US011421034B2

(12) United States Patent
Lewis et al.

(10) Patent No.: US 11,421,034 B2
(45) Date of Patent: Aug. 23, 2022

(54) COMBINATION ANTI-CSF1R AND ANTI-PD-1 ANTIBODY COMBINATION THERAPY FOR PANCREATIC CANCER

(71) Applicants: Five Prime Therapeutics, Inc., South San Francisco, CA (US); Bristol-Myers Squibb Company, Princeton, NJ (US)

(72) Inventors: Katherine E. Lewis, Lake Forest Park, WA (US); Serena Kimi Perna, Philadelphia, PA (US); Michael Carleton, Princeton, NJ (US); Ke Xu, Plainsboro, NJ (US); Penny Phillips, Morristown, NJ (US); Dimple Pandya, Princeton, NJ (US); Brian Wong, Los Altos, CA (US); Julie Hambleton, San Francisco, CA (US); Robert Sikorski, Woodside, CA (US); Emma Masteller, Redwood City, CA (US); Kevin Hestir, Kensington, CA (US); David Bellovin, San Jose, CA (US); Janine Powers, Alameda, CA (US); Ernestine Lee, Kensington, CA (US)

(73) Assignees: Five Prime Therapeutics, Inc., Thousand Oaks, CA (US); Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/646,690

(22) PCT Filed: Sep. 12, 2018

(86) PCT No.: PCT/US2018/050711
§ 371 (c)(1),
(2) Date: Mar. 12, 2020

(87) PCT Pub. No.: WO2019/055537
PCT Pub. Date: Mar. 21, 2019

(65) Prior Publication Data
US 2021/0009697 A1    Jan. 14, 2021

Related U.S. Application Data

(60) Provisional application No. 62/679,612, filed on Jun. 1, 2018, provisional application No. 62/671,887, filed on May 15, 2018, provisional application No. 62/581,962, filed on Nov. 6, 2017, provisional application No. 62/580,154, filed on Nov. 1, 2017, provisional application No. 62/558,161, filed on Sep. 13, 2017.

(51) Int. Cl.
| C07K 16/28 | (2006.01) |
| A61K 47/69 | (2017.01) |
| A61K 47/64 | (2017.01) |
| A61P 35/00 | (2006.01) |
| A61K 31/337 | (2006.01) |
| A61K 31/513 | (2006.01) |
| A61K 31/7068 | (2006.01) |
| A61K 39/395 | (2006.01) |
| C12Q 1/6886 | (2018.01) |
| A61K 39/00 | (2006.01) |

(52) U.S. Cl.
CPC ........ *C07K 16/2866* (2013.01); *A61K 31/337* (2013.01); *A61K 31/513* (2013.01); *A61K 31/7068* (2013.01); *A61K 39/3955* (2013.01); *A61K 47/643* (2017.08); *A61K 47/6929* (2017.08); *A61P 35/00* (2018.01); *C07K 16/2818* (2013.01); *C12Q 1/6886* (2013.01); *A61K 2039/507* (2013.01); *A61K 2039/545* (2013.01); *C07K 2317/21* (2013.01); *C12Q 2600/106* (2013.01); *C12Q 2600/158* (2013.01)

(58) Field of Classification Search
CPC ............ C07K 16/2866; C07K 16/2818; A61K 47/6929; A61K 47/643; A61K 31/337; A61K 31/513; A61K 31/7068; A61K 39/3955; A61P 35/00; C12Q 1/6886
See application file for complete search history.

(56) References Cited

U.S. PATENT DOCUMENTS

| 5,866,114 A | 2/1999 | Pandit et al. |
| 6,184,354 B1 | 2/2001 | Koths et al. |
| 7,108,852 B2 | 9/2006 | Devalaraja et al. |

(Continued)

FOREIGN PATENT DOCUMENTS

| CA | 2388298 A1 | 5/2001 |
| EP | 2241333 A1 | 10/2010 |

(Continued)

OTHER PUBLICATIONS

Zhu et al., "CSF1/CSF1R blockade reprograms tumor-infiltrating macrophages and improves response to T-cell checkpoint immunotherapy in pancreatic cancer models", Cancer Res. Sep. 15, 2014;74(18):5057-69 (Year: 2014).*
The Merck Manuals Online Medical Library, [online]. Merck Research Laboratories, 2006-2007. [retrieved on Oct. 19, 2020]. < URL: https://www.merckmanuals.com/professional/hematology-and-oncology/overview-of-cancer/cellular-and-molecular-basis-of-cancer>. Cellular and Molecular Basis of Cancer (Year: 2007).*
Fujii et al. "Simulation-based analyses reveal stable microsatellite sequences in human pancreatic cancer", Cancer Genet Cytogenet. Feb. 2009;189(1):5-14. (Year: 2009).*
Torres et al. "Serum cytokine profile in patients with pancreatic cancer", Pancreas. Oct. 2014;43(7):1042-9. (Year: 2014).*

(Continued)

*Primary Examiner* — Amy E Juedes
*Assistant Examiner* — Peter Johansen
(74) *Attorney, Agent, or Firm* — McNeill Baur PLLC

(57) ABSTRACT

The present invention relates to methods of treating pancreatic cancer with particular dosage regimes of antibodies that bind colony stimulating factor 1 receptor (CSF1R) (e.g. cabiralizumab) in combination with antibodies that bind programmed cell death 1 (PD-1) (e.g. nivolumab).

15 Claims, 15 Drawing Sheets

Specification includes a Sequence Listing.

(56) References Cited

U.S. PATENT DOCUMENTS

| | | | |
|---|---|---|---|
| 7,247,618 | B2 | 7/2007 | Rajavashisth |
| 7,455,836 | B2 | 11/2008 | Hamilton et al. |
| 7,807,389 | B2 | 10/2010 | Ritchlin et al. |
| 7,919,594 | B2 | 4/2011 | Smith et al. |
| 8,008,449 | B2 | 8/2011 | Korman et al. |
| 8,206,715 | B2 * | 6/2012 | Wong ............... C12N 15/63 424/143.1 |
| 8,513,199 | B2 | 8/2013 | Brasel et al. |
| 8,747,845 | B2 | 6/2014 | Wong et al. |
| 9,765,147 | B2 * | 9/2017 | Wong ............... A61P 1/04 |
| 10,072,082 | B2 * | 9/2018 | Cogswell ............... C07K 16/18 |
| 10,221,244 | B2 * | 3/2019 | Wong ............... C07K 16/3069 |
| 10,556,957 | B2 * | 2/2020 | Beebe ............... A61P 31/00 |
| 10,618,967 | B2 * | 4/2020 | Wong ............... A61P 43/00 |
| 2002/0119494 | A1 | 8/2002 | Jung et al. |
| 2002/0193575 | A1 | 12/2002 | Holmes et al. |
| 2003/0103976 | A1 | 6/2003 | Serizawa et al. |
| 2006/0286102 | A1 | 12/2006 | Jin et al. |
| 2007/0072797 | A1 | 3/2007 | Robinson et al. |
| 2007/0148172 | A1 | 6/2007 | Lawson et al. |
| 2007/0166788 | A1 | 7/2007 | Jin et al. |
| 2008/0219971 | A1 | 9/2008 | Smith et al. |
| 2009/0148883 | A1 | 6/2009 | Manthey |
| 2009/0155164 | A1 | 6/2009 | Brasel et al. |
| 2010/0136006 | A1 | 6/2010 | Lin et al. |
| 2010/0136007 | A1 | 6/2010 | Lin et al. |
| 2011/0123550 | A1 | 5/2011 | Shibayama et al. |
| 2011/0129456 | A1 | 6/2011 | Wang et al. |
| 2011/0243947 | A1 | 10/2011 | Doody et al. |
| 2011/0274683 | A1 | 11/2011 | Wong et al. |
| 2012/0121634 | A1 | 5/2012 | Chen et al. |
| 2013/0302322 | A1 | 11/2013 | Wong et al. |
| 2013/0309250 | A1 | 11/2013 | Cogswell et al. |
| 2014/0079699 | A1 | 3/2014 | Wong et al. |
| 2015/0073129 | A1 | 3/2015 | Herting et al. |
| 2016/0152715 | A1 * | 6/2016 | Wong ............... C07K 16/2818 424/134.1 |
| 2019/0025308 | A1 * | 1/2019 | Cummings ............... G16H 50/20 |
| 2019/0219586 | A1 * | 7/2019 | Fabrizio ............... C12Q 1/6886 |

FOREIGN PATENT DOCUMENTS

| | | | |
|---|---|---|---|
| WO | 8903687 | A1 | 5/1989 |
| WO | 9929345 | A1 | 6/1999 |
| WO | 0134177 | A2 | 5/2001 |
| WO | 2002102972 | A2 | 12/2002 |
| WO | 2004045532 | A2 | 6/2004 |
| WO | 2005070447 | A2 | 8/2005 |
| WO | 2006012451 | A2 | 2/2006 |
| WO | 2007075933 | A2 | 7/2007 |
| WO | 2007081879 | A2 | 7/2007 |
| WO | 2007120252 | A2 | 10/2007 |
| WO | 2008060610 | A2 | 5/2008 |
| WO | 2008124858 | A2 | 10/2008 |
| WO | 2008150383 | A1 | 12/2008 |
| WO | 2009026303 | A1 | 2/2009 |
| WO | 2009058968 | A2 | 5/2009 |
| WO | 2009075344 | A1 | 6/2009 |
| WO | 2009112245 | A1 | 9/2009 |
| WO | 2010062399 | A2 | 6/2010 |
| WO | 2010062401 | A2 | 6/2010 |
| WO | 2011070024 | A1 | 6/2011 |
| WO | 2011107553 | A1 | 9/2011 |
| WO | 2011131407 | A1 | 10/2011 |
| WO | 2011140249 | A2 | 11/2011 |
| WO | 2012082573 | A1 | 6/2012 |
| WO | 2012110360 | A1 | 8/2012 |
| WO | 2013057281 | A1 | 4/2013 |
| WO | 2013057290 | A1 | 4/2013 |
| WO | 2013132044 | A1 | 9/2013 |
| WO | 2013169264 | A1 | 11/2013 |
| WO | 2013173223 | A1 | 11/2013 |
| WO | 2014036357 | A1 | 3/2014 |
| WO | 2015036511 | A1 | 3/2015 |
| WO | 2016069727 | A1 | 5/2016 |
| WO | WO-2016081947 | A2 * | 5/2016 ............... C12Q 1/68 |

OTHER PUBLICATIONS

Lloyd et al., "Modelling the human immune response: performance of a 1011 human antibody repertoire against a broad panel of therapeutically relevant antigens", Protein Engineering, Design and Selection, vol. 22, Issue 3, Mar. 2009, pp. 159-168 (Year: 2009).*

Le Meur et al., Macrophage accumulation at a site of renal inflammation is dependent on the M-CSF/c-fms pathway, J Leukoc Biol, 2002, 72(3):530-537.

Lee et al., Functional Dissection of Structural Domains in the Receptor for Colony-stimulating Factor-1, J. Biol. Chem., vol. 267, Aug. 1992, pp. 16472-16483.

Lenda et al., Negative role of colony-stimulating factor-1 in macrophage, T cell, and B cell mediated autoimmune disease in MRL-Fas(lpr) mice, J Immunol, 2004, 173(7):4744-4754.

Li et al., Conditional Deletion of the Colony Stimulating Factor-1 Receptor (c-fms Proto-Oncogene) in Mice, Genesis, vol. 44, May 2006, pp. 328-335.

Li et al., Role of Dimerization and Modification of the CSF-1 Receptor in its Activation and Internalization During the CSF-1 Response, The EMBO Journal, 1991, pp. 277-288.

Lim et al., Antibody blockade of c-fms suppresses the progression of inflammation and injury in early diabetic nephropathy in obese db/db mice, Diabetologia, vol. 52, 2009, pp. 1669-1679.

Lin et al. Regulation of Myeloid Growth and Differentiation by a Novel Cytokine, Interleukin-34 (IL-34), via the CSF-1 Receptor, poster presented at Cytokines in Health & Disease, Fifteenth Annual Conference of the International Cytokine Society (San Francisco, CA, Oct. 26-30, 2007, 1 page.

Lin et al., Colony-stimulating Factor 1 Promotes Progression of Mammary Tumors to Malignancy, J. Exp. Med., vol. 193, No. 6, Mar. 2001, pp. 727-739.

Lin et al., Discovery of a Cytokine and Its Receptor by Functional Screening of the Extracellular Proteome, Science, vol. 320, May 2008, pp. 807-811.

Lin et al., The Macrophage Growth Factor CSF-1 in Mammary Gland Development and Tumor Progression, J. Mammary Gland Biology and Neoplasia, vol. 7, Apr. 2002, pp. 147-162.

Lipton, Future Treatment of Bone Metastases, Clin. Cancer Res., vol. 12, 20 Suppl., Oct. 2006, pp. 6305s-6308s.

Liu et al., The mechanism of shared but distinct CSF-1R signaling by the non-homologous cytokines IL-34 and CSF-1, Biochimica et Biophysica Acta, 2012, 1824:938-945.

Llosa, et al., "The Vigorous Immune Microenvironment of Microsatellite Instable Colon Cancer is Balanced by Multiple Counter-Inhibitory Checkpoints," Cancer Discov, 2015, 5(1):43-51.

Lopez-Diego et al., Novel Therapeutic Strategies for Multiple Sclerosis—A Multifaceted Adversary, Nature Reviews Drug Discovery, vol. 7, Nov. 2008, pp. 909-925.

MacDonald et al., An Antibody Against the Colony-stimulating Factor 1 Receptor Depletes the Resident Subset of Monocytes and Tissue- and Tumor-associated Macrophages But Does Not Inhibit Inflammation, Blood, vol. 116, Aug. 2010, pp. 3955-3963.

Mancino et al., Breast Cancer Increases Osteoclastogenesis by Secreting M-CSF and Upregulating RANKL in Stromal Cells, J. Surgical Research, vol. 100, Jul. 2001, pp. 18-24.

Masteller, et al., "Targeting IL-34 in Chronic Inflammation," Drug Discov Today, 2014, 19:1212-16.

Menke et al., Circulating CSF-1 Promotes Monocyte and Macrophage Phenotypes that Enhance Lupus Nephritis, j Am Soc Nephrol, 2009, 20:2581-2592.

Menke et al., CSF-1 signals directly to renal tubular epithelial cells to mediate repair in mice, J Clin Invest, 2009, 119(8):2330-2342.

Montell, Metastasis Movies, Macrophages, Molecules and More, EMBO Reports, vol. 4, No. 5, Apr. 2003, pp. 458-462.

(56) References Cited

OTHER PUBLICATIONS

Mroczko et al., Serum Macrophage-colony Stimulating Factor Levels in Colorectal Cancer Patients Correlate with Lymph Node Metastasis and Poor Prognosis, Clinica Chimica Acta., vol. 380, Feb. 2007, pp. 208-212.
Murray et al., SU11248 Inhibits Tumor Growth and CSF-1 R-dependent Osteolysis in an Experimental Breast Dancer Bone Metastasis Model, Clinical & Experimental Metastasis, vol. 2, Aug. 2003, pp. 757-766.
Nishimura, et al., "Autoimmune Dilated Cardiomyopathy in PD-1 Receptor-Deficient Mice," Science, 2001, 291:319-22.
Nishimura, et al., "Development of Lupus-Like Autoimmune Diseases by Distruption of the PD-1 Gene Encoding an TM Motif-Carrying Immunoreceptor," Immunity, 1999, 11:141-51.
Nishimura, et al., "PD-1: An Inhibitory Immunoreceptor Involved in Peripheral Tolerance," Trends Immunol., 2001, 22:265-8.
Notice of Allowance and Fees Due and Examiner initiated interview summary dated Dec. 8, 2011, for U.S. Appl. No. 12/626,583 (9 pages).
Notice of Allowance and Fees Due dated Oct. 13, 2011, for U.S. Appl. No. 12/626,598 (6 pages).
Noy, et al., "Tumor-Associated Macrophages: from Mechanisms to Therapy," Immunity, 2014, 41:49-61.
Office Action dated Jun. 21, 2011, for U.S. Appl. No. 12/626,583 (14 pages).
Office Action dated Mar. 16, 2001, for U.S. Appl. No. 12/626,598 (12 pages).
Office Action dated Nov. 16, 2010, for U.S. Appl. No. 12/626,598 (7 pages).
Ohno et al., A c-Fms Tyrosine Kinase Inhibitor, Ki20227, Suppresses Osteoclast Differentiation and Osteolytic Bone Destruction in a Bone Metastasis, Mol. Cancer Ther., vol. 5, Nov. 2006, pp. 2634.
Ohno et al., The Orally-active and Selective c-FMS tyrosine Kinase Inhibitor Ki20227 Inhibits Disease Progression in a Collagen-induced Arthritis Mouse Model, Eur. J. Immunol., 2008, vol. 38:283-291.
Okazaki, et al., "Autoantibodies against Cardiac Troponin I are Responsible for Dilated Cardiomyopathy in PD-1-Deficient Mice," Nat Med, 2003, 9:1477-83.
Opdivo [package insert]. Princeton, NJ: Bristol-Myers Squibb Company; Mar. 2015.
Opposition Brief in European Patent No. 2287192, dated May 25, 2016, 22 pages.
Paniagua et al., c-Fms-mediated Differentiation and Priming of Monocyte Lineage Cells Plays a Central Role in Autoimmune Arthritis, Arthritis Research & Therapy, vol. 12, No. R32, Feb. 2010, pp. 1-45.
Papadopoulos et al., "First-in-human Study of AMG 820, a Monoclonal Anti-Colony Stimulating Factor 1 Receptor Antibody, in Patients with Advanced Solid Tumors," Clin Cancer Research, 2017, 23(19): 5703-5710.
Pardoll, "Does the Immune System see Tumors as Foreign or Self?" Annu Rev Immunol, 2003, 21:807-39.
Pasternak et al., ACC/AHA/NHLBI Clinical Advisory on the Use and Safety of Statins, J Am College Cardiology, 2002, 40(3):567-572.
Patel & Player, Colony-Stimulating Factor-1 Receptor Inhibitors for the Treatment of Cancer and Inflammatory Disease, Curr Topics Med Chem, 2009, 9:599-610.
Paul, WE, Fundamental Immunology, 3rd Ed., Raven Press, NY, Chapter 9, pp. 292-295 (1993).
Paulus et al., Colony-stimulating Factor-1 Antibody Reverses Chemoresistance in Human MCF-7 Breast Cancer Xenografts, Cancer Res., vol. 66, No. 8, Apr. 2006, pp. 4349-4356.
Pederson et al., Identification of Breast Cancer Cell Line-derived Paracrine Factors That Stimulate Osteoclast Activity, Cancer Research, vol. 59, Nov. 1999, pp. 5849-5855.

Pixley et al., CSF-1 Regulation of the Wandering Macrophage: Complexity in Action, Trends in Cell Biology, vol. 14, No. 11, Nov. 2004, pp. 628-638.
Priceman et al., Targeting distinct tumor-infiltrating myeloid cells by inhibiting CSF-1 receptor: combating tumor evasion of antiangiogenic therapy, Blood, 2010 115(7):1461-1471.
Prince et al., 8: Disorders of Bone and Mineral Other Than Osteoporosis, MJA, vol. 180, Apr. 2004, pp. 354-359.
Pyonteck, et al., "CSF-1R Inhibition Alters Macrophage Polarization and Blocks Glioma Progression," Nat Med, 2013, 19:1264-72.
Qiu et al., Primary Structure of c-kit: Relationship with the CSF-1/PDGF Receptor Kinase Family—Oncogenic Activation of v-kit Involves Deletion of Extracellular Domain and C Terminus, The EMBO Journal, vol. 7, No. 4, Jan. 1988, pp. 1003-1011.
R&D Systems, Inc., Recombinant Human M-CSF R/Fc Chimera, Specifications and Use, Catalog No. 329-MR, Nov. 2007, 2 pages.
Aharinejad et al., Colony-stimulating Factor-1 Antisense Treatment Suppresses Growth of Human Tumor Xenografls in Mice, Cancer Research, vol. 62, Sep. 2002, pp. 5317-5324.
Aharinejad et al., Colony-stimulating Factor-1 Blockade by Antisense Oligonucleotides and Small Interfering RNAs Suppresses Growth of Human Mammary Tumor Xenografls in Mice, Cancer Research, vol. 64, Aug. 2004, pp. 5378-5384.
Aikawa et al., PU.1-mediated upregulation of CSF1R is crucial for leukemia stem cell potential induced by MOZ-TIF2, Nature Medicine, vol. 16, May 2010, pp. 580-585.
Amendment After Final filed Aug. 16, 2011, for U.S. Appl. No. 12/626,598 (8 pages).
Amendment and Response to Restriction Requirement filed Feb. 16, 2011, for U.S. Appl. No. 12/626,598 (7 pages).
Ando et al., Imatinib Mesylate Inhibits Osteoclastogenesis and Joint Destruction in Rats with Collagen-induced Arthritis, J. Bone Miner. Metab., vol. 24, Jan. 2006, pp. 274-282.
Anonymous, "A Study of Cabiralizumab Give with Nivolumab With or Without Chemotherapy in Patients with Advanced Pancreatic Cancer," NCT03336216, Nov. 8, 2017, 8 pages.
Anonymous, "A Study of Cabiralzumab Given by Itself or with Nivolumab in Advanced Cancer or Cancer that has Spread," ClinicalTrials.gov, NCT03158272, May 18, 2017, 7 pages.
Anonymous, "An Adaptive Study to Match Patients with Solid Tumors to Various Immunotherapy Combinations Based Upon a Broad Biomarker Assessment," ClinicalTrials.gov, NCT03335540, Nov. 7, 2017, 7 pages.
Anonymous, "APX005M With Nivolumab and Cabiralizumab in Advanced Melanoma, Non-Small Cell Lung Cancer or Renal Cell Carcinoma," ClinicalTrials.gov, NCT03502330, Apr. 18, 2018, 14 pages.
Anonymous, "Archive History for NCT02713529—Safety and Efficacy Study of AMG 820 and Pembrolizumab Combination in Select Advanced Solid Tumor Cancer," ClinicalTrials.gov, NCT02713529, Sep. 6, 2017, 4 pages.
Anonymous, "Bristol-Myers Squibb and Five Prime Therapeutics Announce Exclusive Clinical Collaboration to Evaluate the Combination of Investigational Immunotherapies Opvido (nivolumab) and FPA008 in Six Tumor Types," XP055243984, Nov. 24, 2014, pp. 1-4.
Anonymous, "Five Prime Therapeutics Provides Update on Phase 2 Trial of Cabiralizumab Combined with Opdivo® in Pancreatic Cancer," Feb. 18, 2020, available at htps://www.fiveprime.com.
Anonymous, Nivolumab + Cabiralizumab + Gemcitabine Versus Gemcitabine in Patients with Stage IV Pancreatic Cancer Achieving Disease Conlrol in Response to First-line Chemotherapy (GemCaN Trial), ClinicalTrials.gov, NCT03697564, Oct. 5, 2018, 7 pages.
Anonymous, "Nivolumab and the Antagonistic CSF-1R Monoclonal Antibody Cabiralizumab (BMS-986227) in Patients with Relapsed/Refractory Peripheral T Cell Lymphoma," ClinicalTrials.gov, NCT03927105, Apr. 25, 2019, 9 pages.
Anonymous, "Safety and Tolerability Study of Nivolumab and Cabiralizumab for Resectable Biliary Tract Cancer," ClinicalTrials.gov, NCT03768531, Dec. 7, 2018, 6 pages.
Anonymous, "Stereotactic Body Radiotherapy (SBRT) Plus Immunotherapy for Cancer (C4-MOSART)," ClinicalTrials.gov, NCT03431948, 9 pages.

(56) References Cited

OTHER PUBLICATIONS

Anonymous, "Study of Cabiralizumab in Combination with Nivolumab in Patients with Selected Advanced Cancers (FPA008-003)," ClinicalTrials.gov, NCT02526017, Aug. 18, 2015, 7 pages.

Anonymous, "Study of Cabiralizumab in Patients with pigmented Villonodular Synovitis / Diffuse Type Tenosynovial Giant Cell Tumor (FPA008-002)", ClinicalTrials.gov, NCT02471716, Jun. 15, 2015, 6 pages.

Anonymous, "Study of FPA008 in Combination with Nivolumab in Patients with Selected Advance Cancers," XP055243978, Aug. 17, 2015, pp. 1-4.

Anonymous, "Study of Nivolumab, Cabiralizumab, and Sterotactic Body Radiotherapy (SBRT) for Locally Advanced Unresectable Pancreatic Cancer," ClinicalTrials.gov, NCT03599362, Jul. 25, 2018, 8 pages.

Ansari, et al., "The Programmed Death-1 (PD-1) Pathway Regulates Autoimmune Diabetes in Nonobese Diabetic (NOD) Mice," J Exp Med., 2003, 198(1):63-9.

Apollo Cytokine Research, Human hex™ M-CSF R, Fc Chimera, Product Information Sheet from http://www.biocompare.com/itemdetails.asp?itemid=837066, Feb. 4, 2008.

Birchenall-Roberts, Inhibition of Murine Monocyte Proliferation by a Colony-stimulating Factor-1 Antisense Oligodeoxynucleotide, J. Immunol., vol. 15, Nov. 1990, pp. 3290-3296.

Bischof et al., Exacerbation of Acute Inflammatory Arthritis by the Colony-stimulating Factors CSF-1 and Granulocyte Macrophage (GM)-CSF: Evidence of Macrophage Infiltration and Local Proliferation, Clin. Exp. Immunol., vol. 119, 2000, pp. 361-367.

Blazar, et al., "Blockade of Programmed Death-1 Engagement Accelerates Graft-Versus-Host Disease Lethality by an IFN-α-Dependent Mechanism," J Immunol., 2003, 171:1272-7.

Bloom et al., Colony stimulating factor-1 in the induction of lupus nephritis, Kidney International, 1993, 43:1000-1009.

Burns & Wilks, c-FMS inhibitors: a patent review, Expert Opin Ther Pat., 2011, 21(2):147-165.

Campbell et al., The Colony-stimulating Factors and Collagen-induced Arthritis: Exacerbation of Disease by M-CSF and G-CSF and Requirement for Endogenous M-CSF, Journal of Leukocyte Biology, vol. 68, Jul. 2000.

Carayannopoulos & Capra, Immunoglobulins: Structure and Function, Fundamental Immunology, 3rd Edition, Paul ed., Raven Press, NY, 1993, 292-295.

Carter et al., "PD-1:PD-L Inhibitory Pathway Affects both CD4+ and CD8+ T Cells and is Overcome by IL-2," Eur J Immunol., 2002, 32(3):634-43.

Gassier et al., "Phase 1 Study of RG7155, a Novel Anti-CSF1R Antibody, in Patients with Locally Advanced Pigmented Villonodular Synovitis (PVNS)," J Clin Oncol suppl., 2014, 32:5 abstract 10504.

Chaika et al., CSF-1 Receptor/Insulin Chimera Permits CSF-1-dependent Differentiation of 3T3-L1 Preadipocytes, J. Biol. Chem., vol. 272, No. 18, May 1997, pp. 11968-11974.

Chara et al., Monocyte populations as markers of response to adalimumab plus MTX in rheumatoid arthritis, Arthritis Research & Therapy, 2012, 14:R175 including supplemental data, 13 pages.

Chemel et al., Interleukin 34 expression is associated with synovitis severity in rheumatoid arthritis patients, Ann Rheum Dis, 2012, 71(1):150-154.

Chemnitz, et al., "SHP-1 and SHP-2 Associate with Immunoreceptor Tyrosine-Based Switch Motif of Programmed Death 1 upon Primary Human T Cell Stimulation, but only Receptor Ligation Prevents T Cell Activation," J Immunol., 2004, 173:945-54.

Chitu et al., Colony-stimulating Factor-1 in Immunity and Inflammation, Current Opinion in Immunology, vol. 18, No. 1, Feb. 2006, pp. 39-48.

Colman, "Effects of amino acid sequence changes on antibody-antigen interactions," Research in Immunology, Elsevier, NY, 145(1): 33-36 (1994).

Conway et al., Effects of the cFMS Kinase Inhibitor 5-(3-Methoxy-4-((4-methoxybenzyl)oxy)benzyl)pyrimidine-2,4-diamine (GW2580) in Normal and Arthritic Rats, J. Pharmacology and Experimental Therapeutics, vol. 326, No. 1, Apr. 2008, pp. 41-50.

Conway et al., Inhibition of Colony-stimulating-factor-1 Signaling in Vivo with the Orally Bioavailable cFMS Kinase Inhibitor GW2580, PNAS, vol. 102, Nov. 2005, pp. 16078.

Cooper et al., FccRIIIa Expression on Monocytes in Rheumatoid Arthritis: Role in Immune-Complex Stimulated TNF Production and Non-Response to Methotrexate Therapy, PLoS One, 2012, 7(1):e28918, 10 pages.

Cros et al., Human CD14dim Monocytes Patrol and Sense Nucleic Acids and Viruses via TLR7 and TLR8 Receptors, Immunity, 2010, 33:375-386.

Dai et al., "Targeted Disruption of the Mouse Colony-Stimulating Factor 1 Receptor Gene Results in Osteopetrosis, Mononuclear Phagocyte Deficiency, Increased Primitive Progenitor Cell Frequencies, and Reproductive Defects," Blood, 2002, 99:111-20.

Dandekar et al., Comparison of the Signaling Abilities of the Cytoplasmic Domains of the Insulin Receptor and the Insulin Receptor-related Receptor in 3T3-L1 Adipocytes, Endocrinology, vol. 139, No. 8, Jan. 2008, pp. 3578-3584.

Dewar et al., Imatinib as a Potential Antiresorptive Therapy for Bone Disease, Blood, vol. 107, No. 11, Jun. 2006, pp. 4334-4337.

Dunn et al., "Cancer Immunoediting: from Immunosurveillance to Tumor Escape," Nat Immunol, 2002, 3:991-8.

Extended European Search Report, European Patent Appl. No. 11778283.9, dated Apr. 22, 2015.

File History of U.S. Appl. No. 16/808,910, filed Mar. 4, 2020.

File History of U.S. Appl. No. 13/100,990, filed May 4, 2011.

File History of U.S. Appl. No. 13/464,503, filed May 4, 2012.

Radi, et al., "Increased Connective Tissue Extracellular Matrix in the Op/Op Model of Osteopetrosis," Pathobiology, 2009, 76:199-203.

Radi, et al., "Increased Serum Enzyme Levels Associated with Kupffer Cell Reduction with No Signs of Hepatic or Skeletal Muscle Injury," Am J Pathol, 2011, 179:240-247.

Rahimi et al., Receptor Chimeras Indicate that the Vascular Endothelial Growth Factor Receptor-1 (VEGFR-1) Modulates Mitogenic Activity of VEGFR-2 in Endothelial Cells, J. Biol. Chem., vol. 275, No. 22, Jun. 2000, pp. 16986-16992.

Rauen & Mertens, Unravelling the pathogenesis of lupus nephritis: novel genetic study confirms decisive contribution of circulating colony-stimulating factor-1 (CSF-1), Int Urol Nephrol, 2010, 42:419-521.

Reply to Office Action filed Aug. 1, 2011, for U.S. Appl. No. 12/626,583 (15 pages).

Reply to Office Action filed Jun. 16, 2011 for U.S. Appl. No. 12/626,598 (7 pages).

Response to Restriction Election Requirement filed May 3, 2011, for U.S. Appl. No. 12/626,583 (3 pages).

Ries, et al., "CSF-1/CSF-1R Targeting Agents in Clinical Development for Cancer Therapy," Current Opinion in Pharmacology, 2015, 23: 45-51.

Ries, et al., "Targeting Tumor-Associated Macrophages with Anti-CSF-1R Antibody Reveals a Strategy for Cancer Therapy," Cancer Cell, 2014, 25(6): 846-859.

Rizvi, et al., "Activity and Safety of Nivolumab, an Anti-PD-1 Immune Checkpoint Inhibitor, for Patients with Advanced, Refractory Squamous Non-Small-Cell Lung Cancer (CheckMate 063): A Phase 2, Single-Arm Trial," Lancet Oncol., 2015, 16(3):257-65.

Ross, M-CSF, c-Fms, and Signaling in Osteoclasts and Their Precursors, Annals NY Acad. Sci., vol. 1068, 2006, pp. 110-116.

Rossol et al., The CD14-bright CD16+ Monocyte Subset Is Expanded in Rheumatoid Arthritis and Promotes Expansion of the Th17 Cell Population, Arthritis & Rheumatism, 2012, 64(3):671-677.

Roussel et al., Colony-stimulating Factor 1-mediated Regulation of a Chimeric c-fms / v-fms Receptor Containing the v-fms-encoded Tyrosine Kinase Domain, PNAS, vol. 85, Aug. 1988, pp. 5903-5907.

Rudikoff et al., "Single amino acid substitution altering antigen-binding specificity," Proc. Natl. Acad. Sci. USA, 79:1979-1983(1982).

Ruffell, et al., "Macrophages and Therapeutic Resistance in Cancer," Cancer Cell, 2015, 27:462-72.

(56) References Cited

OTHER PUBLICATIONS

Rutebemberwa, et al., "High-Programmed Death-1 Levels of Hepatitis C Virus-Specific T Cells During Acute Infection are Associated with Viral Persistence and Require Preservation of Cognate Antigen during Chronic Infection," J Immunol, 2008, 181:8215-25.
Sadis, et al., "Safety, Pharmacokinetics, and Pharmacodynamics of PD-0360324, a Human Monoclonal Antibody to Monocyte/Macrophage Colony Stimulating Factor, in Healthy Volunteers," ACR/ARHP Scientific Meeting Oct. 17-21, 2009, Philadelphia, PA, Poster 408.
Salama, et al., "Critical Role of the Programmed Death-1 (PD-1) Pathway in Regulation of Experimental Autoimmune Encephalomyelitis," J Exp Med, 2003, 198:71-8.
Sapi, The Role of CSF-1 in Normal Physiology of Mammary Gland and Breast Cancer: An Update, Exp. Biol. Med., vol. 229, 2004, pp. 1-11.
Sarma et al., Macrophage Colony-stimulating Factor Induces Substantial Osteoclast Generation and Bone Resorption in Human Bone Marrow Cultures, Blood, vol. 88, No. 7, Oct. 1996, pp. 2531-2540.
Sasmono et al., Mouse neutrophilic granulocytes express mRNA encoding the macrophage colony-stimulating factor receptor (CSF-1R) as well as many other macrophage-specific transcripts and can transdifferentiate into macrophages in vitro in response to CSF-1, J Leukoc Biol, 2007, 82(1):111-123.
Seeff, Should There Be a Standard of Care (SOC) for Drug-Induced Liver Injury (DILI)?, Presentation, Drug-Induced Liver Injury: Are We Ready to Look, Mar. 23-24, 2011, AASLD, FDA/CDER, PhRMA, 20 pages.
Seshan & Jennette, Renal Disease in Systemic Lupus Erythematosus With Emphasis on Classification of Lupus Glomerulonephritis, Arch Pathol Lab Med, 2009, 133:233-248.
Shaposhink et al., Arterial Colony Stimulating Factor-1 Influences Atherosclerotic Lesions by Regulating Monocyte Migration and Apoptosis, J. Lipid Research, vol. 51, 2010, pp. 1962-1970.
Sharpe, et al., "The Function of Programmed Cell Death 1 and its Ligands in Regulating Autoimmunity and Infection," Nature Immunol, 2007, 8:239-45.
Sheppard, et al., "PD-1 Inhibits T-Cell Receptor Induced Phosphorylation of the ZAP70/CD3zeta Signalosome and Downstream Signaling to PKC-theta," FEBS Letters, 2004, 574:37-41.
Sherr et al., Inhibition of Colony-Stimulating Factor-1 Activity by Monoclonal Antibodies to the Human CSF-1 Receptor, Blood, vol. 73, No. 7, May 1989, pp. 1786-1793.
Sherr, Colony-Stimulating Factor-1 Receptor, Blood, vol. 75, No. 1, Jan. 1990, pp. 1-12.
Sigma Product Information, "Macrophage Cologny Stimulating Factor Receptor/Fc Chimera (M-CSF R, CD115) Human, Recombinant, Expressed in mouse NSO cells," Product No. M 7559, no date available.
Sigma Product Information, "Macrophage Cologny Stimulating Factor Receptor/Fc Chimera (M-CSF R, CD115) Human, Recombinant, Expressed in mouse NSO cells," Product No. M 7559, 2011, 2 pages.
Steinman et al., Virtues and Pitfalls of EAE for the Development of Therapies for Multiple Sclerosis, Trends in Immunology, 2005, 26(11):565-571.
Subimerb et al., Circulating CD14+CD16+ monocyte levels predict tissue invasive character of cholangiocarcinoma, Clinical and Experimental Immunology, 2010, 161:471-479.
Suzuki et al., Differences in Bone Responses to Recombinant Human Granulocyte Colony-stimulating Factor Between Mice and Rats, J. Toxicol. Sci., vol. 33, No. 2, 2008, pp. 245-249.
Sweet et al., CSF-1 as a Regulator of Macrophage Activation and Immune Response, AI&TE, vol. 51, 2003, pp. 169-177.
T Tsuboi et al., Leukemia 14: 1460-66 (2000).
Tamura et al., Tyrosine Kinase as Targets for Anti-inflammatory Therapy, Anti-Inflammatory & Anti-Allergy Agents in Medicinal Chemistry, vol. 6, No. 1, 2007, pp. 47-60.

Tanaka et al., Macrophage Colony-stimulating Factor is Indispensable for Both Proliferation and Differentiation of Osteoclast Progenitors, J. Clin. Invest., vol. 91, Jan. 1993, pp. 257-263.
TECOmedical Group, TRAP5b Tartrate-Resistant Acid Phosphatase active isoform 5b, A biomarker for osteoclastic bone-resporption activity, Bone-resporption in renal insufficiency, Catalog, Jul. 2011, 20 pages.
Teitelbaum, Osteoclasts: What Do They Do and How Do They Do It? Am. J. Pathol., vol. 170, No. 2, Feb. 2007, pp. 427-435.
Toh et al., Colony Stimulating Factor 1 Receptor Inhibition Has Anti-Inflammatory and Potent Early Onset Bone and Cartilage Protective Effects, Abstract, ACR/ARHP Scientific Meeting, Nov. 7, 2011, 1 page.
Tumeh, et al., "PD-1 Blockade Induces Responses by Inhibiting Adaptive Immune Resistance," Nature, 2014, 515:568-71.
Uemura et al., The Selective M-CSF Receptor Tyrosine Kinase Inhibitor Ki20227 Suppresses Experimental Autoimmune Encephalomyelitis, J. Neuroimmunology, vol. 195, Jan. 2008, pp. 73-80.
USBiological, CD115, Recombinant, Human, Fc Chimera (BSA Free) (c-fms, Fms, CSF-1 R, M-CSFR), from Google's cache of http://usbio.net/Product.spx?ProdSku+C2447-52E1, as retrieved on Jan. 16, 2008 (1 page).
Van Daalen Wetters et al., Random Mutagenesis of CSF-1 Receptor (FMS) Reveals Multiple Sites for Activating Mutations within the Extracellular Domain, The EMBO Journal, 1992, 11:551-557.
Velu, et al., "Enhancing SIV-Specific Immunity in vivo by PD-1 Blockade," Nature, 2009, 458:206-10.
Virk et al., Tumor Metastasis to Bone, Arthritis Research & Therapy, vol. 9, Suppl. 1, 2007, S5, pp. 1-10.
Wada et al., Systemic autoimmune nephritogenic components induce CSF-1 and TNF-alpha in MRL kidneys, Kidney International, 1997, 52:934-941.
Walsh et al., Post-translational Modifications in the Context of Therapeutic Proteins, Nature Biotechnology, vol. 24, No. 10, Oct. 2006, pp. 1241-1252.
Wang et al., Identification of the Ligand-binding Regions in the Macrophage Colony-stimulating Factor Receptor Extracellular Domain, Mol. Cell Biol., Sep. 1993, pp. 5348-5359.
Wang, et al., "In Vitro Characterization of the Anti-PD-1 Antibody Nivolumab, BMS-936558, and in vivo Toxicology in Non-Human Primates," Cancer Immunol Res., 2014, 2:846-56.
File History of U.S. Appl. No. 13/891,455, filed May 10, 2013.
File History of U.S. Appl. No. 14/014,446, filed Aug. 30, 2013.
File History of U.S. Appl. No. 14/266,209, filed Apr. 30, 2014.
File History of U.S. Appl. No. 14/924,568, filed Oct. 27, 2015.
File History of U.S. Appl. No. 14/925,534, filed Oct. 28, 2015.
File History of U.S. Appl. No. 15/279,853, filed Sep. 29, 2016.
File History of U.S. Appl. No. 15/680,664, filed Aug. 18, 2017.
File History of U.S. Appl. No. 16/243,510, filed Jan. 9, 2019.
Final Office Action dated Aug. 3, 2011, for U.S. Appl. No. 12/626,598 (6 pages).
Freeman, et al., "Engagement of the PD 1 Immunoinhibitory Receptor by a Novel B7 Family Member Leads to Negative Regulation of Lymphocyte Activation," J Exp Med, 2000, 192(7):1027-34.
Gabbay, et al., "A Randomized Crossover Trial of the Impact of Additional Spermicide on Condom Failure Rates," Sex Transm Dis, 2008, 35:862-8.
Garceau, V. et al., "Pivotal Advance: Avian Colony-Stimulating Factor 1 (CSF-1), Interlukin-34 (IL-34), and CSF-1 Receptor Genes and Gene Products," Journal of Leukocyte Biology, 2010, vol. 87, pp. 753-764.
Garcia et al., Colony-Stimulating Factor (CSF)-1 Receptor Blockade Overcomes Overlapping Effects of M-CSF and IL-34 on Myeloid Differentiation and Gene Expression to Reduce Inflammation in Human and Murine Models of Rheumatoid Arthritis, ACR Poster, Nov. 2012, 1 page.
Garnero et al., Biochemical markers of joint tissue turnover in early rheumatoid arthritis, Clin Exp Rheumatol, 2003, 21(Suppl. 31):S54-S58.
Goswami et al., Macrophages Promote the Invasion of Breast Carcinoma Cells via a Colony-stimulating Factor-1/Epidermal Growth Factor . . . , Cancer Research., vol. 65, Jun. 2005.

(56) References Cited

OTHER PUBLICATIONS

Greenwald, et al., "The B7 Family Revisited," Annu Rev Immunol, 2005, 23:515-48.
Habicht, et al., "A Link Between PDL 1 and T Regulatory Cells in Fetomaternal Tolerance," J Immunol, 2007, 179:5211-9.
Haegel, et al., "A Unique Anti-CD115 Monoclonal Antibody Which Inhibits Osteolysis and Skews Human Monocyte Differentiation from M2-Polarized Macrophages Toward Dendritic Cells," mAbs, 2013, 5:5, pp. 736-747.
Haegel, et al., "A Unique Anti-CD115 Monoclonal Antibody Which Inhibits Osteolysis and Skews Human Monocyte Differentiation from M2-Polarized Macrophages Toward Dendritic Cells," mAbs, 5:5, 2013, Suppl., 12 pages.
Hamilton, Colony-stimulating Factors in Inflammation and Autoimmunity, Nature Reviews, vol. 8, Jul. 2008, pp. 533-544.
Hamilton, CSF-1 Signal Transduction, Journal of Leukocyte Biology, vol. 62, Aug. 1997, pp. 145-155.
Hamilton, et al., "Colony Stimulating Factors and Myeloid Cell Biology in Health and Disease," Trends in Immunology, 2013, 34:81-89.
Hegen et al., Utility of Animal Models for Identification of Potential Therapeutics for Rheumatoid Arthritis, Ann. Rheum. Dis., vol. 67, published online Nov. 2007, pp. 1505-1515.
Ide et al., Expression of Colony-stimulating Factor 1 Receptor During Prostate Development and Prostate Cancer Progression, PNAS, vol. 99, No. 22, Oct. 2002, pp. 14404-14409.
Ide et al., Serum Level of Macrophage Colony-stimulating Factor is Increased in Prostate Cancer Patients with Bone Metastasis, Human Cell, vol. 21, No. 1, Feb. 2008, pp. 1-6.
International Search Report and the Written Opinion dated Jan. 31, 2012 for International Patent Application PCT/US2011/035231, filed May 4, 2011.
International Search Report and Written Opinion dated Jan. 7, 2014, for Application No. PCT/US2013/057442, filed Aug. 30, 2013, 15 pages.
International Search Report and Written Opinion dated Jun. 9, 2010 for Application No. PCT/US2009/006299, filed Nov. 25, 2009.
International Search Report and Written Opinion dated May 24, 2010 for Application No. PCT/US2009/006301, filed Nov. 25, 2009.
International Search Report and Written Opinion dated Sep. 7, 2012 for Application No. PCT/US2012/037520, Filed May 11, 2012, 13 pages.
International Search Report for PCT/US2015/057781, dated Feb. 1, 2016, pp. 1-17.
International Search Report for PCT/US2018/050711, dated Feb. 20, 2019, 18 pages.
Irvine et al., A CSF-1 Receptor Kinase Inhibitor Targets Effector Functions and Inhibits Pro-inflammatory Cytokine Production . . . , FASEB, vol. 20, Sep. 2006, pp. E1315-E1326.
Kaufmann, et al., "Programmed Death-1 as a Factor in Immune Exhaustion and Activation in HIV Infection," Curr Opin HIV Aids, 2008, 3(3):362-7.
Kawanaka et al., CD14+, CD16+ Blood Monocytes and Joint Inflammation in Rheumatoid Arthritis, Arthritis & Rheumatism, 2002, 46(10):2578-2586.
Kelley, Leukocyte-Renal Epithelial Cell Interactions Regulate Lupus Nephritis, Semin Nephrol, 27:59-68 Jan. 2007.
Kestelman, et al., "Efficacy of the Simultaneous Use of Condoms and Spermicides," Family Planning Perspectives, 1991, 23(5):226-7.
Kingsley et al., Molecular Biology of Bone Metastasis, Mol. Cancer Ther., vol. 6, No. 10, Oct. 2007, pp. 2609-2617.
Kitaura et al., An M-CSF Receptor c-Fms Antibody Inhibits Mechanical Stress-Induced Root Resorption during Orthodontic Tooth Movement in Mice, Angle Orthodontist, vol. 79, No. 5, 2009, pp. 835-841.
Kitaura et al., M-CSF Mediates TNF-induced Inflammatory Osteolysis, The Journal of Clinical Investigation, vol. 115, No. 12, Dec. 2005, pp. 3418-3427.
Kluger et al., Macrophage Colony-stimulating Factor-1 Receptor Expression is Associated with Poor Outcome in Breast Cancer by Large Cohort Tissue Microarray Analysis, Clinical Cancer Res, vol. 10, Jan. 2004, pp. 173.
Koch et al., Investigating the role of proinflammatory CD16+ monocytes in the pathogenesis of inflammatory bowel disease, Clin Exper Immunol, 2010, 161:332-341.
Komohara, et al, "Clinical Significance of Macrophage Heterogeneity in Human Malignant Tumors," Cancer Sci, 2014, 105:1-8.
Kuang, et al., "Activated Monocytes in Peritumoral Stroma of Hepatocellular Carcinoma Foster Immune Privilege and Disease Progression through PD-L1," J Exp Med, 2009, 206(6):1327-37.
Kubota et al., M-CSF Inhibition Selectively Targets Pathological Angiogenesis and Lymphangiogenesis, J. Exp. Med., vol. 206, No. 5, Apr. 2009, pp. 1089-1102.
Kutza et al., Macrophage Colony-stimulating Factor Antagonists Inhibit Replication of HIV-1 in Human Macrophages, The Journal of Immunology, 2000, vol. 164, pp. 4955-4960.
Kutzelnigg et al., Cortical demyelination and diffuse white matter injury in multiple sclerosis, Brain, 2005, 128:2705-2712.
Latchman, et al., "PD-L2 is a Second Ligand for PD-1 and Inhibits T Cell Activation," Nat Immunol, 2001, 2(3):261-268.
Lavin, et al., "Macrophages: Gate Keepers of Tissue Integrity," Cancer Immunol Res., 2013, 1(4):201-9.
Lavin, et al., "Tissue-Dependent Macrophage Enhancer Landscapes are Shaped by the Local Microenvironment," Cell, 2014, 159:1312-26.
Weber, et al., "Nivolumab Versus Chemotherapy in Patients with Advanced Melanoma who Progressed after Anti-CTLA-4 Treatment (CheckMate 037): A Randomised, Controlled, Open-Label, Phase 3 Trial," Lancet Oncol, 2015, 16(4):375-84.
Wei et al., Functional overlap but differential expression of CSF-1 and IL-34 in their CSF-1 receptor-mediated regulation of myeloid cells, J Leukoc Biol, 2010, 88(3):495-505.
Weihofen et al., Release of Signal Peptide Fragments Into the Cytosol Requires Cleavage in the Transmembrane Region by a Protease Activity That is Specifically Blocked by a Novel Cysteine Protease Inhibitor, J. Biol. Chem., vol. 275, No. 40, Oct. 2000, pp. 30951-30956.
Wentworth & Davis, Systemic lupus erythematosus, Nature Rev, 2009, 8:103-104.
Wijngaarden et al., Fc-gamma receptor expression levels on monocytes are elevated in rheumatoid arthritis patients with high erythrocyte sedimentation rate who do not use anti-rheumatic drugs, Rheumatology, 2003, 42:681-688.
Wolchok, et al., "Guidelines for the Evaluation of Immune Therapy Activity in Solid Tumors: Immune-Related Response Criteria," Clin Cancer Res., 2009, 15:7412-20.
Wu et al., Enhancement of J6-1 Human Leukemic Cell Proliferation by Membrane-bound M-CSF Through a Cell-Cell Contact Mechanism II. Role of an M-CSF Receptor-like Membrane Protein, Leukemia Research, vol. 22, 1998, pp. 55-60.
Wyckoff et al., A Paracrine Loop Between Tumor Cells and Macrophages is Required for Tumor Cell Migration in Mammary Tumors, Cancer Research, vol. 64, Oct. 2004, pp. 7022-7029.
Yang et al., Increase in the level of macrophage colony-stimulating factor in patients with systemic lupus arythematosus, Ann Rheum Dis, 2008, 67:429-430.
Yano et al., Macrophage Colony-Stimulating Factor Gene Transduction into Human Lung Cancer Cells Differentially Regulates Metastasis . . . , Cancer Research, Feb. 1997, pp. 784.
Yao et al., Tumor Necrosis Factor-α Increases Circulating Osteoclast Precursor Numbers by Promoting Their Proliferation and Differentiation in the Bone Marrow Through Up-regulation of c-Fms Expression, J. Biol Chem., vol. 281, Apr. 2006, pp. 11846.
Yoshimoto et al., Elevated levels of Fractalkine Expression and Accumulation of CD16+ Monocytes in Glomeruli of Active Lupus Nephritis, Am. J. Kidney Disease, vol. 50, No. 1, Jul. 2007, pp. 47-58.
Zhang et al., Hyper-Activated Pro-Inflammatory CD16+ Monocytes Correlate with the Severity of Liver Injury and Fibrosis in Patients with Chronic Hepatitis B, PLoS One, 2011, 6:(3):e17484, 10 pages.

(56) References Cited

OTHER PUBLICATIONS

Zheng et al., Expression of Bioactive Human M-CSF Soluble Receptor in Transgenic Tobacco Products, Protein Expression and Purification, 2006, 46:367-373; available online Aug. 15, 2005.
Zhu, et al., "CSF1/CSF1R Blockade Reprograms Tumor-Infiltrating Macrophages and Improves Response to T-cell Checkpoint Immunotherapy in Pancreatic Cancer Models," Cancer Research, 2014, 74(18): 5057-5069.
Ziegler-Heitbrock, The CD14 CD16 blood monocytes: their role in infection and inflammation, J Leuko Biol, 2007, 81:584-592.
Zitvogel, et al., "Cancer Despite Immunosurveillance: Immunoselection and Immunosubversion," Nat Rev Immunol, 2006, 6:715-27.
Extended European Search Report in European Patent Application No. 20207287.2 dated May 18, 2021, 18 pages.
Fend et al., "Therapeutic Effects of Anti-CD115 Monoclonal Antibody in Mouse Cancer Models through Dual Inhibition of Tumor-Associated Macrophages and Osteoclasts," PLOS One, 2013, 8(9):e73310, 11 pages.
Anonymous, Nivolumab and Ipilimumab and Radiation Therapy in MSS and MSI High Colorectal and Pancreatic, ClinicalTrials.gov, NCT03104439, Apr. 7, 2017, 13 pages.
Chiorean et al., "Pancreatic Cancer: Optimizing Treatment Options, New, and Emerging Targeted Therapies," Drug Des Devel Ther, 2015, 9:3529-3545.

\* cited by examiner

Summary of Study Design
Screening Assessments (All Cohorts): Within 28 days of first study drug dose
<u>Cycle = Day 1 to Day 14</u>

| <u>Phase 1a</u><br>1) HuAB1 Monotherapy (two cohorts)<br>2) HuAB1 + Nivolumab Dose Escalation (three cohorts) | | Phase 1b Dose Expansion at the Recommended Combination Dose of HuAB1 + Nivolumab |
|---|---|---|
| <u>HuAB1 Monotherapy (q2w)</u><br>Cohort 1aM1:<br>2 mg/kg HuAB1(FPA008)<br>  Cohort 1aM2:<br>  4 mg/kg HuAB1<br>(6 - 12 pts with advanced cancers) | RD (Recommended Dose) → | Cohort 1b1: Squamous/Non-squamaous NSCLC (Second/third line, anti-PD-1 therapy naïve)<br>Cohort 1b2: NSCLC (Refractory on anti-PD-1 targeting drug)<br>Cohort 1b3: Melanoma (anti-PD-1 therapy naïve)<br>Cohort 1b4: Melanoma (Refractory/Relapse on anti-PD-1 targeting drug)<br>Cohort 1b5: SCCHN (Second line)<br>Cohort 1b6: Pancreatic Cancer (Second line)<br>Cohort 1b7: Colorectal Cancer (Third line)<br>Cohort 1b8: GBM (1$^{st}$ Recurrence)<br><br>(About 30 pts per cohort, a total of 240 pts) |
| <u>3+3 Dose Escalation Combinational Therapy (q2w):</u><br>Cohort 1aC1:<br>1 mg/kg HuAB1 + 3 mg/kg nivolumab<br>  Cohort 1aC2:<br>  2 mg/kg HuAB1 + 3 mg/kg nivolumab<br>    Cohort 1aC3:<br>    4 mg/kg HuAB1 + 3 mg/kg nivolumab<br>(9 - 18 pts with advanced cancers) | | |

Treatment Completion/Early Termination Visit:
28 Days after last dose of study drug(s)

*Fig. 1*

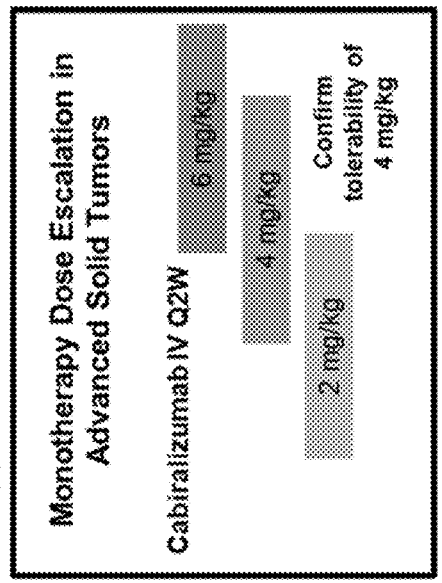
Fig. 6A
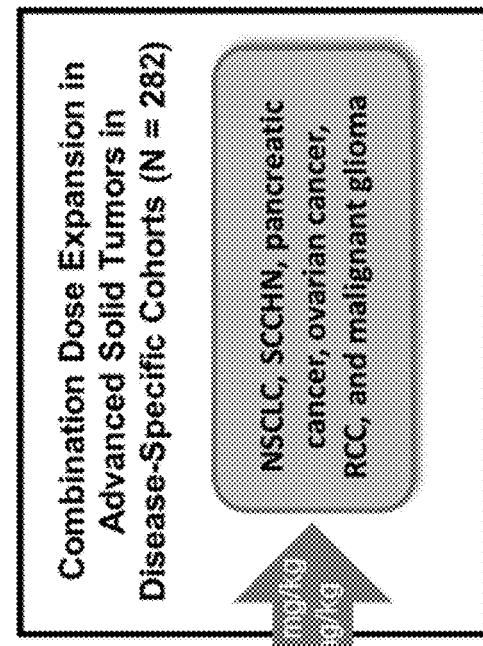
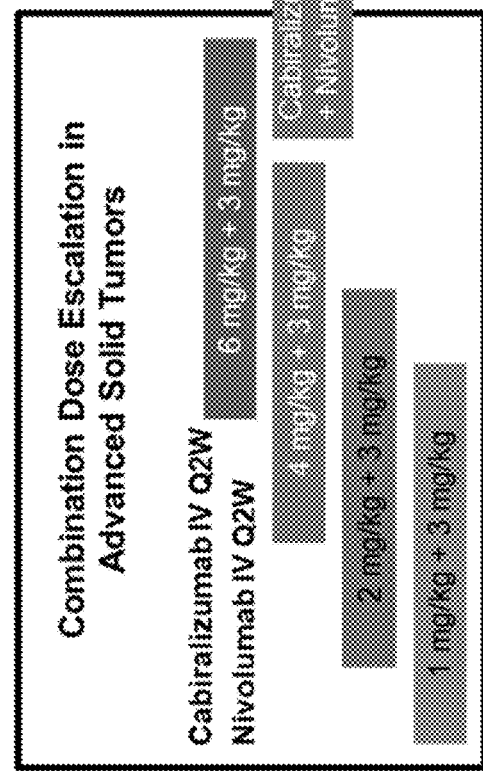
Fig. 6B

COMBINATION ANTI-CSF1R AND ANTI-PD-1 ANTIBODY COMBINATION THERAPY FOR PANCREATIC CANCER

This application is a national stage application of International Patent Application No. PCT/US2018/050711, filed Sep. 12, 2018, which claims priority to U.S. Provisional Application Nos. 62/558,161 filed Sep. 13, 2017, 62/580,154 filed Nov. 1, 2017, 62/581,962 filed Nov. 6, 2017, 62/671,887 filed May 15, 2018, and 62/679,612 filed Jun. 1, 2018, each of which is incorporated in its entirety by reference herein.

TECHNICAL FIELD

The present invention relates to methods of treating pancreatic cancer with particular dosage regimes of antibodies that bind colony stimulating factor 1 receptor (CSF1R) (e.g. cabiralizumab) in combination with antibodies that bind programmed cell death 1 (PD-1) (e.g. nivolumab).

BACKGROUND

Colony stimulating factor 1 receptor (referred to herein as CSF1R; also referred to in the art as FMS, FIM2, C-FMS, M-CSF receptor, and CD115) is a single-pass transmembrane receptor with an N-terminal extracellular domain (ECD) and a C-terminal intracellular domain with tyrosine kinase activity. Ligand binding of CSF1 or the interleukin 34 ligand (referred to herein as IL-34; Lin et al., *Science* 320: 807-11 (2008)) to CSF1R leads to receptor dimerization, upregulation of CSF1R protein tyrosine kinase activity, phosphorylation of CSF1R tyrosine residues, and downstream signaling events. CSF1R activation by CSF1 or IL-34 leads to the trafficking, survival, proliferation, and differentiation of monocytes and macrophages, as well as other monocytic cell lineages such as osteoclasts, dendritic cells, and microglia.

Many tumor cells or tumor stromal cells have been found to produce CSF1, which activates monocyte/macrophage cells through CSF1R. The level of CSF1 in tumors has been shown to correlate with the level of tumor-associated macrophages (TAMs) in the tumor. Higher levels of TAMs have been found to correlate with poorer patient prognoses in the majority of cancers. In addition, CSF1 has been found to promote tumor growth and progression to metastasis in, for example, human breast cancer xenografts in mice. See, e.g., Paulus et al., *Cancer Res.* 66: 4349-56 (2006). Further, CSF1R plays a role in osteolytic bone destruction in bone metastasis. See, e.g., Ohno et al., *Mol. Cancer Ther.* 5: 2634-43 (2006). TAMs promote tumor growth, in part, by suppressing anti-tumor T cell effector function through the release of immunosuppressive cytokines and the expression of T cell inhibitory surface proteins.

Genetic alterations in cancer provide a diverse set of antigens that can mediate anti-tumor immunity. Antigen recognition through T-cell receptors (TCRs) initiate T-cell-responses, which are regulated by a balance between activating and inhibitory signals. The inhibitory signals, or "immune checkpoints," play an important role in normal tissues by preventing autoimmunity. Up-regulation of immune checkpoint proteins allows cancers to evade anti-tumor immunity. Two immune checkpoint proteins have been the focus of clinical cancer immunotherapeutics, cytotoxic T-lymphocyte-associated antigen 4 (CTLA-4) and programmed cell death protein 1 (PD-1). The combination of an anti-CTLA-4 antibody and an anti-PD-1 antibody has been approved for the treatment of metastatic melanoma and several additional clinical trials are also ongoing to study the use of this combination for the treatment of other cancers. Anti-PD-1 antibodies and anti-CTLA-4 antibodies for use as monotherapies are also currently being studied in clinical trials as a treatment for many different types of cancer. Anti-PD-L1 antibodies which bind PD-L1, one of the ligands for PD-1, are also currently in clinical development.

Many tumors often express multiple checkpoint molecules simultaneously, Therefore, combinations of checkpoint modulators are undergoing clinical testing with aim of improved efficacy. Initial clinical results of the combination of an anti-CTLA-4 antibody (anti-CTLA-4 Ab) and an anti-PD-1 antibody (anti-PD-1 Ab) have demonstrated improved overall response rates, increased complete response rates, as well as overall survival rates in metastatic melanoma, compared to anti-CTLA-4 Ab alone or historical controls.

SUMMARY

As described herein, Phase Ia/b studies of an anti-PD-1 antibody in combination with an anti-CSF1R antibody are ongoing. (See, e.g., clinical trial NCT02526017, summary available at the Internet site clinicaltrials (dot) gov.) Based on preliminary safety and pharmacodynamics, a particular dosage regime for a combination of cabiralizumab (anti-CSF1R antibody) and nivolumab (anti-PD-1 antibody) for pancreatic cancer patients has been selected for dose expansion studies.

In some embodiments, this disclosure provides methods of treating cancer, such as solid tumors, e.g., pancreatic cancer, including pancreatic ductal adenocarcinoma, advanced pancreatic cancer, metastatic pancreatic cancer, such as pancreatic cancer having metastasized to the liver and/or lung, and Microsatellite Stable (MSS) pancreatic cancer, in a subject comprising administering to the subject 4 mg/kg of an anti-CSF1R antibody and 3 mg/kg an anti-PD-1 antibody, wherein the antibodies are each administered once every two weeks, and wherein the anti-CSF1R antibody comprises a heavy chain comprising a heavy chain (HC) CDR1 having the sequence of SEQ ID NO: 5, an HC CDR2 having the sequence of SEQ ID NO: 6, and an HC CDR3 having the sequence of SEQ ID NO: 7, and a light chain comprising a light chain (LC) CDR1 having the sequence of SEQ ID NO: 8, a LC CDR2 having the sequence of SEQ ID NO: 9, and a LC CDR3 having the sequence of SEQ ID NO: 10; and wherein the anti-PD-1 antibody comprises a heavy chain comprising a heavy chain (HC) CDR1 having the sequence of SEQ ID NO: 28, an HC CDR2 having the sequence of SEQ ID NO: 30, and an HC CDR3 having the sequence of SEQ ID NO: 32, and a light chain comprising a light chain (LC) CDR1 having the sequence of SEQ ID NO: 35, a LC CDR2 having the sequence of SEQ ID NO: 37, and a LC CDR3 having the sequence of SEQ ID NO: 39. In some embodiments, the anti-CSF1R antibody and/or the anti-PD-1 antibody comprises full length heavy and/or light chains, or alternatively, is a Fab, an Fv, an scFv, a Fab', or a (Fab')$_2$ fragment.

In some embodiments, the anti-PD-1 antibody heavy chain comprises a heavy chain variable region comprising the sequence of SEQ ID NO: 23 and wherein the anti-PD-1 antibody light chain comprises a light chain variable region comprising the sequence of SEQ ID NO: 25. In some embodiments, the anti-PD-1 antibody comprises a heavy chain comprising the sequence of each of SEQ ID NOs: 23 and 24 and wherein the anti-PD-1 antibody comprises a light chain comprising the sequence of each of SEQ ID NOs: 25 and 26. In some embodiments, the anti-PD-1 antibody is nivolumab, pembrolizumab, or PDR001.

In some embodiments, the anti-CSF1R antibody comprises a heavy chain variable region comprising the sequence of SEQ ID NO: 11 and wherein the anti-CSF1R antibody comprises a light chain variable region comprising the sequence of SEQ ID NO: 12. In some embodiments, the anti-CSF1R antibody comprises a heavy chain comprising the sequence of SEQ ID NO: 13 and wherein the anti-CSF1R antibody comprises a light chain comprising the sequence of SEQ ID NO: 14. In some embodiments, the anti-CSF1R antibody is cabiralizumab.

In some embodiments, the anti-PD-1 antibody is administered to the subject before the anti-CSF1R antibody. In some such embodiments, the anti-CSF1R antibody is administered from 30 minutes to 120 minutes after the PD-1/PD-L1 inhibitor. In some embodiments, the anti-PD-1 antibody is infused over a period of 30-60 minutes, and the anti-CSF1R antibody is infused over a period of 30-60 minutes. In some embodiments, the infusion of the anti-CSF1R antibody is initiated 30-120 minutes after the end of the infusion of the anti-PD-1 antibody. In some embodiments, the infusion of the anti-CSF1R antibody is initiated 30-60 minutes (e.g., 30 minutes) after the end of the infusion of the anti-PD-1 antibody.

In some embodiments, the subject has previously failed treatment with a standard therapy for pancreatic cancer or is not indicated for treatment with a standard therapy. In some embodiments, the subject has previously received a PD-1/PD-L1 inhibitor therapy. In some such embodiments, the subject is a PD-1/PD-L1 inhibitor inadequate responder. In some embodiments, the subject is refractory to a PD-1/PD-L1 inhibitor, e.g., after at least 2 doses.

In some embodiments, the subject has a localized adenocarcinoma of the pancreas. In some embodiments, the subject has metastatic adenocarcinoma of the pancreas. In some embodiments, the subject has advanced pancreatic cancer. In some embodiments, the subject does not have active pancreatitis or ascites of Grade 2 or higher. In some embodiments, the subject's pancreatic tumor(s) are PD-L1 positive. In some embodiments, the subject has reduced circulating $CD14^+$ $CD16^{++}$ nonclassical monocytes after at least one dose of each of the anti-CSF1R antibody and the anti-PD-1 antibody. For example, in some cases the CD14+CD16++ nonclassical monocytes are reduced below 10 monocytes per microliter peripheral blood within 3 days after a first dose of each of the anti-CSF1R antibody and the anti-PD-1 antibody and remain below 10 monocytes per microliter peripheral blood for at least 10 further days. In some embodiments, the subject has advanced pancreatic cancer and/or metastatic pancreatic cancer, such as with metastasis to another organ such as liver and/or lung, and/or is a microsatellite-stable (MSS) subject and/or has a microsatellite-stable tumor. In some embodiments, the pancreatic cancer has been determined to be microsatellite-stable (MSS) and/or has been determined to have a tumor mutation burden (TMB) of less than 20 mutations/megabase, less than 15 mutations/megabase, or less than 10 mutations/megabase by the Foundation One® CDx™ assay or less than 400, less than 300, or less than 200 missense mutations by WES. In some embodiments, the subject's pancreatic cancer has progressed after at least one gemcitabine-based or 5-fluorouracil-based chemotherapy regimen.

Encompassed herein are also methods of treating cancer, such as solid tumors, e.g., pancreatic cancer, including pancreatic ductal adenocarcinoma, advanced pancreatic cancer, metastatic pancreatic cancer, such as pancreatic cancer having metastasized to the liver and/or lung, and Microsatellite Stable (MSS) pancreatic cancer, in a subject comprising administering to the subject 2, 3, or 4 mg/kg of an anti-CSF1R antibody once every two weeks and 400-600 mg an anti-PD-1 antibody once every four weeks, wherein the anti-CSF1R antibody comprises a heavy chain comprising a heavy chain (HC) CDR1 having the sequence of SEQ ID NO: 5, an HC CDR2 having the sequence of SEQ ID NO: 6, and an HC CDR3 having the sequence of SEQ ID NO: 7, and a light chain comprising a light chain (LC) CDR1 having the sequence of SEQ ID NO: 8, a LC CDR2 having the sequence of SEQ ID NO: 9, and a LC CDR3 having the sequence of SEQ ID NO: 10; and wherein the anti-PD-1 antibody comprises a heavy chain comprising a heavy chain (HC) CDR1 having the sequence of SEQ ID NO: 28, an HC CDR2 having the sequence of SEQ ID NO: 30, and an HC CDR3 having the sequence of SEQ ID NO: 32, and a light chain comprising a light chain (LC) CDR1 having the sequence of SEQ ID NO: 35, a LC CDR2 having the sequence of SEQ ID NO: 37, and a LC CDR3 having the sequence of SEQ ID NO: 39.

In some embodiments, the subject is administered 4 mg/kg of the anti-CSF1R antibody once every two weeks and 450-500 mg the anti-PD-1 antibody once every four weeks. In some embodiments, the subject is administered 4 mg/kg of the anti-CSF1R antibody once every two weeks and 480 mg the anti-PD-1 antibody once every four weeks.

In some embodiments, the anti-CSF1R antibody comprises full length heavy and/or light chains, or is a Fab, an Fv, an scFv, a Fab', or a (Fab')$_2$ fragment. In some embodiments, the anti-PD-1 antibody comprises full length heavy and/or light chains, or is a Fab, an Fv, an scFv, a Fab', or a (Fab')$_2$ fragment. In some embodiments, the anti-PD-1 antibody heavy chain comprises a heavy chain variable region comprising the sequence of SEQ ID NO: 23 and wherein the anti-PD-1 antibody light chain comprises a light chain variable region comprising the sequence of SEQ ID NO: 25. In some embodiments, the anti-PD-1 antibody comprises a heavy chain comprising the sequence of each of SEQ ID NOs: 23 and 24 and wherein the anti-PD-1 antibody comprises a light chain comprising the sequence of each of SEQ ID NOs: 25 and 26. In some embodiments, the anti-PD-1 antibody is nivolumab, pembrolizumab, or PDR001. In some embodiments, the anti-CSF1R antibody comprises a heavy chain variable region comprising the sequence of SEQ ID NO: 11 and wherein the anti-CSF1R antibody comprises a light chain variable region comprising the sequence of SEQ ID NO: 12. In some embodiments, the anti-CSF1R antibody comprises a heavy chain comprising the sequence of SEQ ID NO: 13 and wherein the anti-CSF1R antibody comprises a light chain comprising the sequence of SEQ ID NO: 14. In some embodiments, the anti-CSF1R antibody is cabiralizumab. In some embodiments, the anti-PD-1 antibody is infused over a period of 30-60 minutes, and the anti-CSF1R antibody is infused over a period of 30-60 minutes. In some embodiments, the subject has previously failed treatment with a standard therapy for pancreatic cancer or is not indicated for treatment with a standard therapy.

In some embodiments, the subject has previously received a PD-1/PD-L1 inhibitor therapy. In some such cases, the subject is a PD-1/PD-L1 inhibitor inadequate responder. In some such cases, the subject is refractory to a PD-1/PD-L1 inhibitor, e.g., after at least 2 doses. In some embodiments, the subject has a localized adenocarcinoma of the pancreas.

In some embodiments, the subject has metastatic adenocarcinoma of the pancreas. In some embodiments, the subject does not have active pancreatitis or ascites of Grade 2 or higher. In some embodiments, the subject's pancreatic tumor(s) are PD-L1 positive. In some embodiments, the subject has reduced circulating $CD14^+$ $CD16^+$ nonclassical monocytes after at least one dose of each of the anti-CSF1R antibody and the anti-PD-1 antibody. In some embodiments, the CD14+CD16++ nonclassical monocytes are reduced below 10 monocytes per microliter peripheral blood within 3 days after a first dose of each of the anti-CSF1R antibody and the anti-PD-1 antibody and remain below 10 monocytes per microliter peripheral blood for at least 10 further days. In some embodiments, subject has advanced pancreatic cancer and/or metastatic pancreatic cancer, such as with metastasis to another organ such as liver and/or lung, and/or is a microsatellite-stable (MSS) subject. In some embodiments, the pancreatic cancer has been determined to be microsatellite-stable (MSS) and/or has been determined to have a tumor mutation burden (TMB) of less than 20 mutations/megabase, less than 15 mutations/megabase, or less than 10 mutations/megabase by the Foundation One® CDx™ assay or less than 400, less than 300, or less than 200 missense mutations by WES. In some embodiments, the subject's pancreatic cancer has progressed after at least one gemcitabine-based or 5-fluorouracil-based chemotherapy regimen.

Encompassed herein are also methods of treating cancer, such as solid tumors, e.g., pancreatic cancer, including pancreatic ductal adenocarcinoma, advanced pancreatic cancer, metastatic pancreatic cancer, such as pancreatic cancer having metastasized to the liver and/or lung, and Microsatellite Stable (MSS) pancreatic cancer, in a subject comprising administering to the subject 2, 3, or 4 mg/kg of an anti-CSF1R antibody once every two weeks and 400-600 mg an anti-PD-1 antibody once every four weeks in combination with chemotherapy comprising gemcitabine or 5-fluorouracil (5-FU), wherein the anti-CSF1R antibody comprises a heavy chain comprising a heavy chain (HC) CDR1 having the sequence of SEQ ID NO: 5, an HC CDR2 having the sequence of SEQ ID NO: 6, and an HC CDR3 having the sequence of SEQ ID NO: 7, and a light chain comprising a light chain (LC) CDR1 having the sequence of SEQ ID NO: 8, a LC CDR2 having the sequence of SEQ ID NO: 9, and a LC CDR3 having the sequence of SEQ ID NO: 10; and wherein the anti-PD-1 antibody comprises a heavy chain comprising a heavy chain (HC) CDR1 having the sequence of SEQ ID NO: 28, an HC CDR2 having the sequence of SEQ ID NO: 30, and an HC CDR3 having the sequence of SEQ ID NO: 32, and a light chain comprising a light chain (LC) CDR1 having the sequence of SEQ ID NO: 35, a LC CDR2 having the sequence of SEQ ID NO: 37, and a LC CDR3 having the sequence of SEQ ID NO: 39.

In some embodiments, the subject is administered 4 mg/kg of the anti-CSF1R antibody once every two weeks and 450-500 mg the anti-PD-1 antibody once every four weeks. In some embodiments, the subject is administered 4 mg/kg of the anti-CSF1R antibody once every two weeks and 480 mg the anti-PD-1 antibody once every four weeks. In some embodiments, the subject is administered chemotherapy comprising gemcitabine and nab-paclitaxel. In some embodiments, the subject is administered chemotherapy comprising 5-FU, leucovorin, and liposomal irinotecan. In some embodiments, the subject is administered chemotherapy comprising FOLFOX. In some embodiments, the anti-CSF1R antibody comprises full length heavy and/or light chains, or alternatively, is a Fab, an Fv, an scFv, a Fab', or a (Fab')$_2$ fragment. In some embodiments, the anti-PD-1 antibody comprises full length heavy and/or light chains, or alternatively, is a Fab, an Fv, an scFv, a Fab', or a (Fab')$_2$ fragment.

In some embodiments, the anti-PD-1 antibody heavy chain comprises a heavy chain variable region comprising the sequence of SEQ ID NO: 23 and wherein the anti-PD-1 antibody light chain comprises a light chain variable region comprising the sequence of SEQ ID NO: 25. In some embodiments, the anti-PD-1 antibody comprises a heavy chain comprising the sequence of each of SEQ ID NOs: 23 and 24 and wherein the anti-PD-1 antibody comprises a light chain comprising the sequence of each of SEQ ID NOs: 25 and 26. In some embodiments, the anti-PD-1 antibody is nivolumab, pembrolizumab, or PDR001. In some embodiments, the anti-CSF1R antibody comprises a heavy chain variable region comprising the sequence of SEQ ID NO: 11 and wherein the anti-CSF1R antibody comprises a light chain variable region comprising the sequence of SEQ ID NO: 12. In some embodiments, the anti-CSF1R antibody comprises a heavy chain comprising the sequence of SEQ ID NO: 13 and wherein the anti-CSF1R antibody comprises a light chain comprising the sequence of SEQ ID NO: 14. In some embodiments, the anti-CSF1R antibody is cabiralizumab. In some embodiments, the anti-PD-1 antibody is infused over a period of 30-60 minutes, and the anti-CSF1R antibody is infused over a period of 30-60 minutes.

In some embodiments, the subject has previously failed treatment with a standard therapy for pancreatic cancer or is not indicated for treatment with a standard therapy. In some embodiments, the subject has previously received a PD-1/PD-L1 inhibitor therapy. In some embodiments, the subject is a PD-1/PD-L1 inhibitor inadequate responder.

In some embodiments, the subject is refractory to a PD-1/PD-L1 inhibitor, e.g., after at least 2 doses. In some embodiments, the subject has a localized adenocarcinoma of the pancreas. In some embodiments, the subject has metastatic adenocarcinoma of the pancreas. In some embodiments, the subject does not have active pancreatitis or ascites of Grade 2 or higher. In some embodiments, the subject's pancreatic tumor(s) are PD-L1 positive. In some embodiments, subject has reduced circulating $CD14^+$ $CD16^{++}$ nonclassical monocytes after at least one dose of each of the anti-CSF1R antibody and the anti-PD-1 antibody. In some embodiments, the CD14+CD16++ classical monocytes are reduced below 10 monocytes per microliter peripheral blood within 3 days after a first dose of each of the anti-CSF1R antibody and the anti-PD-1 antibody and remain below 10 monocytes per microliter peripheral blood for at least 10 further days. In some embodiments, subject has advanced pancreatic cancer and/or metastatic pancreatic cancer, such as with metastasis to another organ such as liver and/or lung, and/or is a microsatellite-stable (MSS) subject. In some embodiments, the pancreatic cancer has been determined to be microsatellite-stable (MSS) and/or has been determined to have a tumor mutation burden (TMB) of less than 20 mutations/megabase, less than 15 mutations/megabase, or less than 10 mutations/megabase, as determined by the Foundation One® CDx™ assay, and/or less than 400, less than 300, or less than 200 missense mutations, as determined by whole exome sequencing (WES). In some embodiments, the subject's pancreatic cancer has progressed after at least one gemcitabine-based or 5-fluorouracil-based chemotherapy regimen.

The disclosure herein also encompasses methods of treating cancer in a subject comprising administering to the subject an anti-CSF1R antibody and an anti-PD-1 antibody, wherein the cancer has been determined to be microsatellite-stable (MSS) and/or has been determined to have a TMB of less than 20, 15 or 10 mutations/megabase, as determined by the Foundation One® CDx™ assay, and/or less than 400, less than 300, or less than 200 missense mutations, as determined by WES. In some embodiments, the cancer has been determined (i) to be MSS and (ii) to have a TMB of less than 20, 15 or 10 mutations/megabase, as determined by the Foundation One® CDx™ assay, and/or less than 400, 300, or 200 missense mutations, as determined by WES. In some embodiments, the cancer has been determined to have a TMB of less than 15 mutations/megabase, as determined by the Foundation One® CDx™ assay, and/or less than 300 missense mutations, as determined by WES. In some embodiments, the cancer has been determined to have a TMB of less than 10 mutations/megabase, as determined by the Foundation One® CDx™ assay, and/or less than 200 missense mutations, as determined by WES. In some such methods, the anti-CSF1R antibody comprises a heavy chain comprising a heavy chain (HC) CDR1 having the sequence of SEQ ID NO: 5, an HC CDR2 having the sequence of SEQ ID NO: 6, and an HC CDR3 having the sequence of SEQ ID NO: 7, and a light chain comprising a light chain (LC) CDR1 having the sequence of SEQ ID NO: 8, a LC CDR2 having the sequence of SEQ ID NO: 9, and a LC CDR3 having the sequence of SEQ ID NO: 10; and the anti-PD-1 antibody comprises a heavy chain comprising a heavy chain (HC) CDR1 having the sequence of SEQ ID NO: 28, an HC CDR2 having the sequence of SEQ ID NO: 30, and an HC CDR3 having the sequence of SEQ ID NO: 32, and a light chain comprising a light chain (LC) CDR1 having the sequence of SEQ ID NO: 35, a LC CDR2 having the sequence of SEQ ID NO: 37, and a LC CDR3 having the sequence of SEQ ID NO: 39. In some methods, the anti-CSF1R antibody is a Fab, an Fv, an scFv, a Fab', or a (Fab')$_2$ fragment and/or the anti-PD-1 antibody is a Fab, an Fv, an scFv, a Fab', or a (Fab')$_2$ fragment. In some such methods, the anti-PD-1 antibody heavy chain comprises a heavy chain variable region comprising the sequence of SEQ ID NO: 23 and wherein the anti-PD-1 antibody light chain comprises a light chain variable region comprising the sequence of SEQ ID NO: 25. In some embodiments, the anti-PD-1 antibody comprises a heavy chain comprising the sequence of each of SEQ ID NOs: 23 and 24 and wherein the anti-PD-1 antibody comprises a light chain comprising the sequence of each of SEQ ID NOs: 25 and 26. In some embodiments, the anti-PD-1 antibody is nivolumab or pembrolizumab or PDR001. In some embodiments, the anti-CSF1R antibody comprises a heavy chain variable region comprising the sequence of SEQ ID NO: 11 and wherein the anti-CSF1R antibody comprises a light chain variable region comprising the sequence of SEQ ID NO: 12. In some embodiments, the anti-CSF1R antibody comprises a heavy chain comprising the sequence of SEQ ID NO: 13 and wherein the anti-CSF1R antibody comprises a light chain comprising the sequence of SEQ ID NO: 14. In some embodiments, the anti-CSF1R antibody is cabiralizumab. In some embodiments, the anti-CSF-1R antibody is emactuzumab (RG7155), AMG 820, or SNDX 6352 (UCB 6352), In some embodiments, a non-antibody anti-CSF-1R agent is used in place of the anti-CSF1R antibody, such as a small molecule, e.g., JNJ-40346527 (now PRV-6527), e.g., an anti-CSF1R tyrosine kinase inhibitor, or other modality.

In some of the above methods, the anti-PD-1 antibody is administered to the subject before the anti-CSF1R antibody. In some embodiments, the anti-CSF1R antibody is administered from 30 minutes to 120 minutes after the anti-PD-1 antibody. In some embodiments, the anti-PD-1 antibody is infused over a period of 30-60 minutes, and the anti-CSF1R antibody is infused over a period of 30-60 minutes. In some embodiments, the infusion of the anti-CSF1R antibody is initiated 30-120 minutes after the end of the infusion of the anti-PD-1 antibody. In some embodiments, the infusion of the anti-CSF1R antibody is initiated 30-60 minutes (e.g., 30 minutes) after the end of the infusion of the anti-PD-1 antibody. In some embodiments, the subject has previously received a PD-1/PD-L1 inhibitor therapy. In some embodiments, the subject is a PD-1/PD-L1 inhibitor inadequate responder. In some embodiments, the subject is refractory to a PD-1/PD-L1 inhibitor, e.g., after at least 2 doses. In some embodiments, the anti-CSF1R antibody is cabiralizumab and the anti-PD-1 antibody is nivolumab, wherein cabiralizumab is administered at a dose of 4 mg/kg once every two weeks, and wherein nivolumab is administered at a dose of 3 mg/kg once every two weeks. In some embodiments, the cancer is pancreatic cancer, ovarian cancer, renal cancer, malignant glioma, melanoma, non-small cell lung cancer (NSCLC), or squamous cell carcinoma of the head and neck (SCCHN).

The disclosure herein also contemplates methods of treating cancer in a subject, comprising administering to the subject at least one dose of an anti-CSF1R antibody and an anti-PD-1 antibody, such as, for example a single dose or two doses of the antibodies, wherein the expression level of at least one marker gene is determined both prior to and following the administration, the at least one marker gene comprising one or more of: CCL19, CCL5, CCL8, CCR7, CD86, CXCL10, CXCL11, CXCL13, CXCL9, IFNG, IL23A, STAT1, TNF, CD72, CD79A, CD79B, MS4A1, TNFRSF17, CD3D, CD8A, CD8B, GZMM, APOL3, CTSW, GNLY, GZMA, GZMH, KLRB1, KLRD1, KLRK1, NKG7, PRF1, BTLA, CD244, CD96, CTLA4, LAG3, PDCD1, TIGIT, and FOXP3. If the expression level data indicates that the expression level of the at least one marker gene increases following the administration, administration of the anti-CSF1R antibody and anti-PD-1 antibody to the subject may then continue. Some embodiments comprise a method of treating cancer in a subject, comprising administering to the subject at least one dose of an anti-CSF1R antibody and an anti-PD-1 antibody, wherein the expression level of at least one marker gene is determined to increase following the administration, the at least one marker gene comprising one or more of: CCL19, CCL5, CCL8, CCR7, CD86, CXCL10, CXCL11, CXCL13, CXCL9, IFNG, IL23A, STAT1, TNF, CD72, CD79A, CD79B, MS4A1, TNFRSF17, CD3D, CD8A, CD8B, GZMM, APOL3, CTSW, GNLY, GZMA, GZMH, KLRB1, KLRD1, KLRK1, NKG7, PRF1, BTLA, CD244, CD96, CTLA4, LAG3, PDCD1, TIGIT, and FOXP3; and then continuing to administer the anti-CSF1R antibody and anti-PD-1 antibody to the subject. In further embodiments, the method comprises first determining or having determined the expression level of the at least one marker gene comprising one or more of: CCL19, CCL5, CCL8, CCR7, CD86, CXCL10, CXCL11, CXCL13, CXCL9, IFNG, IL23A, STAT1, TNF, CD72, CD79A, CD79B, MS4A1, TNFRSF17, CD3D, CD8A, CD8B, GZMM, APOL3, CTSW, GNLY, GZMA, GZMH, KLRB1, KLRD1, KLRK1, NKG7, PRF1, BTLA, CD244, CD96, CTLA4, LAG3, PDCD1, TIGIT, and FOXP3, then administering at least one dose of the anti-CSF1R antibody and the anti-PD-1 antibody, such as one or two doses of the antibodies, and then re-determining or having determined the expression level of the at least one marker gene. If the expression level data indicates that the expression level of the at least one marker gene increases following the administration, administration of the anti-CSF1R antibody and anti-PD-1 antibody to the subject may then continue. In yet further embodiments, the method comprises first determining or having determined the expression level of the at least one marker gene comprising one or more of: CCL19, CCL5, CCL8, CCR7, CD86, CXCL10, CXCL11, CXCL13, CXCL9, IFNG, IL23A, STAT1, TNF, CD72, CD79A, CD79B, MS4A1, TNFRSF17, CD3D, CD8A, CD8B, GZMM, APOL3, CTSW, GNLY, GZMA, KLRB1, KLRD1, KLRK1, NKG7, PRF1, BTLA, CD244, CD96, CTLA4, LAG3, PDCD1, TIGIT, and FOXP3, then administering at least one dose of the anti-CSF1R antibody and the anti-PD-1 antibody, such as one or two doses of the antibodies, and then determining that the expression level of the at least one marker gene has increased following the administration, followed by further administration of the anti-CSF1R antibody and anti-PD-1 antibody to the subject. Embodiments herein also include methods of treating cancer in a subject, comprising administering to the subject at least one dose of an anti-CSF1R antibody and an anti-PD-1 antibody, wherein the expression level of at least one marker gene comprising one or both of CSF-1 and IL-34 is determined both prior to and following the administration; and continuing to administer the anti-CSF1R antibody and anti-PD-1 antibody to the subject if the expression level of the at least one marker gene comprising one or both of CSF-1 and IL-34 increases following the administration of a) compared to the expression level determined prior to administration. Embodiments herein also include methods of treating cancer in a subject, comprising administering to the subject at least one dose of an anti-CSF1R antibody and an anti-PD-1 antibody, wherein the expression level of at least one marker gene comprising one or both of CSF-1 and IL-34 is determined to increase following the administration, and continuing to administer the anti-CSF1R antibody and anti-PD-1 antibody to the subject. Embodiments herein also include methods of treating cancer in a subject, comprising administering to the subject at least one dose of an anti-CSF1R antibody and an anti-PD-1 antibody, determining the expression level of at least one marker gene comprising one or both of CSF-1 and IL-34 both prior to and after the administration, wherein, if the expression level of the at least one marker gene is determined to increase following the administration, then continuing to administer the anti-CSF1R antibody and anti-PD-1 antibody to the subject. Embodiments herein also include methods of treating cancer in a subject, comprising administering to the subject at least one dose of an anti-CSF1R antibody and an anti-PD-1 antibody, determining that the expression level of at least one marker gene comprising one or both of CSF-1 and IL-34 has increased after the administration, then continuing to administer the anti-CSF1R antibody and anti-PD-1 antibody to the subject.

In any of the above methods, the at least one marker gene comprises: (a) at least one pro-inflammatory marker gene comprising: CCL19, CCL5, CCL8, CCR7, CD86, CXCL10, CXCL11, CXCL13, CXCL9, IFNG, IL23A, STAT1, and TNF, (b) at least one B cell marker comprising: CD72, CD79A, CD79B, MS4A1, and TNFRSF17, (c) at least one CD8 T cell marker comprising: CD3D, CD8A, and CD8B, (d) at least one effector T cell cytolytic marker comprising: GZMM, APOL3, CTSW, GNLY, GZMA, GZMH, KLRB1, KLRD1, KLRK1, NKG7, and PRF1; and/or (e) at least one effector T cell receptor marker comprising: BTLA, CD244, CD96, CTLA4, LAG3, PDCD1, TIGIT, and FOXP3. Any of the above methods may further comprise measuring the expression level of one or more of CSF1R, CSF-1 and IL-34, wherein increases in CSF-1 and IL-34 expression levels following administration indicate that the subject is responsive to treatment with the anti-CSF1R antibody and anti-PD-1 antibody while a decrease in CSF1R expression level indicates that the subject is not responsive to treatment with the anti-CSF1R antibody and anti-PD-1 antibody. In some embodiments, the methods further comprise determining the expression level of one or more anti-inflammatory markers comprising: ARG1, C5AR1, CD14, CD163, CXCR1, CXCR2, ILIA, IL1RN, IL8, MRC1, MSR1, PF4, PPBP, S100A12, S100A8, SAA1, S100A9, and TGFB1. In some embodiments, the levels of these markers do not change or do not increase in subjects responsive to treatment with the anti-CSF1R antibody and the anti-PD-1 antibody.

In any of the above methods, the expression level of the at least one marker gene may be the RNA expression level, e.g., measured by transcriptome analysis or reverse transcription PCR. In any of the above methods, the expression level may, for instance, be measured in tumor cells, i.e., in cells from a tumor sample such as a biopsy sample. In any of the above cancer treatment methods, the cancer may have been determined to be MSS and/or has been determined to have a TMB of less than 20, less than 15 or less than 10 mutations/megabase, as determined by the Foundation One® CDx™ assay, and/or less than 400, less than 300, or less than 200 missense mutations, as determined by whole exome sequencing (WES). In some embodiments, the cancer has been determined (i) to be MSS and (ii) to have a TMB of less than 20, less than 15 or less than 10 mutations/megabase, as determined by the Foundation One® CDx™ assay, and/or less than 400, less than 300, or less than 200 missense mutations, as determined by WES. In some embodiments, the cancer has been determined to have a TMB of less than 15 mutations/megabase, as determined by the Foundation One® CDx™ assay, and/or less than 300 missense mutations, as determined by WES. In some embodiments, the cancer has been determined to have a TMB of less than 10 mutations/megabase, as determined by the Foundation One® CDx™ assay, and/or less than 200 missense mutations, as determined by WES.

In some embodiments, the anti-CSF1R antibody may comprise a heavy chain comprising a heavy chain (HC) CDR1 having the sequence of SEQ ID NO: 5, an HC CDR2 having the sequence of SEQ ID NO: 6, and an HC CDR3 having the sequence of SEQ ID NO: 7, and a light chain comprising a light chain (LC) CDR1 having the sequence of SEQ ID NO: 8, a LC CDR2 having the sequence of SEQ ID NO: 9, and a LC CDR3 having the sequence of SEQ ID NO: 10; and the anti-PD-1 antibody may comprise a heavy chain comprising a heavy chain (HC) CDR1 having the sequence of SEQ ID NO: 28, an HC CDR2 having the sequence of SEQ ID NO: 30, and an HC CDR3 having the sequence of SEQ ID NO: 32, and a light chain comprising a light chain (LC) CDR1 having the sequence of SEQ ID NO: 35, a LC CDR2 having the sequence of SEQ ID NO: 37, and a LC CDR3 having the sequence of SEQ ID NO: 39. In some embodiments, the anti-CSF1R antibody is a Fab, an Fv, an scFv, a Fab', or a (Fab')$_2$ fragment. In some embodiments, the anti-PD-1 antibody is a Fab, an Fv, an scFv, a Fab', or a (Fab')$_2$ fragment. In some embodiments, the anti-PD-1 antibody heavy chain comprises a heavy chain variable region comprising the sequence of SEQ ID NO: 23 and wherein the anti-PD-1 antibody light chain comprises a light chain variable region comprising the sequence of SEQ ID NO: 25. In some embodiments, the anti-PD-1 antibody comprises a heavy chain comprising the sequence of each of SEQ ID NOs: 23 and 24 and wherein the anti-PD-1 antibody comprises a light chain comprising the sequence of each of SEQ ID NOs: 25 and 26. In some embodiments, the anti-PD-1 antibody is nivolumab or pembrolizumab or PDR001. In some embodiments, the anti-CSF1R antibody comprises a heavy chain variable region comprising the sequence of SEQ ID NO: 11 and wherein the anti-CSF1R antibody comprises a light chain variable region comprising the sequence of SEQ ID NO: 12. In some embodiments, the anti-CSF1R antibody comprises a heavy chain comprising the sequence of SEQ ID NO: 13 and wherein the anti-CSF1R antibody comprises a light chain comprising the sequence of SEQ ID NO: 14. In some embodiments, the anti-CSF1R antibody is cabiralizumab. In some embodiments, the anti-PD-1 antibody is administered to the subject before the anti-CSF1R antibody. In some embodiments, the anti-CSF1R antibody is administered from 30 minutes to 120 minutes after the anti-PD-1 antibody. In some embodiments, the anti-PD-1 antibody is infused over a period of 30-60 minutes, and the anti-CSF1R antibody is infused over a period of 30-60 minutes. In some embodiments, the infusion of the anti-CSF1R antibody is initiated 30-120 minutes after the end of the infusion of the anti-PD-1 antibody. In some embodiments, the infusion of the anti-CSF1R antibody is initiated 30-60 minutes (e.g., 30 minutes) after the end of the infusion of the anti-PD-1 antibody. In some embodiments, the subject has previously received a PD-1/PD-L1 inhibitor therapy. In some embodiments, the subject is a PD-1/PD-L1 inhibitor inadequate responder. In some embodiments, the subject is refractory to a PD-1/PD-L1 inhibitor, e.g., after at least 2 doses. In some embodiments, the anti-CSF1R antibody is cabiralizumab and the anti-PD-1 antibody is nivolumab, wherein cabiralizumab is administered at a dose of 4 mg/kg once every two weeks, and wherein nivolumab is administered at a dose of 3 mg/kg once every two weeks. In some embodiments, the cancer is pancreatic cancer, ovarian cancer, renal cancer, malignant glioma, melanoma, non-small cell lung cancer (NSCLC), or squamous cell carcinoma of the head and neck (SCCHN). In some embodiments, the anti-CSF-1R antibody is emactuzumab (RG7155), AMG 820, or SNDX 6352 (UCB 6352). In some embodiments, a non-antibody CSF-1R inhibitor is used in place of the anti-CSF1R antibody, such as a small molecule, e.g., JNJ-40346527 (now PRV-6527), e.g., an anti-CSF1R tyrosine kinase inhibitor, or other modality.

The present disclosure also includes a method of determining responsiveness of a subject with cancer to treatment with a combination of an anti-CSF1R antibody and an anti-PD-1 antibody, the method comprising determining the expression level of at least one marker gene before and after the subject is administered at least one dose of the anti-CSF1R antibody and the anti-PD-1 antibody, the at least one marker gene comprising one or more of: CCL19, CCL5, CCL8, CCR7, CD86, CXCL10, CXCL11, CXCL13, CXCL9, IFNG, IL23A, STAT1, TNF, CD72, CD79A, CD79B, MS4A1, TNFRSF17, CD3D, CD8A, CD8B, GZMM, APOL3, CTSW, GNLY, GZMA, GZMH, KLRB1, KLRD1, KLRK1, NKG7, PRF1, BTLA, CD244, CD96, CTLA4, LAG3, PDCD1, TIGIT, and FOXP3. A increase in the expression level of the at least one marker gene indicates responsiveness in some embodiments. In any of the above methods, the at least one marker gene comprises: (a) at least one pro-inflammatory marker gene comprising: CCL19, CCL5, CCL8, CCR7, CD86, CXCL10, CXCL11, CXCL13, CXCL9, IFNG, IL23A, STAT1, and TNF, (b) at least one B cell marker comprising: CD72, CD79A, CD79B, MS4A1, and TNFRSF17, (c) at least one CD8 T cell marker comprising: CD3D, CD8A, and CD8B, (d) at least one effector T cell cytolytic marker comprising: GZMM, APOL3, CTSW, GNLY, GZMA, GZMH, KLRB1, KLRD1, KLRK1, NKG7, and PRF1; and/or (e) at least one effector T cell receptor marker comprising: BTLA, CD244, CD96, CTLA4, LAG3, PDCD1, TIGIT, and FOXP3. Any of the above methods may further comprise measuring the expression level of one or more of CSF1R, CSF-1 and IL-34, wherein increases in CSF-1 and IL-34 expression levels following administration indicate that the subject is responsive to treatment with the anti-CSF1R antibody and anti-PD-1 antibody while a decrease in CSF1R expression level indicates that the subject is not responsive to treatment with the anti-CSF1R antibody and anti-PD-1 antibody. Also included herein are methods of determining responsiveness of a subject with cancer to treatment with a combination of an anti-CSF1R antibody and an anti-PD-1 antibody, the method comprising determining the expression level of at least one marker gene before and after the subject is administered at least one dose of the anti-CSF1R antibody and the anti-PD-1 antibody, the at least one marker gene comprising one or both of CSF-1 and IL-34, wherein an increase in the expression level of the at least one marker gene following administration indicates that the subject is responsive to treatment with the combination of the anti-CSF1R antibody and the anti-PD-1 antibody.

In some embodiments, the methods further comprise determining the expression level of one or more anti-inflammatory markers comprising: ARG1, C5AR1, CD14, CD163, CXCR1, CXCR2, IL1A, IL1RN, IL8, MRC1, MSR1, PF4, PPBP, S100A12, S100A8, SAA1, S100A9, and TGFB1. In some embodiments, the levels of these markers do not change or do not increase in subjects responsive to treatment with the anti-CSF1R antibody and the anti-PD-1 antibody. In some embodiments, the subject is administered one or two doses of the anti-CSF1R antibody and anti-PD-1 antibody between determinations of the expression level of the at least one marker gene. In some embodiments, the methods further comprise determining the expression level of one or more anti-inflammatory markers comprising: ARG1, C5AR1, CD14, CD163, CXCR1, CXCR2, IL1A, IL1RN, IL8, MRC1, MSR1, PF4, PPBP, S100A12, S100A8, SAA1, S100A9, and TGFB1. In some embodiments, the levels of these markers do not change or do not increase in subjects responsive to treatment with the anti-CSF1R antibody and the anti-PD-1 antibody. In any of the above methods, the expression level of the at least one marker gene may be the RNA expression level, e.g., measured by transcriptome analysis or reverse transcription PCR. In any of the above methods, the expression level may, for instance, be measured in tumor cells, i.e., in cells from a tumor sample such as a biopsy sample. In any of the above methods, the cancer may have been determined to be MSS and/or has been determined to have a TMB of less than 20, less than 15 or less than 10 mutations/megabase, as determined by the Foundation One® CDx™ assay, and/or less than 400, less than 300, or less than 200 missense mutations, as determined by WES. In some embodiments, the cancer has been determined (i) to be MSS and (ii) to have a TMB of less than 20, less than 15 or less than 10 mutations/megabase, as determined by the Foundation One® CDx™ assay, and/or less than 400, less than 300, or less than 200 missense mutations, as determined by WES. In some embodiments, the cancer has been determined to have a TMB of less than 15 mutations/megabase, as determined by the Foundation One® CDx™ assay, and/or less than 300 mutations/megabase, as determined by WES. In some embodiments, the cancer has been determined to have a TMB of less than 10 mutations/megabase, as determined by the Foundation One® CDx™ assay, and/or less than 200 missense mutations, as determined by WES.

In some embodiments, the anti-CSF1R antibody may comprise a heavy chain comprising a heavy chain (HC) CDR1 having the sequence of SEQ ID NO: 5, an HC CDR2 having the sequence of SEQ ID NO: 6, and an HC CDR3 having the sequence of SEQ ID NO: 7, and a light chain comprising a light chain (LC) CDR1 having the sequence of SEQ ID NO: 8, a LC CDR2 having the sequence of SEQ ID NO: 9, and a LC CDR3 having the sequence of SEQ ID NO: 10; and the anti-PD-1 antibody may comprise a heavy chain comprising a heavy chain (HC) CDR1 having the sequence of SEQ ID NO: 28, an HC CDR2 having the sequence of SEQ ID NO: 30, and an HC CDR3 having the sequence of SEQ ID NO: 32, and a light chain comprising a light chain (LC) CDR1 having the sequence of SEQ ID NO: 35, a LC CDR2 having the sequence of SEQ ID NO: 37, and a LC CDR3 having the sequence of SEQ ID NO: 39. In some embodiments, the anti-CSF1R antibody is a Fab, an Fv, an scFv, a Fab', or a (Fab')$_2$ fragment. In some embodiments, the anti-PD-1 antibody is a Fab, an Fv, an scFv, a Fab', or a (Fab')$_2$ fragment. In some embodiments, the anti-PD-1 antibody heavy chain comprises a heavy chain variable region comprising the sequence of SEQ ID NO: 23 and wherein the anti-PD-1 antibody light chain comprises a light chain variable region comprising the sequence of SEQ ID NO: 25. In some embodiments, the anti-PD-1 antibody comprises a heavy chain comprising the sequence of each of SEQ ID NOs: 23 and 24 and wherein the anti-PD-1 antibody comprises a light chain comprising the sequence of each of SEQ ID NOs: 25 and 26. In some embodiments, the anti-PD-1 antibody is nivolumab or pembrolizumab or PDR001. In some embodiments, the anti-CSF1R antibody comprises a heavy chain variable region comprising the sequence of SEQ ID NO: 11 and wherein the anti-CSF1R antibody comprises a light chain variable region comprising the sequence of SEQ ID NO: 12. In some embodiments, the anti-CSF1R antibody comprises a heavy chain comprising the sequence of SEQ ID NO: 13 and wherein the anti-CSF1R antibody comprises a light chain comprising the sequence of SEQ ID NO: 14. In some embodiments, the anti-CSF1R antibody is cabiralizumab. In some embodiments, the anti-CSF-1R antibody is emactuzumab (RG7155), AMG 820, or SNDX 6352 (UCB 6352). In some embodiments, a non-antibody CSF1R inhibitor is used in place of the anti-CSF1R antibody, such as a small molecule, e.g., JNJ-40346527 (now PRV-6527), e.g., an anti-CSF1R tyrosine kinase inhibitor, or other modality.

In some embodiments, the subject has previously received a PD-1/PD-L1 inhibitor therapy. In some embodiments, the subject is a PD-1/PD-L1 inhibitor inadequate responder. In some embodiments, the subject is refractory to a PD-1/PD-L1 inhibitor, e.g., after at least 2 doses. In some embodiments, the anti-CSF1R antibody is cabiralizumab and the anti-PD-1 antibody is nivolumab, wherein cabiralizumab is administered at a dose of 4 mg/kg once every two weeks, and wherein nivolumab is administered at a dose of 3 mg/kg once every two weeks. In some embodiments, the cancer is pancreatic cancer, ovarian cancer, renal cancer, malignant glioma, melanoma, non-small cell lung cancer (NSCLC), or squamous cell carcinoma of the head and neck (SCCHN).

BRIEF DESCRIPTION OF THE FIGURES AND ADDITIONAL MATERIALS

FIG. 1 is a description of the treatment cohorts for clinical experiments described in Examples 3 and 4 involving cabiralizumab (also called FPA008 or HuAb1 herein) and nivolumab.

Figure 3A:
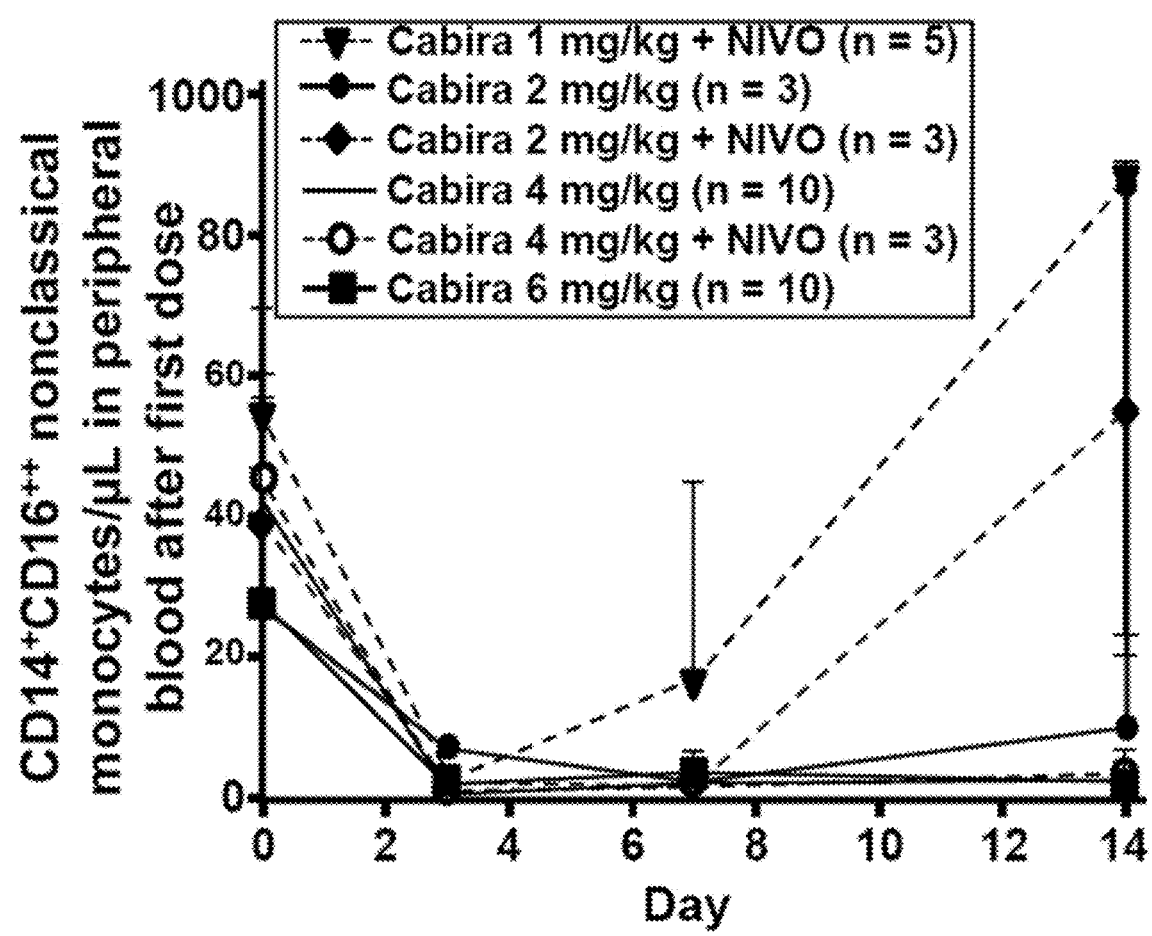
Figure 3B:
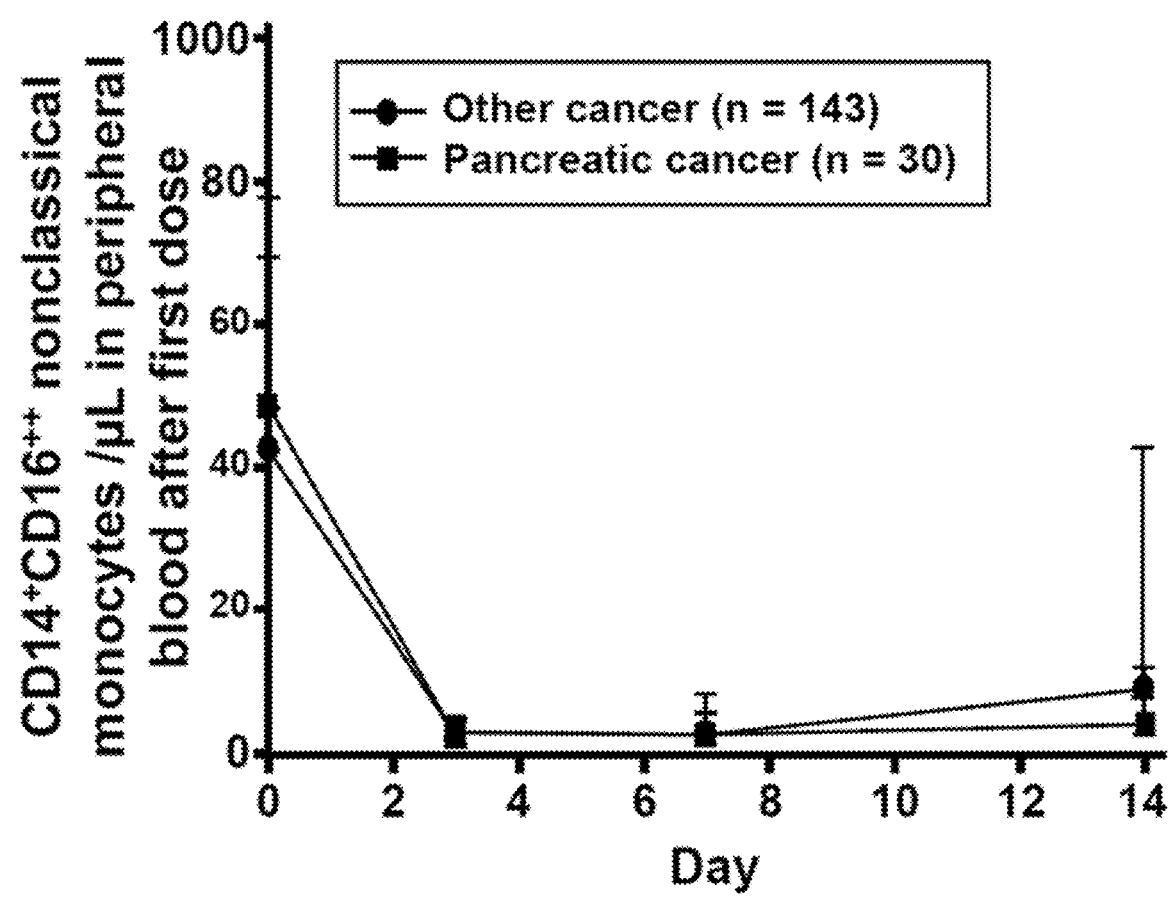

FIG. 3A shows the level of CD14+CD16++ nonclassical monocytes in peripheral blood after a first dose of either cabiralizumab ("cabira") or combination cabiralizumab and nivolumab ("cabira" and "NIVO"). The value "n" is the number of patients receiving each dosage of cabiralizumab or the combination. The highest, dashed line in the graph to the left of the page is from the Cabira 1 mg/kg+NIVO data set while the second dashed line is from the Cabira 2 mg/kg+NIVO data set, while the third highest, solid line is from the Cabira 2 mg/kg data set. The remaining lines generally superimpose on the graph. FIG. 3B shows the level of peripheral blood CD14+CD16++ monocytes in a dose expansion of 173 cancer patients after a first dose of 4 mg/kg cabiralizumab every 2 weeks (Q2W), separated into two categories for "pancreatic cancer" and "other cancer." The levels of peripheral CD14+CD16++ monocytes in the two groups of patients generally superimpose, with the "other cancer" line being the lower of the two lines on Day 0 and the higher of the two on Day 14.

Figure 4:
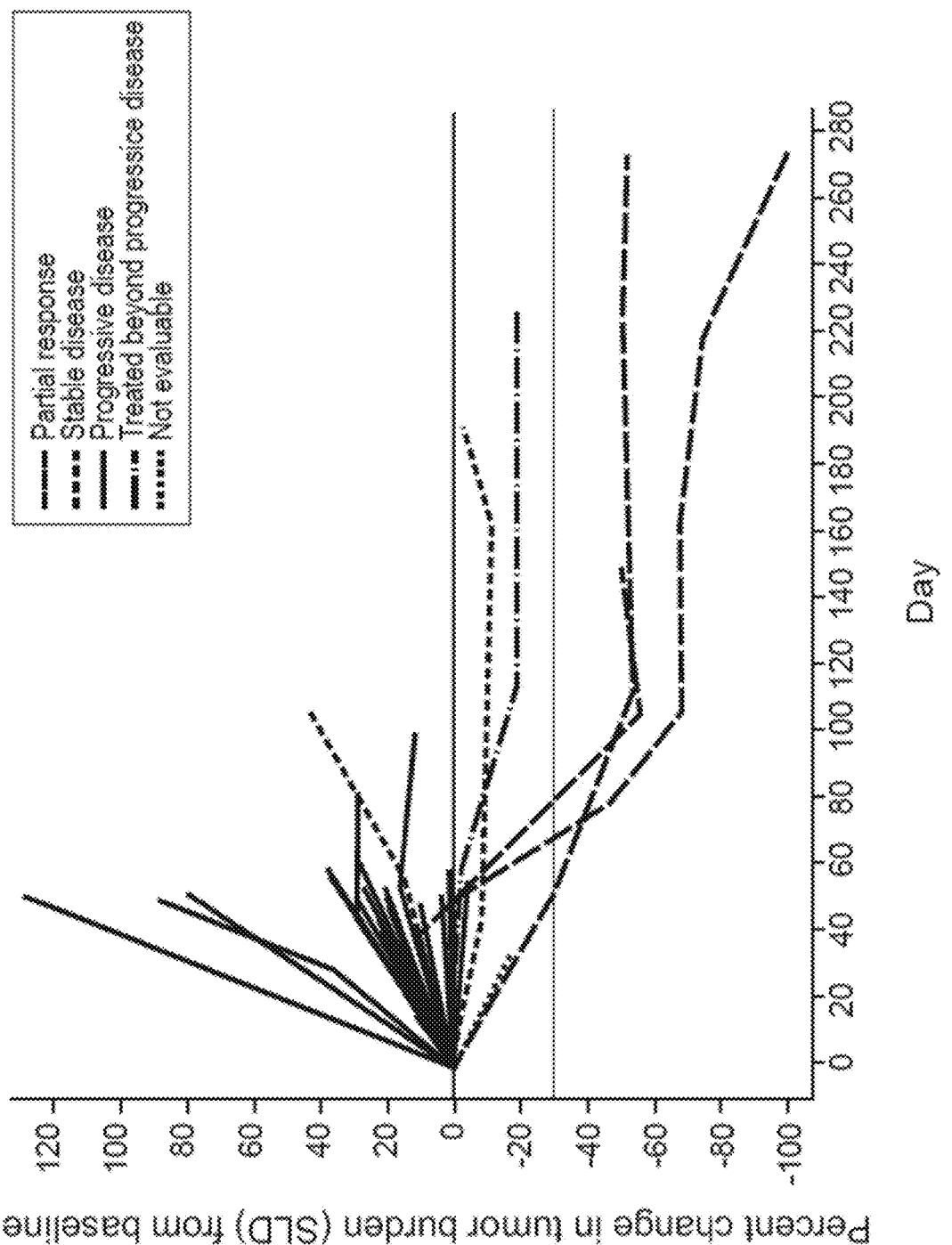

FIG. 4 shows a spliderplot of responsiveness of pancreatic cancer patients to a combination of 4 mg/kg cabiralizumab and 3 mg/kg nivolumab every two weeks. The 3 bottom lines correspond to patients having a confirmed partial response. As shown, tumor burden in those 3 patients falls by at least 30% within 50-100 days of the start of the treatment. The line above these 3 corresponds to a patient treated beyond progressive disease; the next higher line corresponds to a patient having stable disease, and the lines above the zero line of the graph correspond to patients having progressive disease, except for one having stable disease.

Figure 5:
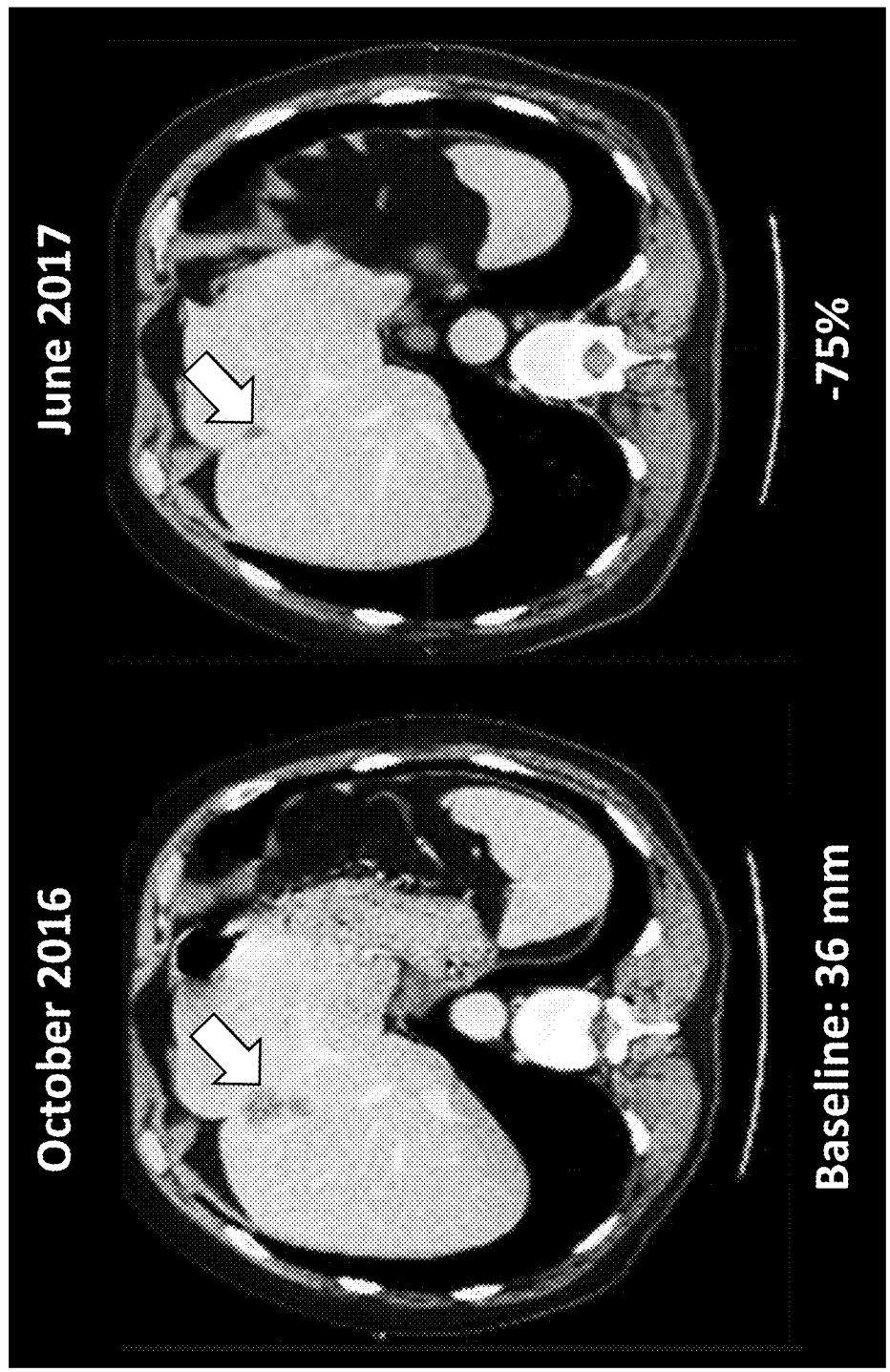

FIG. 5 shows a liver scan from a patient whose pancreatic cancer had metastasized to the liver with images taken after 4 different chemotherapy regimens but prior to treatment with a combination of 4 mg/kg cabiralizumab and 3 mg/kg nivolumab every two weeks (baseline; October 2016) and following treatment with the cabiralizumab/nivolumab combination (−75%; June 2017). The scan shows a 75% drop in tumor burden measured as a reduction in size of the 36 mm diameter liver metastasis.

FIGS. 6A and B together show a diagram of patient cohorts in a Phase Ia/Ib study of cabiralizumab monotherapy (FIG. 6A) and cabiralizumab in combination with nivolumab (FIG. 6B) in patients with advanced solid tumors. The combination treatment study was initiated after corresponding monotherapy doses were deemed tolerable. Abbreviations: IV=intravenous; NSCLC=non-small cell lung cancer; Q2W=every 2 weeks; RCC=renal cell carcinoma; SCCHN=squamous cell carcinoma of the head and neck.

Figure 7:
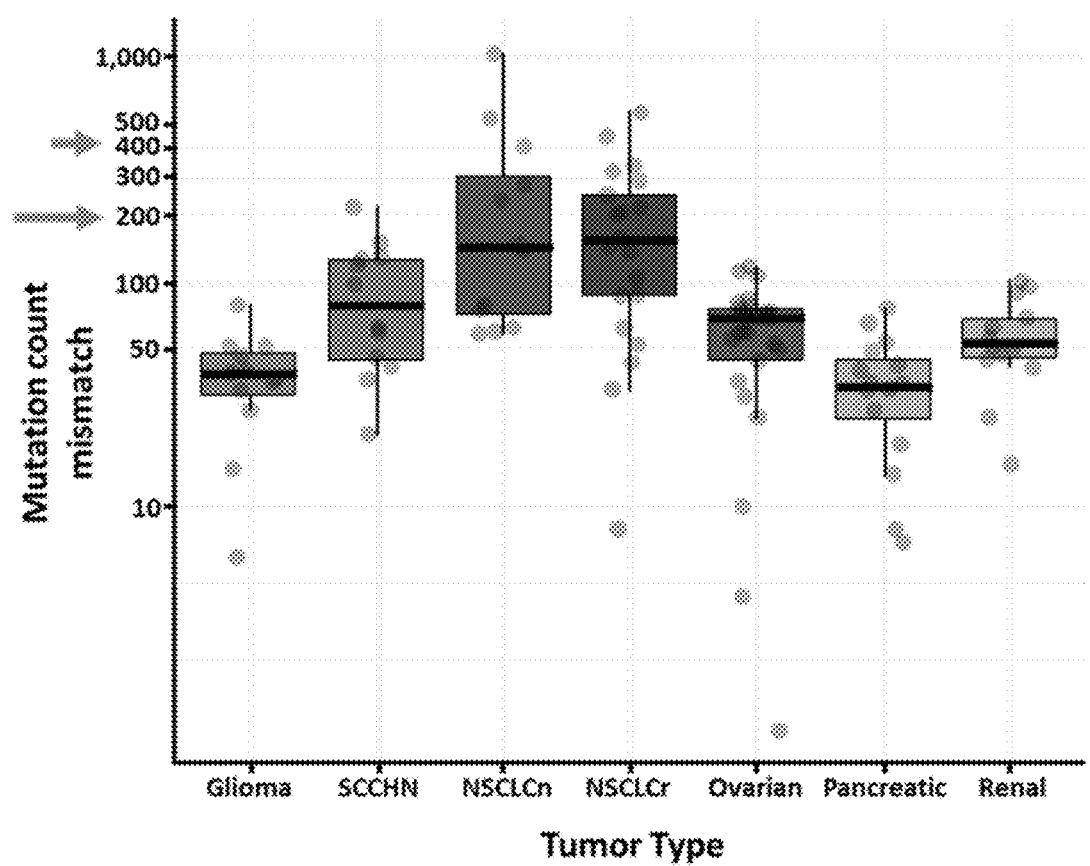

FIG. 7 shows tumor mutation burden (TMB), determined by RNA sequencing, (correspondence with TMB values obtained by a Foundation Medicine, Inc. Foundation One® CDx assay are shown as described herein), in patients receiving cabiralizumab plus nivolumab broken down by type of tumor. The plot shows the number of mismatch mutations for both individual patients (grey dots) and for the patients in each tumor group. The left-hand arrow is the cut-off line of 200 total missense mutations as determined by WES, which corresponds to a TMB of 10 mismatch mutations per megabase as determined by the Foundation Medicine Foundation One® CDx™ assay used in the CM026 clinical trial (see Szustakowski et al. Presented at the AACR 2018 Annual Meeting; Apr. 14-18, 2018; Chicago. Abstract 5528). NSCLCn stands for PD-1 naïve NSCLC while NSCLCr stands for de novo or acquired resistance NSCLC.

Figures 8A, 8B:
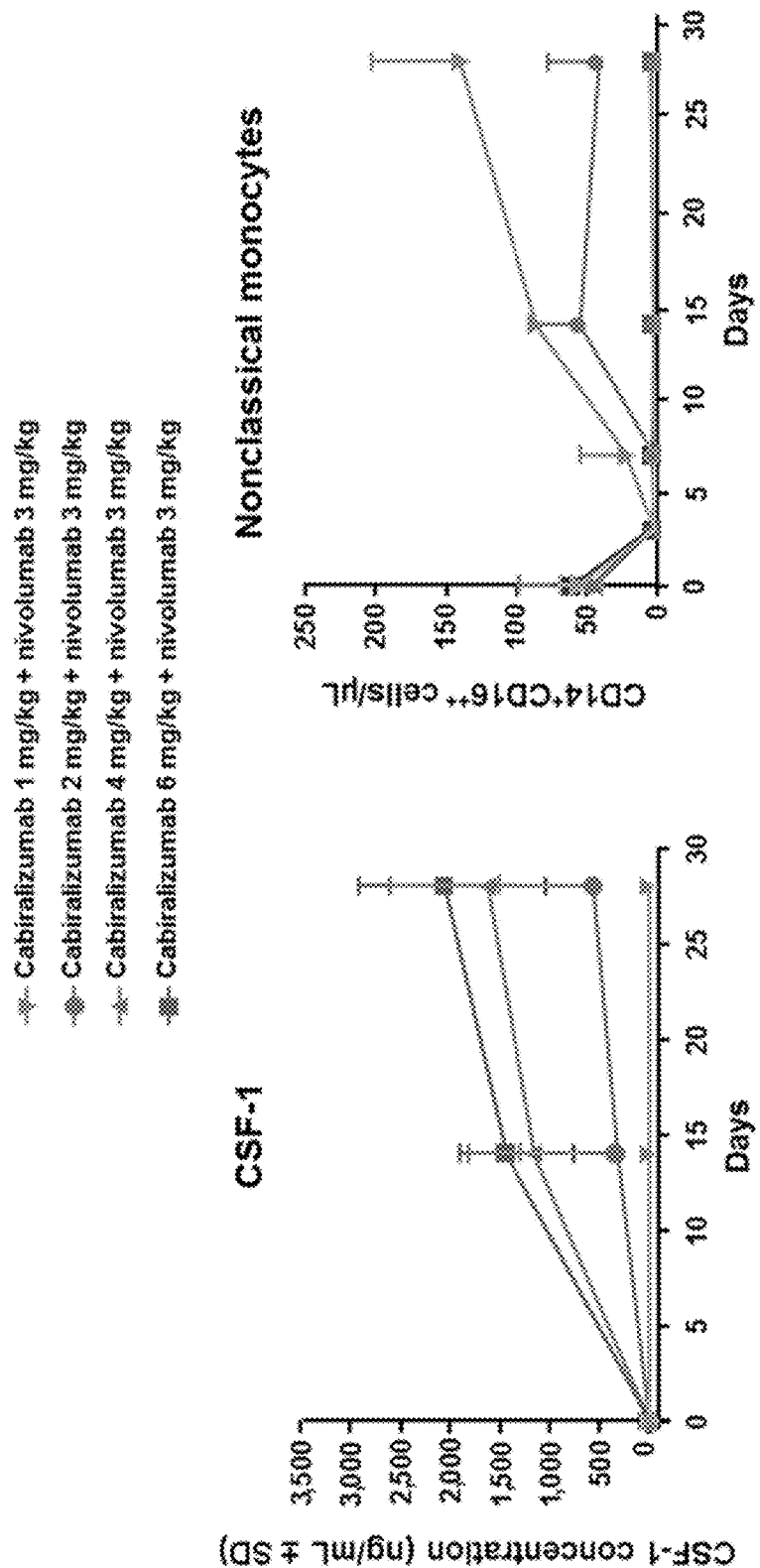

FIG. 8 illustrates that dose-dependent changes in peripheral CSF-1 and nonclassical monocytes were observed with cabiralizumab ≥4 mg/kg and nivolumab. FIG. 8A shows CSF-1 concentration in ng/mL in peripheral blood at 0-30 days following the start of treatment with 1, 2, 4, or 6 mg/kg cabiralizumab plus 3 mg/kg nivolumab Q2W, indicating that CSF-1 increased in patients treated with cabiralizumab doses ≥4 mg/kg+nivolumab 3 mg/kg Q2W. FIG. 8B shows concentration in peripheral blood of nonclassical monocytes (CD14+CD16++) 0-30 days following the start of treatment with 1, 2, 4, or 6 mg/kg cabiralizumab plus 3 mg/kg nivolumab Q2W, showing durable depletion of nonclassical monocytes in patients treated with cabiralizumab doses ≥4 mg/kg+nivolumab 3 mg/kg Q2W.

Figure 9B:
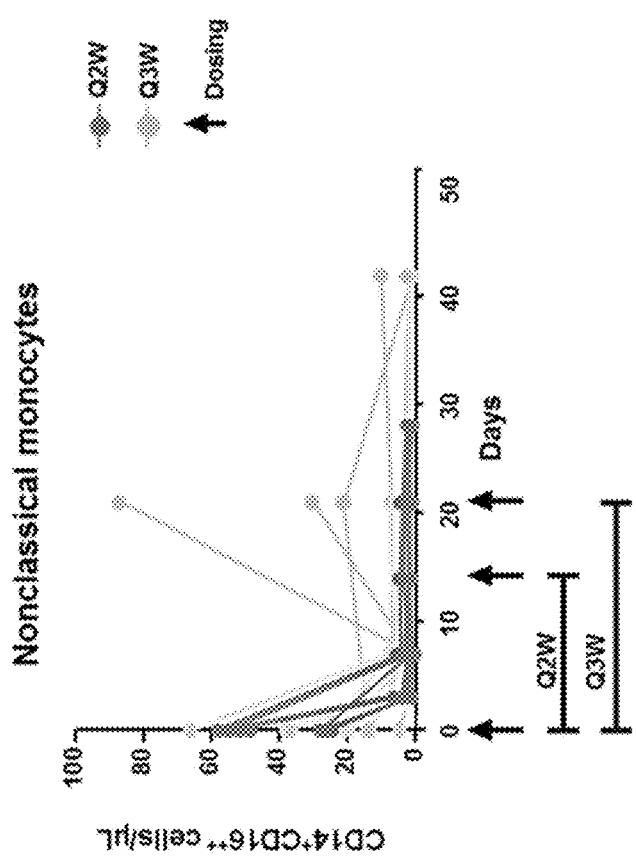
Figure 9A:
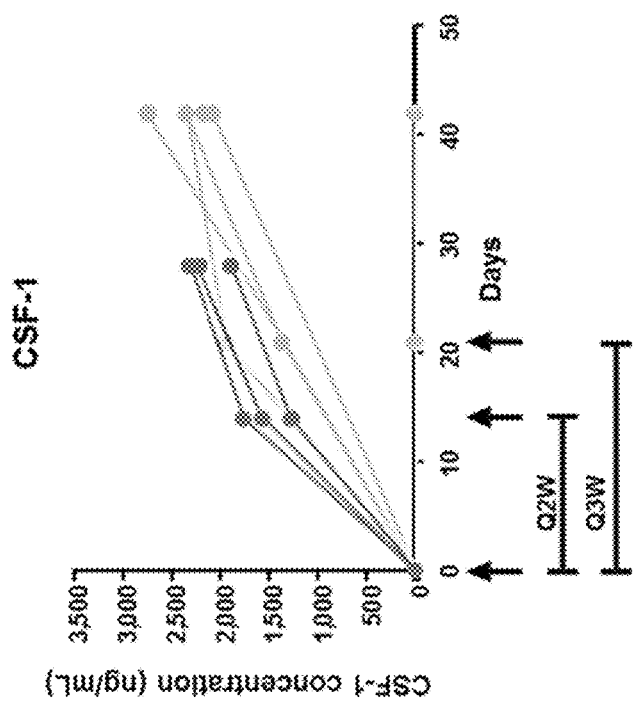
Figure 10:
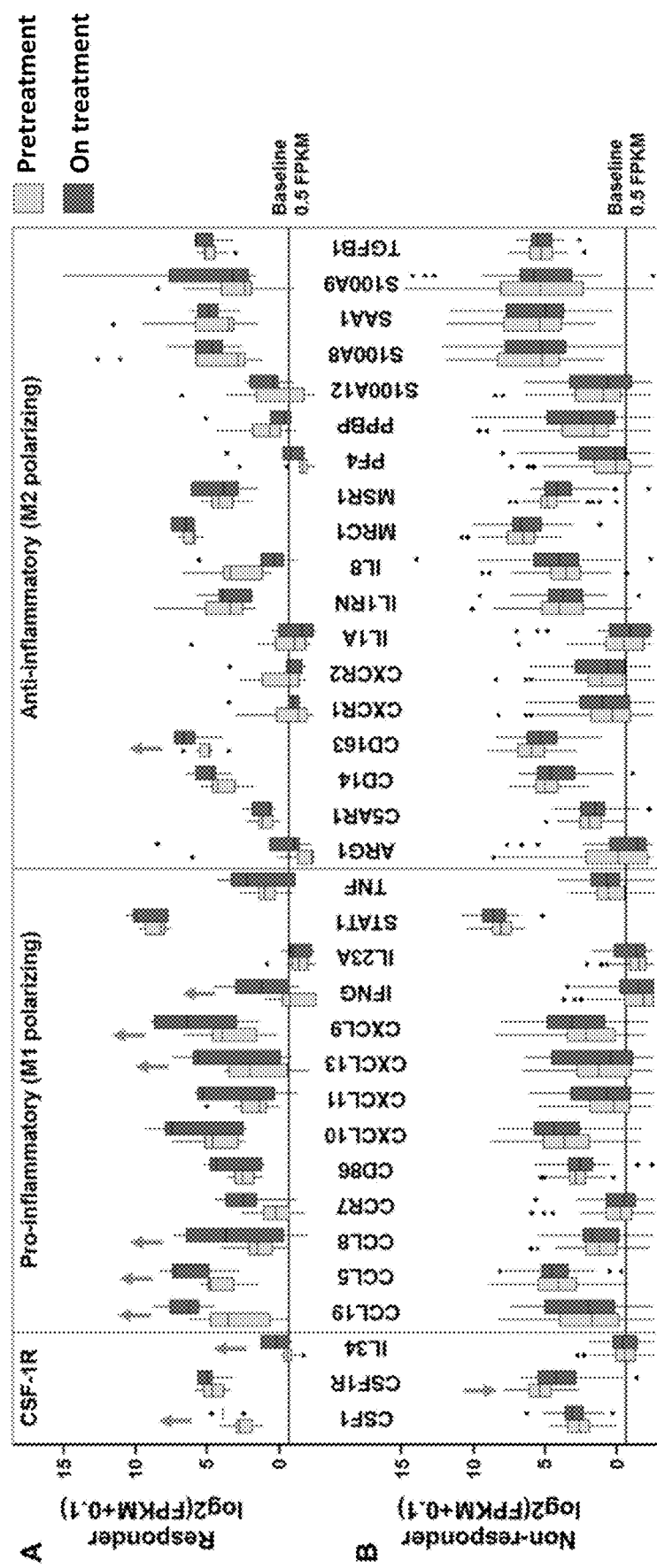

FIG. 9 illustrates that schedule-dependent changes in peripheral CSF-1 and nonclassical monocytes had optimal kinetics with the Q2W regimen. FIG. 9A shows CSF-1 concentration, while FIG. 9B shows nonclassical monocyte concentration, comparing a Q2W with a Q3W dosing schedule of the cabiralizumab plus nivolumab combination. FIG. 9A shows that CSF-1 results were similar with the Q2W and every 3 weeks (Q3W) regimens, with the exception of 1 patient treated with the Q3W regimen, whose CSF-1 levels did not increase. FIG. 9B shows that nonclassical monocytes decreased consistently with the Q2W regimen but varied with the Q3W regimen FIG. 10 shows that expression of CSF-1R ligands and pro-inflammatory genes increased in tumors of responders but not in nonresponders FIGS. 10A and 10B show plots of expression levels of various markers at pretreatment baseline (light shading) and following 4 weeks of treatment (dark shading) in cabiralizumab plus nivolumab responders (FIG. 10A) and nonresponders (FIG. 10B). FIG. 10A shows that significant increases in the expression of CSF-1R ligands and pro-inflammatory markers were observed in patients who responded to treatment with cabiralizumab+nivolumab. FIG. 10B shows that a decrease in CSF1R was the only significant change observed in patients who did not respond. FPKM=fragments per kilobase of transcript per million mapped reads. Pretreatment and on-treatment analysis includes 133 pre- and 55 on-treatment samples. Arrows denote statistically significant changes determined by DSEq2 package in R criteria >2-fold change and <0.05 FDR.

Figure 11:
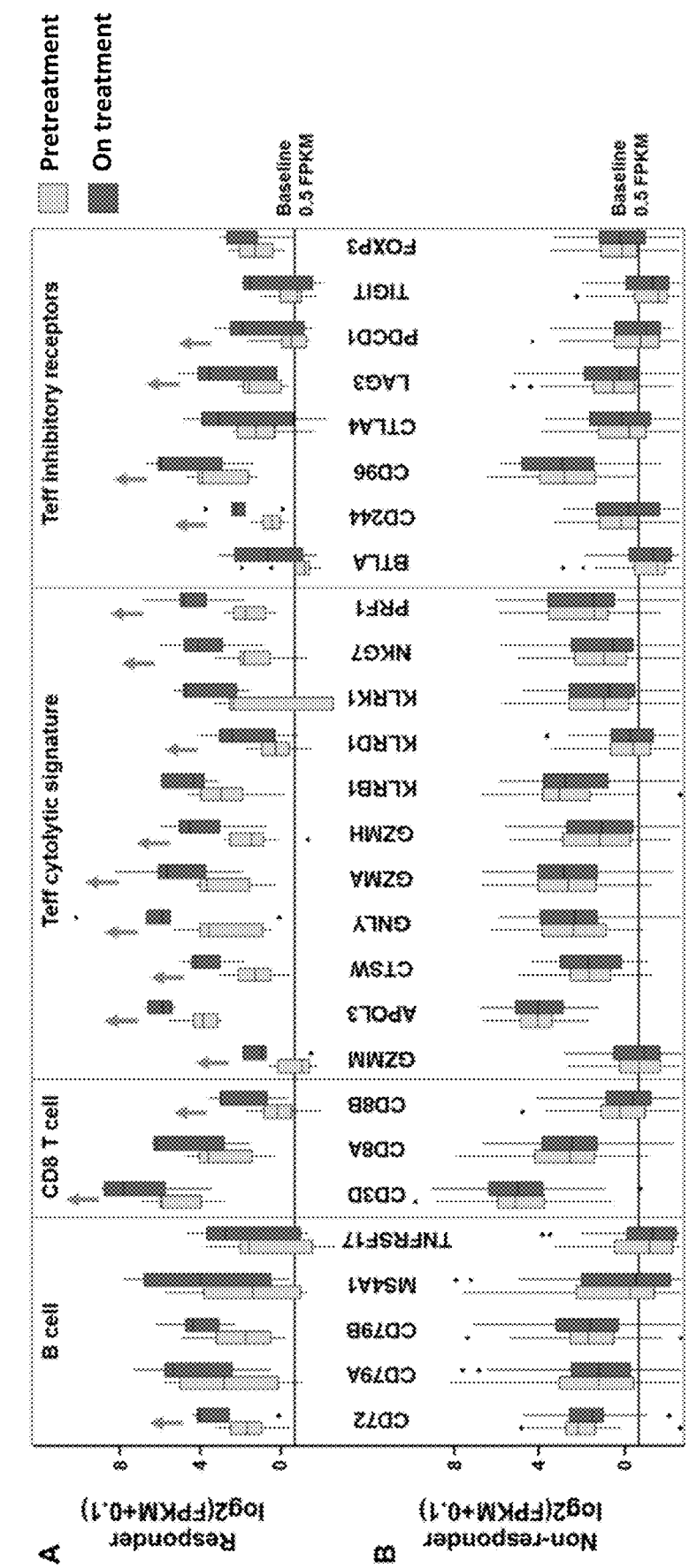

FIG. 11 shows that expression of genes associated with B cells, CD8+ T cells, and CD8+ T-cell activation increased in tumors in responders but not in nonresponders. FIGS. 11A and 11B show plots of expression levels of various additional markers at pretreatment baseline (light shading) and following 4 weeks of treatment (dark shading) in cabiralizumab plus nivolumab responders (FIG. 11A) and nonresponders (FIG. 11B). FIG. 11A shows that significant increases in the expression of genes associated with CD8+ T cells and CD8+ T-cell cytolytic and inhibitory receptor signatures were observed in patients who responded to the combination. FIG. 11B shows that no significant changes were observed in nonresponders. FPKM=fragments per kilobase of transcript per million mapped reads. Pretreatment and on-treatment analysis includes 133 pre- and 55 on-treatment samples. Arrows denote statistically significant changes determined by DSEq2 package in R criteria >2-fold change and <0.05 FDR.

Figure 12:
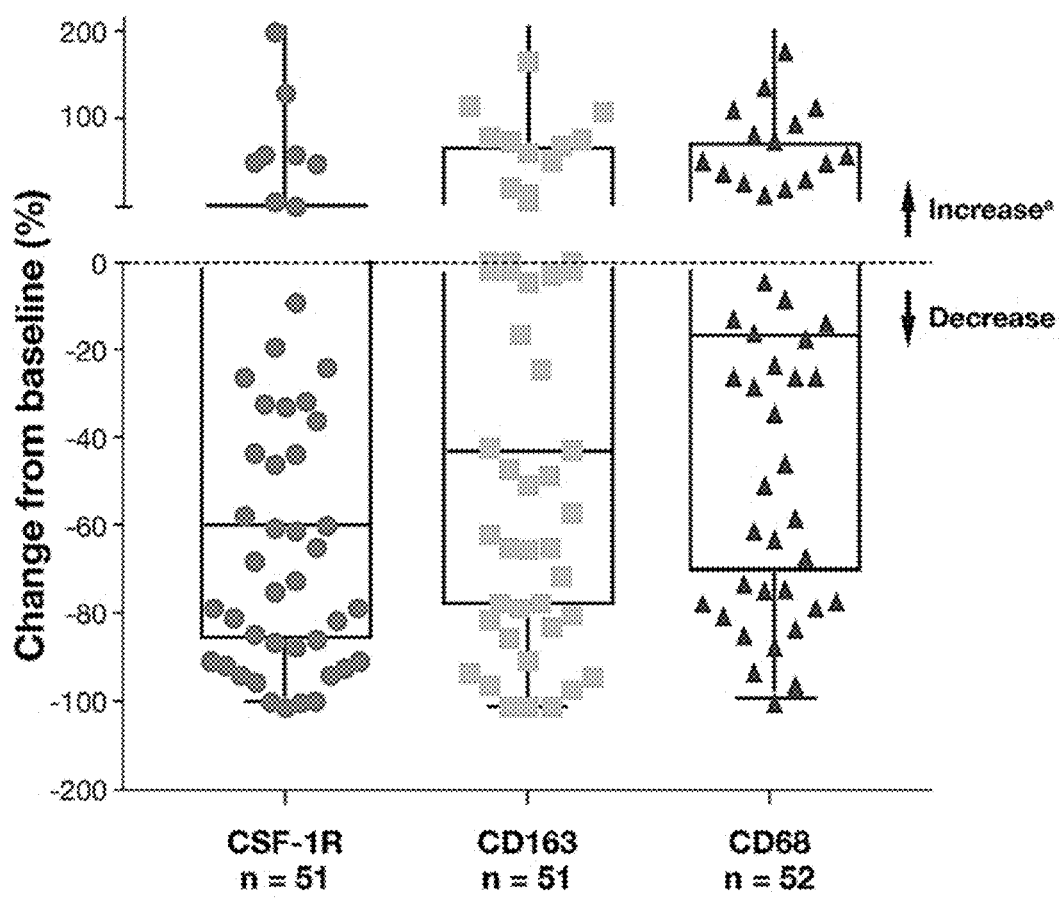

FIG. 12 shows that CSF1R and M2 macrophages decreased in tumors of patients treated with cabiralizumab and nivolumab. Specifically, CSF1R and CD163, which are markers of M2 macrophages, showed pronounced decreases from baseline on day 28 of treatment, as shown in the left and center panels of the graph. CD68, which is a marker for M1 and M2 macrophages, decreased to a lesser extent. In the graph, "n" equals the number of patient samples tested. The graph does not show increases in marker levels of above 200%. Greater than 200% increases in CSF1R were observed in 5 patients, >200% increases in CD163 in 7 patients, and >200% increases in CD68 in 6 patients.

Figure 13:
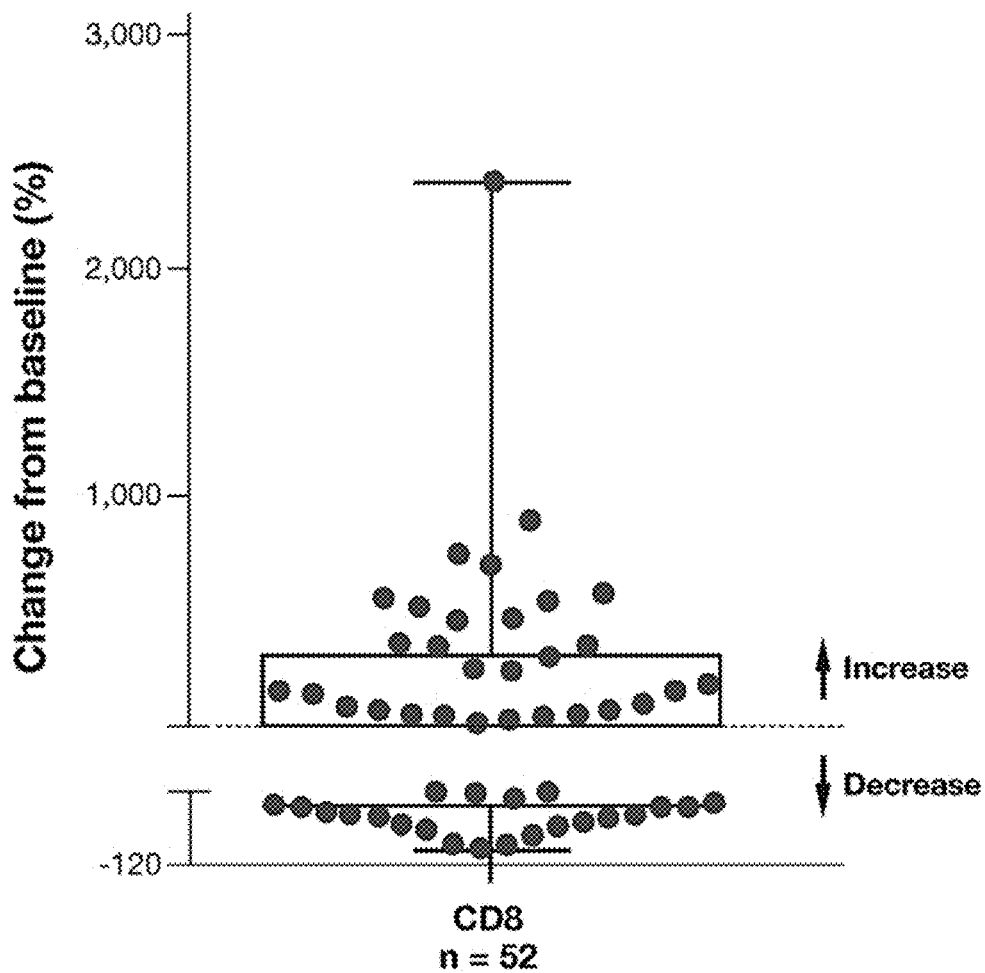

FIG. 13 shows that CD8+ effector T cells increased in tumors of patients treated with cabiralizumab and nivolumab. The graph shows percent change from baseline for 52 patients.

Figure 14:
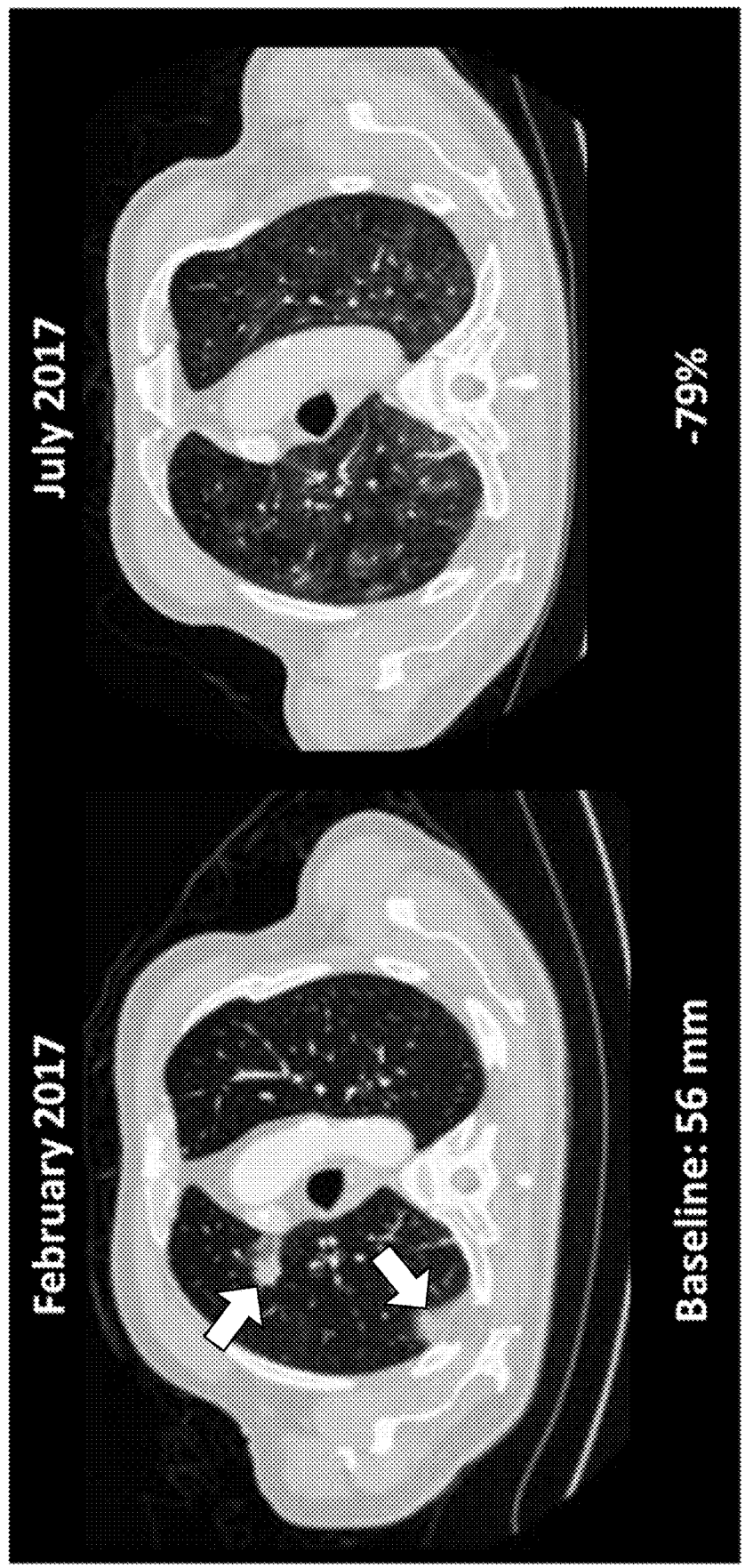

FIG. 14 shows images of the lung of a heavily pretreated patient with MSS pancreatic cancer treated with a combination of cabiralizumab and nivolumab both before treatment (February 2017; lesions indicated by white arrows in image) and after several months of treatment (July 2017). The images show a durable response to treatment in the lung. The patient is a 63-year old male who received 4 prior chemotherapy regimens (adjuvant FOLFIRINOX, FOLFIRINOX, capecitabine, gemcitabine plus nab-paclitaxel). The patient achieved a partial response with a best change in tumor burden of −50%. CA19-9 levels declined by 96%. As of November 2017, the patient's response was ongoing.

DETAILED DESCRIPTION

Tumor-associated macrophages (TAMs) are implicated in the pathogenesis of many cancers, and correlate with poor prognosis. Inhibition of CSF1R can reduce immunosuppressive TAMs in mouse models and human tumors. See, e.g., Ries et al., 2014, *Cancer Cell*, 25: 846-859; Pyontech et al., 2013, *Nature Med.*, 19: 1264-1272; and Zhu et al., 2014, *Cancer Res.*, 74: 5057-5069. Small molecule inhibition of CSF1R synergizes with immune checkpoint blockade in a pancreatic tumor model. See Zhu et al., 2014, *Cancer Res.*, 74: 5057-5069. While not intending to be bound by any particular theory, the present invention is directed to methods of treating tumors that may have both CSF1R-expressing TAMs and PD-1-expressing T cells, e.g., CD8+ T cells, and will be sensitive to combination therapy with an anti-CSF1R antibody and a PD-1/PD-L1 inhibitor. In some instances, tumors that have both CSF1R-expressing TAMs and PD-1-expressing T cells, e.g., CD8+ T cells, may be resistant to PD-1/PD-L1 monotherapy, but should be sensitive to the combination therapy. For example, without intending to be bound by any particular theory, tumors that have high levels of CSF1R-expressing TAMs, which are suppressing PD-1-expressing T cells, e.g., CD8+ T cells, may be sensitive to combination therapy, for example, because inhibition of TAMs with an anti-CSF1R antibody may boost PD-1 expressing T cells, e.g., CD8+ T cells, rendering the tumor sensitive to a PD-1/PD-L1 inhibitor. Accordingly, the present invention provides methods of treating cancer comprising administering an anti-CSF1R antibody and a PD-1 antibody in a particular dosage regime identified through Phase Ia/b clinical testing.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

Exemplary techniques used in connection with recombinant DNA, oligonucleotide synthesis, tissue culture and transformation (e.g., electroporation, lipofection), enzymatic reactions, and purification techniques are known in the art. Many such techniques and procedures are described, e.g., in Sambrook et al. *Molecular Cloning: A Laboratory Manual* (2nd ed., Cold Spring Harbor Laboratory Press, Cold Spring Harbor, N.Y. (1989)), among other places. In addition, exemplary techniques for chemical syntheses, chemical analyses, pharmaceutical preparation, formulation, and delivery, and treatment of patients are also known in the art.

In this application, the use of "or" means "and/or" unless stated otherwise. In the context of a multiple dependent claim, the use of "or" refers back to more than one preceding independent or dependent claim in the alternative only. Also, terms such as "element" or "component" encompass both elements and components comprising one unit and elements and components that comprise more than one subunit unless specifically stated otherwise.

As described herein, any concentration range, percentage range, ratio range or integer range is to be understood to include the value of any integer within the recited range and, when appropriate, fractions thereof (such as one tenth and one hundredth of an integer), unless otherwise indicated.

Units, prefixes, and symbols are denoted in their Système International de Unites (SI) accepted form. Numeric ranges are inclusive of the numbers defining the range. The headings provided herein are not limitations of the various aspects of the disclosure, which can be had by reference to the specification as a whole. Instead, the section headings used herein are for organizational purposes only.

Accordingly, the terms defined immediately below are more fully defined by reference to the specification in its entirety.

All references cited herein, including patent applications and publications, are incorporated herein by reference in their entireties for any purpose.

As utilized in accordance with the present disclosure, the following terms, unless otherwise indicated, shall be understood to have the following meanings:

"Administering" refers to the physical introduction of a composition comprising a therapeutic agent to a subject, using any of the various methods and delivery systems known to those skilled in the art. Routes of administration for the anti-PD-1 Ab and/or the anti-PD-L1 Ab and anti-CSF-1R antibody include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. Non-parenteral routes include a topical, epidermal or mucosal route of administration, for example, orally, intranasally, vaginally, rectally, sublingually or topically. Administering can also be performed, for example, once, a plurality of times, and/or over one or more extended periods.

The terms "colony stimulating factor 1 receptor" and "CSF1R" or "CSF-1R" refer herein to the full-length, human CSF1R, which includes the N-terminal ECD, the transmembrane domain, and the intracellular tyrosine kinase domain, either with or without an N-terminal leader sequence, unless it is clearly expressed otherwise (e.g. "murine CSF1R," or "CSF1R ECD," etc.). In some embodiments, the CSF1R has the amino acid sequence of SEQ ID NO: 1 (mature, without signal sequence) or SEQ ID NO: 2 (precursor, with signal sequence).

An "antibody that binds CSF1R" or an "anti-CSF1R antibody" as referred to herein is an antibody that binds CSF1R and that may block the binding of CSF1R to one or both of its ligands CSF-1 and IL-34.

The terms "programmed cell death protein 1" and "PD-1" refer to a full-length, human PD-1 protein, unless clearly expressed otherwise (e.g., "murine PD-1" and the like). PD-1 is expressed predominantly on previously activated T cells in vivo, and binds to two ligands, PD-L1 and PD-L2. The complete PD-1 sequence can be found under GenBank Accession No. U64863. In some embodiments, PD-1 has the amino acid sequence of SEQ ID NO: 19 (precursor, with signal sequence) or SEQ ID NO: 20 (mature, without signal sequence).

"Programmed cell death 1 ligand 1" and "PD-L1" (also known as B7 homolog-1; B7-H1; or CD274) and "Programmed Death Ligand-2" and "PD-L2" (also known as B7-DC; or CD273) are two cell surface glycoprotein ligands for PD-1 that downregulate T-cell activation and cytokine secretion upon binding to PD-1. The terms refer to full-length human PD-L1 and human PD-L2 unless particularly specified otherwise. The complete PD-L1 sequence can be found under GenBank Accession No. Q9NZQ7. In some embodiments, PD-L1 has the amino acid sequence of SEQ ID NO: 21 (precursor, with signal sequence) or SEQ ID NO: 22 (mature, without signal sequence).

"Cytotoxic T-Lymphocyte Antigen-4" and "CTLA-4" is an immunoinhibitory receptor belonging to the CD28 family. The terms refer to the full length human protein unless particularly specified otherwise. CTLA-4 is expressed exclusively on T cells in vivo, and binds to two ligands, CD80 and CD86 (also called B7-1 and B7-2, respectively). The complete CTLA-4 sequence can be found under GenBank Accession No. AAB59385.

The term "PD-1/PD-L1 inhibitor" refers to a moiety that disrupts the PD-1/PD-L1 signaling pathway. In some embodiments, the inhibitor inhibits the PD-1/PD-L1 signaling pathway by binding to PD-1 and/or PD-L1. In some embodiments, the inhibitor also binds to PD-L2. In some embodiments, a PD-1/PD-L1 inhibitor blocks binding of PD-1 to PD-L1 and/or PD-L2. Such an inhibitor may be, for example, an antibody, a fusion protein, or a small molecule inhibitor of the PD-1/PD-L1 signaling pathway.

The term "antibody that inhibits PD-1" or an "anti-PD-1 antibody" herein refers to an antibody that inhibits PD-1 and/or PD-L1 signaling. In some embodiments, the antibody inhibits PD-1 binds to PD-1 and blocks binding of PD-L1 and/or PD-L2 to PD-1. In some embodiments, the antibody inhibits PD-1 binds to PD-L1 and blocks binding of PD-1 to PD-L1.

"PD-L1 positive" as used herein can be interchangeably used with "PD-L1 expression of at least about 5%." PD-L1 expression can be measured by any methods known in the art. In some embodiments, the PD-L1 expression is measured by an automated IHC. A PD-L1 positive tumor can thus have at least about 5%, at least about 10%, or at least about 20% of tumor cells expressing PD-L1 as measured by an automated IHC. In certain embodiments, "PD-L1 positive" means that there are at least 100 cells that express PD-L1 on the surface of the cells.

"PD-L2 positive" as used herein can be interchangeably used with "PD-L2 expression of at least about 5%." PD-L2 expression can be measured by any methods known in the art. In some embodiments, the PD-L2 expression is measured by an automated IHC. A PD-L2 positive tumor can thus have at least about 5%, at least about 10%, or at least about 20% of tumor cells expressing PD-L2 as measured by an automated IHC. In certain embodiments, "PD-L2 positive" means that there are at least 100 cells that express PD-L2 on the surface of the cells.

With reference to anti-CSF1R antibodies the term "blocks binding of" a ligand, such as CSF1 and/or IL-34, and grammatical variants thereof, is used to refer to the ability to inhibit the interaction between CSF1R and a CSF1R ligand, such as CSF1 and/or IL-34. Such inhibition may occur through any mechanism, including direct interference with ligand binding, e.g., because of overlapping binding sites on CSF1R, and/or conformational changes in CSF1R induced by the antibody that alter ligand affinity, etc. Antibodies and antibody fragments referred to as "functional" are characterized by having such properties. As used herein, the terms "CSF1" and "IL-34" refer to the human, full-length proteins unless explicitly noted otherwise.

With reference to anti-PD-1 antibodies the term "blocks binding of" a ligand, such as PD-L1, and grammatical variants thereof, is used to refer to the ability to inhibit the interaction between PD-1 and a PD-1 ligand, such as PD-L1. Such inhibition may occur through any mechanism, including direct interference with ligand binding, e.g., because of overlapping binding sites on PD-1, and/or conformational changes in PD-1 induced by the antibody that alter ligand affinity, etc. Antibodies and antibody fragments referred to as "functional" are characterized by having such properties. As used herein, the terms "PD-L1" refers to the human, full-length protein unless explicitly noted otherwise.

The term "antibody" as used herein (abbreviated "Ab") refers to a molecule comprising at least complementarity-determining region (CDR) 1, CDR2, and CDR3 of a heavy chain and at least CDR1, CDR2, and CDR3 of a light chain, wherein the molecule is capable of binding to antigen. The term antibody includes, but is not limited to, fragments that are capable of binding antigen, such as Fv, single-chain Fv (scFv), Fab, Fab', and (Fab')$_2$. The term also encompasses molecules with full length heavy and/or light chains. The term antibody also includes, but is not limited to, chimeric antibodies, humanized antibodies, and antibodies of various species such as mouse, human, cynomolgus monkey, etc.

In some embodiments, an antibody comprises a heavy chain variable region and a light chain variable region. In some embodiments, an antibody comprises at least one heavy chain comprising a heavy chain variable region and at least a portion of a heavy chain constant region, and at least one light chain comprising a light chain variable region and at least a portion of a light chain constant region. In some embodiments, an antibody comprises two heavy chains, wherein each heavy chain comprises a heavy chain variable region and at least a portion of a heavy chain constant region, and two light chains, wherein each light chain comprises a light chain variable region and at least a portion of a light chain constant region. As used herein, a single-chain Fv (scFv), or any other antibody that comprises, for example, a single polypeptide chain comprising all six CDRs (three heavy chain CDRs and three light chain CDRs) is considered to have a heavy chain and a light chain. In some such embodiments, the heavy chain is the region of the antibody that comprises the three heavy chain CDRs and the light chain in the region of the antibody that comprises the three light chain CDRs.

The term "heavy chain variable region" as used herein refers to a region comprising heavy chain CDR1, framework (FR) 2, CDR2, FR3, and CDR3. In some embodiments, a heavy chain variable region also comprises at least a portion of an FR1 and/or at least a portion of an FR4. In some embodiments, a heavy chain CDR1 corresponds to Kabat residues 26 to 35; a heavy chain CDR2 corresponds to Kabat residues 50 to 65; and a heavy chain CDR3 corresponds to Kabat residues 95 to 102. See, e.g., Kabat Sequences of Proteins of Immunological Interest (1987 and 1991, NIH, Bethesda, Md.); and FIG. 1. In some embodiments, a heavy chain CDR1 corresponds to Kabat residues 31 to 35; a heavy chain CDR2 corresponds to Kabat residues 50 to 65; and a heavy chain CDR3 corresponds to Kabat residues 95 to 102. See id.

The term "heavy chain constant region" as used herein refers to a region comprising at least three heavy chain constant domains, $C_H1$, $C_H2$, and $C_H3$. Nonlimiting exemplary heavy chain constant regions include γ, δ, and α. Nonlimiting exemplary heavy chain constant regions also include ε and μ. Each heavy constant region corresponds to an antibody isotype. For example, an antibody comprising a γ constant region is an IgG antibody, an antibody comprising a δ constant region is an IgD antibody, and an antibody comprising an α constant region is an IgA antibody. Further, an antibody comprising a μ constant region is an IgM antibody, and an antibody comprising an ε constant region is an IgE antibody. Certain isotypes can be further subdivided into subclasses. For example, IgG antibodies include, but are not limited to, IgG1 (comprising a $γ_1$ constant region), IgG2 (comprising a $γ_2$ constant region), IgG3 (comprising a $γ_3$ constant region), and IgG4 (comprising a $γ_4$ constant region) antibodies; IgA antibodies include, but are not limited to, IgA1 (comprising an $α_1$ constant region) and IgA2 (comprising an $α_2$ constant region) antibodies; and IgM antibodies include, but are not limited to, IgM1 and IgM2.

In some embodiments, a heavy chain constant region comprises one or more mutations (or substitutions), additions, or deletions that confer a desired characteristic on the antibody. A nonlimiting exemplary mutation is the S241P mutation in the IgG4 hinge region (between constant domains $C_H1$ and $C_H2$), which alters the IgG4 motif CPSCP to CPPCP, which is similar to the corresponding motif in IgG1. That mutation, in some embodiments, results in a more stable IgG4 antibody. See, e.g., Angal et al., *Mol. Immunol.* 30: 105-108 (1993); Bloom et al., *Prot. Sci.* 6: 407-415 (1997); Schuurman et al., *Mol. Immunol.* 38: 1-8 (2001).

The term "heavy chain" (abbreviated HC) as used herein refers to a polypeptide comprising at least a heavy chain variable region, with or without a leader sequence. In some embodiments, a heavy chain comprises at least a portion of a heavy chain constant region. The term "full-length heavy chain" as used herein refers to a polypeptide comprising a heavy chain variable region and a heavy chain constant region, with or without a leader sequence.

The term "light chain variable region" as used herein refers to a region comprising light chain CDR1, framework (FR) 2, CDR2, FR3, and CDR3. In some embodiments, a light chain variable region also comprises an FR1 and/or an FR4. In some embodiments, a light chain CDR1 corresponds to Kabat residues 24 to 34; a light chain CDR2 corresponds to Kabat residues 50 to 56; and a light chain CDR3 corresponds to Kabat residues 89 to 97. See, e.g., Kabat Sequences of Proteins of Immunological Interest (1987 and 1991, NIH, Bethesda, Md.).

The term "light chain constant region" as used herein refers to a region comprising a light chain constant domain, CL. Nonlimiting exemplary light chain constant regions include δ0 and κ.

The term "light chain" (abbreviate LC) as used herein refers to a polypeptide comprising at least a light chain variable region, with or without a leader sequence. In some embodiments, a light chain comprises at least a portion of a light chain constant region. The term "full-length light chain" as used herein refers to a polypeptide comprising a light chain variable region and a light chain constant region, with or without a leader sequence.

A "chimeric antibody" as used herein refers to an antibody comprising at least one variable region from a first species (such as mouse, rat, cynomolgus monkey, etc.) and at least one constant region from a second species (such as human, cynomolgus monkey, etc.). In some embodiments, a chimeric antibody comprises at least one mouse variable region and at least one human constant region. In some embodiments, a chimeric antibody comprises at least one cynomolgus variable region and at least one human constant region. In some embodiments, a chimeric antibody comprises at least one rat variable region and at least one mouse constant region. In some embodiments, all of the variable regions of a chimeric antibody are from a first species and all of the constant regions of the chimeric antibody are from a second species.

A "humanized antibody" as used herein refers to an antibody in which at least one amino acid in a framework region of a non-human variable region has been replaced with the corresponding amino acid from a human variable region. In some embodiments, a humanized antibody comprises at least one human constant region or fragment thereof. In some embodiments, a humanized antibody is a Fab, an scFv, a (Fab')$_2$, etc.

A "CDR-grafted antibody" as used herein refers to a humanized antibody in which the complementarity determining regions (CDRs) of a first (non-human) species have been grafted onto the framework regions (FRs) of a second (human) species.

A "human antibody" as used herein refers to antibodies produced in humans, antibodies produced in non-human animals that comprise human immunoglobulin genes, such as XenoMouse®, and antibodies selected using in vitro methods, such as phage display, wherein the antibody repertoire is based on a human immunoglobulin sequences.

The term "leader sequence" refers to a sequence of amino acid residues located at the N terminus of a polypeptide that facilitates secretion of a polypeptide from a mammalian cell. A leader sequence may be cleaved upon export of the polypeptide from the mammalian cell, forming a mature protein. Leader sequences may be natural or synthetic, and they may be heterologous or homologous to the protein to which they are attached. Exemplary leader sequences include, but are not limited to, antibody leader sequences, such as, for example, the amino acid sequences of SEQ ID NOs: 3 and 4, which correspond to human light and heavy chain leader sequences, respectively. Nonlimiting exemplary leader sequences also include leader sequences from heterologous proteins. In some embodiments, an antibody lacks a leader sequence. In some embodiments, an antibody comprises at least one leader sequence, which may be selected from native antibody leader sequences and heterologous leader sequences.

The term "isolated" as used herein refers to a molecule that has been separated from at least some of the components with which it is typically found in nature. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, e.g., in the case of an RNA polynucleotide. Thus, a DNA polynucleotide that is contained in a vector inside a host cell may be referred to as "isolated" so long as that polynucleotide is not found in that vector in nature.

The term "elevated level" means a higher level of a protein in a particular tissue of a subject relative to the same tissue in a control, such as an individual or individuals who are not suffering from cancer or other condition described herein. The elevated level may be the result of any mechanism, such as increased expression, increased stability, decreased degradation, increased secretion, decreased clearance, etc., of the protein.

The term "reduce" or "reduces" means to lower the level of a protein in a particular tissue of a subject by at least 10%. In some embodiments, an agent, such as an antibody that binds CSF1R or a PD-1/PD-L1 inhibitor, reduces the level of a protein in a particular tissue of a subject by at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90%. In some embodiments, the level of a protein is reduced relative to the level of the protein prior to contacting with an agent, such as an antibody that binds CSF1R or a PD-1/PD-L1 inhibitor.

The term "resistant," when used in the context of resistance to a therapeutic agent, means a decreased response or lack of response to a standard dose of the therapeutic agent, relative to the subject's response to the standard dose of the therapeutic agent in the past, or relative to the expected response of a similar subject with a similar disorder to the standard dose of the therapeutic agent. Thus, in some embodiments, a subject may be resistant to therapeutic agent although the subject has not previously been given the therapeutic agent, or the subject may develop resistance to the therapeutic agent after having responded to the agent on one or more previous occasions.

The terms "subject" and "patient" are used interchangeably herein to refer to a human.

The term "sample," as used herein, refers to a composition that is obtained or derived from a subject that contains a cellular and/or other molecular entity that is to be characterized, quantitated, and/or identified, for example based on physical, biochemical, chemical and/or physiological characteristics. An exemplary sample is a tissue sample.

The term "tissue sample" refers to a collection of similar cells obtained from a tissue of a subject. The source of the tissue sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, synovial fluid, or interstitial fluid; cells from any time in gestation or development of the subject. In some embodiments, a tissue sample is a synovial biopsy tissue sample and/or a synovial fluid sample. In some embodiments, a tissue sample is a synovial fluid sample. The tissue sample may also be primary or cultured cells or cell lines. Optionally, the tissue sample is obtained from a disease tissue/organ. The tissue sample may contain compounds that are not naturally intermixed with the tissue in nature such as preservatives, anticoagulants, buffers, fixatives, nutrients, antibiotics, or the like. A "control sample" or "control tissue", as used herein, refers to a sample, cell, or tissue obtained from a source known, or believed, not to be afflicted with the disease for which the subject is being treated.

For the purposes herein a "section" of a tissue sample means a part or piece of a tissue sample, such as a thin slice of tissue or cells cut from a solid tissue sample.

The term "cancer" is used herein to refer to a group of cells that exhibit abnormally high levels of proliferation and growth. A cancer may be benign (also referred to as a benign tumor), pre-malignant, or malignant. Cancer cells may be solid cancer cells or leukemic cancer cells. The term "cancer growth" is used herein to refer to proliferation or growth by a cell or cells that comprise a cancer that leads to a corresponding increase in the size or extent of the cancer.

Examples of cancer include but are not limited to, carcinoma, lymphoma, blastoma, sarcoma, and leukemia. More particular nonlimiting examples of such cancers include squamous cell cancer, small-cell lung cancer, pituitary cancer, esophageal cancer, astrocytoma, soft tissue sarcoma, non-small cell lung cancer (including squamous cell non-small cell lung cancer), adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, renal cell carcinoma, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer (including squamous cell carcinoma of the head and neck).

The term "recurrent cancer" refers to a cancer that has returned after a previous treatment regimen, following which there was a period of time during which the cancer could not be detected.

The term "progressive cancer" is a cancer that has increased in size or tumor spread since the beginning of a treatment regimen. In certain embodiments, a progressive cancer is a cancer that has increased in size or tumor spread by at least 10%, at least 20%, at least 30%, at least 40%, or at least 50% since the beginning of a treatment regimen.

In some embodiments, the subject has pancreatic cancer. "Pancreatic cancer" includes, for example, pancreatic ductal adenocarcinoma (PDAC), advanced pancreatic cancer including locally advanced pancreatic cancer, metastatic pancreatic cancer, for example, such as pancreatic cancer having metastasized to other organs such as the liver and/or lung, and Microsatellite Stable (MSS) pancreatic cancer.

By way of example, an "anti-cancer agent" promotes cancer regression in a subject. In some embodiments, a therapeutically effective amount of the drug promotes cancer regression to the point of eliminating the cancer. "Promoting cancer regression" means that administering an effective amount of the drug, alone or in combination with an anti-cancer agent, results in a reduction in tumor growth or size, necrosis of the tumor, a decrease in severity of at least one disease symptom, an increase in frequency and duration of disease symptom-free periods, or a prevention of impairment or disability due to the disease affliction. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

By way of example for the treatment of tumors, a therapeutically effective amount of an anti-cancer agent can inhibit cell growth, inhibit tumor growth, or reduce tumor size or tumor growth rate by at least about 5%, at least about 10%, by at least about 15%, at least about 20%, by at least about 25%, by at least about 30%, by at least about 40%, by at least about 50%, by at least about 60%, by at least about 70%, or by at least about 80%, by at least about 90%, by at least about 95%, or by at least about 100% relative to untreated subjects, relative to baseline, or, in certain embodiments, relative to patients treated with a standard-of-care therapy. In other embodiments of the invention, tumor regression can be observed and continue for a period of at least about 20 days, at least about 40 days, or at least about 60 days. Notwithstanding these ultimate measurements of therapeutic effectiveness, evaluation of immunotherapeutic drugs must also make allowance for "immune-related" response patterns.

By way of example for the treatment of tumors, a therapeutically effective amount of an anti-cancer agent can inhibit cell growth or tumor growth by at least about 20%, by at least about 30%, by at least about 40%, by at least about 50%, by at least about 60%, by at least about 70%, or by at least about 80% relative to untreated subjects.

In other embodiments of the invention, tumor regression can be observed and continue for a period of at least about 20 days, at least about 40 days, or at least about 60 days. Notwithstanding these ultimate measurements of therapeutic effectiveness, evaluation of immunotherapeutic drugs must also make allowance for "immune-related" response patterns.

An "immune-related" response pattern refers to a clinical response pattern often observed in cancer patients treated with immunotherapeutic agents that produce antitumor effects by inducing cancer-specific immune responses or by modifying native immune processes. This response pattern is characterized by a beneficial therapeutic effect that follows an initial increase in tumor burden or the appearance of new lesions, which in the evaluation of traditional chemotherapeutic agents would be classified as disease progression and would be synonymous with drug failure. Accordingly, proper evaluation of immunotherapeutic agents can require long-term monitoring of the effects of these agents on the target disease.

A "chemotherapeutic agent" is a chemical compound useful in the treatment of cancer. Examples of chemotherapeutic agents include, but are not limited to, alkylating agents such as thiotepa and Cytoxan® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, *Chem Intl. Ed. Engl.,* 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, Adriamycin® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., Taxol® paclitaxel (Bristol-Myers Squibb Oncology, Princeton, N.J.), Abraxane® Cremophor-free, albumin-engineered nanoparticle formulation of paclitaxel (American Pharmaceutical Partners, Schaumberg, Ill.), and Taxotere® doxetaxel (Rhone-Poulenc Rorer, Antony, France); chloranbucil; Gemzar® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; Navelbine® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluorometlhylornithine (DMFO); retinoids such as retinoic acid; capecitabine; combretastatin; leucovorin (LV); oxaliplatin, including the oxaliplatin treatment regimen (FOLFOX); inhibitors of PKC-alpha, Raf, H-Ras, EGFR (e.g., erlotinib)(Tarceva® and VEGF-A that reduce cell proliferation and pharmaceutically acceptable salts, acids or derivatives of any of the above.

Further nonlimiting exemplary chemotherapeutic agents include anti-hormonal agents that act to regulate or inhibit hormone action on cancers such as anti-estrogens and selective estrogen receptor modulators (SERMs), including, for example, tamoxifen (including Nolvadex® tamoxifen), raloxifene, droloxifene, 4-hydroxytamoxifen, trioxifene, keoxifene, LY117018, onapristone, and Fareston® toremifene; aromatase inhibitors that inhibit the enzyme aromatase, which regulates estrogen production in the adrenal glands, such as, for example, 4(5)-imidazoles, aminoglutethimide, Megase® megestrol acetate, Aromasin® exemestane, formestanie, fadrozole, Rivisor® vorozole, Femara® letrozole, and Arimidex® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., Angiozyme® ribozyme) and a HER2 expression inhibitor; vaccines such as gene therapy vaccines, for example, Allovectin® vaccine, Leuvectin® vaccine, and Vaxid® vaccine; Proleukin® rIL-2; Lurtotecan® topoisomerase 1 inhibitor; Abarelix® rmRH; and pharmaceutically acceptable salts, acids or derivatives of any of the above.

An "anti-angiogenesis agent" or "angiogenesis inhibitor" refers to a small molecular weight substance, a polynucleotide (including, e.g., an inhibitory RNA (RNAi or siRNA)), a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenesis agent includes those agents that bind and block the angiogenic activity of the angiogenic factor or its receptor. For example, an anti-angiogenesis agent is an antibody or other antagonist to an angiogenic agent, e.g., antibodies to VEGF-A (e.g., bevacizumab (Avastin®)) or to the VEGF-A receptor (e.g., KDR receptor or Flt-1 receptor), anti-PDGFR inhibitors such as Gleevec® (Imatinib Mesylate), small molecules that block VEGF receptor signaling (e.g., PTK787/ZK2284, SU6668, Sutent®/SU11248 (sunitinib malate), AMG706, or those described in, e.g., international patent application WO 2004/113304). Anti-angiogensis agents also include native angiogenesis inhibitors, e.g., angiostatin, endostatin, etc. See, e.g., Klagsbrun and D'Amore (1991) *Annu. Rev. Physiol.* 53:217-39; Streit and Detmar (2003) *Oncogene* 22:3172-3179 (e.g., Table 3 listing anti-angiogenic therapy in malignant melanoma); Ferrara & Alitalo (1999) *Nature Medicine* 5(12): 1359-1364; Tonini et al. (2003) *Oncogene* 22:6549-6556 (e.g., Table 2 listing known anti-angiogenic factors); and, Sato (2003) *Int. J. Clin. Oncol.* 8:200-206 (e.g., Table 1 listing anti-angiogenic agents used in clinical trials).

A "growth inhibitory agent" as used herein refers to a compound or composition that inhibits growth of a cell (such as a cell expressing VEGF) either in vitro or in vivo. Thus, the growth inhibitory agent may be one that significantly reduces the percentage of cells (such as a cell expressing VEGF) in S phase. Examples of growth inhibitory agents include, but are not limited to, agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., *The Molecular Basis of Cancer*, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (Taxotere®, Rhone-Poulenc Rorer), derived from the European yew, is a semisynthetic analogue of paclitaxel (Taxol®, Bristol-Myers Squibb). Paclitaxel and docetaxel promote the assembly of microtubules from tubulin dimers and stabilize microtubules by preventing depolymerization, which results in the inhibition of mitosis in cells.

The term "anti-neoplastic composition" refers to a composition useful in treating cancer comprising at least one active therapeutic agent. Examples of therapeutic agents include, but are not limited to, e.g., chemotherapeutic agents, growth inhibitory agents, cytotoxic agents, agents used in radiation therapy, anti-angiogenesis agents, cancer immunotherapeutic agents, apoptotic agents, anti-tubulin agents, and other-agents to treat cancer, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib)(Tarceva®, platelet derived growth factor inhibitors (e.g., Gleevec® (Imatinib Mesylate)), a COX-2 inhibitor (e.g., celecoxib), interferons, CTLA-4 inhibitors (e.g., anti-CTLA antibody ipilimumab (YERVOY®)), PD-1 inhibitors (e.g., anti-PD-1 antibodies, BMS-936558), PD-L1 inhibitors (e.g., anti-PD-L1 antibodies, MPDL3280A), PD-L2 inhibitors (e.g., anti-PD-L2 antibodies), TIM3 inhibitors (e.g., anti-TIM3 antibodies), cytokines, antagonists (e.g., neutralizing antibodies) that bind to one or more of the following targets ErbB2, ErbB3, ErbB4, PDGFR-beta, BlyS, APRIL, BCMA, PD-1, PD-L1, PD-L2, CTLA-4, TIM3, or VEGF receptor(s), TRAIL/Apo2, and other bioactive and organic chemical agents, etc. Combinations thereof are also included in the invention.

As used herein, the term "FOLFOX" refers to a combination chemotherapy treatment regimen of 5-fluorouracil (5-FU), leucovorin, and oxaliplatin.

An agent "antagonizes" factor activity when the agent neutralizes, blocks, inhibits, abrogates, reduces, and/or interferes with the activity of the factor, including its binding to one or more receptors when the factor is a ligand.

"Treatment," as used herein, refers to therapeutic treatment, for example, wherein the object is or slow down (lessen) the targeted pathologic condition or disorder as well as, for example, wherein the object is to inhibit recurrence of the condition or disorder. In certain embodiments, the term "treatment" covers any administration or application of a therapeutic for disease in a patient, and includes inhibiting or slowing the disease or progression of the disease; partially or fully relieving the disease, for example, by causing regression, or restoring or repairing a lost, missing, or defective function; stimulating an inefficient process; or causing the disease plateau to have reduced severity. The term "treatment" also includes reducing the severity of any phenotypic characteristic and/or reducing the incidence, degree, or likelihood of that characteristic. Those in need of treatment include those already with the disorder as well as those at risk of recurrence of the disorder or those in whom a recurrence of the disorder is to be prevented or slowed down.

"Pre-treatment" or "baseline," as used herein, refers to the status of a subject prior to administration of a particular therapy, e.g., prior to administration of an anti-cancer agent, e.g., an immunotherapy, e.g., an anti-PD-1 Ab or an antigen binding portion thereof or an anti-CSF1R Ab or an antigen binding portion thereof "Pre-treatment" can refer to the status of a treatment naïve subject or to a subject who has had one or more prior therapies. Accordingly, it is possible that a subject may be considered to be "pre-treatment" even though the subject received some form of treatment or therapy at some time prior to the present treatment or therapy. Furthermore, "pre-treatment" can refer to any moment up until the moment that a treatment is administered. For example, "pre-treatment" can include weeks, days, hours, minutes, or seconds before administration of the treatment. In one particular embodiment, a "pre-treatment" sample can be collected from a subject immediately before administration of a first dose of the treatment or therapy. "Pre-treatment" and "baseline" are used interchangeably herein.

"On-treatment," as used herein, refers to the status of a subject who has received one or more initial dose of a particular therapy, e.g., an anti-cancer agent, e.g., an immunotherapy, e.g., an anti-PD-1 Ab or an antigen binding portion thereof or an anti-CSF1R Ab or an antigen binding portion thereof. "On-treatment" can refer to a subject who has only received a single dose or a subject who has received multiple doses of the anti-PD-1 Ab or an antigen binding portion thereof or the anti-CSF1R Ab or an antigen binding portion thereof. In some aspects, "on-treatment" refers to a subject who is receiving an ongoing regimen of a particular therapy, e.g., the subject is being treated with an anti-PD-1 Ab or an antigen binding portion thereof or an anti-CSF1R Ab or an antigen binding portion thereof. In certain embodiments, the "on-treatment" sample can be collected from a subject on about day 1, on about day 2, on about day 3, on about day 4, on about day 5, on about day 6, on about day 7, on about day 8, on about day 9, on about day 10, on about day 11, on about day 12, on about day 13, on about day 14, on about day 15, on about day 16, on about day 17, on about day 18, on about day 19, on about day 20, on about day 21, or any combination thereof, wherein the treatment is administered on day 1. In certain embodiments, the treatment is administration of an anti-PD-1 Ab or an antigen binding portion thereof or an anti-PD-L1 Ab or an antigen binding portion thereof. In some embodiments, the anti-PD-1 Ab or an antigen binding portion thereof or the anti-CSF1R Ab or an antigen binding portion thereof is administered on day 1 of every 21-day cycle. In certain embodiments, the on-treatment sample is collected from the subject on about day 1, on about day 2, on about day 3, on about day 4, on about day 5, on about day 6, on about day 7, on about day 8, on about day 9, on about day 10, on about day 11, on about day 12, on about day 13, on about day 14, on about day 15, on about day 16, on about day 17, on about day 18, on about day 19, on about day 20, or on about day 21 of the 21 day cycle, or any combination thereof. In one particular embodiment, the on-treatment sample is collected on day 1 of cycle 1, day 1 of cycle 2, day 8 of cycle 2, on day 1 of cycle 4, or any combination thereof. In one embodiment, the on-treatment sample is collect on day 8 of cycle 2.

Pre-treatment and on-treatment samples may be collected in the form of a tumor biopsy (e.g., a core needle biopsy), partial or complete surgical resection, blood draw, or any other method known in the art. In certain embodiments, tumor sites selected for biopsy have not received previous radiation therapy.

The term "immunotherapy" refers to the treatment of a subject afflicted with, or at risk of contracting or suffering a recurrence of, a disease by a method comprising inducing, enhancing, suppressing or otherwise modifying an immune response.

The term "effective amount" or "therapeutically effective amount" refers to an amount of a drug effective to treat a disease or disorder in a subject. In certain embodiments, an effective amount refers to an amount effective, at dosages and for periods of time necessary, to achieve the desired therapeutic or prophylactic result. A therapeutically effective amount of an anti-CSF1R antibody and/or a PD-1/PD-L1 inhibitor of the invention may vary according to factors such as the disease state, age, sex, and weight of the individual, and the ability of the antibody or antibodies to elicit a desired response in the individual. A therapeutically effective amount encompasses an amount in which any toxic or detrimental effects of the antibody or antibodies are outweighed by the therapeutically beneficial effects. In some embodiments, the expression "effective amount" refers to an amount of the antibody that is effective for treating the cancer. A "therapeutic amount" refers to a dosage of a drug that has been approved for use by a regulatory agency. A "subtherapeutic amount" as used herein refers to a dosage of a drug or therapeutic agent that is significantly lower than the approved dosage. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount would be less than the therapeutically effective amount.

A subject may be characterized as having one or more "prior therapies" or as being "treatment naïve." As used herein, unless otherwise indicated, a "prior therapy" refers to any previous systemic therapy for a cancer. A "treatment naïve" subject is one that has never received any previous systemic therapy in the metastatic or adjuvant setting. As used herein, a "standard therapy" or "standard treatment" means a therapy considered to be the current best practice or standard of care for treatment of a particular disease, e.g. pancreatic cancer. The effectiveness of the treatment methods herein, may, for example, be compared against that of the current "standard therapy."

As used herein, the term "first dose" includes a single dose, but can be more than one dose, i.e., multiple doses (at least two doses, at least three doses, or more) that are administered prior to the administration of "a second dose" if the multiple doses are administered to determine the susceptibility of the patient for an anti-PD-1 Ab or anti-CSF1R Ab therapy, i.e., differential expression of certain proteins (e.g., PD-L1). The term "first dose" can also be a therapeutic dose, a dose higher than a therapeutic dose, or a subtherapeutic dose.

The term "second dose" as used herein can also include a single dose or multiple doses that are administered after the first dose (single dose or multiple doses). The second dose can be a therapeutic dose.

The use of the term "fixed dose ratio" with regard to a composition or method described herein means that two or more different antibodies in a single composition are present in the composition in particular (fixed) ratios with each other. In some embodiments, the fixed dose is based on the weight (e.g., mg) of the antibodies. In certain embodiments, the fixed dose is based on the concentration (e.g., mg/ml) of the antibodies. In some embodiments, the ratio is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1 mg first antibody to mg second antibody. For example, the 3:1 ratio of a first antibody and a second antibody can mean that a vial can contain about 240 mg of the first antibody and 80 mg of the second antibody or about 3 mg/ml of the first antibody and 1 mg/ml of the second antibody.

The use of the term "flat dose" with regard to the composition of the invention means a dose that is administered to a patient without regard for the weight or body surface area (BSA) of the patient. The flat dose is, therefore, not provided as a mg/kg dose, but rather as an absolute amount of the agent (e.g., the anti-CSF1R antibody and/or PD-1/PD-L1 inhibitor). For example, a 60 kg person and a 100 kg person would receive the same dose of the composition (e.g., 240 mg of an anti-PD-1 antibody and 80 mg of an anti-CSF1R antibody in a single fixed dosing formulation vial containing both 240 mg of an anti-PD-1 antibody and 80 mg of an anti-CSF1R antibody (or two fixed dosing formulation vials containing 120 mg of an anti-PD-1 antibody and 40 mg of an anti-CSF1R antibody, etc.)).

The term "weight based dose" as referred to herein means that a dose that is administered to a patient is calculated based on the weight of the patient. For example, when a patient with 60 kg body weight requires 3 mg/kg of an anti-PD-1 antibody in combination with 1 mg/kg of an anti-CSF1R antibody, one can draw the appropriate amounts of the anti-PD-1 antibody (i.e., 180 mg) and the anti-CSF1R antibody (i.e., 60 mg) at once from a 3:1 ratio fixed dosing formulation of an anti-PD1 antibody and an anti-CSF1R antibody.

Administration "in combination with" one or more further therapeutic agents includes simultaneous (concurrent) and consecutive (sequential) administration in any order.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. For example, if the therapeutic agent is to be administered orally, the carrier may be a gel capsule. If the therapeutic agent is to be administered subcutaneously, the carrier ideally is not irritable to the skin and does not cause injection site reaction.

The term "refractory" as applied to a treatment means a lack of partial or complete clinical response to that treatment. For example, patients may be considered refractory to a PD-1 or PD-L1 inhibitor if they do not show at least a partial response after receiving at least 2 doses of the inhibitor.

Expressions such as "determining an expression level" or "detecting an increased expression level" and the like are broadly intended to include requesting the determination or detection of the expression level by others, and, for example, reviewing the results of such a determination or detection by others, as well as conducting the determination or detection directly.

The term "tumor mutation burden" or "TMB" is a measure of the total number of mutations per coding area of tumor genome. As used herein, TMB is measured from a biopsy sample using Foundation Medicine's analytically validated assay, Foundation One® CDx™ and reported as "mismatches/megabase" or "mutations/megabase" (both terms being used interchangeably), or it is measured using whole exome sequencing (WES) and reported as a total number of missense mutations.

The term "microsatellite instable" or "MSI" refers to a tumor characterized by mutations in one or more mismatch repair genes. Mutations in these genes may cause mutations in microsatellite DNA sequences and genes close to those sequences. The term "microsatellite stable" or "MSS" refers to a tumor that is not microsatellite instable (MSI) or that is not characterized by having mutations in DNA mismatch repair genes. MSS status may be confirmed, for example, based on sequencing or PCR methods.

Anti-CSF1R Antibodies

Exemplary anti-CSF1R antibodies used herein comprise the heavy and light chain CDRs, or the heavy and light chain variable domains, or the heavy and light chains of the humanized anti-CSF1R antibody cabiralizumab (also referred to as FPA008 or huAb1 herein), disclosed, for example in U.S. Pat. No. 8,206,715 and PCT Publication No. WO2011/140249. In some embodiments, an anti-CSF1R antibody comprises a set of heavy chain CDR1, CDR2, and CDR3 of SEQ ID NOs: 5, 6, and 7 and a set of light chain CDR1, CDR2, and CDR3 of SEQ ID NOs: 8, 9, and 10.

In some embodiments, an anti-CSF1R antibody comprises a heavy chain comprising a variable region sequence that is at least 90%, at least 91%, at least 92%, at least 93%, at least 94%, at least 95%, at least 96%, at least 97%, at least 98%, or at least 99% identical to the sequence of SEQ ID NO: 11. In some embodiments, an anti-CSF1R antibody comprises a light chain comprising a variable region sequence that is at least 90%, at least 91%, at least 92%, at least 93%, at least 94%, at least 95%, at least 96%, at least 97%, at least 98%, or at least 99% identical to the sequence of SEQ ID NO: 12. In some embodiments, an anti-CSF1R antibody comprises a heavy chain comprising a variable region sequence that is at least 90%, at least 91%, at least 92%, at least 93%, at least 94%, at least 95%, at least 96%, at least 97%, at least 98%, or at least 99% identical to the sequence of SEQ ID NO: 11; and a light chain comprising a variable region sequence that is at least 90%, at least 91%, at least 92%, at least 93%, at least 94%, at least 95%, at least 96%, at least 97%, at least 98%, or at least 99% identical to the sequence SEQ ID NO: 12.

In some embodiments, an anti-CSF1R antibody comprises a set of heavy chain CDR1, CDR2, and CDR3 of SEQ ID NOs: 5, 6, and 7 and a set of light chain CDR1, CDR2, and CDR3 of SEQ ID NOs: 8, 9, and 10 and further comprises a heavy chain comprising a variable region sequence that is at least 90%, at least 91%, at least 92%, at least 93%, at least 94%, at least 95%, at least 96%, at least 97%, at least 98%, or at least 99% identical to the sequence of SEQ ID NO: 11. In some embodiments, an anti-CSF1R antibody comprises a set of heavy chain CDR1, CDR2, and CDR3 of SEQ ID NOs: 5, 6, and 7 and a set of light chain CDR1, CDR2, and CDR3 of SEQ ID NOs: 8, 9, and 10, and further comprises a light chain comprising a variable region sequence that is at least 90%, at least 91%, at least 92%, at least 93%, at least 94%, at least 95%, at least 96%, at least 97%, at least 98%, or at least 99% identical to the sequence of SEQ ID NO: 12. In some embodiments, an anti-CSF1R antibody comprises a set of heavy chain CDR1, CDR2, and CDR3 of SEQ ID NOs: 5, 6, and 7 and a set of light chain CDR1, CDR2, and CDR3 of SEQ ID NOs: 8, 9, and 10, and further comprises a heavy chain comprising a variable region sequence that is at least 90%, at least 91%, at least 92%, at least 93%, at least 94%, at least 95%, at least 96%, at least 97%, at least 98%, or at least 99% identical to the sequence of SEQ ID NO: 11; and also a light chain comprising a variable region sequence that is at least 90%, at least 91%, at least 92%, at least 93%, at least 94%, at least 95%, at least 96%, at least 97%, at least 98%, or at least 99% identical to the sequence of SEQ ID NO: 12. In some embodiments, the anti-CSF1R antibody comprises the complete heavy chain and light chain variable domain sequences of cabiralizumab (SEQ ID NOs: 11 and 12).

As used herein, whether a particular polypeptide is, for example, at least 95% identical to an amino acid sequence can be determined using, e.g., a computer program. When determining whether a particular sequence is, for example, 95% identical to a reference sequence, the percentage of identity is calculated over the full length of the reference amino acid sequence. In some embodiments, one or more of the amino acid substitutions are conservative amino acid substitutions. One skilled in the art can select one or more suitable conservative amino acid substitutions for a particular CDR sequence, wherein the suitable conservative amino acid substitutions are not predicted to significantly alter the binding properties of the antibody comprising the mutated CDR.

In some embodiments, an anti-CSF1R antibody comprises a heavy chain comprising a sequence that is at least 90%, at least 91%, at least 92%, at least 93%, at least 94%, at least 95%, at least 96%, at least 97%, at least 98%, or at least 99% identical to the sequence of SEQ ID NO: 13. In some embodiments, an anti-CSF1R antibody comprises a light chain comprising a sequence that is at least 90%, at least 91%, at least 92%, at least 93%, at least 94%, at least 95%, at least 96%, at least 97%, at least 98%, or at least 99% identical to the sequence of SEQ ID NO: 14. In some embodiments, an anti-CSF1R antibody comprises a heavy chain comprising a sequence that is at least 90%, at least 91%, at least 92%, at least 93%, at least 94%, at least 95%, at least 96%, at least 97%, at least 98%, or at least 99% identical to the sequence of SEQ ID NO: 13; and a light chain comprising a sequence that is at least 90%, at least 91%, at least 92%, at least 93%, at least 94%, at least 95%, at least 96%, at least 97%, at least 98%, or at least 99% identical to the sequence SEQ ID NO: 14.

In some embodiments, an anti-CSF1R antibody comprises a set of heavy chain CDR1, CDR2, and CDR3 of SEQ ID NOs: 5, 6, and 7 and a set of light chain CDR1, CDR2, and CDR3 of SEQ ID NOs: 8, 9, and 10 and further comprises a heavy chain comprising a sequence that is at least 90%, at least 91%, at least 92%, at least 93%, at least 94%, at least 95%, at least 96%, at least 97%, at least 98%, or at least 99% identical to the sequence of SEQ ID NO: 13. In some embodiments, an anti-CSF1R antibody comprises a set of heavy chain CDR1, CDR2, and CDR3 of SEQ ID NOs: 5, 6, and 7 and a set of light chain CDR1, CDR2, and CDR3 of SEQ ID NOs: 8, 9, and 10, and further comprises a light chain comprising a sequence that is at least 90%, at least 91%, at least 92%, at least 93%, at least 94%, at least 95%, at least 96%, at least 97%, at least 98%, or at least 99% identical to the sequence of SEQ ID NO: 14. In some embodiments, an anti-CSF1R antibody comprises a set of heavy chain CDR1, CDR2, and CDR3 of SEQ ID NOs: 5, 6, and 7 and a set of light chain CDR1, CDR2, and CDR3 of SEQ ID NOs: 8, 9, and 10, and further comprises a heavy chain comprising a sequence that is at least 90%, at least 91%, at least 92%, at least 93%, at least 94%, at least 95%, at least 96%, at least 97%, at least 98%, or at least 99% identical to the sequence of SEQ ID NO: 13; and also a light chain comprising a sequence that is at least 90%, at least 91%, at least 92%, at least 93%, at least 94%, at least 95%, at least 96%, at least 97%, at least 98%, or at least 99% identical to the sequence of SEQ ID NO: 14. In some embodiments, the anti-CSF1R antibody comprises the complete heavy chain and light chain sequences of cabiralizumab (SEQ ID NOs: 13 and 14). In some embodiments, the anti-CSF1R antibody consists of the complete heavy chain and light chain sequences of cabiralizumab (SEQ ID NOs: 13 and 14).

Anti-CSF1R antibodies usable in the methods of the disclosed invention also include antigen-binding fragments. It has been amply demonstrated that the antigen-binding function of an Ab can be performed by fragments of a full-length Ab. Examples of binding fragments include (i) a Fab fragment, a monovalent fragment consisting of the $V_L$, $V_H$, $C_L$ and $C_{H1}$ domains; (ii) a F(ab')2 fragment, a bivalent fragment comprising two Fab fragments linked by a disulfide bridge at the hinge region; (iii) a Fd fragment consisting of the $V_H$ and $C_{H1}$ domains; and (iv) a Fv fragment consisting of the $V_L$ and $V_H$ domains of a single arm of an Ab. In some embodiments, the antigen binding fragments comprise a set of heavy chain CDR1, CDR2, and CDR3 of SEQ ID NOs: 5, 6, and 7 and a set of light chain CDR1, CDR2, and CDR3 of SEQ ID NOs: 8, 9, and 10. Thus, in some embodiments, the anti-CSF1R antibody is a full length antibody, or alternatively, is a Fab, an Fv, an scFv, a Fab', or a (Fab')$_2$ fragment.

In some embodiments, the antigen binding fragments comprise a heavy chain variable region sequence that is at least 90%, at least 91%, at least 92%, at least 93%, at least 94%, at least 95%, at least 96%, at least 97%, at least 98%, or at least 99% identical to the sequence of SEQ ID NO: 11. In some embodiments, the antigen binding fragments comprise a light chain variable region sequence that is at least 90%, at least 91%, at least 92%, at least 93%, at least 94%, at least 95%, at least 96%, at least 97%, at least 98%, or at least 99% identical to the sequence of SEQ ID NO: 12. In some embodiments, the antigen binding fragments comprise a heavy chain variable region sequence that is at least 90%, at least 91%, at least 92%, at least 93%, at least 94%, at least 95%, at least 96%, at least 97%, at least 98%, or at least 99% identical to the sequence of SEQ ID NO: 11; and a light chain variable region sequence that is at least 90%, at least 91%, at least 92%, at least 93%, at least 94%, at least 95%, at least 96%, at least 97%, at least 98%, or at least 99% identical to the sequence SEQ ID NO: 12.

In some embodiments, the antigen binding fragments comprise a set of heavy chain CDR1, CDR2, and CDR3 of SEQ ID NOs: 5, 6, and 7 and a set of light chain CDR1, CDR2, and CDR3 of SEQ ID NOs: 8, 9, and 10 and further comprise a heavy chain variable region sequence that is at least 90%, at least 91%, at least 92%, at least 93%, at least 94%, at least 95%, at least 96%, at least 97%, at least 98%, or at least 99% identical to the sequence of SEQ ID NO: 11. In some embodiments, the antigen binding fragments comprise a set of heavy chain CDR1, CDR2, and CDR3 of SEQ ID NOs: 5, 6, and 7 and a set of light chain CDR1, CDR2, and CDR3 of SEQ ID NOs: 8, 9, and 10, and further comprise a light chain variable region sequence that is at least 90%, at least 91%, at least 92%, at least 93%, at least 94%, at least 95%, at least 96%, at least 97%, at least 98%, or at least 99% identical to the sequence of SEQ ID NO: 12. In some embodiments, the antigen binding fragments comprise a set of heavy chain CDR1, CDR2, and CDR3 of SEQ ID NOs: 5, 6, and 7 and a set of light chain CDR1, CDR2, and CDR3 of SEQ ID NOs: 8, 9, and 10, and further comprises a heavy chain variable region sequence that is at least 90%, at least 91%, at least 92%, at least 93%, at least 94%, at least 95%, at least 96%, at least 97%, at least 98%, or at least 99% identical to the sequence of SEQ ID NO: 11; and also a light chain variable region sequence that is at least 90%, at least 91%, at least 92%, at least 93%, at least 94%, at least 95%, at least 96%, at least 97%, at least 98%, or at least 99% identical to the sequence of SEQ ID NO: 12. In some embodiments, the antigen binding fragments comprise the complete heavy chain and light chain variable domain sequences of cabiralizumab (SEQ ID NOs: 11 and 12).

Exemplary Anti-CSF1R Antibody Constant Regions

In some embodiments, an anti-CSF1R antibody described herein comprises one or more human constant regions. In some embodiments, the human heavy chain constant region is of an isotype selected from IgA, IgG, and IgD. In some embodiments, the human light chain constant region is of an isotype selected from κ and λ. In some embodiments, a humanized antibody described herein comprises a human IgG constant region. In some embodiments, a humanized antibody described herein comprises a human IgG4 heavy chain constant region. In some such embodiments, a humanized antibody described herein comprises an S241P mutation (Kabat numbering; S241P corresponds to an S228P mutation in EU numbering) in the human IgG4 constant region. (See SEQ ID NO: 17.) In some embodiments, a humanized antibody described herein comprises a human IgG4 constant region and a human κ light chain.

The choice of heavy chain constant region can determine whether or not an antibody will have effector function in vivo. Such effector function, in some embodiments, includes antibody-dependent cell-mediated cytotoxicity (ADCC) and/or complement-dependent cytotoxicity (CDC), and can result in killing of the cell to which the antibody is bound. In some methods of treatment, including methods of treating some cancers, cell killing may be desirable, for example, when the antibody binds to a cell that supports the maintenance or growth of the tumor. Exemplary cells that may support the maintenance or growth of a tumor include, but are not limited to, tumor cells themselves, cells that aid in the recruitment of vasculature to the tumor, and cells that provide ligands, growth factors, or counter-receptors that support or promote tumor growth or tumor survival. In some embodiments, when effector function is desirable, an anti-CSF1R antibody comprising a human IgG1 heavy chain or a human IgG3 heavy chain is selected.

An antibody may be humanized by any method. Nonlimiting exemplary methods of humanization include methods described, e.g., in U.S. Pat. Nos. 5,530,101; 5,585,089; 5,693,761; 5,693,762; 6,180,370; Jones et al., *Nature* 321: 522-525 (1986); Riechmann et al., *Nature* 332: 323-27 (1988); Verhoeyen et al., *Science* 239: 1534-36 (1988); and U.S. Publication No. US 2009/0136500.

As noted above, a humanized antibody is an antibody in which at least one amino acid in a framework region of a non-human variable region has been replaced with the amino acid from the corresponding location in a human framework region. In some embodiments, at least two, at least three, at least four, at least five, at least six, at least seven, at least eight, at least nine, at least 10, at least 11, at least 12, at least 15, or at least 20 amino acids in the framework regions of a non-human variable region are replaced with an amino acid from one or more corresponding locations in one or more human framework regions.

In some embodiments, some of the corresponding human amino acids used for substitution are from the framework regions of different human immunoglobulin genes. That is, in some such embodiments, one or more of the non-human amino acids may be replaced with corresponding amino acids from a human framework region of a first human antibody or encoded by a first human immunoglobulin gene, one or more of the non-human amino acids may be replaced with corresponding amino acids from a human framework region of a second human antibody or encoded by a second human immunoglobulin gene, one or more of the non-human amino acids may be replaced with corresponding amino acids from a human framework region of a third human antibody or encoded by a third human immunoglobulin gene, etc. Further, in some embodiments, all of the corresponding human amino acids being used for substitution in a single framework region, for example, FR2, need not be from the same human framework. In some embodiments, however, all of the corresponding human amino acids being used for substitution are from the same human antibody or encoded by the same human immunoglobulin gene.

In some embodiments, an antibody is humanized by replacing one or more entire framework regions with corresponding human framework regions. In some embodiments, a human framework region is selected that has the highest level of homology to the non-human framework region being replaced. In some embodiments, such a humanized antibody is a CDR-grafted antibody.

In some embodiments, following CDR-grafting, one or more framework amino acids are changed back to the corresponding amino acid in a mouse framework region. Such "back mutations" are made, in some embodiments, to retain one or more mouse framework amino acids that appear to contribute to the structure of one or more of the CDRs and/or that may be involved in antigen contacts and/or appear to be involved in the overall structural integrity of the antibody. In some embodiments, ten or fewer, nine or fewer, eight or fewer, seven or fewer, six or fewer, five or fewer, four or fewer, three or fewer, two or fewer, one, or zero back mutations are made to the framework regions of an antibody following CDR grafting.

In some embodiments, a humanized antibody also comprises a human heavy chain constant region and/or a human light chain constant region.

In some embodiments, the anti-CSF1R antibody is a human antibody. Human antibodies can be made by any suitable method. Nonlimiting exemplary methods include making human antibodies in transgenic mice that comprise human immunoglobulin loci. See, e.g., Jakobovits et al., *Proc. Natl. Acad. Sci. USA* 90: 2551-55 (1993); Jakobovits et al., *Nature* 362: 255-8 (1993); Lonberg et al., *Nature* 368: 856-9 (1994); and U.S. Pat. Nos. 5,545,807; 6,713,610; 6,673,986; 6,162,963; 5,545,807; 6,300,129; 6,255,458; 5,877,397; 5,874,299; and 5,545,806.

Nonlimiting exemplary methods also include making human antibodies using phage display libraries. See, e.g., Hoogenboom et al., *J. Mol. Biol.* 227: 381-8 (1992); Marks et al., *J. Mol. Biol.* 222: 581-97 (1991); and PCT Publication No. WO 99/10494.

In some embodiments, when effector function is desirable, a human anti-CSF1R antibody comprising a human IgG1 heavy chain constant region or a human IgG3 heavy chain constant region is selected. In some embodiments, when effector function is not desirable, a human anti-CSF1R antibody comprising a human IgG4 or IgG2 heavy chain constant region is selected.

Exemplary Properties of Anti-CSF1R Antibodies

In some embodiments, an antibody as described above binds to the CSF1R with a binding affinity ($K_D$) of less than 1 nM, blocks binding of CSF1 and/or IL-34 to CSF1R, and inhibits CSF1R phosphorylation induced by CSF1 and/or IL-34.

In some embodiments, an anti-CSF1R antibody binds to the extracellular domain of CSF1R (CSF1R-ECD). In some embodiments, an anti-CSF1R antibody has a binding affinity ($K_D$) for CSF1R of less than 1 nM, less than 0.5 nM, less than 0.1 nM, or less than 0.05 nM. In some embodiments, an anti-CSF1R antibody has a $K_D$ of between 0.01 and 1 nM, between 0.01 and 0.5 nM, between 0.01 and 0.1 nM, between 0.01 and 0.05 nM, or between 0.02 and 0.05 nM.

In some embodiments, an anti-CSF1R antibody blocks ligand binding to CSF1R. In some embodiments, an anti-CSF1R antibody blocks binding of CSF1 to CSF1R. In some embodiments, an anti-CSF1R antibody blocks binding of IL-34 to CSF1R. In some embodiments, an anti-CSF1R antibody blocks binding of both CSF1 and IL-34 to CSF1R. In some embodiments, an antibody that blocks ligand binding binds to the extracellular domain of CSF1R. In some embodiments, an antibody blocks ligand binding to CSF1R when it reduces the amount of detectable binding of a ligand to CSF1R by at least 50%, using the assay described, e.g., U.S. Pat. No. 8,206,715 B2, Example 7, which is incorporated herein by reference for any purpose. In some embodiments, an antibody reduces the amount of detectable binding of a ligand to CSF1R by at least 60%, at least 70%, at least 80%, or at least 90%. In some such embodiments, the antibody is said to block ligand binding by at least 50%, at least 60%, at least 70%, etc.

In some embodiments, an anti-CSF1R antibody inhibits ligand-induced CSF1R phosphorylation. In some embodiments, an anti-CSF1R antibody inhibits CSF1-induced CSF1R phosphorylation. In some embodiments, an anti-CSF1R antibody inhibits IL-34-induced CSF1R phosphorylation. In some embodiments, an anti-CSF1R antibody inhibits both CSF1-induced and IL-34-induced CSF1R phosphorylation. In some embodiments, an antibody is considered to "inhibit ligand-induced CSF1R phosphorylation" when it reduces the amount of detectable ligand-induced CSF1R phosphorylation by at least 50%, using the assay described, e.g., U.S. Pat. No. 8,206,715 B2, Example 6, which is incorporated herein by reference for any purpose. In some embodiments, an antibody reduces the amount of detectable ligand-induced CSF1R phosphorylation by at least 60%, at least 70%, at least 80%, or at least 90%. In some such embodiments, the antibody is said to inhibit ligand-induced CSF1R phosphorylation by at least at least 50%, at least 60%, at least 70%, etc.

In some embodiments, an antibody inhibits monocyte proliferation and/or survival responses in the presence of CSF1 and/or IL-34. In some embodiments, an antibody is considered to "inhibit monocyte proliferation and/or survival responses" when it reduces the amount of monocyte proliferation and/or survival responses in the presence of CSF1 and/or IL-34 by at least 50%, using the assay described, e.g., U.S. Pat. No. 8,206,715 B2, Example 10, which is incorporated herein by reference for any purpose. In some embodiments, an antibody reduces the amount of monocyte proliferation and/or survival responses in the presence of CSF1 and/or IL-34 by at least 60%, at least 70%, at least 80%, or at least 90%. In some such embodiments, the antibody is said to inhibit monocyte proliferation and/or survival responses by at least at least 50%, at least 60%, at least 70%, etc.

Exemplary Anti-PD-1 Antibodies

PD-1 is a key immune checkpoint receptor expressed by activated T and B cells and mediates immunosuppression. PD-1 is a member of the CD28 family of receptors, which includes CD28, CTLA-4, ICOS, PD-1, and BTLA. Two cell surface glycoprotein ligands for PD-1 have been identified, Programmed Death Ligand-1 (PD-L1) and Programmed Death Ligand-2 (PD-L2), that are expressed on antigen-presenting cells as well as many human cancers and have been shown to down regulate T cell activation and cytokine secretion upon binding to PD-1. Inhibition of the PD-1/PD-L1 interaction mediates potent antitumor activity in preclinical models.

Exemplary anti-PD-1 antibodies used herein comprise the heavy and light chain CDRs, or the heavy and light chain variable domains, or the heavy and light chains of the anti-PD-1 antibody nivolumab (also known as "Opdivo®"; formerly designated 5C4, BMS-936558, MDX-1106, or ONO-4538), which is a fully human IgG4 (S241P) anti-PD-1 antibody that selectively prevents interaction of PD-1 with ligands PD-L1 and PD-L2, thereby blocking the down-regulation of antitumor T-cell functions. Nivolumab is described in U.S. Pat. No. 8,008,449 and Wang et al., 2014 *Cancer Immunol Res.* 2(9):846-56. In some embodiments, an anti-PD-1 antibody herein comprises heavy chain CDR1, CDR2, and CDR3 comprising SEQ ID NOs: 28, 30, and 32. In some embodiments, an anti-PD-1 antibody comprises light chain CDR1, CDR2, and CDR3 comprising SEQ ID NOs: 35, 37, and 39. In some embodiments, an anti-PD-1 antibody comprises heavy chain CDR1, CDR2, and CDR3 comprising SEQ ID NOs: 28, 30, and 32, and light chain CDR1, CDR2, and CDR3 comprising SEQ ID NOs: 35, 37, and 39.

In some embodiments, the anti-PD-1 antibody comprises a heavy chain variable region comprising SEQ ID NO: 23. In some embodiments, the anti-PD-1 antibody comprises a light chain variable region comprising SEQ ID NO: 25. In some embodiments, the anti-PD-1 antibody comprises a heavy chain variable region comprising SEQ ID NO: 23 and a light chain variable region comprising SEQ ID NO: 25. In some embodiments, the anti-PD-1 antibody comprises a heavy chain constant region comprising SEQ ID NO: 24 and/or a light chain constant region comprising SEQ ID NO: 26. In some embodiments, the anti-PD-1 antibody comprises a heavy chain comprising SEQ ID NOs: 23 and 24 and/or a light chain comprising SEQ ID NOs: 25 and 26.

In some embodiments, an anti-PD-1 antibody comprises a heavy chain comprising a variable region sequence that is at least 90%, at least 91%, at least 92%, at least 93%, at least 94%, at least 95%, at least 96%, at least 97%, at least 98%, or at least 99% identical to SEQ ID NO:23. In some embodiments, an anti-PD-1 antibody comprises a light chain comprising a variable region sequence that is at least 90%, at least 91%, at least 92%, at least 93%, at least 94%, at least 95%, at least 96%, at least 97%, at least 98%, or at least 99% identical to SEQ ID NO:25. In some embodiments, an anti-PD-1 antibody comprises a heavy chain comprising a variable region sequence that is at least 90%, at least 91%, at least 92%, at least 93%, at least 94%, at least 95%, at least 96%, at least 97%, at least 98%, or at least 99% identical to SEQ ID NO:23; and a light chain comprising a variable region sequence that is at least 90%, at least 91%, at least 92%, at least 93%, at least 94%, at least 95%, at least 96%, at least 97%, at least 98%, or at least 99% identical to SEQ ID NO:25.

In some embodiments, an anti-PD-1 antibody comprises heavy chain CDR1, CDR2, and CDR3 comprising SEQ ID NOs: 28, 30, and 32, and light chain CDR1, CDR2, and CDR3 comprising SEQ ID NOs: 35, 37, and 39, and also comprises a heavy chain comprising a variable region sequence that is at least 90%, at least 91%, at least 92%, at least 93%, at least 94%, at least 95%, at least 96%, at least 97%, at least 98%, or at least 99% identical to SEQ ID NO:23. In some embodiments, an anti-PD-1 antibody comprises heavy chain CDR1, CDR2, and CDR3 comprising SEQ ID NOs: 28, 30, and 32, and light chain CDR1, CDR2, and CDR3 comprising SEQ ID NOs: 35, 37, and 39, and also comprises a light chain comprising a variable region sequence that is at least 90%, at least 91%, at least 92%, at least 93%, at least 94%, at least 95%, at least 96%, at least 97%, at least 98%, or at least 99% identical to SEQ ID NO:25. In some embodiments, an anti-PD-1 antibody comprises heavy chain CDR1, CDR2, and CDR3 comprising SEQ ID NOs: 28, 30, and 32, and light chain CDR1, CDR2, and CDR3 comprising SEQ ID NOs: 35, 37, and 39, and also comprises a heavy chain comprising a variable region sequence that is at least 90%, at least 91%, at least 92%, at least 93%, at least 94%, at least 95%, at least 96%, at least 97%, at least 98%, or at least 99% identical to SEQ ID NO:23; and a light chain comprising a variable region sequence that is at least 90%, at least 91%, at least 92%, at least 93%, at least 94%, at least 95%, at least 96%, at least 97%, at least 98%, or at least 99% identical to SEQ ID NO:25.

In some embodiments, an anti-PD-1 antibody comprises a heavy chain comprising a sequence that is at least 90%, at least 91%, at least 92%, at least 93%, at least 94%, at least 95%, at least 96%, at least 97%, at least 98%, or at least 99% identical to SEQ ID NOs:23 and 24. In some embodiments, an anti-PD-1 antibody comprises a light chain comprising a sequence that is at least 90%, at least 91%, at least 92%, at least 93%, at least 94%, at least 95%, at least 96%, at least 97%, at least 98%, or at least 99% identical to SEQ ID NOs:25 and 26. In some embodiments, an anti-PD-1 antibody comprises a heavy chain comprising a sequence that is at least 90%, at least 91%, at least 92%, at least 93%, at least 94%, at least 95%, at least 96%, at least 97%, at least 98%, or at least 99% identical to SEQ ID NOs:23 and 24; and a light chain comprising a sequence that is at least 90%, at least 91%, at least 92%, at least 93%, at least 94%, at least 95%, at least 96%, at least 97%, at least 98%, or at least 99% identical to SEQ ID NOs:25 and 26.

In some embodiments, an anti-PD-1 antibody comprises heavy chain CDR1, CDR2, and CDR3 comprising SEQ ID NOs: 28, 30, and 32, and light chain CDR1, CDR2, and CDR3 comprising SEQ ID NOs: 35, 37, and 39, and also comprises a heavy chain comprising a sequence that is at least 90%, at least 91%, at least 92%, at least 93%, at least 94%, at least 95%, at least 96%, at least 97%, at least 98%, or at least 99% identical to SEQ ID NOs:23 and 24. In some embodiments, an anti-PD-1 antibody comprises heavy chain CDR1, CDR2, and CDR3 comprising SEQ ID NOs: 28, 30, and 32, and light chain CDR1, CDR2, and CDR3 comprising SEQ ID NOs: 35, 37, and 39, and also comprises a light chain comprising a sequence that is at least 90%, at least 91%, at least 92%, at least 93%, at least 94%, at least 95%, at least 96%, at least 97%, at least 98%, or at least 99% identical to SEQ ID NOs:25 and 26. In some embodiments, an anti-PD-1 antibody comprises heavy chain CDR1, CDR2, and CDR3 comprising SEQ ID NOs: 28, 30, and 32, and light chain CDR1, CDR2, and CDR3 comprising SEQ ID NOs: 35, 37, and 39, and also comprises a heavy chain comprising a sequence that is at least 90%, at least 91%, at least 92%, at least 93%, at least 94%, at least 95%, at least 96%, at least 97%, at least 98%, or at least 99% identical to SEQ ID NOs:23 and 24; and a light chain comprising a sequence that is at least 90%, at least 91%, at least 92%, at least 93%, at least 94%, at least 95%, at least 96%, at least 97%, at least 98%, or at least 99% identical to SEQ ID NOs:25 and 26.

In some embodiments, an anti-PD-1 antibody comprises at least one of the CDRs discussed herein. That is, in some embodiments, an anti-PD-1 antibody comprises at least one CDR selected from a heavy chain CDR1 discussed herein, a heavy chain CDR2 discussed herein, a heavy chain CDR3 discussed herein, a light chain CDR1 discussed herein, a light chain CDR2 discussed herein, and a light chain CDR3 discussed herein. Further, in some embodiments, an anti-PD-1 antibody comprises at least one mutated CDR based on a CDR discussed herein, wherein the mutated CDR comprises 1, 2, 3, or 4 amino acid substitutions relative to the CDR discussed herein. In some embodiments, one or more of the amino acid substitutions are conservative amino acid substitutions. One skilled in the art can select one or more suitable conservative amino acid substitutions for a particular CDR sequence, wherein the suitable conservative amino acid substitutions are not predicted to significantly alter the binding properties of the antibody comprising the mutated CDR.

In some embodiments, the anti-PD-1 antibody is an antigen binding fragment. It has been amply demonstrated that the antigen-binding function of an Ab can be performed by fragments of a full-length Ab. Examples of binding fragments include (i) a Fab fragment, a monovalent fragment consisting of the $V_L$, $V_H$, $C_L$ and $C_{H1}$ domains; (ii) a F(ab')2 fragment, a bivalent fragment comprising two Fab fragments linked by a disulfide bridge at the hinge region; (iii) a Fd fragment consisting of the $V_H$ and $C_{H1}$ domains; and (iv) a Fv fragment consisting of the $V_L$ and $V_H$ domains of a single arm of an Ab. Thus, in some embodiments, the anti-PD-1 antibody is a full length antibody, or alternatively, is a Fab, an Fv, an scFv, a Fab', or a (Fab')$_2$ fragment.

In some embodiments, the anti-PD-1 antibodies exhibit one or more of the following characteristics: (a) binds to human PD-1 with a $K_D$ of $1 \times 10^{-7}$ M or less, as determined by surface plasmon resonance using a Biacore biosensor system; (b) does not substantially bind to human CD28, CTLA-4 or ICOS; (c) increases T-cell proliferation in a Mixed Lymphocyte Reaction (MLR) assay; (d) increases interferon-γ production in an MLR assay; (e) increases IL-2 secretion in an MLR assay; (f) binds to human PD-1 and cynomolgus monkey PD-1; (g) inhibits the binding of PD-L1 and/or PD-L2 to PD-1; (h) stimulates antigen-specific memory responses; (i) stimulates Ab responses; and/or (j) inhibits tumor cell growth in vivo. Anti-PD-1 Abs usable in the present invention include mAbs that bind specifically to human PD-1 and exhibit at least one, at least two, at least three, at least four or at least five of the preceding characteristics.

In some embodiments, an anti-PD-1 antibody described herein comprises one or more human constant regions. In some embodiments, the human heavy chain constant region is of an isotype selected from IgA, IgG, and IgD. In some embodiments, the human light chain constant region is of an isotype selected from κ and λ. In some embodiments, a humanized antibody described herein comprises a human IgG constant region. In some embodiments, a humanized antibody described herein comprises a human IgG4 heavy chain constant region. In some such embodiments, a humanized antibody described herein comprises an S241P mutation (Kabat numbering; S241P corresponds to an S228P mutation in EU numbering) in the human IgG4 constant region. (See SEQ ID NO: 17.) In some embodiments, a humanized antibody described herein comprises a human IgG4 constant region and a human κ light chain.

Therapeutic Compositions and Methods
Methods of Treating Cancer

Resistance to immunotherapy may be related to the activity of several immunosuppressive cell types. Depletion of tumor-associated macrophages (TAMs) may promote a pro-inflammatory state, increasing antitumor T cell responses. For example, TAMs inhibit antitumor T-cell activity in the tumor microenvironment. (See Ries C. H. et al. *Cancer Cell* 25: 846-859 (2014) and Cannarile M. et al. *J. Immuo. Ther. Cancer* 5: 53 (2017).) In pancreatic and other cancers, high levels of TAMs are associated with poor prognosis. (See Hu H. et al. *Tumour Biol.* 37: 8659-8664 (2016); Kurahara H. et al. *J. Surg. Res.* 167: e211-e219 (2011); Goswami K. K. et al. *Cell Imunol.* 316: 1-10 (2017).) Signaling through the CSF1 receptor promotes the maintenance and function of TAMs. (See Ries and Cannarile.)

Cabiralizumab binds to CSF1R and blocks cytokine signaling that is needed for TAM activation. Cabiralizumab may block CSF1R in a way that leads to the depletion of TAMs and to upregulation of PD-L1 expression. Accordingly, cabiralizumab may synergize with PD-1 blockade. (Zhu Y. et al. *Cancer Res.* 74: 5057-5069 (2014).) The result may be to modify the immunosuppressive tumor environment while simultaneously suppressing the PD-1 checkpoint pathway, enhancing the benefits of anti-PD-1 antibody therapy, even in patients for whom anti-PD-1 monotherapy has limited clinical benefit (e.g. in pancreatic cancer). Adverse events observed in the combination of cabiralizumab and nivolumab treatment include elevations of creatine kinase and liver enzymes. These are hypothesized to be secondary to cabiralizumab's depletion of Kupffer cells (macrophages).

In some embodiments, methods for treating cancer are provided. In some embodiments, the cancer is selected from non-small cell lung cancer (NSCLC), melanoma, squamous cell carcinoma of the head and neck, ovarian cancer, pancreatic cancer, renal cell carcinoma, hepatocellular carcinoma, bladder cancer, and endometrial cancer. In some embodiments, the cancer is a central nervous system neoplasm. In some embodiments, the central nervous system neoplasm is a malignant glioma or glioblastoma. In some embodiments, the cancer is recurrent or progressive after a therapy selected from surgery, chemotherapy, radiation therapy, or a combination thereof. In some embodiments, the patient has stage III or stage IV cancer, as defined in the definitions section below with respect to particular cancers. In some embodiments, the patient's cancer is metastatic. In some such embodiments, the cancer is NSCLC and the NSCLC patient has Stage IIIB or IV disease and/or has demonstrated disease progression or recurrence during and/or after a platinum doublet-based or other chemotherapy regimen for advanced or metastatic disease. In some such embodiments, the patient has Stage III or IV melanoma. In some embodiments, the melanoma patient has demonstrated disease progression during or after treatment with at least one BRAF inhibitor, or is BRAF wild-type. In some embodiments, the patient has squamous cell cancer of the head and neck (SSCHN), such as Stage III or IV SSCHN or recurrent or metastatic SSCHN. In some embodiments, the SSCHN patient has previously received chemotherapy, such as platinum therapy, but has demonstrated tumor progression or recurrence. In some embodiments, the SSCHN patient has previously received radiation therapy, optionally along with platinum therapy, but has demonstrated tumor progression or recurrence. In some embodiments, the patient has adenocarcinoma of the colon or rectum. In some embodiments, the patient has metastatic colorectal cancer. In some embodiments, the patient has metastatic colorectal cancer despite prior treatment with one or more of fluoropyrimidine, oxaliplatin, irinotecan, bevacizumab, cetuximab, or panitumumab. In some embodiments, the patient has malignant glioma (e.g. glioblastoma or gliosarcoma). In some embodiments, the malignant glioma patient has previously been treated with surgery, radiotherapy, and/or temozolomide. In some embodiments, the malignant glioma patient has Grade IV malignant glioma. In some embodiments, the subject is a PD-1/PD-L1 inhibitor inadequate responder or is refractory to prior treatment with a PD-1/PD-L1 inhibitor. In some embodiments, the subject has previously received PD-1/PD-L1 inhibitor therapy, and in other embodiments the subject has not previously received PD-1/PD-L1 inhibitor therapy. In some embodiments, the patient has previously received one or more of chemotherapy, radiation therapy, or surgery; in some such embodiments the patient has documented tumor progression in spite of such prior treatment.

In some embodiments, methods for treating pancreatic cancer are provided, comprising administering an effective amount of an anti-CSF1R antibody and an effective amount of an anti-PD-1 antibody. The pancreatic cancer in embodiments herein may be pancreatic ductal adenocarcinoma (PDAC), advanced pancreatic cancer, locally advanced pancreatic cancer, metastatic pancreatic cancer, or microsatellite stable (MSS) pancreatic cancer. In some embodiments, the subject is a PD-1/PD-L1 inhibitor inadequate responder or is refractory to prior treatment with a PD-1/PD-L1 inhibitor. In some embodiments, the subject has previously received PD-1/PD-L1 inhibitor therapy, and in other embodiments the subject has not previously received PD-1/PD-L1 inhibitor therapy. In some embodiments, the patient has previously received one or more of chemotherapy, radiation therapy, or surgery; in some such embodiments the patient has documented tumor progression in spite of such prior treatment. In some embodiments, the cancer is metastatic pancreatic cancer. In some such cases, the cancer may have metastasized to other organs such as the liver and/or lung.

Pancreatic cancer is associated with high TAM infiltration and poor prognosis. (See Hu H. et al. *Tumour Biol.* 37: 8659-8664 (2016); Kurahara H. et al. *J. Surg. Res.* 167: e211-e219 (2011).) In some embodiments, a combination of cabiralizumab and nivolumab plus or minus chemotherapy may benefit patients with pancreatic cancer by reduction of TAMs and inhibition of PD-1 signaling. Pancreatic cancer often presents as a metastatic disease with a 1-year survival rate of 17-23% and a 5-year survival rate of only 1-3%. (See Von Hoff D. D. et al. *N. Engl. J. Med.* 369: 1691-1703 (2013); Am. Cancer Society, Pancreatic cancer: https www (dot) cancer (dot) org (slash) cancer (slash) pancreatic-cancer (dot) html, (last accessed Oct. 20, 2017); Foley K. et al. *Cancer Lett.* 381: 244-251 (2016).) Over 95% of pancreatic cancer patients are MSS pancreatic cancer patients and a majority are PD-1/PD-L1 inhibitor inadequate responders. (See Goggins M. et al. *Am. J. Pathol.* 1501-1507 (1998); Luttges J. et al. *Mod. Pathol.* 16: 537-542 (2003); Laghi L. et al. *PLOS One* 7: e46002 (2012); Brahmer J R et al. *N. Engl. J. Med.* 366: 2455-2465 (2012).)

In some embodiments, the methods herein comprise treating pancreatic cancer in a subject comprising administering to the subject 4 mg/kg of an anti-CSF1R antibody and 3 mg/kg of an anti-PD-1 antibody, wherein the antibodies are each administered once every two weeks. The amounts of 4 mg/kg and 3 mg/kg herein are rounded to one significant figure and thus, include amounts that round to 4 or that round to 3, respectively. Administration once every two weeks means every 12-16 days, every 13-15 days, or every 12, 13, 14, 15, or 16 days. In some embodiments, the antibodies are administered every 14 days. In some embodiments, they are administered every 13-15 days. The antibodies do not have to be administered in the same setting or during one single medical appointment, but can be administered sequentially in a staggered fashion as well based on convenience to the patient and physician. For example, the antibodies may be administered on different days from each other.

In some embodiments, the methods herein comprise treating pancreatic cancer in a subject comprising administering to the subject 1, 2, 3, 4, 5, or 6 mg/kg of an anti-CSF1R antibody once every two weeks and 200-600 mg of an anti-PD-1 antibody once every 4 weeks. The amounts above are rounded to one significant figure. In some embodiments, 2, 3, or 4 mg/kg of anti-CSF1R antibody is administered. In some embodiments, 400-600 mg of anti-PD-1 antibody is administered. In some embodiments, 200, 300, 400, 450, 480, 500, 520, 550, or 600 mg of anti-PD-1 antibody is administered. Administration once every two weeks includes every 12-16 days, such as every 13-15 days, or every 12, 13, 14, 15, or 16 days. Administration once every 4 weeks includes every 28 plus or minus 4 days, such as every 24-32 days, or every 26-30 days, or every 24, 25, 26, 27, 28, 29, 30, 31, or 32 days. The antibodies do not have to be administered in the same setting or during one single medical appointment, but can be administered sequentially in a staggered fashion as well based on convenience to the patient and physician. For example, the antibodies may be administered on different days from each other.

In some embodiments, the cancer patient may also receive chemotherapy in addition to the combination of anti-CSF1R antibody and anti-PD-1 antibody, such as the standard, first or second-line chemotherapy regimen for that patient's cancer. In some such embodiments, the patient may have progressed after receiving a course of first-line chemotherapy treatment for their cancer.

For example, in pancreatic cancer patients, the patient may also receive a combination of gemcitabine and nab-paclitaxel (Abraxane®). In some embodiments, the patient may receive 500-1500 mg/m$^2$, 800-1200 mg/m$^2$, or 1000, 800, or 600 mg/m$^2$ gemcitabine by IV every 2, 3, or 4 weeks and 75-150 mg/m$^2$, 100 mg/m$^2$, or 125 mg/m$^2$ nab-paclitaxel by IV every 2, 3, or 4 weeks. For example, some patients may receive 1000, 800, or 600 mg/m$^2$ gemcitabine and 125, 100, or 75 mg/m$^2$ nab-paclitaxel each every 2 weeks. For example, in pancreatic cancer patients, the patient may also receive a combination of 5-fluorouracil (5-FU), leucovorin and irinotecan liposome injection (Onivyde®). In pancreatic cancer patients, the patient may also receive a combination of 5-FU, leucovorin, and oxaliplatin (FOLFOX). The FOLFOX treatment may involve administering 50-100 mg/m$^2$ oxaliplatin, such as 50, 60, 75, 85, or 100 mg/m$^2$, and may involve administering 200-500 mg/m$^2$ leucovorin, such as 200, 300, 400, or 500 mg/m², and may involve administering 5-FU as an initial bolus at 200, 300, 400, or 500 mg/m² followed by a longer IV infusion over 24-48 hours of 1600-3000 mg/m², such as 1600, 2000, 2400, or 3000 mg/m² administered over 46-48 hours by IV. In some embodiments in which FOLFOX is administered, oxaliplatin is administered at 85 mg/m². In some embodiments in which FOLFOX is administered, leucovorin is administered at 400 mg/m². In some embodiments in which FOLFOX is administered, 5-FU is administered as a 400 mg/m² bolus followed by a 2400 mg/m² IV infusion over 46 hours. In some embodiments, the FOLFOX regimen is 85 mg/m² oxaliplatin, 400 mg/m² leucovorin, 400 mg/m² bolus 5-FU, followed by 2400 mg/m² 5-FU by infusion over 46 hours, all every 2 weeks.

Exemplary Molecules for Treatment

In the methods herein, the anti-CSF1R antibody and anti-PD-1 antibody may be any of the antibodies described herein, such as in the earlier sections of this disclosure. For example, in some such embodiments, the anti-CSF1R antibody comprises a heavy chain comprising a heavy chain (HC) CDR1 having the sequence of SEQ ID NO: 5, an HC CDR2 having the sequence of SEQ ID NO: 6, and an HC CDR3 having the sequence of SEQ ID NO: 7, and a light chain comprising a light chain (LC) CDR1 having the sequence of SEQ ID NO: 8, a LC CDR2 having the sequence of SEQ ID NO: 9, and a LC CDR3 having the sequence of SEQ ID NO: 10; and wherein the anti-PD-1 antibody comprises a heavy chain comprising a heavy chain (HC) CDR1 having the sequence of SEQ ID NO: 28, an HC CDR2 having the sequence of SEQ ID NO: 30, and an HC CDR3 having the sequence of SEQ ID NO: 32, and a light chain comprising a light chain (LC) CDR1 having the sequence of SEQ ID NO: 35, a LC CDR2 having the sequence of SEQ ID NO: 37, and a LC CDR3 having the sequence of SEQ ID NO: 39. In some embodiments, the anti-PD-1 antibody heavy chain comprises the heavy chain variable region sequence of SEQ ID NO: 23 and the anti-PD-1 antibody light chain comprises the light chain variable region sequence of SEQ ID NO: 25. In some embodiments, the anti-PD-1 antibody heavy chain comprises a heavy chain variable region that is at least 95%, 97%, 98%, or 99% identical to the sequence of SEQ ID NO: 23 and the anti-PD-1 antibody light chain comprises the light chain variable region that is at least 95%, 97%, 98%, or 99% identical to the sequence of SEQ ID NO: 25. For instance, the sequence may comprise each of the heavy and light chain CDRs of SEQ ID NOs: 28, 30, 32, 35, 37, and 39 and also comprise a heavy chain variable region that is at least 95%, 97%, 98%, or 99% identical to the sequence of SEQ ID NO: 23 and a light chain variable region that is at least 95%, 97%, 98%, or 99% identical to the sequence of SEQ ID NO: 25. In some embodiments, the anti-PD-1 antibody heavy chain comprises the sequence of each of SEQ ID NO: 23 and 24 and the anti-PD-1 antibody light chain comprises the sequence of each of SEQ ID NO: 25 and 26. In some embodiments, the anti-PD-1 antibody heavy chain comprises a sequence that is at least 95%, 97%, 98%, or 99% identical to a sequence comprising each of SEQ ID NOs: 23 and 24 and the anti-PD-1 antibody light chain comprises a sequence that is at least 95%, 97%, 98%, or 99% identical to a sequence of each of SEQ ID NOs: 25 and 26. For instance, the sequence may comprise each of the heavy and light chain CDRs of SEQ ID NOs: 28, 30, 32, 35, 37, and 39 and also comprise a heavy chain that is at least 95%, 97%, 98%, or 99% identical to a sequence comprising each of SEQ ID NOs: 23 and 24 and a light chain that is at least 95%, 97%, 98%, or 99% identical to a sequence comprising each of SEQ ID NOs: 25 and 26. In some embodiments, the anti-PD-1 antibody is nivolumab. In other embodiments, the anti-PD-1 antibody is pembrolizumab or PDR-001.

In some embodiments, the anti-CSF1R antibody heavy chain comprises the heavy chain variable region sequence of SEQ ID NO: 11 and the anti-CSF1R antibody light chain comprises the light chain variable region sequence of SEQ ID NO: 12. In some embodiments, the anti-CSF1R antibody heavy chain comprises a heavy chain variable region that is at least 95%, 97%, 98%, or 99% identical to the sequence of SEQ ID NO: 11 and a light chain variable region that is at least 95%, 97%, 98%, or 99% identical to the sequence of SEQ ID NO: 12. For instance, the sequence may comprise each of the heavy and light chain CDRs of SEQ ID NOs: 5, 6, 7, 8, 9, and 10, and also comprise a heavy chain variable region that is at least 95%, 97%, 98%, or 99% identical to the sequence of SEQ ID NO: 11 and a light chain variable region that is at least 95%, 97%, 98%, or 99% identical to the sequence of SEQ ID NO: 12. In some embodiments, the anti-CSF1R antibody heavy chain comprises the sequence of SEQ ID NO: 13 and the anti-CSF1R antibody light chain comprises the sequence of SEQ ID NO: 14. In some embodiments, the anti-CSF1R antibody heavy chain comprises a sequence that is at least 95%, 97%, 98%, or 99% identical to the sequence of SEQ ID NO: 13 and the light chain comprises a sequence that is at least 95%, 97%, 98%, or 99% identical to the sequence of SEQ ID NO: 14. For instance, the sequence may comprise each of the heavy and light chain CDRs of SEQ ID NOs: 5, 6, 7, 8, 9, and 10, and also comprise a heavy chain that is at least 95%, 97%, 98%, or 99% identical to the sequence of SEQ ID NO: 13 and a light chain that is at least 95%, 97%, 98%, or 99% identical to the sequence of SEQ ID NO: 14. In some embodiments, the anti-CSF1R antibody is cabiralizumab.

In certain embodiments, the anti-PD-1 antibody is an antibody that specifically binds to PD-1 or PD-L1 and comprises pembrolizumab, avelumab, durvalumab, atezolizumab, or PDR001, or is replaced with a non-antibody PD-1/PD-L1 inhibitor such as AMP-224. Certain methods comprise administering to a subject having pancreatic cancer a therapeutically effective amount of AMG820 and pembrolizumab. Certain methods comprise administering to a subject having pancreatic cancer a therapeutically effective amount of PDR001 and BLZ945 or MCS-110. In such embodiments, a cancer patient such as a pancreatic cancer patient may be administered 4 mg/kg of anti-CSF1R antibody and 3 mg/kg of anti-PD-1 antibody comprising pembrolizumab, avelumab, durvalumab, atezolizumab, or is replaced with a non-antibody PD-1/PD-L1 inhibitor such as AMP-224 or PDR001. In such embodiments, a cancer patient such as a pancreatic cancer patient may be administered 1, 2, 3, 4, 5, or 6 mg/kg of anti-CSF1R antibody every 2 weeks and 300-600 mg/kg of anti-PD-1 antibody every month comprising pembrolizumab, avelumab, durvalumab, atezolizumab, or is replaced with a non-antibody PD-1/PD-L1 inhibitor such as AMP-224 or PDR001. AMP-224 or PDR001, each given once every two weeks. In some such embodiments, the anti-CSF1R antibody may be cabiralizumab or any of the antibodies listed in the preceding paragraphs and sections herein.

In some embodiments, the anti-CSF1R antibody is an antibody species disclosed in any of international publications WO2013/132044, WO2009/026303, WO2011/140249, or WO2009/112245, such as RG7155 (emactuzumab), AMG820, SNDX 6352 (UCB 6352), CXIIG6, IMC-CS4, JNJ-40346527, MCS110, or the anti-CSF1R antibody in the methods is replaced with an anti-CSF1R inhibitor or anti-CSF1 inhibitor such as BLZ-945, pexidartinib (PLX3397, PLX108-01), AC-708, pexidartinib, PLX-5622, PLX7486, ARRY-382, or PLX-73086. Certain methods described herein, accordingly, comprise administering to a subject having pancreatic cancer a therapeutically effective amount of atezolizumab and RG7155 (emactuzumab); peridartinib and pembrolizumab or durvalumab; ARRY-382 and pembrolizumab; BLZ945 and PDR001; emactuzumab and atezolizumab; AMG820 and pembrolizumab, IMC-CS4 and durvalumab, MCS110 and PDR001, or PD-0360324 and avelumab. In some embodiments, the anti-CSF1R antibody in the methods is replaced with an anti-CSF1R inhibitor or anti-CSF1 inhibitor such as BLZ-945, pexidartinib, or PLX-73086 (or others described herein). Thus, in some embodiments, the anti-CSF-1R antibody is emactuzumab (RG7155), AMG 820, or SNDX 6352 (UCB 6352), In some embodiments, a non-antibody CSF1R inhibitor is used in place of the anti-CSF1R antibody, such as a small molecule, e.g., JNJ-40346527 (now PRV-6527), e.g., an anti-CSF1R tyrosine kinase inhibitor, or other modality.

In some embodiments, the cancer patient such as a pancreatic cancer patient may be administered 4 mg/kg of anti-CSF1R antibody (or other anti-CSF1R or anti-CSF1 inhibitor) and 3 mg/kg of anti-PD-1 antibody, each given once every two weeks. In such embodiments, the cancer patient such as a pancreatic cancer patient may be administered 1, 2, 3, 4, 5, or 6 mg/kg of anti-CSF1R antibody (or other anti-CSF1R or anti-CSF1 inhibitor) every 2 weeks and 300-600 mg of anti-PD-1 antibody every 4 weeks. In some such embodiments, the anti-PD-1 antibody may be nivolumab, pembrolizumab, avelumab, durvalumab, atezolizumab, AMP-224 and/or PDR001, or any of the antibodies listed in the preceding paragraphs and sections herein. In other such embodiments, the anti-PD-1 antibody may comprise pembrolizumab, avelumab, durvalumab, atezolizumab, or PDR001, or is replaced with a non-antibody PD-1/PD-L1 inhibitor such as AMP-224.

The treatments described herein may be generally applicable to any anti-CSF-1R inhibitor and any anti-PD-1 inhibitor, e.g., atezolizumab and RG7155 (emactuzumab); peridartinib and pembrolizumab or durvalumab; ARRY-382 and pembrolizumab; BLZ945 and PDR001; emactuzumab and atezolizumab; AMG820 and pembrolizumab, IMC-CS4 and durvalumab, MCS110 and PDR001, or PD-0360324 and avelumab.

In embodiments herein, the anti-CSF1R and anti-PD-1 antibodies may be fragments that are capable of binding antigen, such as Fv, single-chain Fv (scFv), Fab, Fab', and (Fab')$_2$, or they may alternatively comprise full length heavy and/or light chains, and they may be humanized, chimeric, or human antibodies, as further described earlier in this disclosure.

Administration of Anti-CSF1R and Anti-PD-1 Antibodies

In some embodiments, the anti-CSF1R antibody and the anti-PD-1 antibody are administered concurrently. In some embodiments, the anti-CSF1R antibody and the anti-PD-1 antibody are administered sequentially. In some embodiments, the anti-PD-1 antibody is infused over a period of 30-60 minutes, and the anti-CSF1R antibody is infused over a period of 30-60 minutes. In some embodiments, the infusion of the anti-CSF1R antibody is initiated 30-120 minutes after the end of the infusion of the anti-PD-1 antibody. In some embodiments, the infusion of the anti-CSF1R antibody is initiated 30-60 minutes, e.g. 30 minutes, 45 minutes, or 60 minutes, after the end of the infusion of the anti-PD-1 antibody. In some methods, a anti-PD-1 antibody may be a infused first, followed by a period of rest of 30-120 minutes, and infusion of an anti-CSF1R antibody.

In some embodiments, a subject has received, or is receiving, PD-1/PD-L1 inhibitor therapy, such as anti-PD-1 antibody therapy, and an anti-CSF1R antibody is added to the therapeutic regimen. In some embodiments of the methods described herein, the pancreatic cancer subject is a PD-1/PD-L1 inhibitor inadequate responder. A subject who is a PD-1/PD-L1 inhibitor inadequate responder, may have previously responded to a PD-1/PD-L1 inhibitor, such as an anti-PD-1 antibody, but may have become less responsive to the PD-1/PD-L1 inhibitor, or the subject may have never responded to the PD-1/PD-L1 inhibitor. Inadequate response to a PD-1/PD-L1 inhibitor means that aspects of the condition that would be expected to improve following a standard dose of the PD-1/PD-L1 inhibitor do not improve, and/or improvement only occurs if greater than a standard dose is administered. In some embodiments, a PD-1/PD-L1 inhibitor inadequate responder has experienced, or is experiencing, an inadequate response to the PD-1/PD-L1 inhibitor after receiving a standard dose for at least two weeks, at least three weeks, at least four weeks, at least six weeks, or at least twelve weeks. A "standard" dose is determined by a medical professional, and may depend on the subject's age, weight, healthy history, severity of disease, the frequency of dosing, etc. In some embodiments, a PD-1/PD-L1 inhibitor inadequate responder has experienced, or is experiencing, an inadequate response to an anti-PD-1 antibody and/or an anti-PD-L1 antibody. In some embodiments, a PD-1/PD-L1 inhibitor inadequate responder has experienced, or is experiencing, an inadequate response to a PD-1/PD-L1 inhibitor selected from nivolumab, pembrolizumab, avelumab, durvalumab, atezolizumab, AMP-224 and/or PDR001. In some embodiments, the pancreatic patient who is an inadequate responder to a PD-1/PD-L1 inhibitor becomes refractory to therapy with the inhibitor after at least 2 doses, such as after 2, 3, 4, 5, or 6 doses of a PD-1/PD-L1 inhibitor, e.g., nivolumab, pembrolizumab, avelumab, durvalumab, atezolizumab, AMP-224 and/or PDR001. In some embodiments, the subject has failed standard treatment(s) for pancreatic cancer or is not indicated for standard treatments for pancreatic cancer.

Exemplary Cancer Treatment Methods

In some embodiments, cancer patients, such as solid tumor patients or advanced cancer patients are treated with 4 mg/kg cabiralizumab and 3 mg/kg nivolumab every 2 weeks, either with our without chemotherapy. In some embodiments, pancreatic cancer patients are treated with 4 mg/kg cabiralizumab and 3 mg/kg nivolumab every 2 weeks, either with our without chemotherapy. In some embodiments, advanced pancreatic cancer patients are treated with 4 mg/kg cabiralizumab and 3 mg/kg nivolumab every 2 weeks, either with our without chemotherapy. In some embodiments, metastatic pancreatic cancer patients are treated with 4 mg/kg cabiralizumab and 3 mg/kg nivolumab every 2 weeks, either with our without chemotherapy. In some embodiments, the cancer has metastasized to other organs such as the liver and/or lung. In some embodiments, the cancer patients are also microsatellite stable.

In some embodiments, pancreatic cancer patients have already received at least one chemotherapy regimen. In some embodiments, patients have already received a chemotherapy regimen comprising gemcitabine or 5-FU and have progressed despite that regimen.

In some embodiments, pancreatic cancer patients are treated with a combination of cabiralizumab, nivolumab, and a chemotherapy regimen comprising either gemcitabine or 5-FU. In some embodiments, the chemotherapy regimen is gemcitabine/nab-paclitaxel and in other embodiments, the chemotherapy regimen is FOLFOX (5-FU, leucovorin, oxaliplatin). In other embodiments, the chemotherapy regimen is a combination of 5-FU, leucovorin, and liposomal irinotecan.

In some embodiments, pancreatic cancer patients are treated with a combination of 1, 2, 3, 4, 5, of 6 mg/kg cabiralizumab once every 2 weeks and 300, 400, 450, 480, 500, 550, or 600 mg nivolumab once every 4 weeks. In some embodiments, pancreatic cancer patients are treated with a combination of 4 mg/kg cabiralizumab once every 2 weeks and 480 mg nivolumab once every 4 weeks. In some embodiments, advanced pancreatic cancer patients are treated with a combination of 1, 2, 3, 4, 5, of 6 mg/kg cabiralizumab once every 2 weeks and 300, 400, 450, 480, 500, 550, or 600 mg nivolumab once every 4 weeks. In some embodiments, advanced pancreatic cancer patients are treated with a combination of 4 mg/kg cabiralizumab once every 2 weeks and 480 mg nivolumab once every 4 weeks. In some embodiments, metastatic pancreatic cancer patients are treated with a combination of 1, 2, 3, 4, 5, of 6 mg/kg cabiralizumab once every 2 weeks and 300, 400, 450, 480, 500, 550, or 600 mg nivolumab once every 4 weeks. In some embodiments, metastatic pancreatic cancer patients are treated with a combination of 4 mg/kg cabiralizumab once every 2 weeks and 480 mg nivolumab once every 4 weeks. In some embodiments, the metastatic cancer has spread to other organs such as the liver and/or lung. In some embodiments, the cancer patients are also microsatellite stable. In some embodiments, the patients have progressed despite prior chemotherapy treatment.

In some embodiments, pancreatic cancer patients are treated with a combination of 1, 2, 3, 4, 5, of 6 mg/kg cabiralizumab once every 2 weeks and 300, 400, 450, 480, 500, 550, or 600 mg nivolumab once every 4 weeks in addition to gemcitabine/nab-paclitaxel chemotherapy. In some embodiments, pancreatic cancer patients are treated with a combination of 4 mg/kg cabiralizumab once every 2 weeks and 480 mg nivolumab once every 4 weeks in addition to gemcitabine/nab-paclitaxel chemotherapy. In some embodiments, advanced pancreatic cancer patients are treated with a combination of 1, 2, 3, 4, 5, of 6 mg/kg cabiralizumab once every 2 weeks and 300, 400, 450, 480, 500, 550, or 600 mg nivolumab once every 4 weeks in addition to gemcitabine/nab-paclitaxel chemotherapy. In some embodiments, advanced pancreatic cancer patients are treated with a combination of 4 mg/kg cabiralizumab once every 2 weeks and 480 mg nivolumab once every 4 weeks in addition to gemcitabine/nab-paclitaxel chemotherapy. In some embodiments, metastatic pancreatic cancer patients are treated with a combination of 1, 2, 3, 4, 5, of 6 mg/kg cabiralizumab once every 2 weeks and 300, 400, 450, 480, 500, 550, or 600 mg nivolumab once every 4 weeks in addition to gemcitabine/nab-paclitaxel chemotherapy. In some embodiments, metastatic pancreatic cancer patients are treated with a combination of 4 mg/kg cabiralizumab once every 2 weeks and 480 mg nivolumab once every 4 weeks in addition to gemcitabine/nab-paclitaxel chemotherapy. In some embodiments, the metastatic cancer has spread to other organs such as the liver and/or lung. In some embodiments, the cancer patients are also microsatellite stable. In some embodiments, the patients have progressed despite prior chemotherapy treatment. In some embodiments the gemcitabine/nab-paclitaxel chemotherapy comprises administering 600, 800, or 1000 mg/m$^2$ gemcitabine and 75, 100, or 125 mg/m$^2$ nab-paclitaxel every 2 weeks. In some embodiments the gemcitabine/nab-paclitaxel chemotherapy comprises administering 600, 800, or 1000 mg/m$^2$ gemcitabine and 75, 100, or 125 mg/m$^2$ nab-paclitaxel on days 1, 8, and 15 of each 28-day cycle.

In some embodiments, pancreatic cancer patients are treated with a combination of 1, 2, 3, 4, 5, of 6 mg/kg cabiralizumab once every 2 weeks and 300, 400, 450, 480, 500, 550, or 600 mg nivolumab once every 4 weeks in addition to FOLFOX chemotherapy. In some embodiments, pancreatic cancer patients are treated with a combination of 4 mg/kg cabiralizumab once every 2 weeks and 480 mg nivolumab once every 4 weeks in addition to FOLFOX chemotherapy. In some embodiments, advanced pancreatic cancer patients are treated with a combination of 1, 2, 3, 4, 5, of 6 mg/kg cabiralizumab once every 2 weeks and 300, 400, 450, 480, 500, 550, or 600 mg nivolumab once every 4 weeks in addition to FOLFOX chemotherapy. In some embodiments, advanced pancreatic cancer patients are treated with a combination of 4 mg/kg cabiralizumab once every 2 weeks and 480 mg nivolumab once every 4 weeks in addition to FOLFOX chemotherapy. In some embodiments, metastatic pancreatic cancer patients are treated with a combination of 1, 2, 3, 4, 5, of 6 mg/kg cabiralizumab once every 2 weeks and 300, 400, 450, 480, 500, 550, or 600 mg nivolumab once every 4 weeks in addition to FOLFOX chemotherapy. In some embodiments, metastatic pancreatic cancer patients are treated with a combination of 4 mg/kg cabiralizumab once every 2 weeks and 480 mg nivolumab once every 4 weeks in addition to FOLFOX chemotherapy. In some embodiments, the metastatic cancer has spread to other organs such as the liver and/or lung. In some embodiments, the cancer patients are also microsatellite stable. In some embodiments, the patients have progressed despite prior chemotherapy treatment. In some embodiments the FOLFOX chemotherapy comprises administering 50, 70, or 85 mg/m$^2$ oxaliplatin and 200, 300, or 400 mg/m$^2$ leucovorin, and 200, 300, or 400 mg/m$^2$ 5-FU as a bolus followed by 1600, 2000, or 2400 mg/m$^2$ 5-FU as a 46-48 hour IV infusion every 2 weeks.

In some embodiments, pancreatic cancer patients are treated with a combination of 1, 2, 3, 4, 5, of 6 mg/kg cabiralizumab once every 2 weeks and 300, 400, 450, 480, 500, 550, or 600 mg nivolumab once every 4 weeks in addition to 5-FU/leucovorin/liposomal irinotecan chemotherapy. In some embodiments, pancreatic cancer patients are treated with a combination of 4 mg/kg cabiralizumab once every 2 weeks and 480 mg nivolumab once every 4 weeks in addition to 5-FU/leucovorin/liposomal irinotecan chemotherapy. In some embodiments, advanced pancreatic cancer patients are treated with a combination of 1, 2, 3, 4, 5, of 6 mg/kg cabiralizumab once every 2 weeks and 300, 400, 450, 480, 500, 550, or 600 mg nivolumab once every 4 weeks in addition to 5-FU/leucovorin/liposomal irinotecan chemotherapy. In some embodiments, advanced pancreatic cancer patients are treated with a combination of 4 mg/kg cabiralizumab once every 2 weeks and 480 mg nivolumab once every 4 weeks in addition to 5-FU/leucovorin/liposomal irinotecan chemotherapy. In some embodiments, metastatic pancreatic cancer patients are treated with a combination of 1, 2, 3, 4, 5, of 6 mg/kg cabiralizumab once every 2 weeks and 300, 400, 450, 480, 500, 550, or 600 mg nivolumab once every 4 weeks in addition to 5-FU/leucovorin/liposomal irinotecan chemotherapy. In some embodiments, metastatic pancreatic cancer patients are treated with a combination of 4 mg/kg cabiralizumab once every 2 weeks and 480 mg nivolumab once every 4 weeks in addition to 5-FU/leucovorin/liposomal irinotecan chemotherapy. In some embodiments, the metastatic cancer has spread to other organs such as the liver and/or lung. In some embodiments, the cancer patients are also microsatellite stable. In some embodiments, the patients have progressed despite prior chemotherapy treatment.

In some embodiments above, the cabiralizumab may be substituted with another anti-CSF1R antibody or inhibitor such as RG7155 (emactuzumab) or AMG820, or with an CSF1R inhibitor or CSF1 inhibitor such as BLZ-945, pexidartinib, or PLX-73086 (or any other described herein). In some embodiments, the anti-CSF1R antibody is emactuzumab (RG7155), AMG 820, or SNDX 6352 (UCB 6352), or another anti-CSF1R antibody, CSF1R inhibitor, or CSF1 inhibitor as described herein, such as a small molecule, e.g., JNJ-40346527 (now PRV-6527), e.g., an anti-CSF1R tyrosine kinase inhibitor, or other modality. In some embodiments above, the nivolumab may be substituted with an anti-PD-1 antibody comprising pembrolizumab, avelumab, durvalumab, atezolizumab, or PDR001, or with a non-antibody PD-1/PD-L1 inhibitor such as AMP-224.

Methods of Selecting Patients for Treatment

In some embodiments, a method of selecting a pancreatic patient for combination therapy with an anti-CSF1R antibody and an anti-PD-1 antibody with or without chemotherapy is provided, comprising determining the levels of TAMs and/or CD8+ T cells in the patient. In some embodiments, if a patient's TAM levels are high, the patient is selected for combination therapy. In some embodiments, if a patient's TAM and CD8+ T cell levels are high, the patient is selected for combination therapy. The level of TAMs or CD8+ T cells is considered "high" if it is at least 10%, at least 20%, at least 30%, at least 40%, at least 50%, at least 75%, or at least 100% higher than the level in an individual who does not have cancer. In some embodiments, the level of TAMs or CD8+ T cells is considered "high" if it is above the median level found in individuals with cancer. In some embodiments, if a patient's TAM levels are high and CD8+ T cell levels are low, the patient is selected for combination therapy with an anti-CSF1R antibody and a PD-1/PD-L1 inhibitor. The level of CD8+ T cells is considered "low" if it is at or below the median level found in individuals with cancer. In some embodiment, the level of CD8+ T cells is considered "low" if it is at least 10%, at least 20%, at least 30%, at least 40%, at least 50%, at least 75%, or at least 100% lower than the level in an individual who does not have cancer. In some embodiments, expression of CSF1R on the patient's TAMs is determined. In some embodiments, if the patient's TAMs express CSF1R, the patient is selected for combination therapy. In some embodiments, if the patient's TAMs express elevated levels of CSF1R, the patient is selected for combination therapy. In some embodiments, a patient's TAMs are considered to express "elevated" levels of CSF1R if the level of CSF1R is at or above the median level of CSF1R found expressed on TAMS in individuals with cancer. In some embodiments, if the patient's CSF1R expression shows a high correlation with the level of CD8+ T cells, T cells or PD-1/PD-L1 expression, the patient is selected for combination therapy. The correlation of the expressions is considered "high" if it is at or above the median level found in individuals with cancer.

Levels of TAMs, CSF1R expression, CD8+ T cells, regulatory T cells, and/or PD-1 expression may be measured by methods in the art. Nonexemplary methods include immunohistochemistry (IHC), fluorescence-activated cell sorting (FACS), protein arrays, and gene expression assays, such as RNA sequencing, gene arrays, and quantitative PCR. In some embodiments, one or more markers selected from CSF1R, CD68, CD163, CD8, FoxP3, PD-1, and PD-L1 may be detected by IHC, FACS, or gene expression assay on tumor sections, or dissociated cells from tumor sections.

Reduction of Nonclassical Monocytes and Tumor Burden

In some embodiments, methods of treating cancer, e.g., solid tumors, e.g., advanced cancer (e.g., metastatic cancer) are provided, comprising administering to a subject having cancer, e.g., solid tumors, e.g., advanced cancer (e.g., metastatic cancer), a therapeutically effective amount of a CSF1R inhibitor, such as an antibody, and a PD-1/PD-L1 inhibitor, e.g., an antibody. In certain embodiments, an anti-CSF1R antibody is administered in an amount sufficient to reduce, e.g., deplete, the number of circulating CD14+CD16++ nonclassical monocytes, e.g., to that of healthy (i.e., control) subjects.

In some embodiments, the anti-CSF1R antibody and the anti-PD-1 antibody are administered to a cancer patient, such as a solid tumor patient or an advanced cancer patient or a pancreatic cancer patient such that peripheral blood levels of CD16+ monocytes or CD14+/CD16++ nonclassical monocytes fall to less than 10 monocytes per microliter peripheral blood within 3 days of the first antibody dosage and remain at less than 10 monocytes per microliter peripheral blood for at least 10 further days, such as until the next dosage of anti-CSF1R antibody. In some embodiments, the methods herein may reduce tumor burden in cancer patients. For example, in pancreatic cancer patients, tumor burden may be reduced by at least 30% in some patients within 50-100 days from the start of treatment with a combination of an anti-CSF1R antibody and an anti-PD-1 antibody. In some embodiments, pancreatic cancer patients treated with 4 mg/kg cabiralizumab and 3 mg/kg nivolumab every 2 weeks, either with our without chemotherapy, may show such reductions in CD14+CD16++ monocytes and/or tumor burden. In some embodiments, pancreatic cancer patients treated with 1, 2, 3, 4, 5, or 6 mg/kg cabiralizumab every 2 weeks and 300-600 mg nivolumab every 4 weeks, either with our without chemotherapy, may show such reductions in CD14+CD16++ monocytes and/or tumor burden. In some embodiments, pancreatic cancer patients treated with 4 mg/kg cabiralizumab every 2 weeks and 450-500 mg nivolumab every 4 weeks, either with our without chemotherapy, may show such reductions in CD14+CD16++ monocytes and/or tumor burden. In some embodiments, the pancreatic cancer is metastatic pancreatic cancer has spread to other organs such as the liver and/or lung and the treatment may allow reduction in tumor burden (i.e. decreases in tumor size) in one or more sites of metastasis such as in the liver or lung.

Additional Cancer Treatment Methods

The disclosure herein also encompasses methods of treating cancer in a subject comprising administering to the subject a CSF1R or CSF1 inhibitor as described herein, such as an anti-CSF1R antibody, CSF-1 inhibitor, or a CSF-1R inhibitor as described herein, in combination with a PD-1/PD-L1 inhibitor as described herein, such as an anti-PD-1 antibody, a PD-1 inhibitor, or a PD-L1 inhibitor as described herein, wherein the cancer has been determined to be microsatellite-stable (MSS) and/or has been determined to have a TMB of less than 20, less than 15 or less than 10 mutations/megabase by the Foundation One® CDx™ assay or less than 400, less than 300, or less than 200 missense mutations by WES. The disclosure herein also encompasses methods of treating cancer in a subject comprising administering to the subject a anti-CSF1R antibody and an anti- PD-1 antibody, wherein the cancer has been determined to be microsatellite-stable (MSS) and/or has been determined to have a TMB of less than 20, less than 15 or less than 10 mutations/megabase by the Foundation One® CDx™ assay or less than 400, less than 300, or less than 200 missense mutations by WES. In some embodiments, the cancer has been determined to be MSS and to have a TMB of less than 20, less than 15 or less than 10 mutations/megabase by the Foundation One® CDx™ assay or less than 400, less than 300, or less than 200 missense mutations by WES. In some embodiments, the cancer has been determined to have a TMB of less than 15 mutations/megabase by the Foundation One® CDx™ assay or less than 300 missense mutations by WES. In some embodiments, the cancer has been determined to have a TMB of less than 10 mutations/megabase by the Foundation One® CDx™ assay or less than 200 missense mutations by WES. Generally, patients with cancers determined to be MSS and with a low TMB of, for example, less than 20, less than 15, or less than 10 mutations/megabase by the Foundation One® CDx™ assay or less than 400, less than 300, or less than 200 missense mutations by WES have not responded to PD-1/PD-L1 inhibitor monotherapy.

In some such methods, the anti-CSF1R antibody comprises a heavy chain comprising a heavy chain (HC) CDR1 having the sequence of SEQ ID NO: 5, an HC CDR2 having the sequence of SEQ ID NO: 6, and an HC CDR3 having the sequence of SEQ ID NO: 7, and a light chain comprising a light chain (LC) CDR1 having the sequence of SEQ ID NO: 8, a LC CDR2 having the sequence of SEQ ID NO: 9, and a LC CDR3 having the sequence of SEQ ID NO: 10; and the anti-PD-1 antibody comprises a heavy chain comprising a heavy chain (HC) CDR1 having the sequence of SEQ ID NO: 28, an HC CDR2 having the sequence of SEQ ID NO: 30, and an HC CDR3 having the sequence of SEQ ID NO: 32, and a light chain comprising a light chain (LC) CDR1 having the sequence of SEQ ID NO: 35, a LC CDR2 having the sequence of SEQ ID NO: 37, and a LC CDR3 having the sequence of SEQ ID NO: 39. In some methods, the anti-CSF1R antibody is a Fab, an Fv, an scFv, a Fab', or a (Fab')$_2$ fragment and/or the anti-PD-1 antibody is a Fab, an Fv, an scFv, a Fab', or a (Fab')$_2$ fragment. In some such methods, the anti-PD-1 antibody heavy chain comprises a heavy chain variable region comprising the sequence of SEQ ID NO: 23 and wherein the anti-PD-1 antibody light chain comprises a light chain variable region comprising the sequence of SEQ ID NO: 25. In some embodiments, the anti-PD-1 antibody comprises a heavy chain comprising the sequence of each of SEQ ID NOs: 23 and 24 and wherein the anti-PD-1 antibody comprises a light chain comprising the sequence of each of SEQ ID NOs: 25 and 26. In some embodiments, the anti-PD-1 antibody is nivolumab or pembrolizumab or PDR001. In some embodiments, the anti-CSF1R antibody comprises a heavy chain variable region comprising the sequence of SEQ ID NO: 11 and wherein the anti-CSF1R antibody comprises a light chain variable region comprising the sequence of SEQ ID NO: 12. In some embodiments, the anti-CSF1R antibody comprises a heavy chain comprising the sequence of SEQ ID NO: 13 and wherein the anti-CSF1R antibody comprises a light chain comprising the sequence of SEQ ID NO: 14. In some embodiments, the anti-CSF1R antibody is cabiralizumab. In some embodiments, the anti-CSF1R antibody is emactuzumab (RG7155), AMG 820, or SNDX 6352 (UCB 6352), or another anti-CSF1R antibody, or is replaced by a CSF1R inhibitor or CSF1 inhibitor as described herein, such as a small molecule, e.g., JNJ-40346527 (now PRV-6527) e.g., an anti-CSF1R tyrosine kinase inhibitor, or other modality.

In some of the above methods, the anti-PD-1 antibody is administered to the subject before the anti-CSF1R antibody. In some embodiments, the anti-CSF1R antibody is administered from 30 minutes to 120 minutes after the anti-PD-1 antibody. In some embodiments, the anti-PD-1 antibody is infused over a period of 30-60 minutes, and the anti-CSF1R antibody is infused over a period of 30-60 minutes. In some embodiments, the infusion of the anti-CSF1R antibody is initiated 30-120 minutes after the end of the infusion of the anti-PD-1 antibody. In some embodiments, the infusion of the anti-CSF1R antibody is initiated 30-60 minutes (e.g., 30 minutes) after the end of the infusion of the anti-PD-1 antibody. In some embodiments, the subject has previously received a PD-1/PD-L1 inhibitor therapy. In some embodiments, the subject is a PD-1/PD-L1 inhibitor inadequate responder. In some embodiments, the subject is refractory to a PD-1/PD-L1 inhibitor, e.g., after at least 2 doses. In some embodiments, the anti-CSF1R antibody is cabiralizumab and the anti-PD-1 antibody is nivolumab, wherein cabiralizumab is administered at a dose of 4 mg/kg once every two weeks, and wherein nivolumab is administered at a dose of 3 mg/kg once every two weeks. In some embodiments, the cancer is pancreatic cancer, ovarian cancer, renal cancer, malignant glioma, melanoma, non-small cell lung cancer (NSCLC), or squamous cell carcinoma of the head and neck (SCCHN). In some embodiments, the cancer is pancreatic cancer.

Methods of Determining Responsiveness to Anti-CSF1R and Anti-PD-1 Antibody Combination Therapy The disclosure herein also contemplates methods of treating cancer in a subject, comprising administering to the subject at least one dose of a CSF1R or CSF1 inhibitor as described herein, such as an anti-CSF1R antibody, CSF-1 inhibitor, or a CSF-1R inhibitor as described herein, in combination with a PD-1/PD-L1 inhibitor as described herein, such as an anti-PD-1 antibody, a PD-1 inhibitor, or a PD-L1 inhibitor as described herein, (for example administering to the subject an anti-CSF1R antibody and an anti-PD-1 antibody), such as, for example, in a single dose or two doses, wherein the expression level of at least one marker gene is determined both prior to and following the administration, the at least one marker gene comprising one or more of: CCL19, CCL5, CCL8, CCR7, CD86, CXCL10, CXCL11, CXCL13, CXCL9, IFNG, IL23A, STAT1, TNF, CD72, CD79A, CD79B, MS4A1, TNFRSF17, CD3D, CD8A, CD8B, GZMM, APOL3, CTSW, GNLY, GZMA, GZMH, KLRB1, KLRD1, KLRK1, NKG7, PRF1, BTLA, CD244, CD96, CTLA4, LAG3, PDCD1, TIGIT, and FOXP3. If the expression level data indicates that the expression level of the at least one marker gene increases following the administration, administration of the treatment, e.g., anti-CSF1R antibody and anti-PD-1 antibody, to the subject may then continue. Some embodiments comprise a method of treating cancer in a subject, comprising administering to the subject at least one dose of a CSF1R or CSF1 inhibitor as described herein, such as an anti-CSF1R antibody, CSF-1 inhibitor, or a CSF-1R inhibitor as described herein, in combination with a PD-1/PD-L1 inhibitor, such as an anti-PD-1 antibody, a PD-1 inhibitor, or a PD-L1 inhibitor as described herein, such as an anti-CSF1R antibody and an anti-PD-1 antibody, such as one or two doses, wherein the expression level of at least one marker gene is determined to increase following the administration, the at least one marker gene comprising one or more of: CCL19, CCL5, CCL8, CCR7, CD86, CXCL10, CXCL11, CXCL13, CXCL9, IFNG, IL23A, STAT1, TNF, CD72, CD79A, CD79B, MS4A1, TNFRSF17, CD3D, CD8A, CD8B, GZMM, APOL3, CTSW, GNLY, GZMA, KLRB1, KLRD1, KLRK1, NKG7, PRF1, BTLA, CD244, CD96, CTLA4, LAG3, PDCD1, TIGIT, and FOXP3; and then continuing to administer the treatment, e.g., anti-CSF1R antibody and anti-PD-1 antibody, to the subject. In further embodiments, the method comprises first determining or having determined the expression level of the at least one marker gene comprising one or more of: CCL19, CCL5, CCL8, CCR7, CD86, CXCL10, CXCL11, CXCL13, CXCL9, IFNG, IL23A, STAT1, TNF, CD72, CD79A, CD79B, MS4A1, TNFRSF17, CD3D, CD8A, CD8B, GZMM, APOL3, CTSW, GNLY, GZMA, GZMH, KLRB1, KLRD1, KLRK1, NKG7, PRF1, BTLA, CD244, CD96, CTLA4, LAG3, PDCD1, TIGIT, and FOXP3, then administering at least one dose of the combination treatment, such as anti-CSF1R antibody and the anti-PD-1 antibody, such as one or two doses, and then re-determining or having determined the expression level of the at least one marker gene. If the expression level data indicates that the expression level of the at least one marker gene increases following the administration, administration of the treatment, e.g., an anti-CSF1R antibody and anti-PD-1 antibody, to the subject may then continue. In yet further embodiments, the method comprises first determining or having determined the expression level of the at least one marker gene comprising one or more of: CCL19, CCL5, CCL8, CCR7, CD86, CXCL10, CXCL11, CXCL13, CXCL9, IFNG, IL23A, STAT1, TNF, CD72, CD79A, CD79B, MS4A1, TNFRSF17, CD3D, CD8A, CD8B, GZMM, APOL3, CTSW, GNLY, GZMA, GZMH, KLRB1, KLRD1, KLRK1, NKG7, PRF1, BTLA, CD244, CD96, CTLA4, LAG3, PDCD1, TIGIT, and FOXP3, then administering at least one dose of a CSF1R or CSF1 inhibitor as described herein, such as an anti-CSF1R antibody, CSF-1 inhibitor, or a CSF-1R inhibitor as described herein, in combination with a PD-1/PD-L1 inhibitor, such as an anti-PD-1 antibody, a PD-1 inhibitor, or a PD-L1 inhibitor as described herein, such as an anti-CSF1R antibody and an anti-PD-1 antibody, such as one or two doses, and then determining that the expression level of the at least one marker gene has increased following the administration, followed by further administration of the treatment, such as an anti-CSF1R antibody and anti-PD-1 antibody, to the subject.

In any of the above methods, the at least one marker gene may comprise: (a) at least one pro-inflammatory marker gene comprising: CCL19, CCL5, CCL8, CCR7, CD86, CXCL10, CXCL11, CXCL13, CXCL9, IFNG, IL23A, STAT1, and TNF, (b) at least one B cell marker comprising: CD72, CD79A, CD79B, MS4A1, and TNFRSF17, (c) at least one CD8 T cell marker comprising: CD3D, CD8A, and CD8B, (d) at least one effector T cell cytolytic marker comprising: GZMM, APOL3, CTSW, GNLY, GZMA, GZMH, KLRB1, KLRD1, KLRK1, NKG7, and PRF1; and/or (e) at least one effector T cell receptor marker comprising: BTLA, CD244, CD96, CTLA4, LAG3, PDCD1, TIGIT, and FOXP3. In the above methods, the at least one marker gene may further comprise measuring the expression level of one or more of CSF1R, CSF-1 and IL-34, wherein increases in CSF-1 and IL-34 expression levels following administration indicate that the subject is responsive to the treatment while a decrease in CSF1R expression level indicates that the subject is not responsive to the treatment. In some embodiments, the methods further comprise determining the expression level of one or more anti-inflammatory markers comprising: ARG1, C5AR1, CD14, CD163, CXCR1, CXCR2, IL1A, IL1RN, IL8, MRC1, MSR1, PF4, PPBP, S100A12, S100A8, SAA1, S100A9, and TGFB1. In some embodiments, the levels of these markers do not change or do not increase in subjects responsive to treatment.

In any of the above methods, the expression level of the at least one marker gene may be measured by RNA sequencing of RNA extracted from or present in tumor biopsy samples. In some embodiments, the expression level of the at least one marker gene may be measured at the protein level, such as by immunohistochemistry (IHC) on a tumor sample. In some embodiments, the tumor biopsy samples are obtained from the subject before the start of treatment and after about 4 weeks of treatment (or two doses Q2W).

In some embodiments, the peripheral concentration of CSF1R ligands (CSF-1 and IL34) and/or the level of non-classical monocytes (CD14$^{DIM}$CD16$^{BRIGHT}$; i.e., CD14$^+$CD16$^{++}$) are measured in subjects before and after administration of the combination therapy described above, optionally in conjunction with measurement of the marker gene expression levels above. Changes in peripheral concentrations of CSF1R ligands may be measured by enzyme-linked immunosorbent assay (ELISA) and changes in non-classical monocytes may be measured by flow cytometry, for example. A lower level of peripheral concentration of a CSF1R ligand and/or level of nonclassical monocytes, for example after one or two doses of treatment or 4 weeks on treatment relative to the baseline level prior to the start of the treatment, may indicate that the patient responds to the treatment. Methods of treatment may include measurement of the peripheral concentration of CSF1R ligands and/or the level of nonclassical monocytes.

In some embodiments, the RNA expression levels of CSF1R and/or its ligands CSF-1 and IL34 are measured in subjects before and after administration of the combination therapy described above, optionally in conjunction with measurement of the marker gene expression levels above and/or optionally in conjunction with measurement of the peripheral concentration of these molecules or the level of nonclassical monocytes. Changes in these expression levels may be measured by RNA sequencing of RNA extracted from our found in tumor biopsy samples, for example. In some embodiments, the tumor biopsy samples are obtained from the subject before the start of treatment and after about 4 weeks of treatment (or two doses Q2W). An increase in the expression of CSF-1 and/or IL-34, for example after one or two doses of treatment or 4 weeks on treatment relative to the baseline level prior to the start of the treatment, may indicate that the patient responds to the treatment. An increase in the expression of CSF1R over this same period may indicate that the patient is not responsive.

In any of the above cancer treatment methods, the cancer may have been determined to be MSS and/or has been determined to have a TMB of less than 20, less than 15 or less than 10 mutations/megabase by the Foundation One® CDx™ assay or less than 400, less than 300, or less than 200 missense mutations by WES. In some embodiments, the cancer has been determined to be MSS and to have a TMB of less than 20, less than 15 or less than 10 mutations/megabase by the Foundation One® CDx™ assay or less than 400, less than 300, or less than 200 missense mutations by WES. In some embodiments, the cancer has been determined to have a TMB of less than 15 mutations/megabase by the Foundation One® CDx™ assay or less than 300 missense mutations by WES. In some embodiments, the cancer has been determined to have a TMB of less than 10 mutations/megabase by the Foundation One® CDx™ assay or less than 200 missense mutations by WES.

In some embodiments, the anti-CSF1R antibody may comprise a heavy chain comprising a heavy chain (HC) CDR1 having the sequence of SEQ ID NO: 5, an HC CDR2 having the sequence of SEQ ID NO: 6, and an HC CDR3 having the sequence of SEQ ID NO: 7, and a light chain comprising a light chain (LC) CDR1 having the sequence of SEQ ID NO: 8, a LC CDR2 having the sequence of SEQ ID NO: 9, and a LC CDR3 having the sequence of SEQ ID NO: 10; and the anti-PD-1 antibody may comprise a heavy chain comprising a heavy chain (HC) CDR1 having the sequence of SEQ ID NO: 28, an HC CDR2 having the sequence of SEQ ID NO: 30, and an HC CDR3 having the sequence of SEQ ID NO: 32, and a light chain comprising a light chain (LC) CDR1 having the sequence of SEQ ID NO: 35, a LC CDR2 having the sequence of SEQ ID NO: 37, and a LC CDR3 having the sequence of SEQ ID NO: 39. In some embodiments, the anti-CSF1R antibody is a Fab, an Fv, an scFv, a Fab', or a (Fab')₂ fragment. In some embodiments, the anti-PD-1 antibody is a Fab, an Fv, an scFv, a Fab', or a (Fab')₂ fragment. In some embodiments, the anti-PD-1 antibody heavy chain comprises a heavy chain variable region comprising the sequence of SEQ ID NO: 23 and wherein the anti-PD-1 antibody light chain comprises a light chain variable region comprising the sequence of SEQ ID NO: 25. In some embodiments, the anti-PD-1 antibody comprises a heavy chain comprising the sequence of each of SEQ ID NOs: 23 and 24 and wherein the anti-PD-1 antibody comprises a light chain comprising the sequence of each of SEQ ID NOs: 25 and 26. In some embodiments, the anti-PD-1 antibody is nivolumab or pembrolizumab or PDR001. In some embodiments, the anti-CSF1R antibody comprises a heavy chain variable region comprising the sequence of SEQ ID NO: 11 and wherein the anti-CSF1R antibody comprises a light chain variable region comprising the sequence of SEQ ID NO: 12. In some embodiments, the anti-CSF1R antibody comprises a heavy chain comprising the sequence of SEQ ID NO: 13 and wherein the anti-CSF1R antibody comprises a light chain comprising the sequence of SEQ ID NO: 14. In some embodiments, the anti-CSF1R antibody is cabiralizumab. In some embodiments, the anti-CSF1R antibody is emactuzumab (RG7155), AMG 820, or SNDX 6352 (UCB 6352), or another anti-CSF1R antibody, or is instead a CSF1R inhibitor, or CSF1 inhibitor as described herein, such as a small molecule, e.g., JNJ-40346527 (now PRV-6527), e.g., an anti-CSF1R tyrosine kinase inhibitor, or other modality.

In some embodiments, the anti-PD-1 antibody is administered to the subject before the anti-CSF1R antibody. In some embodiments, the anti-CSF1R antibody is administered from 30 minutes to 120 minutes after the anti-PD-1 antibody. In some embodiments, the anti-PD-1 antibody is infused over a period of 30-60 minutes, and the anti-CSF1R antibody is infused over a period of 30-60 minutes. In some embodiments, the infusion of the anti-CSF1R antibody is initiated 30-120 minutes after the end of the infusion of the anti-PD-1 antibody. In some embodiments, the infusion of the anti-CSF1R antibody is initiated 30-60 minutes (e.g., 30 minutes) after the end of the infusion of the anti-PD-1 antibody. In some embodiments, the subject has previously received a PD-1/PD-L1 inhibitor therapy. In some embodiments, the subject is a PD-1/PD-L1 inhibitor inadequate responder. In some embodiments, the subject is refractory to a PD-1/PD-L1 inhibitor, e.g., after at least 2 doses. In some embodiments, the anti-CSF1R antibody is cabiralizumab and the anti-PD-1 antibody is nivolumab, wherein cabiralizumab is administered at a dose of 4 mg/kg once every two weeks, and wherein nivolumab is administered at a dose of 3 mg/kg once every two weeks. In some embodiments, the cancer is pancreatic cancer, ovarian cancer, renal cancer, malignant glioma, melanoma, non-small cell lung cancer (NSCLC), or squamous cell carcinoma of the head and neck (SCCHN). In some embodiments, the cancer is pancreatic cancer.

The present disclosure also includes a method of determining or predicting responsiveness of a subject with cancer to treatment with a CSF1R or CSF1 inhibitor as described herein, such as an anti-CSF1R antibody, CSF-1 inhibitor, or a CSF-1R inhibitor as described herein, in combination with a PD-1/PD-L1 inhibitor, such as an anti-PD-1 antibody, a PD-1 inhibitor, or a PD-L1 inhibitor as described herein, such as with a combination of an anti-CSF1R antibody and an anti-PD-1 antibody, the method comprising determining the expression level of at least one marker gene before and after the subject is administered at least one dose of the combination treatment, the at least one marker gene comprising one or more of: CCL19, CCL5, CCL8, CCR7, CD86, CXCL10, CXCL11, CXCL13, CXCL9, IFNG, IL23A, STAT1, TNF, CD72, CD79A, CD79B, MS4A1, TNFRSF17, CD3D, CD8A, CD8B, GZMM, APOL3, CTSW, GNLY, GZMA, GZMH, KLRB1, KLRD1, KLRK1, NKG7, PRF1, BTLA, CD244, CD96, CTLA4, LAG3, PDCD1, TIGIT, and FOXP3. A increase in the expression level of the at least one marker gene indicates responsiveness in some embodiments. In any of the above methods, the at least one marker gene comprises: (a) at least one pro-inflammatory marker gene comprising: CCL19, CCL5, CCL8, CCR7, CD86, CXCL10, CXCL11, CXCL13, CXCL9, IFNG, IL23A, STAT1, and TNF, (b) at least one B cell marker comprising: CD72, CD79A, CD79B, MS4A1, and TNFRSF17, (c) at least one CD8 T cell marker comprising: CD3D, CD8A, and CD8B, (d) at least one effector T cell cytolytic marker comprising: GZMM, APOL3, CTSW, GNLY, GZMA, GZMH, KLRB1, KLRD1, KLRK1, NKG7, and PRF1; and/or (e) at least one effector T cell receptor marker comprising: BTLA, CD244, CD96, CTLA4, LAG3, PDCD1, TIGIT, and FOXP3. In some embodiments, methods may further comprise measuring the expression level of one or more of CSF1R, CSF-1 and IL-34, wherein increases in CSF-1 and IL-34 expression levels following administration indicate that the subject is responsive to treatment with the anti-CSF1R antibody and anti-PD-1 antibody while a decrease in CSF1R expression level indicates that the subject is not responsive to treatment with the anti-CSF1R antibody and anti-PD-1 antibody. In some embodiments, the methods further comprise determining the expression level of one or more anti-inflammatory markers comprising: ARG1, C5AR1, CD14, CD163, CXCR1, CXCR2, IL1A, IL1RN, IL8, MRC1, MSR1, PF4, PPBP, S100A12, S100A8, SAA1, S100A9, and TGFB1. In some embodiments, the levels of these markers do not change or do not increase in subjects responsive to treatment with the anti-CSF1R antibody and the anti-PD-1 antibody. In some embodiments, the subject is administered one or two doses of the anti-CSF1R antibody and anti-PD-1 antibody between determinations of the expression level of the at least one marker gene. In some embodiments, the methods further comprise determining the expression level of one or more anti-inflammatory markers comprising: ARG1, C5AR1, CD14, CD163, CXCR1, CXCR2, IL1A, IL1RN, IL8, MRC1, MSR1, PF4, PPBP, S100A12, S100A8, SAA1, S100A9, and TGFB1. In some embodiments, the levels of these markers do not change or do not increase in subjects responsive to treatment with the anti-CSF1R antibody and the anti-PD-1 antibody. In any of the above methods, the expression level of the at least one marker gene may be the RNA expression level, e.g., measured by transcriptome analysis or reverse transcription PCR. In any of the above methods, the cancer may have been determined to be MSS and/or has been determined to have a TMB of less than 20, less than 15 or less than 10 mutations/megabase by the Foundation One® CDx™ assay or less than 400, less than 300, or less than 200 missense mutations by WES. In some embodiments, the cancer has been determined to be MSS and to have a TMB of less than 20, less than 15 or less than 10 mutations/megabase by the Foundation One® CDx™ assay or less than 400, less than 300, or less than 200 missense mutations by WES. In some embodiments, the cancer has been determined to have a TMB of less than 15 mutations/megabase by the Foundation One® CDx™ assay or less than 300 missense mutations by WES. In some embodiments, the cancer has been determined to have a TMB of less than 10 mutations/megabase by the Foundation One® CDx™ assay or less than 200 missense mutations by WES.

In any of the above methods, the expression level of the at least one marker gene may be measured by RNA sequencing of RNA extracted from or present in tumor biopsy samples. In some embodiments, the expression level of the at least one marker gene may be measured at the protein level, such as by immunohistochemistry (IHC) on a tumor sample. In some embodiments, the tumor biopsy samples are obtained from the subject before the start of treatment and after about 4 weeks of treatment (or two doses Q2W).

In some embodiments, determining or predicting responsiveness involves measuring the peripheral concentration of CSF1R ligands (CSF-1 and IL34) and/or the level of non-classical monocytes ($CD14^{DIM}CD16^{BRIGHT}$; i.e., $CD14^+$ $CD16^{++}$) in subjects before and after administration of the combination therapy described above, optionally in conjunction with measurement of the marker gene expression levels above. Changes in peripheral concentrations of CSF1R ligands may be measured by enzyme-linked immunosorbent assay (ELISA) and changes in nonclassical monocytes may be measured by flow cytometry, for example. A lower level of peripheral concentration of a CSF1R ligand and/or level of nonclassical monocytes, for example after one or two doses of treatment or 4 weeks on treatment relative to the baseline level prior to the start of the treatment, may indicate that the patient responds to the treatment. Methods of treatment may include measurement of the peripheral concentration of CSF1R ligands and/or the level of nonclassical monocytes.

In some embodiments, the RNA expression levels of CSF1R and/or its ligands CSF-1 and IL34 are measured in subjects before and after administration of the combination therapy described above, optionally in conjunction with measurement of the marker gene expression levels above and/or optionally in conjunction with measurement of the peripheral concentration of these molecules or the level of nonclassical monocytes, as a means of determining or predicting responsiveness to treatment with the combination. Changes in these expression levels may be measured by RNA sequencing of RNA extracted from our found in tumor biopsy samples, for example. In some embodiments, the tumor biopsy samples are obtained from the subject before the start of treatment and after about 4 weeks of treatment (or two doses Q2W). An increase in the expression of CSF-1 and/or IL-34, for example after one or two doses of treatment or 4 weeks on treatment relative to the baseline level prior to the start of the treatment, may indicate that the patient responds to the treatment. An increase in the expression of CSF1R over this same period may indicate that the patient is not responsive.

In some embodiments, the anti-CSF1R antibody may comprise a heavy chain comprising a heavy chain (HC) CDR1 having the sequence of SEQ ID NO: 5, an HC CDR2 having the sequence of SEQ ID NO: 6, and an HC CDR3 having the sequence of SEQ ID NO: 7, and a light chain comprising a light chain (LC) CDR1 having the sequence of SEQ ID NO: 8, a LC CDR2 having the sequence of SEQ ID NO: 9, and a LC CDR3 having the sequence of SEQ ID NO: 10; and the anti-PD-1 antibody may comprise a heavy chain comprising a heavy chain (HC) CDR1 having the sequence of SEQ ID NO: 28, an HC CDR2 having the sequence of SEQ ID NO: 30, and an HC CDR3 having the sequence of SEQ ID NO: 32, and a light chain comprising a light chain (LC) CDR1 having the sequence of SEQ ID NO: 35, a LC CDR2 having the sequence of SEQ ID NO: 37, and a LC CDR3 having the sequence of SEQ ID NO: 39. In some embodiments, the anti-CSF1R antibody is a Fab, an Fv, an scFv, a Fab', or a $(Fab')_2$ fragment. In some embodiments, the anti-PD-1 antibody is a Fab, an Fv, an scFv, a Fab', or a $(Fab')_2$ fragment. In some embodiments, the anti-PD-1 antibody heavy chain comprises a heavy chain variable region comprising the sequence of SEQ ID NO: 23 and wherein the anti-PD-1 antibody light chain comprises a light chain variable region comprising the sequence of SEQ ID NO: 25. In some embodiments, the anti-PD-1 antibody comprises a heavy chain comprising the sequence of each of SEQ ID NOs: 23 and 24 and wherein the anti-PD-1 antibody comprises a light chain comprising the sequence of each of SEQ ID NOs: 25 and 26. In some embodiments, the anti-PD-1 antibody is nivolumab or pembrolizumab or PDR001. In some embodiments, the anti-CSF1R antibody comprises a heavy chain variable region comprising the sequence of SEQ ID NO: 11 and wherein the anti-CSF1R antibody comprises a light chain variable region comprising the sequence of SEQ ID NO: 12. In some embodiments, the anti-CSF1R antibody comprises a heavy chain comprising the sequence of SEQ ID NO: 13 and wherein the anti-CSF1R antibody comprises a light chain comprising the sequence of SEQ ID NO: 14. In some embodiments, the anti-CSF1R antibody is cabiralizumab. In some embodiments, the anti-CSF1R antibody is emactuzumab (RG7155), AMG 820, or SNDX 6352 (UCB 6352), or another anti-CSF1R antibody, or is instead a CSF1R inhibitor, or CSF1 inhibitor as described herein, such as a small molecule, e.g., JNJ-40346527 (now PRV-6527), e.g., an anti-CSF1R tyrosine kinase inhibitor, or other modality.

In some embodiments, the subject has previously received a PD-1/PD-L1 inhibitor therapy. In some embodiments, the subject is a PD-1/PD-L1 inhibitor inadequate responder. In some embodiments, the subject is refractory to a PD-1/PD-L1 inhibitor, e.g., after at least 2 doses. In some embodiments, the anti-CSF1R antibody is cabiralizumab and the anti-PD-1 antibody is nivolumab, wherein cabiralizumab is administered at a dose of 4 mg/kg once every two weeks, and wherein nivolumab is administered at a dose of 3 mg/kg once every two weeks. In some embodiments, the cancer is pancreatic cancer, ovarian cancer, renal cancer, malignant glioma, melanoma, non-small cell lung cancer (NSCLC), or squamous cell carcinoma of the head and neck (SCCHN). In some embodiments, the cancer is pancreatic cancer.

Routes of Administration and Carriers

In various embodiments, antibodies may be administered in vivo by various routes, including, but not limited to, oral, intra-arterial, parenteral, intranasal, intravenous, intramuscular, intracardiac, intraventricular, intratracheal, buccal, rectal, intraperitoneal, intradermal, topical, transdermal, and intrathecal, or otherwise by implantation or inhalation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols.

In various embodiments, compositions comprising antibodies are provided in formulations with a wide variety of pharmaceutically acceptable carriers (see, e.g., Gennaro, *Remington: The Science and Practice of Pharmacy with Facts and Comparisons: Drugfacts Plus*, 20$^{th}$ ed. (2003); Ansel et al., *Pharmaceutical Dosage Forms and Drug Delivery Systems*, 7$^{th}$ ed., Lippencott Williams and Wilkins (2004); Kibbe et al., *Handbook of Pharmaceutical Excipients*, 3$^{rd}$ ed., Pharmaceutical Press (2000)). Various pharmaceutically acceptable carriers, which include vehicles, adjuvants, and diluents, are available. Moreover, various pharmaceutically acceptable auxiliary substances, such as Ph adjusting and buffering agents, tonicity adjusting agents, stabilizers, wetting agents and the like, are also available. Non-limiting exemplary carriers include saline, buffered saline, dextrose, water, glycerol, ethanol, and combinations thereof.

In various embodiments, compositions comprising antibodies may be formulated for injection, including subcutaneous administration, by dissolving, suspending, or emulsifying them in an aqueous or nonaqueous solvent, such as vegetable or other oils, synthetic aliphatic acid glycerides, esters of higher aliphatic acids, or propylene glycol; and if desired, with conventional additives such as solubilizers, isotonic agents, suspending agents, emulsifying agents, stabilizers and preservatives. In various embodiments, the compositions may be formulated for inhalation, for example, using pressurized acceptable propellants such as dichlorodifluoromethane, propane, nitrogen, and the like. The compositions may also be formulated, in various embodiments, into sustained release microcapsules, such as with biodegradable or non-biodegradable polymers. A non-limiting exemplary biodegradable formulation includes poly lactic acid-glycolic acid polymer. A non-limiting exemplary non-biodegradable formulation includes a polyglycerin fatty acid ester. Certain methods of making such formulations are described, for example, in EP 1 125 584 A1.

Pharmaceutical packs and kits comprising one or more containers, each containing one or more doses of an antibody or combination of antibodies are also provided. In some embodiments, a unit dosage is provided wherein the unit dosage contains a predetermined amount of a composition comprising an antibody or combination of antibodies, with or without one or more additional agents. In some embodiments, such a unit dosage is supplied in single-use prefilled syringe for injection, for example, or as a kit. In various embodiments, the composition contained in the unit dosage may comprise saline, sucrose, or the like; a buffer, such as phosphate, or the like; and/or be formulated within a stable and effective Ph range. Alternatively, in some embodiments, the composition may be provided as a lyophilized powder that may be reconstituted upon addition of an appropriate liquid, for example, sterile water. In some embodiments, the composition comprises one or more substances that inhibit protein aggregation, including, but not limited to, sucrose and arginine. In some embodiments, a composition of the invention comprises heparin and/or a proteoglycan.

Further Combination Therapy

Antibodies may be administered alone or with other modes of treatment. They may be provided before, substantially contemporaneous with, or after other modes of treatment, for example, surgery, further chemotherapy, radiation therapy, or the administration of a biologic, such as another therapeutic antibody. In some embodiments, the cancer has recurred or progressed following a therapy selected from surgery, chemotherapy, and radiation therapy, or a combination thereof.

For treatment of pancreatic cancer, as discussed herein, the antibodies may be administered in conjunction with one or more additional anti-cancer agents, such as the chemotherapeutic agent, growth inhibitory agent, anti-angiogenesis agent and/or anti-neoplastic composition. Nonlimiting examples of chemotherapeutic agent, growth inhibitory agent, anti-angiogenesis agent, anti-cancer agent and anti-neoplastic composition that can be used in combination with the antibodies of the present invention are provided herein under "Definitions."

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Combination of Cabiralizumab and Nivolumab in Advanced Pancreatic Cancer Patients As part of a phase 1a dose escalation study, NCT02526017, a complete protocol for which is provided below in Example 3 and summarized in Example 2, patients with advanced solid tumors were treated with cabiralizumab at dosages of 1, 2, 4, and 6 mg/kg alone and then in combination with nivolumab 3 mg/kg. Both antibodies were administered intravenously once every two weeks (IV Q2W), in a 3+3+3 design. Dose expansion is ongoing across a range of solid tumor types. As of August 2017, 205 patients have been treated with a combination of cabiralizumab and nivolumab. The majority received 4 mg/kg Q2W cabiralizumab plus 3 mg/kg Q2W nivolumab. Cabiralizumab, alone or with nivolumab, demonstrated target-mediated clearance and dose-dependent increase in exposure, and pharmacodynamic activity as evidenced by reduced circulating CD14$^+$ CD16$^+$ nonclassical monocytes. Grade 3-5 treatment-related adverse events (TRAEs) attributed to cabiralizumab occurred in 43% of patients, with 13% of patients discontinuing due to adverse events (AEs). Elevations in creatinine phosphokinase (14%) and aspartate aminotransferase (AST) (7%) were among the most common grade 3 TRAEs but were secondary to cabiralizumab's depletion of macrophages and were reversible without significant clinical sequelae.

Among the cohort of prior chemotherapy-treated and immunotherapy-naive patients with pancreatic cancer, 31 were efficacy evaluable. There were 3 confirmed partial responses in microsatellite-stable patients (293, 275, and 168 days on study) and 1 prolonged stable disease (182 days); 1 patient treated beyond progressive disease experienced >40% reduction in baseline target lesions (247 days on study). The 6-month disease control rate was 13%, and objective response rate was 10%.

Based on these data thus far, cabiralizumab plus nivolumab demonstrated a tolerable safety profile across a several cohorts and promising preliminary antitumor activity in pancreatic cancer. These results show a potential immunotherapeutic strategy to treat patients with tumors resistant to anti-PD-1 blockade.

Example 2

Combination Therapy with an Anti-CSF1R Antibody and an Anti-PD-1 Antibody

This example summarizes a Phase 1 trial protocol for a combination of cabiralizumab and nivolumab, and was previously disclosed as Example 6 in International Publication No. WO2016/069727.

Anti-CSF1R antibody cabiralizumab (comprising the heavy and light chain sequences of SEQ ID NOs: 13 and 14) is administered in combination with anti-PD-1 antibody nivolumab (comprising the heavy and light chain sequences of SEQ ID NOs: 23 and 24 and 25 and 26) at increasing dosages in subjects with a variety of tumor types, including NSCLC, melanoma, SCCHN, bladder cancer, and pancreatic cancer. The anti-CSF1R antibody is administered at doses ranging from 1 mg/kg to 10 mg/kg. The anti-CSF1R antibody and the anti-PD-1 antibody are dosed concurrently every 2 weeks.

Anti-CSF1R antibody and anti-PD-1 antibody are administered to three subsets of patients with melanoma: naïve (have never received either antibody), acquired resistance (have progressed after an initial anti-PD-1 antibody response), and de novo resistance (did not respond to PD-1/PD-L1 inhibitor therapy).

Pre- and post-treatment core needle biopsies are obtained in a subset of subjects to evaluate potential changes in immune cells, stroma, and tumor cells after treatment. In addition to hematoxylin and eosin staining to assess the overall cellularity of the tumor, specific assays are used to monitor macrophage numbers and subtypes, Patients are additionally monitored for overall response, immune-related response, and overall survival.

For some, most, or all patients, the number of CD8+ T cells increases after treatment with the combination and/or the number of Treg cells decreases after treatment with the combination. In addition, for some, most, or all patients, the number of tumor enhancing M2 macrophages decreases and the number of tumor suppressing M1 macrophages increases after treatment with the combination. Finally, for some, most, or all patients, tumor necrosis increases after treatment with the combination.

Example 3

Summary of a Monotherapy and Combination Therapy Clinical Trial with an Anti-CSF1R Antibody and an Anti-PD-1 Antibody This example provides a more detailed Phase 1 trial protocol for a combination of cabiralizumab and nivolumab, and was previously disclosed as Example 7 in International Publication No. WO2016/069727.

Anti-CSF1R antibody cabiralizumab is given as a monotherapy and in combination with the anti-PD-1 antibody nivolumab in patients with selected advanced cancers and who have not previously received a CSF1R pathway inhibitor in an open-label, multicenter, dose escalation and dose expansion study. Nivolumab has previously been approved for use in melanoma, metastatic NSCLC, and in combination with ipilmumab, an anti-CTLA-4 antibody, for the treatment of metastatic melanoma. For the combination arms of the study, cabiralizumab and nivolumab will be given on Day 1 of each 14-day treatment cycle; nivolumab will be given as an IV infusion over 30 minutes first, with a 30-minute rest between 2 infusions, followed by a 30-minute cabiralizumab IV infusion.

The first phase of the study (Phase 1a) comprises two cabiralizumab monotherapy reference cohorts (1aM1 and 1aM2) and three dose-escalation cohorts of cabiralizumab in combination with nivolumab (1aC1, 1aC2, and 1aC3). The second phase of the study (Phase 1b) comprises eight cohorts (1b1 through 1b8) across six cancer types. Approximately 270 total patients will take part in the study, 30 in the first phase and 240 in the second phase with 30 in each of the 8 cohorts of the second phase. Individual patients will be enrolled in no more than one of the study arms 1aM, 1aC, or 1b. FIG. 1 shows a schematic of the study design.

In Phase 1a, monotherapy patients in cohorts 1aM1 and 1aM2 are given 2, 4, or 6 mg/Kg cabiralizumab once every 14 days (q2w). Combination therapy cohorts 1aC1, 1aC2, and 1aC3 are given 1, 2, or 4 mg/Kg cabiralizumab and 3 mg/Kg nivolumab once every 14 days (q2w). Patients in the 1aM1 and 1aC1 cohorts are treated for a total of two 14-day cycles within a 28-day period, followed by the other cohorts. A 3 mg/Kg cabiralizumab and 3 mg/Kg nivolumab cohort may also be included. In Phase 1a, patients may be included in either the monotherapy or combination therapy cohorts if they have a histologically or cytologically confirmed solid tumor that is locally recurrent or metastatic and has progressed following standard treatment or is not appropriate for standard treatment. Patients with any prior exposure to any PD-1 pathway targeting drug are excluded.

In Phase 1b, eight patient cohorts are treated, as follows.

Cohort 1b1: NSCLC (Anti-PD-1 Therapy naïve, Second or Third Lines).

This cohort may include patients with histologically or cytologically documented squamous or non-squamous NSCLC who present with Stage IIIB or IV disease (according to version 7 of the international association for the Study of Lung Cancer Staging manual in Thoracic oncology) and with recurrent or progressive disease following multi-modal therapy (radiation therapy, surgical resection or definitive chemoradiation) for locally advanced or metastatic disease. It may include patients with progression or recurrence during/after a platinum doublet-based chemotherapy regimen for advanced or metastatic disease. Patients with any prior exposure to any PD-1 pathway targeting drug are excluded.

Cohort 1b2: NSCLC (Patients Refractory to Anti-PD-1 Targeting Drugs).

This cohort may include patients with histologically or cytologically documented NSCLC who present with Stage IIIB locally advanced or Stage IV disease, and patients with radiological evidence of disease progression during treatment with a PD-1 pathway targeting drug that did not produce a clinical response (i.e., neither CR nor PR) and with progressive disease as the best response. In the context of this cohort, refractory patients are patients that have had no clinical response after receiving at least 2 doses of any PD-1 targeting drug. Patients that are intolerant to any PD-1 pathway targeting drug are excluded, where intolerance is defined as any treatment-related Grade 4 adverse event, or any treatment-related Grade 2 or 3 adverse event that is unacceptable to the patient and persists despite standard countermeasures.

Cohort 1b3: Melanoma (Anti-PD-1 Therapy Naïve)

This cohort may include patients with histologically or cytologically documented Stage III or IV melanoma as per the American Joint Committee on Cancer (AJCC) staging system who are either refractory to, intolerant to, or have refused, standard therapy for treatment of metastatic melanoma. Included patients may demonstrate objective evidence of disease progression despite treatment with a BRAF inhibitor or may be BRAF wild-type. Patients with any prior exposure to any PD-1 pathway targeting drug, who are BRAF mutant, or whose BRAF mutational status is not known or cannot be determined are excluded.

Cohort 1b4: Melanoma (Refractory or Relapsed on Anti-PD-1 Targeting Drug)

Patients in this cohort may have histologically or cytologically documented unresectable Stage III or IV melanoma as per the AJCC staging system. Included patents may show radiological evidence of disease progression during treatment with a Checkpoint inhibitor or a PD-1 targeting drug that did not produce a clinical benefit, or may show, while receiving treatment with a PD-1 targeting drug, progressive disease as the best response or disease progression after an initial clinical benefit. In the context of this cohort, refractory patients are patients that have had no clinical response after receiving at least 2 doses of any PD-1 targeting drug. Included patients may demonstrate objective evidence of disease progression despite treatment with a BRAF inhibitor or may be BRAF wild-type. Any prior anticancer therapy including dacarbazine, BRAF inhibitor (if BRAF V600 mutation positive) and/or ipilimumab and palliative radiotherapy are completed at least 3 weeks prior to study drug administration and treatment with a PD-1 targeting drug is discontinued at least 6 weeks prior to first dose of the study drug. Patients that are intolerant to any PD-1 pathway targeting drug as defined above are excluded, as are pateints who are BRAF mutant or whose BRAF mutational status is either unknown or cannot be determined.

Cohort 1b5: Squamous Cell Carcinoma of the Head and Neck (SCCHN) (Second Line)

Patients with histologically or cytologically documented recurrent or metastatic SCCHN (oral cavity, pharynx, larynx), stage III or IV and not amenable to local therapy with curative intent (surgery or radiation therapy with or without chemotherapy) may be included in this cohort. Patients may also have progression or recurrence within 6 months of the last dose of platinum therapy in the adjuvant (i.e. with radiation after surgery), primary (i.e., with radiation), recurrent, or metastatic setting. Clinical progression after platinum therapy is an allowable event for entry and is defined as progression of a lesion at least 10 mm in size that is amenable to caliper measurement (e.g., superficial skin lesion as per RECIST v1.1) or a lesion that has been visualized and photographically recorded with measurements and shown to have progressed. Patients with prior exposure to an anti-PD-1 drug are excluded.

Cohort 1b6: Pancreatic Cancer (Second Line)

Included patients may have histologically or cytologically documented localized or metastatic adenocarcinoma of the pancreas, which has failed (or are not indicated for) standard. therapy. Patients may also have received prior surgery, radiation therapy for the management of locally advanced or metastatic adenocarcinoma of the pancreas providing that disease progression has been documented. All toxicities should be resolved, and the last fraction of radiation treatment was completed at least 4 weeks prior to first study drug administration. Patients with prior exposure to an anti-PD-1 drug are excluded.

Cohort 1b7: Colorectal Cancer (Third Line)

Included patients may have histologically or cytologically documented adenocarcinoma of colon or rectum, and they may have metastatic colorectal cancer with documented disease progression after the last administration of standard therapies or intolerance to standard therapies (and approved therapies had to include a fluoropyrimidine, oxaliplatin, irinotecan, bevacizumab, and, if KRAS wild-type, cetuximab or panitumumab). Patients with prior exposure to an anti-PD-1 drug are excluded.

Cohort 1b8: Malignant Glioma (First Recurrence)

Patients in this cohort may have histologically or cytologically documented advanced World Health Organization (WHO) Grade IV malignant glioma (glioblastoma or gliosarcoma) and may have had previous treatment with surgery, radiotherapy and temozolomide. Patients may have a documented first recurrence by diagnostic biopsy or contrast-enhanced MRI performed within 21 days of first study drug administration per Response Assessment in Neurooncology (RANO) criteria. Patients are excluded if they have received prior treatment with bevacizumab or another VEGF or VEGF receptor targeting agent, more than 1 recurrence of glioblastoma or gliosarcoma, or prior exposure to any PD-1 targeting drug.

Monotherapy patients are administered cabiralizumab as a 30 minute IV infusion. Combination therapy patients receive the nivolumab infusion first at a dose of 3 mg/kg as a 30-minute IV infusion, on Day 1 of each 14-day treatment cycle. They receive cabiralizumab following the nivolumab infusion on Day 1 of each 14-day treatment cycle, with a 30-minute rest between the two infusions.

A biopsy at the tumor site is collected prior to Day 1 of the first cycle of the study and again on Day 29. Patients are also assessed for overall survival post-study, progression-free survival, and duration of response for those patients with confirmed responses, based on the criteria of RECIST v1.1. CT/MRI (chest, abdomen, pelvis, and brain) are performed before Day 1, during treatment, and following the study, and measurements of tumor burden are taken. The primary response parameter is the objective response rate, which is the number of patients with complete or partial response divided by the total number of treated patients with measurable disease at baseline. Tumor response is assessed using RECIST v1.1, Appendix F.

Example 4

Complete Clinical Trial Phase 1a and 1b Protocol—Monotherapy and Combination Therapy Clinical Trial with an Anti-CSF1R Antibody (Cabiralizumab) and an Anti-PD-1 Antibody (Nivolumab)

This example summarizes a Phase 1 trial protocol for a combination of cabiralizumab and nivolumab, and was previously disclosed as Example 8 in International Publication No. WO2016/069727.

1 INTRODUCTION AND STUDY RATIONALE

Colony Stimulating Factor 1 Receptor and Tumor-Associated Macrophages

Macrophages are myeloid-derived cells that carry out a variety of functions in the human body. They can colonize tissues (and tumors) through two distinct mechanisms: hematogenous seeding from circulating monocytes or local self-renewal in the form of tissue-resident macrophages (Lavin, 2013). Recent studies have shown that macrophages exert their physiological effect within, and play roles unique to, the tissues in which they are active (Lavin, 2014). Macrophage regulation is complex as these cells actively secrete and respond to multiple cytokine and chemokine gradients within their local environment.

Tumor-associated macrophages (TAMs) are among the most abundant immune cell types in the tumor microenvironment. Substantial evidence suggests that TAMs are polarized towards an anti-inflammatory phenotype (M2) that inhibits anti-tumor immune responses (Noy, 2014) through both cell-cell contact and soluble factors such as immunosuppressive cytokines. Consistent with this, increased levels of TAMs are associated with a poor prognosis in a majority of cancers (Komohara, 2014).

Following treatment with anti-CSF1R agents, the macrophages that have not been depleted may be repolarized from an M2 immunosuppressive state to an M1 anti-tumor state which would support T-cell responses. This conversion, associated with concurrent treatment modalities, such as anti-PD-1 treatment, could have an increased effect on reduction of tumor growth (Ruffell, 2015).

Response rates in ongoing PD-L1 studies have been shown to correlate with the concentration of PD-1/PD-L1 in the tumor stroma (Tumeh, 2014). Of note, there is also a significant amount of macrophages in the tumor stroma as recruitment of monocytes into the tumor stroma leads to their development into suppressive M2 macrophages. The association of monocytes and macrophages with PD-L1 has been shown to suppress tumor-specific T-cell immunity and correlate with poor survival in patients. Predictably, blockade of monocyte-associated PD-L1 positive cells in vivo was demonstrated to improve tumor-specific T-cell immunity. In vitro studies have also shown that activated monocytes expressing PD-L1 demonstrate considerable prevention of tumor-specific T-cell proliferation, cytokine production, and cytotoxic potential (Kuang, 2009).

Colony stimulating factor 1 receptor (CSF1R) signaling plays a fundamental role in the differentiation, maintenance, and function of macrophages and a subset of other myeloid lineage cells that includes monocytes, and osteoclasts (Hamilton, 2013). The two known ligands for CSF1R are CSF1 and IL34. Both of these agonists bind to overlapping regions of CSF1R with similar affinity (Masteller, 2014), even though they have little amino acid homology in common. Mice lacking CSF1R have deficiencies in macrophages, underscoring the essential role of the CSF1R pathway in the biology of this cell type (Dai, 2002). Pharmacologic treatments that block CSF1R in cancer settings are expected to reduce or reprogram TAMs and reduce immune suppression. Overall, this could produce a tumor microenvironment that is more conducive to immune-based anti-cancer therapies.

Cabiralizumab is a recombinant, humanized immunoglobulin G4 (IgG4) monoclonal antibody that binds to human CSF1R. The interaction of Cabiralizumab and CSF1R antagonizes the binding of both CSF1 and IL34 to CSF1R, thereby preventing receptor activation. Cabiralizumab inhibits both CSF1 and IL34-induced CSF1R phosphorylation in a cell line engineered to overexpress CSF1R (CHO-CSF1R), demonstrating experimentally that Cabiralizumab blocks the activation of ligand-induced CSF1R signaling pathways. Cabiralizumab also inhibits CSF1 and IL34-induced proliferation and survival of peripheral blood monocytes in vitro, demonstrating that Cabiralizumab inhibits not only the initiation of CSF1 and IL34 signaling pathways, but also the subsequent physiologic responses of primary human monocytes to these ligands.

Taken together, these and other emerging data suggest that blocking CSF1R with Cabiralizumab treatment could alleviate the immunosuppressive tumor environment that is generated by TAMs and could improve the efficacy of immune-based anti-cancer therapies.

PD-1

Programmed Cell Death-1 (PD-1; CD279) is a cell surface signaling receptor that delivers inhibitory signals that regulate the balance between T-cell activation and tolerance by interacting with its ligands, PD-L1 (CD274; B7-H1) and PD-L2 (B7-DC/CD273). It is a 55 kD type I transmembrane protein that is a member of the CD28 family of T-cell costimulatory receptors, which also includes inducible co-stimulator (ICOS), cytotoxic T lymphocyte antigen-4 (CTLA-4), and B- and T-lymphocyte attenuator (BTLA) (Freeman, 2000). PD-1 contains an intracellular membrane proximal immunoreceptor tyrosine inhibitory motif (ITIM) and a membrane distal immunoreceptor tyrosine-based switch motif (ITSM). PD-1 is primarily expressed on activated T cells, B cells, and myeloid cells (Nishimura, 2001a). Its ligands, PD-L1 and PD-L2, have been shown to downregulate T-cell activation upon binding to PD-1 in both murine and human systems (Carter, 2002; Latchman, 2001). PD-1 delivers a negative signal by the recruitment of SHP-2 to the phosphorylated tyrosine residue in the ITSM in its cytoplasmic region (Chemnitz, 2004; Sheppard, 2004).

Evidence for a negative regulatory role of PD-1 comes from studies of PD-1-deficient mice, which develop various autoimmune phenotypes, including dilated cardiomyopathy and a lupus-like syndrome with arthritis and nephritis (Nishimura, 1999; Nishimura, 2001b; Okazaki, 2003). The emergence of these autoimmune phenotypes is dependent on the genetic background of the mouse strain; many of these phenotypes emerge at different times and show variable penetrance. In addition to the phenotypes of null mutations, PD-1 inhibition by antibody-mediated blockade in several murine models has been found to play a role in the development of autoimmune diseases such as encephalomyelitis, graft-versus-host disease, and type I diabetes (Ansari, 2003; Blazar, 2003; Salama, 2003). Taken together, these results suggest that PD-1 blockade has the potential to activate anti-self T-cell responses, but these responses are variable and dependent upon various host genetic factors. Thus, PD-1 deficiency or inhibition is not accompanied by a universal loss of tolerance to self-antigens.

The PD-1 targeting agent, nivolumab has been clinically tested in several tumor types including NSCLC, melanoma, and renal cell carcinoma (RCC) as a single agent or in combination with other treatments. Some of the efficacy data from the nivolumab Investigator's Brochure (IB) are shown in Table 1, below. Nivolumab as a single agent has remarkable durable efficacy in a subpopulation of patients. The enhanced effect of nivolumab combinations suggests the potential for opportunities with further benefits for patients as a combination regimen with other untested agents.

Nivolumab is currently FDA-approved for unresectable or metastatic melanoma and disease progression following ipilimumab and, if BRAF V600 mutation positive, a BRAF inhibitor. It is also approved for metastatic squamous non-small cell lung cancer (NSCLC) with progression on or after platinum-based chemotherapy.

but combining PD-1 blockade with CSF1R inhibition potently elicited tumor regression even in large, established tumors.

TABLE 1

Summary of nivolumab clinical efficacy data in melanoma, NSCLC, and RCC

| Study Number | Study Drugs | Tumor Type | Response ORR | DOR | OS |
|---|---|---|---|---|---|
| MDX1106-03 | Nivolumab | NSCLC | 17% | 17 months | 24% @ 24 mo |
| CA209012 | Nivolumab | NSCLC | 30% | NR | — |
|  | Nivolumab + ipilimumab | NSCLC | 13-20% | NR | — |
|  | Nivolumab + chemotherapy | NSCLC | 33-47% | 25.4-45 weeks | — |
|  | Nivolumab + erlotinib | NSCLC | 19% | NR | — |
| CA209017[a] | Nivolumab | NSCLC | — | — | 9.2 months |
| CA209063[b] | Nivolumab | NSCLC | 14.5% | NR | — |
| MDX1106-03 | Nivolumab | Melanoma | 31% | >6 months | 48% @ 24 mo |
| CA209004 | Nivolumab + ipilimumab | Melanoma | 42-43% | — | 85% @ 12 mo |
| CA209037[c] | Nivolumab | Melanoma | 31.7% | — | — |
| CA209038 | Nivolumab | Melanoma | 18-32% | — | — |
| MDX1106-03 | Nivolumab | RCC | 21% | >6 months | 48% @ 24 mo |
| CA209010 | Nivolumab | RCC | 20-22% | — | 18.2 months |
| CA209016 | Nivolumab + ipilimumab | RCC | 43-48% | — | — |
|  | Nivolumab + sunitinib | RCC | 52% | — | — |
|  | Nivolumab + pazopanib | RCC | 45% | — | — |

[a]Opdivo Package Insert, 2015
[b]Rizvi, 2015
[c]Weber, 2015

1.1 Rationale for Cabiralizumab and Nivolumab Combination Therapy

Cabiralizumab is a humanized monoclonal antibody directed against CSF1R. Targeting the CSF1R pathway with antibodies or small molecule inhibitors has been shown to be effective in syngeneic mouse tumor models. In an MC38 colon adenocarcinoma model in mice, a CSF1R targeting antibody resulted in a significant reduction of TAMs, which was accompanied by a positive shift of the CD8$^+$ to CD4$^+$ ratio towards cytotoxic CD8$^+$ T cells. In a recent clinical study, RG7155 (a CSF1R targeting antibody) was tested in patients with solid tumors and was shown to substantially reduce CSF1R$^+$CD163$^+$ macrophages in tumors (Ries, 2014). This reduction in macrophages was also associated with a decrease in FOXP3$^+$ regulatory T cells. These data suggest that other immune effector cells were indirectly influenced by CSF1R blockade. In a mouse proneural glioblastoma multiforme (GBM) model, small molecule inhibition of CSF1R significantly increased survival and regressed established tumors (Pyonteck, 2013). In this model, TAMs were not depleted, but instead converted to a more pro-inflammatory phenotype in the presence of CSF1R inhibition.

In an orthotopic pancreatic ductal adenocarcinoma (PDAC) model, CSF1R pathway blockade with a small molecule or an anti-CSF1 antibody selectively decreased immunosuppressive TAMs, subsequently reducing immunosuppression. This decrease in immunosuppressive TAMs enabled the remaining pro-inflammatory TAMs to support antigen presentation and bolster the anti-tumor T-cell response (Zhu, 2014). This, in turn, led to an increased interferon response that upregulated T-cell checkpoint inhibitors, including PD-L1, on tumor cells. This counter-regulation served to limit the anti-tumor T-cell response through engagement of the T-cell inhibitor PD-1. Importantly, anti-PD-1 treatment was able to overcome the PD-L1-mediated inhibition. Targeting PD-1 as a single agent showed limited efficacy in restraining PDAC tumor growth, Together, these data suggest that reprogramming the TAM compartment in tumors via Cabiralizumab-mediated CSF1R blockade could reduce immunosuppressive TAMs in the tumor microenvironment and improve the efficacy of checkpoint-based immunotherapies such as nivolumab.

1.2 Rationale for Cabiralizumab/Nivolumab Combination Therapy in Selected Tumor Types TAMs can potently suppress anti-tumor immune responses. CSF1R is a cell surface receptor that is expressed on TAMs and regulates their survival and function. CSF1R-blocking antibodies have been shown to reduce TAMs in both murine and human tumors (Ries, 2014). TAMs are present in many human cancers suggesting that CSF1R blocking antibodies, such as Cabiralizumab, could be used to treat multiple tumor types. In addition, TAMs have been shown to correlate with poor prognosis in a number of cancers, including lung, pancreatic, head and neck, and melanoma, among others (Komohara, 2014). Furthermore, analysis of The Cancer Genome Atlas shows high correlation of CSF1R with PD-1/PD-L1 co-expression, and T-cell signatures in head and neck, lung, and melanoma cancers, as well as others. In preclinical models, CSF1R inhibition has also been shown to alter macrophage polarization and block glioma progression (Pyonteck, 2013). CSF1R blockade also reduces TAMs and synergizes with PD-1 and CTLA4 checkpoint blockade in pancreatic cancer models (Zhu, 2014). It was also shown that colorectal tumor cells express relatively lower levels of PD-L1 compared to melanoma or lung cancers and that the levels of PD-L1 observed are present on infiltrating myeloid cells (Llosa, 2015).

Nivolumab is currently being tested in multiple tumor types, including all of the tumor types proposed for the Phase 1b portion of this study. As the nivolumab data mature, they will help inform the Phase 1b expansion of this study into selected tumor types.

In addition to the ongoing studies, nivolumab has been approved for use in melanoma and squamous NSCLC. The melanoma approval was based on the results of the CheckMate 037 study. In this study, the efficacy and safety of nivolumab were compared with investigator's choice of chemotherapy (ICC) as a second-line or later-line treatment in patients with advanced melanoma. In this study, 272 patients were randomized to nivolumab and 133 to ICC. Confirmed objective responses were reported in 32% of the first 120 patients in the nivolumab group versus 11% of patients in the ICC group. Grade 3-4 adverse events attributed to nivolumab included increased lipase, increased ALT, anemia, and fatigue (1% each); for ICC, these included neutropenia (14%), thrombocytopenia (6%), and anemia (5%). There were also Grade 3-4 drug-related SAEs in 5% of nivolumab-treated patients and 9% of patients in the ICC group. No treatment-related deaths occurred (Weber, 2015).

The approval in NSCLC for nivolumab was based on the results of the CheckMate 017 and CheckMate 063 studies. CheckMate 017 enrolled patients with metastatic squamous NSCLC who had experienced disease progression during or after one prior platinum doublet-based chemotherapy regimen. OS with nivolumab treatment was 9.2 months, versus 6.0 months with docetaxel (Opdivo Package Insert, 2015). CheckMate 063 assessed the activity of nivolumab in patients with advanced, refractory, squamous NSCLC. The study enrolled and treated 117 patients. Of these, 14.5% of patients had an objective response as assessed by an independent radiology review committee and 26% had stable disease. Median time to response was 3.3 months and median duration of response was not reached. Of the 17 responses, 77% were ongoing at the time of analysis. Of the 117 patients, 17% reported Grade 3-4 treatment-related AEs, including: fatigue (4%), pneumonitis (3%), and diarrhea (3%). There were two treatment-associated deaths caused by pneumonia and ischemic stroke that occurred in patients with multiple comorbidities in the setting of progressive disease (Rizvi, 2015).

The data reported above support investigation of Cabiralizumab in combination with nivolumab in melanoma, NSCLC, head and neck, pancreatic, colorectal, and glioma cancers.

1.3 Rationale for Starting Dose for Cabiralizumab Monotherapy and Combination Dose Escalation The Sponsor has already initiated a first-in-human Phase 1 clinical study designed in 3 parts to evaluate safety, PK and biomarkers of single agent Cabiralizumab in healthy volunteers and rheumatoid arthritis (RA) patients (Study FPA008-001). In Parts 1 and 2 of this study, Cabiralizumab was tested in healthy volunteers at doses of 0.2, 1, 3, and 10 mg/kg body weight. In the healthy volunteer group, at 1 mg/kg, 7 subjects received a single dose and 5 subjects received 2 doses; at 3 mg/kg, 10 subjects received a single dose and 2 subjects received 2 doses; at 10 mg/kg, 6 subjects received a single dose of Cabiralizumab. Multiple-dose cohorts were given doses 14 days apart and all subjects were followed up for dose limiting toxicities (DLTs) through a 28-day window.

As of Sep. 23, 2014, 48 subjects have completed Parts 1 and 2 of the study. No DLTs were reported in Parts 1 or 2. All adverse events (AEs) were Grade 1 or 2 and self-limited with the most common Cabiralizumab treatment-related toxicities being pruritus, eyelid edema along with facial swelling, fatigue, and headache. Temporary elevations in serum enzymes such as creatinine kinase (CK), lactate dehydrogenase (LDH), alanine aminotransferase (ALT) and aspartate aminotransferase (AST) were observed.

In the ongoing Part 3 arm of the Phase 1 study, RA patients who did not respond to disease-modifying anti-rheumatic drugs (DMARDs) are participating in an open-label study at different dose levels of Cabiralizumab at 1, 3, and 6 mg/kg body weight. These patients are required to be on a stable weekly dose of methotrexate before and during the study and will receive 2 doses of Cabiralizumab, 14 days apart. In addition to other analyses, the patients are being followed for safety, pharmacokinetics (PK), and pharmacodynamics (PD) after the 2-dose regimen.

In summary, 36 healthy volunteers and 6 RA patients have received Cabiralizumab to date, no DLTs were reported in Parts 1 or 2, and no significant treatment-related toxicities have been reported from RA patients in the 1 mg/kg or 3 mg/kg dose levels. The safety profile of nivolumab is well established and supported by the recent U.S. marketing authorizations for the treatment of melanoma and squamous NSCLC. The number of subjects dosed, the dose levels evaluated, and the current overall AE profile of Cabiralizumab and nivolumab support concurrent initiation of the 2 mg/kg Cabiralizumab monotherapy and 1 mg/kg Cabiralizumab with 3 mg/kg nivolumab combination therapy cohorts in this study.

The Phase 1a portion of this study will consist of a two-step monotherapy dose escalation of Cabiralizumab at 2 mg/kg followed by 4 mg/kg Cabiralizumab. There will also be a three-step dose escalation of a fixed dose of 3 mg/kg nivolumab in combination with 1 mg/kg Cabiralizumab, followed by 2 mg/kg Cabiralizumab, then 4 mg/kg Cabiralizumab.

Figure 2:
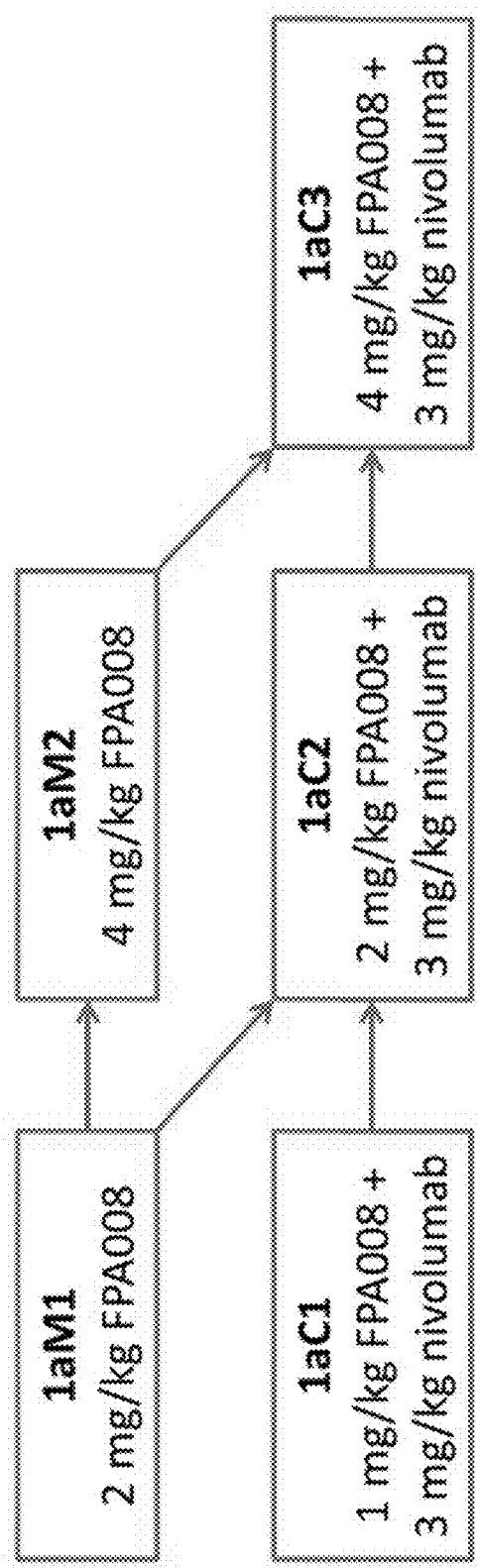
FIG. 2 shows dose escalation criteria for the clinical experiments of Examples 3 and 4.

The 4 mg/kg Cabiralizumab monotherapy cohort will be opened after the 28-day DLT period clears in the 2 mg/kg Cabiralizumab monotherapy cohort. The 2 mg/kg Cabiralizumab/nivolumab combination cohort will only start after the DLT period clears in the 1 mg/kg Cabiralizumab/nivolumab combination cohort and 2 mg/kg Cabiralizumab monotherapy cohort. The 4 mg/kg Cabiralizumab/nivolumab combination cohort will be opened after the DLT period clears in the 1 mg/kg and 2 mg/kg Cabiralizumab/nivolumab combination cohorts and in the 2 mg/kg and 4 mg/kg Cabiralizumab monotherapy cohorts. The dose escalation schematic is shown in FIG. 2.

All patients will be on a continuous dosing schedule every 14 days and followed up until disease progression, unacceptable toxicity or withdrawal of consent.

1.4 Rationale for 30-Minute Infusion Administration for Each Study Drug

Long infusion times, especially when multiple agents are administered sequentially to an individual, place a burden on patients and treatment centers.

Cabiralizumab, a CSF1R inhibitor, has been dosed over 30 minutes in studies in healthy volunteers and also for patients with RA.

Nivolumab has been administered safely over 60 minutes at doses ranging up to 10 mg/kg over extended treatment durations. In Study CA209010, (a Phase 2, randomized, double blinded, dose-ranging study of nivolumab in subjects with advanced/metastatic clear-cell RCC), a dose association was observed for infusion site reactions and hypersensitivity reactions (1.7% at 0.3 mg/kg, 3.7% at 2 mg/kg and 18.5% at 10 mg/kg). All events were Grade 1 or 2 and manageable. An infusion duration of 30 minutes for 3 mg/kg nivolumab (30% of the dose provided at 10 mg/kg) is not expected to present more serious safety concerns compared to the prior experience of 10 mg/kg nivolumab infused over 60 minutes.

Overall, infusion reactions, including high-grade hypersensitivity reactions, have been uncommon across nivolumab and Cabiralizumab clinical studies. Furthermore, a 30 minute break following the nivolumab infusion in the combination cohorts will ensure time for appropriate safety monitoring before the start of the Cabiralizumab infusion.

Overall, a variation in the safety profile is not anticipated with a 30-minute infusion of nivolumab or Cabiralizumab either alone or in combination.

1.5 Research Purposes

The purpose of the Phase 1a arm of this trial is to evaluate safety and tolerability following administration of Cabiralizumab monotherapy as well as in combination with nivolumab in patients with advanced cancers and to identify the recommended dose (RD) of Cabiralizumab for the Phase 1b combination arm of this study.

The purpose of the Phase 1b arm of this trial is to further characterize the safety profile of Cabiralizumab in combination with nivolumab and to evaluate the clinical benefit at the RD of Cabiralizumab/nivolumab combination therapy in patients with selected, advanced cancers.

1.6 Objectives

1.6.1 Phase 1a Objectives

1.6.1.1 Primary

To assess the safety and tolerability of Cabiralizumab as monotherapy

To assess the safety and tolerability of Cabiralizumab in combination with nivolumab To determine the RD of Cabiralizumab in combination with a fixed dose of nivolumab

1.6.1.2 Secondary

To characterize the PK profile of Cabiralizumab

To characterize the PK peak and trough concentration profile of nivolumab when administered in combination with Cabiralizumab To characterize the PD profile of Cabiralizumab and nivolumab To characterize the immunogenicity of Cabiralizumab and nivolumab To assess the association of selected biomarker measures and clinical efficacy measures using pre-treatment and on-treatment tumor biopsies

1.6.1.3 Exploratory

To further characterize the PD profile of Cabiralizumab and nivolumab

1.6.2 Phase 1b Objectives

1.6.2.1 Primary

To evaluate the clinical benefit of Cabiralizumab in combination with nivolumab in patients with selected advanced cancers through the analysis of objective response rate (ORR).

To evaluate the safety and tolerability of Cabiralizumab in combination with nivolumab in patients with selected advanced cancers treated at the RD

1.6.2.2 Secondary

To evaluate the clinical benefit of Cabiralizumab in combination with nivolumab in patients with selected advanced cancers through the analysis of overall survival (OS), duration of response (DOR), and progression free survival (PFS)

To characterize the PK profile of Cabiralizumab

To characterize the PK peak and trough concentration profile of nivolumab when administered in combination with Cabiralizumab To characterize the PD profile of Cabiralizumab and nivolumab To characterize the immunogenicity of Cabiralizumab and nivolumab To assess the association of selected biomarker measures and clinical efficacy measures using pre-treatment and on-treatment tumor biopsies

1.6.2.3 Exploratory

To further characterize the PD profile of Cabiralizumab and nivolumab

1.7 Product Development Background

1.7.1 Mechanism of Action

1.7.1.1 Cabiralizumab

Cabiralizumab is a recombinant, humanized IgG4 monoclonal antibody that binds to human CSF1R. Binding of Cabiralizumab to CSF1R antagonizes its natural ligands, CSF1 and IL34, thereby preventing activation of CSF1R. Cabiralizumab contains a single amino acid substitution in the hinge region to prevent hemi-dimer exchange.

Cabiralizumab inhibits both CSF1 and IL34-induced CSF1R phosphorylation in a cell line engineered to overexpress CSF1R (CHO-CSF1R), demonstrating that Cabiralizumab blocks the activation of ligand-induced CSF1R signaling pathways. Cabiralizumab also inhibits CSF1 and IL34-induced proliferation and survival of peripheral blood monocytes in vitro, demonstrating that Cabiralizumab inhibits not only the initiation of CSF1 and IL34 signaling pathways, but also the subsequent physiologic responses of primary human monocytes to these ligands.

CSF1R is expressed on cells of the monocyte/macrophage lineage and signaling through CSF1R via its ligands, CSF1 and IL34, supports differentiation, maintenance, and function of monocytes, macrophages, and osteoclasts. TAMs are among the most abundant immune cell types in the tumor microenvironment. Substantial evidence suggests that TAMs are polarized towards an anti-inflammatory phenotype and through both cell surface inhibitors and soluble factors, such as immunosuppressive cytokines, play a major role in inhibiting anti-tumor immune responses (Noy, 2014). CSF1 is a major survival factor for TAMs and targeting CSF1R through Cabiralizumab should reduce TAM-mediated immune suppression resulting in strengthening the anti-tumor response to immunotherapy. Therefore, a drug that inhibits CSF1R should limit the immune-suppressive influence of TAMs on the tumor microenvironment and could be complementary and augment current cancer therapies.

Since Cabiralizumab does not cross-react to mouse CSF1R, a surrogate antibody, cmCabiralizumab, was developed that binds and blocks mouse CSF1R with similar potency observed for Cabiralizumab against human CSF1R. cmCabiralizumab contains rat variable regions and a mouse IgG1 Fc region. Binding of cmCabiralizumab to mouse CSF1R was demonstrated in a direct binding enzyme-linked immunosorbent assay (ELISA), and cmCabiralizumab inhibitory activity was demonstrated by its ability to inhibit CSF1-induced and IL34-induced proliferation of a CSF1/IL34-dependent cell line (mNFS60). The $EC_{50}$ value for cmCabiralizumab binding to mouse CSF1R is 2.4 ng/mL, and the $IC_{50}$ values for inhibition of mouse CSF1-induced and mouse IL34-induced proliferation/survival of mNFS60 cells are 32.9 and 9.1 ng/mL, respectively.

1.7.1.2 Nivolumab

Cancer immunotherapy rests on the premise that tumors can be recognized as foreign rather than as self and can be effectively attacked by an activated immune system. An effective immune response in this setting is thought to rely on immune surveillance of tumor antigens expressed on cancer cells that ultimately results in an adaptive immune response and cancer cell death. Meanwhile, tumor progression may depend upon acquisition of traits that allow cancer cells to evade immunosurveillance and escape effective innate and adaptive immune responses (Dunn, 2002; Jemal, 2011; Pardoll, 2003; Zitvogel, 2006). Current immunotherapy efforts attempt to break the apparent tolerance of the immune system to tumor cells and antigens by either introducing cancer antigens by therapeutic vaccination or by modulating regulatory checkpoints of the immune system.

T-cell stimulation is a complex process involving the integration of numerous positive as well as negative co-stimulatory signals in addition to antigen recognition by the T-cell receptor (TCR) (Greenwald, 2004). Collectively, these signals govern the balance between T-cell activation and tolerance. PD-1 signaling has been shown to inhibit CD28-mediated upregulation of IL-2, IL-10, IL-13, interferon-gamma (IFN-γ) and Bcl-xL. PD-1 signaling has also been noted to inhibit T-cell activation, and expansion of previously activated cells. Evidence for a negative regulatory role of PD-1 comes from studies of PD-1 deficient mice, which develop a variety of autoimmune phenotypes (Sharpe, 2007). These results suggest that PD-1 blockade has the potential to promote anti-self T-cell responses, but these responses are variable and dependent upon various host genetic factors. Thus, PD-1 deficiency or inhibition is not accompanied by a universal loss of tolerance to self antigens.

In vitro, nivolumab binds to PD-1 with high affinity ($EC_{50}$ 0.39-2.62 nM), and inhibits the binding of PD-1 to its ligands, PD-L1 and PD-L2 ($IC_{50}$ □ 1 nM). Nivolumab binds specifically to PD-1 and not to related members of the CD28 family such as CD28, ICOS, CTLA-4 and BTLA. Blockade of the PD-1 pathway by nivolumab results in a reproducible enhancement of both proliferation and IFN-γ release in a mixed lymphocyte reaction (MLR). Using a cytomegalovirus (CMV) re-stimulation assay with human peripheral blood mononuclear cells (PBMCs), the effect of nivolumab on antigen-specific recall response is indicative of nivolumab-augmented IFN-γ secretion from CMV-specific memory T cells in a dose-dependent manner versus an isotype-matched control. In vivo blockade of PD-1 by a murine analog of nivolumab enhances the anti-tumor immune response and results in tumor rejection in several immunocompetent mouse tumor models (MC38, SA1N, and PAN02) (Wolchok, 2009).

1.7.2 Preclinical Summary
1.7.2.1 Cabiralizumab

The ability of cmCabiralizumab to inhibit cancer growth in vivo was studied in an MC38 colon cancer model in immune-competent mice. These mice were selected to allow for the establishment of an intact tumor-immune interaction. Treatment with cmCabiralizumab began when tumors reached approximately 100 mm³. Mice were treated once per week by intraperitoneal injection of cmCabiralizumab at 30 mg/kg, and the tumor growth was compared to mice treated with albumin alone. cmCabiralizumab significantly reduced the growth of MC38 tumors compared to control-treated mice. Flow cytometry analysis of control mice showed that the $CD11b^+$ myeloid compartment in MC38 tumors was dominated by $CD206^+$ macrophages. CD206 is a marker of immunosuppressive M2 macrophages. These $CD206^+$ M2 immunosuppressive macrophages were significantly reduced upon treatment with cmCabiralizumab. The reduction of M2 macrophages was accompanied by an increase in $CD8^+$ cytotoxic T cells relative to total $CD4^+$ T cells or regulatory T cells defined as $CD4+CD25^{high}$ cells. These data suggest reduction of immunosuppressive macrophages by cmCabiralizumab results in a shift towards a greater cytotoxic T cell response in the tumor.

The PK profile of Cabiralizumab is complex and characterized by nonlinear clearance that is likely mediated by binding to CSF1R on cells. As monocyte and macrophage cells are dependent on CSF1R for viability, these target-bearing cells are reduced in number following Cabiralizumab treatment, resulting in a decrease of target-mediated clearance. As target-mediated clearance becomes saturated at high or repeat doses, Cabiralizumab clearance is similar to other human IgG antibodies.

Three PD biomarkers correlate with Cabiralizumab exposure in nonclinical studies: CSF1 serum levels, circulating CD16-positive peripheral blood monocytes ($CD16^+$ monocytes), and serum markers of bone resorption (Trap5b and CTX). CSF1 serum levels rapidly rise and $CD16^+$ monocyte levels rapidly fall in a dose-dependent manner that correlates closely with Cabiralizumab plasma concentration. Saturation of the PD response is achieved at a low dose of Cabiralizumab (3 mg/kg weekly) in cynomolgus monkeys. The half-maximal response ($IC_{50}$) for reduction of $CD16^+$ monocytes occurs at a serum concentration of approximately 3 µg/mL and the maximal response occurs at approximately 10 µg/mL. The level of CD16-negative ($CD16^-$) monocytes does not change with exposure to Cabiralizumab.

In the in vivo toxicology studies in cynomolgus monkeys, Cabiralizumab was generally well tolerated. Test article-related findings included clinical observations, hematology and clinical chemistry changes, and histopathological changes. The majority of these observations were considered non-adverse. The most prominent clinical observation was reversible periorbital edema, seen after prolonged exposure to Cabiralizumab. The onset of the edema did not show a clear relationship to exposure levels, but edema resolved after systemic clearance of the drug. Periorbital edema is a known side effect of drugs affecting the CSF1 pathway (Cassier, 2014; Ries, 2014). The main hematologic change was a reversible decrease in circulating $CD16^+$ monocytes, which was considered a PD effect. Cabiralizumab-related clinical chemistry effects included reversible increased ALT, AST, CK, and LDH serum levels. These laboratory abnormalities were not associated with any histopathological evidence of liver, cardiac, or muscle tissue injury. Additionally, cardiac troponin, skeletal troponin (SkTnI), myoglobin, and aldolase did not show any changes further confirming the lack of any liver or muscle injury. The increased serum levels are attributed to diminished clearance of ALT, AST, CK, and LDH molecules from serum due to a reduced number of liver Kupffer cells (Radi, 2011). Accordingly, ALT, AST, CK, and LDH elevations are considered nontoxic and an indirect PD effect of Cabiralizumab exposure.

A noteworthy histopathological finding was the reversible expansion of the submucosal collagen fibers by clear space and varying amounts of a blue, granular extracellular matrix (ECM) in a variety of tissues. This change was neither associated with inflammatory cells nor with any sign of degeneration or other alteration of the collagen fibers, fibroblasts, or the smooth muscle cells within the area of expansion. A similar observation was also seen in op/op mice that lack functional CSF1. The reduction of tissue macrophages is the likely cause of the observed accumulation of ECM due to a decreased clearance of glycosaminoglycans, especially hyaluronic acid, that are prominent in connective tissue and are normally catabolized by macrophages (Radi, 2009). This change is also considered to be an indirect PD effect of Cabiralizumab.

Cardiac troponin I was below the limit of quantitation (LOQ) in all samples except for one female monkey in the 150 mg/kg group at Day 28. This animal did have a corresponding microscopic finding in the heart. While elevations of cardiac troponin I are highly specific for myocardial injury, the level detected in this monkey (0.26 ng/mL) was marginally above the assay LOQ (0.20 ng/mL) and much lower than what would be expected for an adverse cardiac event.

The no-observable-adverse-effect level (NOAEL) for Cabiralizumab was determined to be 100 mg/kg when administered for 13 weekly doses to cynomolgus monkeys, which provides a 32-fold safety factor based on body surface area calculation for the starting dose of 1 mg/kg in humans.

The minimum anticipated biological effect level (MABEL) was evaluated to guide starting dose decisions in healthy volunteers in the first-in-human study. The PD markers identified as representative of a biological effect were changes in $CD16^+$ monocyte levels, elevation of plasma CSF1, and elevation of serum ALT, AST, CK, and LDH. The lowest Cabiralizumab plasma concentration at which a biological effect occurred for each marker ranged from 5 μg/mL to 105 μg/mL, and the Cabiralizumab dose that corresponded to 5 μg/mL at the maximum serum concentration ($C_{max}$) was estimated to be 0.2 mg/kg, the recommended starting dose in healthy volunteers.

1.7.2.2 Nivolumab

Nivolumab has been shown to bind specifically to the human PD-1 receptor and not to related members of the CD28 family, such as ICOS, CTLA-4, and BTLA (Nivolumab IB, 2014). Nivolumab inhibits the interaction of PD-1 with its ligands, PD-L1 and PD-L2, resulting in enhanced T-cell proliferation and IFN-γ release in vitro (Velu, 2009; Nivolumab IB, 2014). Fluorescent-activated cell sorter (FACS) analysis confirmed that nivolumab binds to transfected Chinese hamster ovary (CHO) and activated human T cells expressing cell surface PD-1 and to cynomolgus monkey PD-1, but not to rat or rabbit PD-1 molecules. Nivolumab has also been shown to bind to PD-1 on virus-specific $CD8^+$ T cells from chronically infected hepatitis C virus patients (Kaufmann, 2008; Rutebemberwa, 2008).

PD-1 inhibition in an MLR resulted in a reproducible concentration-dependent enhancement of IFN-γ release in the MLR up to 50 μg/mL. No effect was observed with a human IgG4 isotype control or $CD4^+$ T cells and dendritic cell (DC) controls (Wang, 2014).

In intravenous (IV) repeat-dose toxicology studies in cynomolgus monkeys, nivolumab was well tolerated at doses up to 50 mg/kg, administered weekly for 5 weeks, and at doses up to 50 mg/kg, administered twice weekly for 27 doses. Nivolumab-related findings were limited to a reversible decrease of 28% in triiodothyronine ($T_3$) among the females administered 27 doses of 50 mg/kg nivolumab. No corresponding changes in the level of thyroxine ($T_4$), thyroid-stimulating hormone (TSH), or histologic changes in the thyroid were observed. While nivolumab alone was well tolerated in cynomolgus monkeys, combination studies have highlighted the potential for enhanced toxicity when combined with other immunostimulatory agents (Nivolumab IB, 2014).

Ipilimumab (BMS-734016), an anti-CTLA-4 monoclonal antibody (mAb) that blocks the down-regulation of T-cell activation, was used in combination with nivolumab to investigate the effects of concurrent inhibition of the PD-1 and CTLA-4 receptors in nonhuman primates (Nivolumab IB, 2014). Although gastrointestinal (GI) toxicity has not been observed in cynomolgus monkeys treated with nivolumab alone, dose-dependent GI toxicity was evident in cynomolgus monkeys treated weekly for 4 weeks with a combination of nivolumab+ipilimumab at combinations of 10 and 3 mg/kg and 50 and 10 mg/kg, respectively. GI effects have also been observed at a low incidence after ipilimumab administration (Nivolumab IB).

In addition, an enhanced pre- and post-natal development (ePPND) study in pregnant cynomolgus monkeys with nivolumab was conducted (Nivolumab IB, 2014). Administration of nivolumab at up to 50 mg/kg every 2 weeks was well tolerated by pregnant monkeys; however, nivolumab was determined to be a selective developmental toxicant when administered from the period of organogenesis to parturition at ≥10 mg/kg (area under the concentration-time curve [AUC] from time zero to 168 hours [AUC(0-168 h)] 117,000 μg·h/mL). Specifically, increased developmental mortality (including late gestational fetal losses and extreme prematurity with associated neonatal mortality) was noted in the absence of overt maternal toxicity. There were no nivolumab-related changes in surviving infants tested throughout the 6-month postnatal period. Although the cause of these pregnancy failures was undetermined, nivolumab-related effects on pregnancy maintenance are consistent with the established role of PD-L1 in maintaining fetomaternal tolerance in mice (Habicht, 2007).

1.7.3 Clinical Summary 1.7.3.1 Cabiralizumab 1.7.3.1.1 Ongoing Study Summary of Cabiralizumab Cabiralizumab is currently being evaluated in a double-blind, randomized, placebo-controlled first-in-human trial designed in 3 parts to study safety, PK, and PD in healthy volunteers and RA patients. The first two parts of the study were conducted in healthy volunteers and have been completed. In Part 1, 8 healthy volunteers were randomized (3:1) to receive a single IV infusion of Cabiralizumab or placebo, per dose cohort of 0.2, 1, 3, or 10 mg/kg. In Part 2, 8 healthy volunteers were randomized (3:1) to receive 2 doses of Cabiralizumab or placebo administered 14 days apart, at 1 mg/kg or 3 mg/kg. Part 3 of the study will evaluate Cabiralizumab in RA patients and is currently ongoing. The data for Parts 1 and 2 are summarized below.

1.7.3.1.2 Clinical Pharmacology Summary of Cabiralizumab

The PK of Cabiralizumab was evaluated by measuring systemic drug levels over time in all 36 subjects who received Cabiralizumab in Parts 1 and 2. Blood samples for determination of serum Cabiralizumab concentrations were collected pre-dose and at various time points up to 112 days (for Part 1) or 98 days (for Part 2) post-first dose. In addition, blood samples for determination of anti-Cabiralizumab antibodies were collected pre-dose and at various time points from Day 15 to Day 85 (for Part 1) or Day 15 to Day 99 (for Part 2).

Following a single administration of Cabiralizumab at 0.2, 1, 3, and 10 mg/kg, total clearance decreased with increasing dose and ranged from 38.7 to 2.55 mL/day/kg. The total clearance of 2.55 mL/day/kg at 10 mg/kg is within the range for a typical human IgG monoclonal antibody. The $C_{max}$ increased proportionally with dose, but the AUC did not. Following 2 doses given 14 days apart, there was no accumulation at 1 mg/kg. However, when the dose increased to 3 mg/kg, a mean of 1.60-fold drug accumulation was observed between the first and the second dose for the AUC from Day 1 to Day 15, while minimum accumulation was observed for $C_{max}$ at the same dose level. The observed PK data suggested that CSF1R expressed on monocyte/macrophage lineage and other cell types contributed to target-mediated clearance of Cabiralizumab. As monocyte and macrophage cells are dependent on CSF1R for viability, these target-bearing cells are reduced in number following Cabiralizumab treatment, resulting in a decrease of target-mediated clearance. Once target-mediated clearance is saturated at high or repeat doses, Cabiralizumab clearance is similar to other human IgG antibodies.

Immunogenicity of Cabiralizumab was assessed using a validated electrochemiluminescence assay (ECLA) that measured total anti-Cabiralizumab antibodies in serum. The limit of detection (sensitivity) of the assay was 39.1 ng/mL. Three subjects in cohort 2 (1 mg/kg single dose) had trace positive antibody titers, resulting in 8.3% incidence (3 of 36 subjects that received Cabiralizumab). The trace positive antibody titers were first observed on Day 15 for 2 subjects and on Day 57 for 1 subject. Two subjects still had ADA-positive titers on Day 85 (the last time point tested). The presence of ADAs had negligible impact on Cabiralizumab exposure, if any, when compared to the subjects without ADAs in the same dose cohort, and there were no associated clinical sequelae based on the available data.

Cabiralizumab treatment induced a dose-dependent reduction of nonclassical $CD16^+$ monocytes as a PD marker for Cabiralizumab treatment. The relationship between Cabiralizumab serum concentration and reduction of nonclassical $CD16^+$ monocytes was analyzed and found to be concentration-dependent based on the data collected 72 hours post-treatment until the end of the study. At ≥5 µg/mL Cabiralizumab in serum, maximum reduction of nonclassical $CD16^+$ monocytes was noted. Therefore, the dose to achieve trough serum concentration at ≥5 µg/mL in majority of patients is expected to be the target dose for maximum reduction of nonclassical $CD16^+$ monocytes. The optimal exposure required to achieve clinical efficacy remains to be explored in clinical trials using Cabiralizumab in patients.

In summary, Cabiralizumab exhibited nonlinear clearance in the dose range tested. The PK characteristics observed in healthy volunteers support dosing of Cabiralizumab once every 2 weeks or less frequently to maintain desired drug exposure.

1.7.3.1.3 Clinical Safety Summary of Cabiralizumab

The total number of subjects that received Cabiralizumab was 36 for both Part 1 and Part 2 with 6 subjects in each dose cohort. Dose escalation decisions were based on the incidence of DLTs plus attributed AEs beyond the DLT period.

Cabiralizumab was well tolerated in healthy volunteers up to 3 mg/kg multiple doses. The most common Cabiralizumab treatment-related toxicities were pruritus, eyelid edema along with facial swelling, fatigue, and headache. The events were Grade 1 or 2, and self-limited. The AE profile is similar to what has been reported in other compounds targeting the CSF1R pathway (Cassier, 2014). At 10 mg/kg, all 6 active subjects experienced moderate (Grade 2) eyelid edema or facial swelling, some accompanied with swelling in hands and feet, blurry vision, and weight increase. The events lasted up to 3 months and coincided with prolonged Cabiralizumab exposure at this dose level.

Cabiralizumab has shown elevation of liver enzymes, peaking at 2-8 weeks following drug administration and returning to normalization 12 weeks after discontinuation of drug. Dose-dependent elevations of CK up to 6.8 times the upper limit of normal (ULN) and LDH up to 3.2 times ULN were noted at 1 mg/kg and above; AST elevations up to 2.4 times ULN occurred at 3 mg/kg and above and occurred in a greater percentage of healthy volunteers with increasing dose; and mild ALT elevation up to 1.2 times ULN occurred at 10 mg/kg in 1 subject. These elevations were considered to be due more to the mechanism of action of Cabiralizumab-mediated inhibition of Kupffer cells, rather than any organic failure or injury and were not considered clinically significant. Cabiralizumab was initially tested in healthy volunteers at a dose of 1 mg/kg and 3 mg/kg body weight. At 1 mg/kg, 7 subjects received a single dose and 5 subjects received 2 doses at 14 day intervals and were followed up through the 28 day DLT window. In the 3 mg/kg healthy volunteer group, 10 subjects received a single dose and 2 subjects received 2 doses 14 days apart and were followed up for DLTs. Only 1 subject in the 3 mg/kg cohort had a Grade 1 concurrent increase of alkaline phosphatase and AST.

1.7.3.2 Nivolumab 1.7.3.2.1 Clinical Pharmacology Summary of Nivolumab

Single-dose PK of nivolumab was evaluated in patients with multiple tumor types in CA209001, whereas multiple-dose PK is being evaluated in patients in CA209003. In addition, a preliminary population pharmacokinetic (PPK) model has been developed with data from 350 patients from CA209001, CA209002, and CA209003.

The PK of nivolumab was studied in patients over a dose range of 0.1 to 20 mg/kg administered as a single dose or as multiple doses every 2 or 3 weeks. Based on a PPK analysis using data from 909 patients, the clearance (CL) (CV %) is 9.5 mL/h (49.7%), geometric mean volume of distribution at steady state (Vss) is 8.0 L (30.4%), and geometric mean elimination half-life ($t_{1/2}$) is 26.7 days (101%). Steady-state concentrations of nivolumab were reached by 12 weeks when administered at 3 mg/kg every 2 weeks, and systemic accumulation was approximately 3-fold. The exposure to nivolumab increased dose proportionally over the dose range of 0.1 to 10 mg/kg administered every 2 weeks (Opdivo Package Insert, 2015).

Based on a population PK analysis using data from 909 patients, the clearance of nivolumab increased with increasing body weight supporting a weight-based dose. The population PK analysis suggested that the following factors had no clinically important effect on the clearance of nivolumab: age (29 to 87 years), gender, race, baseline LDH, PD-L1 expression, tumor type, tumor size, renal impairment, and mild hepatic impairment (Opdivo Package Insert, 2015).

1.7.3.2.2 Safety Summary of Nivolumab

Overall, the safety profile of nivolumab monotherapy as well as combination therapy is manageable and generally consistent across completed and ongoing clinical trials with no MTD reached at any dose tested up to 10 mg/kg. There was no pattern in the incidence, severity, or causality of AEs to the nivolumab dose level. Most AEs were low-grade (Grade 1 to 2) with relatively few related high-grade (Grade 3 to 4) AEs. Most high-grade events were manageable with the use of corticosteroids or hormone replacement therapy (endocrinopathies) as instructed in the management algorithms provided in the nivolumab D3 (Nivolumab IB, 2014).

A total of 39 and 306 patients with selected recurrent or treatment-refractory malignancies have been treated in a completed Phase 1 single-dose study (CA209001) and an ongoing Phase 1 multi-dose study (CA209003), respectively. As the safety profile from CA209003 to date is consistent with that observed for CA209001, only data from the larger and more recent study, CA209003, are presented below.

In CA209003 (n=306, including 129 patients with NSCLC), as of the 5 Mar. 2013 database lock, drug-related AEs of any grade occurred in 75% of patients. The most frequent drug-related AEs occurring in at least 5% of patients included fatigue (28%), rash (15%), diarrhea (13%), pruritus (11%), nausea (9%), decreased appetite (9%), decreased hemoglobin (6%), and pyrexia (6%). The majority of events were low grade, with Grade 3/4 drug-related AEs observed in 17% of patients. The most common Grade 3/4 drug-related AEs occurring in at least 1% of patients were fatigue (2%), pneumonitis (1%), diarrhea (1%), abdominal pain (1%), hypophosphatemia (1%), and lymphopenia (1%). Drug-related SAES occurred in 14% of patients; 8% were Grade 3/4 including pneumonitis (1%) and diarrhea (1%). The spectrum, frequency, and severity of drug-related AEs were generally similar across the dose levels tested. A review of the safety data by tumor type (RCC, NSCLC, metastatic castration-resistant prostate cancer [mCRPC], colorectal cancer [CRC], and melanoma) also did not show any clinically meaningful differences in the proportion of patients with AEs noted across tumor type.

Select AEs with potential immune-related causality, previously termed "immune-related adverse events" or "adverse events of special interest" were also analyzed taking into account multiple events, with rates adjusted for treatment duration. Most events occurred within the first 6 months of therapy; cumulative or novel toxicities were not observed with prolonged drug exposure. Nineteen of 306 patients (6%) experienced Grade 3/4 treatment-related select AEs. Fifty-two of 230 patients (23%) with drug-related AEs required management with systemic glucocorticoids and/or other immunosuppressive agents. Twenty-one of 52 (40%) resumed nivolumab therapy after toxicity resolved, while the others discontinued therapy.

Although tumor progression was the most common cause of mortality, there were 3 drug-related deaths associated with Grade 3/4 pneumonitis. Pneumonitis (any grade) occurred in 12 of 306 patients (4%), and Grade 3/4 pneumonitis occurred in 4 patients (1%), with clinical presentations ranging from asymptomatic radiographic abnormalities to progressive, diffuse pulmonary infiltrates associated with cough, fever, and/or dyspnea. No clear relationship between the occurrence of pneumonitis and tumor type, dose level, or treatment duration was noted. In 9 of 12 patients, pneumonitis was reversible after treatment discontinuation and/or with immunosuppressive therapy (glucocorticoids, infliximab, mycophenolate).

Additional details on the safety profile of nivolumab, including results from other clinical studies, are also available in the D3 and package insert (Nivolumab IB, 2014; Opdivo Package Insert, 2015).

1.8 Overall Risk/Benefit Assessment

A number of drug candidates that target the CSF1R pathway are being studied in the clinic. These include antibodies that block agonist ligand binding to CSF1R or inhibit CSF1R dimerization as well as small molecules that block the kinase activity of CSF1R. The safety, PK, and PD of PD-0360324, an antibody to CSF1, in healthy volunteers has been reported (Sadis, 2009). The most significant treatment-emergent findings (increased liver enzyme levels) and AEs (i.e., periorbital edema) exhibited with PD-0360324 treatment are consistent with the data obtained to date with Cabiralizumab.

A clinical study of RG7155 (an anti-dimerization CSF1R antibody) included patients with diffuse-type giant cell tumors (Dt-GCT). All seven evaluable patients showed partial metabolic response in FDG-PET imaging (according to the European Organization for Research and Treatment of Cancer), with two patients approaching a complete metabolic response. Five of the seven patients went on to achieve partial responses at the first assessment. As with other agents targeting the CSF1R pathway, periorbital edema was the most common AE (Ries, 2014). CSF1 is a major survival factor for TAMs and targeting CSF1R through Cabiralizumab should reduce TAM-mediated immunosuppression, resulting in strengthening the anti-tumor response to immunotherapy. Inhibition of CSF1R by Cabiralizumab could limit the influence of TAMs on the tumor microenvironment and be complementary to, and augment current cancer therapies.

Nivolumab has demonstrated clinical activity across several tumor types, particularly melanoma and NSCLC, where it has already been granted FDA approval. Nivolumab has also demonstrated a manageable safety profile. The most common AEs included fatigue, rash, pruritus, diarrhea, and nausea.

Preliminary reports of specific CSF1R inhibitors suggest that Cabiralizumab may be a beneficial treatment for patients with solid tumor malignancies. The robust clinical activity demonstrated by nivolumab in patients with advanced melanoma, NSCLC and RCC in combination with a manageable safety profile supports the further development of this treatment in patients with advanced cancers.

Based on available clinical safety data, toxicities for Cabiralizumab and nivolumab do not overlap (with the notable exception of liver enzyme elevations, discussed below) and therefore, cumulative toxicities are not expected as a result of this combination. Cabiralizumab has been linked to periorbital edema, and there has been only one case of peripheral edema with nivolumab. Additionally, nivolumab has been linked to immune-related AEs, and there have been no immune-related AEs with Cabiralizumab to date.

There is a temporary increase in liver enzymes (CK, AST, ALT, and LDH) in patients taking Cabiralizumab due to a reduction of Kupffer cells, and this has not been associated with any histopathological evidence of liver, cardiac, or skeletal tissue damage. Nivolumab is known to cause hepatic toxicities at a low frequency. Because of the potential for the combination of Cabiralizumab and nivolumab to yield elevated liver enzymes with different underlying mechanisms, risk mitigation guidelines have been designed to rapidly detect, and appropriately respond to, any evidence of liver perturbation during this study (Appendix E).

There remains an unmet medical need for cancer patients. Given the robust nonclinical and clinical data supporting these two molecules, the non-redundant, immune-based mechanisms of actions, and current body of safety data from multiple clinical studies, the logical combination of these two drugs may be beneficial for patients with cancer who are in need of expanded therapeutic options.

2 INVESTIGATIONAL PLAN 2.1 Study Design and Duration

This study is a Phase 1a and 1b, open-label, multicenter, dose escalation and dose expansion study to evaluate the safety, tolerability, PK, and PD of Cabiralizumab as monotherapy and in combination with nivolumab in patients with selected advanced cancers. Cabiralizumab is a humanized monoclonal antibody directed against CSF1R and nivolumab is a fully human monoclonal antibody directed against PD-1. For the combination arms of the study, Cabiralizumab and nivolumab will be given on Day 1 of each 14-day treatment cycle; nivolumab will be given as an IV infusion over 30 minutes first, with a 30-minute rest between 2 infusions, followed by a 30-minute Cabiralizumab IV infusion.

The study will include a Phase 1a dose escalation and a Phase 1b dose expansion. Phase 1a consists of two Cabiralizumab monotherapy reference cohorts (1aM1 and 1aM2) and three dose-escalation cohorts of Cabiralizumab in combination with nivolumab (1aC1, 1aC2, and 1aC3). Phase 1b consists of eight cohorts (1b1 through 1b8) across six cancer types. Patients will be enrolled into either Phase 1aM, 1aC, or Phase 1b of the study, but not two or all three. The study schematic is shown in FIG. 6.

The study will consist of 3 periods including screening (up to 28 days), treatment, and follow-up/survival follow-up.

2.1.1 Screening Period

All screening evaluations must be completed and reviewed by the Investigator following the Study Reference Manual for the enrollment process to confirm that patients meet all eligibility criteria before the first infusion of study drug. Written informed consent for participation in the study must be obtained before performing any study specific screening tests or procedures, which are not considered standard of care. Screening assessments will be performed within 28 days prior to the first dose of study drug unless otherwise specified.

Study procedure-related AEs that occur after signing of the ICF and before administration of the first study drug dose will be collected during this period.

2.1.2 Treatment Period 2.1.2.1 Phase 1a Monotherapy Cohorts (1aM1 and 1aM2) and Combination Dose Escalation Cohorts (1aC1, 1aC2, and 1aC3)

Phase 1a consists of two Cabiralizumab monotherapy reference cohorts and three dose-escalation cohorts of Cabiralizumab in combination with nivolumab with minimum of 3 patients enrolled in each cohort. The planned dose levels and schedules for the Phase 1a cohorts are as follows:

Cohort 1aM1: 2 mg/kg Cabiralizumab, q2w
Cohort 1aM2: 4 mg/kg Cabiralizumab, q2w
Cohort 1aC1: 1 mg/kg Cabiralizumab+3 mg/kg nivolumab, q2w
Cohort 1aC2: 2 mg/kg Cabiralizumab+3 mg/kg nivolumab, q2w
Cohort 1aC3: 4 mg/kg Cabiralizumab+3 mg/kg nivolumab, q2w The 2 mg/kg Cabiralizumab monotherapy cohort (1aM1) and the 1 mg/kg Cabiralizumab+nivolumab combination cohort (1aC1) will be initiated first in parallel with sequential enrollment order, following a 3+3 design, starting with the 1aM1 monotherapy cohort. Patients in these cohorts will be treated for a total of two 14-day treatment cycles within the 28-day DLT period.

The 4 mg/kg Cabiralizumab monotherapy cohort (1aM2) will open after the DLT period is cleared in the 2 mg/kg Cabiralizumab monotherapy cohort (1aM1); the 2 mg/kg Cabiralizumab/nivolumab combination cohort will only start after the DLT periods are cleared in both the 1aC1 Cabiralizumab/nivolumab combination and 1aM1 Cabiralizumab monotherapy cohorts. The 4 mg/kg Cabiralizumab/nivolumab combination cohort (1aC3) will open only after the DLT periods are cleared in the 1aC2 Cabiralizumab/nivolumab combination and 1aM2 Cabiralizumab monotherapy cohorts. Depending on the outcome of the 4 mg/kg Cabiralizumab monotherapy cohort, higher or a lower intermedian dose cohorts for both monotherapy and combination therapy (e.g., 3 mg/kg Cabiralizumab alone or in combination with nivolumab) may be opened up per the decision of Cohort Review Committee. All dose escalation decisions will be based on assessment of DLTs, overall safety, and tolerability. Dose escalation decisions will be agreed upon between the Investigators and the Sponsor. Prior to initiating each new dose level or expanding an existing dose level, a safety teleconference will be held wherein the Investigator(s) and Sponsor will review patient data, including, but not limited to, demographics, drug dosing, concomitant medications, hematology and serum chemistry, and AEs; and confer and document agreement that dose escalation or expanding an existing dose level is considered appropriate. If the Investigator(s) and Sponsor collectively agree, following review of safety, PK, and PD data, that a different dose escalation scheme (e.g., an intermediate Cabiralizumab dose of 3 mg/kg alone or in combination with nivolumab) should be used than the one outlined, this will be permitted. Review of safety, PK, and PD parameters may inform decisions to add cohorts with alternative dose levels or dose regimens (e.g., less frequent dosing) in order to reach an optimal target exposure.

DLT evaluation and enrollment decisions will follow the guidance in the Table 2 below:

TABLE 2

Algorithm for Phase 1a dose escalation decisions

| Number of Patients with DLT at a Given Dose Level | Dose Escalation Decision Rule |
| --- | --- |
| 0/3 | Escalation will occur into the next highest dose cohort |
| 1/3 | Enroll three more patients in same cohort |
| ≥2/3 | Stop enrollment. Enter three more patients at the lower dose level, if only three were previously entered |
| 1/6 | Open next cohort |
| ≥2/6 | Stop enrollment. Enter three more patients at the lower dose level, if only three were previously entered |

Dose escalation will continue in the monotherapy and combination treatment arms until either the MTD or maximum planned dose of Cabiralizumab is reached, with a minimum of 3 patients enrolled in each cohort.

The MTD is defined as the highest dose associated with DLTs in less than 33% of patients (less than 2 out of 6 patients) receiving Cabiralizumab or Cabiralizumab+nivolumab combination therapy, administered during the 28-day DLT period. This will normally be the dose recommended for further study; however, based on review of safety, PK, and PD data, the RD could be lower than the MTD. If the MTD is not reached, and the highest evaluated Cabiralizumab dose alone or in combination with nivolumab is well tolerated, the data will be reviewed to assess whether further dose escalations up to 6 mg/kg Cabiralizumab are warranted.

If the MTD is not reached during the Phase 1a combination dose escalation, or subsequent cycles of treatment in cleared Phase 1a combination cohorts provide additional insight on the safety profile, an RD may be selected based on overall tolerability, safety, PK, and PD.

If a patient in Phase 1aC does not receive 2 doses of each study drug and does not complete the safety assessment (e.g., safety lab and/or AE reporting) in the 28-day DLT period for reasons other than drug-related AEs (e.g., disease progression or withdrawal of consent), then an additional patient will be enrolled into the cohort so that the cohort has at least three patients evaluable for the DLT period. All such discussions and decisions will be documented as part of the dose escalation decision-making process.

Upon completion of the 28-day DLT period, Phase 1a patients may participate in an Extended Treatment Period following the guidelines in Section 4.1.2.2.

2.1.2.1.1 Dose Limiting Toxicity

A DLT is defined as a study drug-related ≥Grade 3 AE (using National Cancer Institute [NCI] Common Terminology Criteria for Adverse Events [CTCAE] v4.03) occurring during the first 28-day DLT period, excluding: Grade 3 tumor flare (defined as local pain, irritation, or rash localized at sites of known or suspected tumor), Grade 3 rash, Grade 3 immune-related adverse event (irAE, defined below) that resolved to a Grade 1 or less within 28 days, or a transient (resolving within 6 hours of onset) Grade 3 infusion-related AE. An irAE is defined as a clinically significant AE that is associated with study drug exposure, of unknown etiology, and is consistent with an immune-mediated mechanism.

2.1.2.2 Phase 1a Extended Treatment Period

Upon completion of the DLT period, patients from the Phase 1aM and 1aC cohorts may participate in an Extended Treatment Period, which begins on Day 1 of Cycle 3 (Study Day 29).

Patients from the Phase 1aM cohorts are allowed to continue to receive Cabiralizumab monotherapy at the same Cabiralizumab dose level and patients from the Phase 1aC cohorts are allowed to continue to receive Cabiralizumab in combination with nivolumab at the same dose levels until disease progression, unacceptable toxicity, or other reason for treatment discontinuation.

2.1.2.3 Phase 1b Expansion Cohorts

To further characterize safety and efficacy of Cabiralizumab in combination with nivolumab, Phase 1b will enroll up to 8 expansion cohorts in 6 advanced cancer types. Enrollment in Phase 1b will begin when an RD has been identified by the Cohort Review Committee based on overall safety, tolerability, PK, and PD data.

2.1.3 Follow-Up Period

Patients who discontinue treatment while showing clinical benefit (complete response [CR], partial response [PR], or stable disease [SD]) for reasons other than disease progression should have follow-up for tumor assessments and any study drug-related AEs as specified below. The follow-up period begins at the Treatment Completion/Early Termination visit.

Follow-up visits include the following (refer to Section 6 for the full schedule):

Tumor assessments will continue every 12 (±2) weeks.

Review of study drug-related AEs, until these AEs resolve, return to baseline or are stabilized per treating Investigator's assessment. All AEs will be documented for a minimum of 100 days after the last dose OR until any one of the above conditions is met.

During the follow-up period, if the patient undergoes local therapy (e.g., resection, radiation) or a new systemic therapy is initiated, the patient should be followed for survival every 3 months (Section 4.1.4).

2.1.4 Survival Follow-Up

A patient who agrees to survival follow-up after withdrawal from study treatment, discontinues from study drug treatment due to progression of disease, or discontinues follow-up visits described in Section 4.1.3 will be followed every 3 months for survival, or more frequently as needed. Follow-up for survival may be conducted by telephone, rather than a required in-person visit.

2.1.5 Study Duration

Patients who receive study drug(s) may continue as long as they experience clinical benefit in the opinion of the investigator or until unacceptable toxicity or symptomatic deterioration attributed to disease progression as determined by the investigator after an integrated assessment of radiographic data, biopsy results (if available), and clinical status, or withdrawal of consent.

2.1.6 Stopping Rules 2.1.6.1 Stopping Rules for Phase 1a

If 2 or more patients in any dose level experience a DLT within the 28-day DLT evaluation period, the Investigators and Sponsor will review the data and follow the guidelines in Table 2 (Section 4.1.2.1). If dose escalation is terminated due to DLTs, then the evaluated dose below that which the stopping rule was invoked will be declared the MTD.

2.1.6.2 Stopping Rules for All Cohorts

Management of drug-related Grade 4 or 5 toxicities will follow the Adverse Event Management Tables (Appendix E and F).

The Sponsor will discuss such cases with the Cohort Review Committee and the study Investigators as appropriate to determine further enrollment. IRBs will be notified by the Investigators of all cases and decisions regarding continued enrollment.

2.1.6.3 Stopping Rules for Clinical Deterioration

Accumulating clinical evidence indicates that the emergence of objective responses to agents that activate anti-tumor immune responses may follow delayed kinetics of weeks or months, and can be preceded by initial apparent progression of disease with the appearance of new lesions or some enlarging of lesions while certain index lesions are regressing ("mixed response"). It is thus reasonable to allow patients experiencing apparent progression to continue to receive treatment until progression is confirmed at the next imaging assessment (Section 5.3.8). These considerations should be balanced by clinical judgment as to whether the patient is clinically deteriorating and unlikely to receive any benefit from continued treatment.

Such deterioration will be assessed to have occurred after a clinical event that, in the Investigator's opinion, is attributable to disease progression and is unlikely to reverse with continued study treatment and therefore indicates that the patient is not benefiting from study treatment and cannot be managed by the addition of supportive care. The decision to stop treatment should be discussed with the Sponsor's Medical Monitor or designee. Examples of events that may, in the Investigator's opinion, indicate a lack of clinical benefit include, but are not limited to, the following:

Eastern Cooperative Oncology Group (ECOG) score increase of at least 2 points from baseline (e.g. from 0 to 2).

Habitual changes such as changes in activities and symptoms including reduction in appetite and/or sleep, altered awareness, and increased pain-related symptoms due to cancer.

Progression of disease confirmed by the treating Investigator.

Any setting where the initiation of new anti-neoplastic therapy has been deemed beneficial to the patient even in the absence of any such documented clinical events.

2.2 Study Population 2.2.1 Planned Number of Patients and Study Centers

The total number of patients planned for this study is estimated to be 270; approximately 30 patients in Part 1a and 240 patients in Part 1b (approximately 30 patients for each of the eight Phase 1b cohorts). There will be 65 to 70 study centers participating in this study. During enrollment of any expansion cohort, if the observed number of responses makes it unlikely to achieve a target response rate for that indication (e.g., 10%), then further recruitment to that cohort may be suspended or terminated.

2.2.2 Inclusion Criteria for All Cohorts

For entry into the study, ALL of the following criteria must be met.

1. Measurable disease by Computed tomography (CT)/ magnetic resonance imaging (MRI) as per Response Evaluation Criteria in Solid Tumors (RECIST) v1.1 and preferably performed within 28 days of first dose.
2. Patients must have at least 1 tumor site that can be biopsied and are willing to recommended pre-treatment, on-treatment, and post-progression biopsies (except for patients in the Glioblastoma cohort); post-progression biopsy is optional for patients in Phase 1b cohorts. Biopsies will be performed according to treating institution's own guidelines from minimum of 10 patients in each Phase 1b cohort.
3. Archival formalin-fixed paraffin-embedded (FFPE) tumor material, if available
4. Understand and sign an IRB/IEC-approved ICF prior to any study-specific evaluation
5. Age ≥18 years
6. ECOG performance status of 0 or 1
7. Willing and able to comply with all study procedures
8. Prior focal radiotherapy must be completed at least 2 weeks before first dose of study drug administration. No radiopharmaceuticals (strontium, samarium) within 8 weeks before study drug administration.
9. Prior surgery that requires general anesthesia must be completed at least 2 weeks before study drug administration. Surgery requiring local/epidural anesthesia must be completed at least 72 hours before study drug administration and patients should be recovered.
10. Screening laboratory values must meet the following criteria:
Hematological
   a. White blood cells (WBCs) ≥2000 cells/µL
   b. Neutrophils ≥1500 cells/µL
   c. Platelets ≥100×10³/µL
   d. Hemoglobin ≥9.0 g/dL
      Serum creatinine ≤1.5×ULN or creatinine clearance of ≥40 mL/minute (using Cockcroft/Gault Formula)

$$\text{Female } CrCl = \frac{(140 - \text{age in years}) \times (\text{weight in kg}) \times 0.85}{72 \times (\text{serum creatinine in mg}/dL)}$$

$$\text{Male } CrCl = \frac{(140 - \text{age in years}) \times (\text{weight in kg})}{72 \times (\text{serum creatinine in mg}/dL)}$$

e. PT/INR ≤1.5×ULN and PTT (aPTT) ≤1.5×ULN
Hepatic
   a. AST or ALT ≤3×ULN without, and ≤5×ULN with hepatic metastasis
   b. Bilirubin ≤1.5×ULN (except patients with Gilbert's syndrome, who must have total bilirubin <3 mg/dL)
11. Women of childbearing potential (WOCBP) must have a negative serum β-human chorionic gonadotropin (β-hCG) at Screening and agree to use a reliable form of contraception (e.g., oral contraceptives, intrauterine device or double barrier method of condom and spermicidal) for at least 28 days prior to the first dose of any study drug during the Treatment Period (and Treatment/Follow-up if receiving study drug), and for at least 23 weeks after the last dose of any study drug. Specific country requirements will be followed (e.g., in the United Kingdom, women of childbearing potential and male patients and their partners of childbearing potential must use two methods of contraception, one of which must be a barrier method, for the duration of the study).
12. Men who are sexually active with WOCBP must agree to follow instructions for method(s) of contraception for the duration of treatment with study drug plus 31 weeks post-treatment completion.

2.2.3 Exclusion Criteria of All Cohorts

Patients who meet ANY of the following criteria will be excluded from study entry.
1. Current or history of clinically significant muscle disorders (e.g., myositis), recent unresolved muscle injury, or any condition known to elevate serum CK levels
2. Immunosuppressive doses of systemic medications, such as steroids or absorbed topical steroids (doses >10 mg/day prednisone or equivalent daily) must be discontinued at least 2 weeks before study drug administration except in the case of tumor-related AE treatment. Patients with a condition requiring chronic systemic treatment with either corticosteroids (inhaled or topical steroids and adrenal replacement steroid doses >10 mg/day prednisone equivalent) or other immunosuppressive medications within 2 weeks of treatment are permitted in the absence of active autoimmune disease.
3. Decreased cardiac function with NYHA >Class 2
4. Uncontrolled or significant heart disorder such as unstable angina
5. Significant abnormalities on ECG at screening. QTcF >450 msec for males or >470 msec for females at screening
6. History of anti-drug antibodies, severe allergic, anaphylactic, or other infusion-related reaction to a previous biologic agent
7. Known history of sensitivity to Tween 20 (polysorbate 20) and polysorbate 80 containing infusions
8. Consumption of non-pasteurized milk on a regular basis, or known significant risk of exposure to opportunistic intracellular infections such as listeria or other such pathogens
9. Non-oncology vaccine therapies for prevention of infectious diseases (e.g., HPV vaccine) within 4 weeks of study drug administration. The inactivated seasonal influenza vaccine can be given to subjects before treatment and while on therapy without restriction. Influenza vaccines containing live virus or other clinically indicated vaccinations for infectious diseases (i.e., pneumovax, varicella, etc.) may be permitted; but must be discussed with the Sponsor's Medical Monitor and may require a study drug washout period prior to and after administration of vaccine.
10. Current unresolved infection or history of chronic, active, clinically significant infection (viral, bacterial, fungal, or other) which, in the opinion of the Investigator, would preclude the patient from exposure to a biologic agent, or pose a risk to patient safety
11. Positive test for latent tuberculosis (TB) at Screening (Quantiferon test) or evidence of active TB
12. Lack of peripheral venous access or any condition that would interfere with drug administration or collection of study samples
13. Any uncontrolled medical condition or psychiatric disorder which, in the opinion of the Investigator, would pose a risk to patient safety or interfere with study participation or interpretation of individual patient results 14. Concomitant use of statins while on study. However, a patient using statins for over 3 months prior to study drug administration and in stable status without CK rise may be permitted to enroll
15. Pregnant or breastfeeding
16. Active, known or suspected autoimmune disease. Patients with type I diabetes mellitus, hypothyroidism requiring only hormone replacement, skin disorders (such as vitiligo, psoriasis, or alopecia) not requiring systemic treatment, or conditions not expected to recur in the absence of an external trigger are permitted to enroll.
17. Participation in a another investigational drug trial within 28 days prior to first dose of study drug administration, or while on this study
18. Known history of testing positive for human immunodeficiency virus (HIV) 1&2 or known acquired immunodeficiency syndrome (AIDS)
19. Positive test for hepatitis B virus surface antigen (HBsAg) or detectable hepatitis C virus ribonucleic acid (HCV RNA) indicating acute or chronic infection
20. Symptomatic interstitial lung disease or inflammatory pneumonitis
21. Untreated or active central nervous system (CNS) or leptomeningeal metastases.

Patients are eligible if metastases have been treated and patients are neurologically returned to baseline (except for residual signs or symptoms related to the CNS treatment) for at least 2 weeks prior to first dose of study drug administration 22. Evidence of hepatic cirrhosis, confirmed by alkaline phosphatase elevations and concomitantly elevated ALT/AST ratio and hypoalbuminemia (<3.0 g/dL)
23. Evidence of coagulopathy or bleeding diathesis
24. Any uncontrolled inflammatory GI disease including Crohn's Disease and ulcerative colitis.
25. Prior exposure to any CSF1R pathway inhibitors
26. Transfusion completed within 72 hours prior to first dose of study drug administration 2.2.4 Additional Inclusion and Exclusion Criteria for Selected Cohorts
2.2.4.1 Phase 1a
2.2.4.1.1 Cabiralizumab Monotherapy Cohorts
Inclusion:
1. Histologically or cytologically confirmed solid tumor that is locally recurrent or metastatic and has progressed following standard treatment or is not appropriate for standard treatment 2.2.4.1.2 Cabiralizumab+Nivolumab Combination Cohorts
Inclusion:
1. Histologically or cytologically confirmed solid tumor that is locally recurrent or metastatic and has progressed following standard treatment or is not appropriate for standard treatment
Exclusion
1. Prior exposure to any PD-1 pathway targeting drug 2.2.4.2 Phase 1b
2.2.4.2.1 Cohort 1b1: NSCLC, (Anti-PD-1 Therapy Naïve, Second or Third Lines)
Inclusion:
1. Patients with histologically or cytologically documented squamous or non-squamous NSCLC who present with Stage IIIB or IV disease (according to version 7 of the international association for the Study of Lung Cancer Staging manual in Thoracic oncology) and with recurrent or progressive disease following multi-modal therapy (radiation therapy, surgical resection or definitive chemoradiation) for locally advanced or metastatic disease
2. Disease progression or recurrence during/after a platinum doublet-based chemotherapy regimen for advanced or metastatic disease.

Maintenance therapy following platinum doublet-based chemotherapy is not considered a separate therapy regimen.
Subjects who received platinum-containing adjuvant, neoadjuvant or definitive chemoradiation therapy given for locally advanced disease, and developed recurrent (local or metastatic) disease within 6 months of completing therapy are eligible.
Subjects with recurrent disease >6 months after platinum-containing adjuvant, neoadjuvant or definitive chemoradiation therapy given for locally advanced disease, who also subsequently progressed during or after a platinum doublet-based regimen given to treat the recurrence, are eligible.
Exclusion:
1. Prior exposure to any PD-1 pathway targeting drug 2.2.4.2.2 Cohort 1b2: NSCLC (Refractory on Anti-PD-1 targeting drugs)
Inclusion
1. Patients with histologically or cytologically documented NSCLC who present with Stage IIIB locally advanced or Stage IV disease.
2. Patient has radiological evidence of disease progression during treatment with a PD-1 pathway targeting drug that did not produce a clinical response (i.e., neither CR nor PR) and with progressive disease as the best response.
3. To be considered refractory, patients should have had no clinical response after receiving at least 2 doses of any PD-1 targeting drug
Exclusion
1. Intolerance to any PD-1 pathway targeting drug.

Intolerance is defined as any treatment-related Grade 4 AE, or any treatment-related Grade 2 or 3 AE that is unacceptable to the patient and persists despite standard countermeasures.

2.2.4.2.3 Cohort 1b3 Melanoma (Anti-PD-1 Therapy Naïve)
Inclusion
1. Patients with histologically or cytologically documented Stage III or IV melanoma as per the American Joint Committee on Cancer (AJCC) staging system who are either refractory to, intolerant to, or have refused, standard therapy for treatment of metastatic melanoma.
2. Objective evidence of disease progression (clinical or radiological) during or after at least 1 BRAF inhibitor (if BRAF V600 mutation positive)
3. Known BRAF wild-type as per regionally acceptable V600 mutational status testing
Exclusion
1. Prior therapy with any PD-1 pathway targeting drug.
2. BRAF mutant subjects and those with indeterminate or unknown BRAF status are not permitted to participate in this study 2.2.4.2.4 Cohort 1b4: Melanoma (Refractory or Relapsed on Anti-PD-1 targeting drug)
Inclusion:
1. Patients with histologically or cytologically documented unresectable Stage III or IV melanoma as per the AJCC staging system 2. Patient has radiological evidence of disease progression during treatment with a Checkpoint inhibitor or PD-1 targeting drug that did not produce a clinical benefit (no CR, PR, or SD) and progressive disease as the best response or disease progression after the initial clinical benefit of either CR, PR or SD while receiving treatment with a PD-1 targeting drug
3. To be considered refractory, patients should have had no response after receiving at least 2 doses of any PD-1 targeting drug
4. Objective evidence of disease progression (clinical or radiological) during or after at least 1 BRAF inhibitor (if BRAF V600 mutation positive)
5. Prior anticancer therapy including dacarbazine, BRAF inhibitor (if BRAF V600 mutation positive) and/or ipilimumab and palliative radiotherapy must have been completed at least 3 weeks prior to study drug administration
6. No prior treatment with PD-1 targeting drug within 6 weeks prior to first dose of study drug Exclusion:
1. BRAF mutant subjects and those with indeterminate or unknown BRAF status are not permitted to participate in this study
2. Ocular melanoma.
3. Prior intolerance to any PD-1 targeting drug Intolerance is defined as any treatment-related Grade 4 AE, or any treatment-related Grade 2 or 3 AE that is unacceptable to the patient and persists despite standard countermeasures. The reason for intolerance should be fully documented.

2.2.4.2.5 Cohort 1b5: Squamous Cell Carcinoma of the Head and Neck (SCCHN) (Second Line)
Inclusion:
1. Patients with histologically or cytologically documented recurrent or metastatic SCCHN (oral cavity, pharynx, larynx), stage III or IV and not amenable to local therapy with curative intent (surgery or radiation therapy with or without chemotherapy)
2. Tumor progression or recurrence within 6 months of the last dose of platinum therapy in the adjuvant (i.e. with radiation after surgery), primary (i.e., with radiation), recurrent, or metastatic setting. Clinical progression after platinum therapy is an allowable event for entry and is defined as progression of a lesion at least 10 mm in size that is amenable to caliper measurement (e.g., superficial skin lesion as per RECIST v1.1) or a lesion that has been visualized and photographically recorded with measurements and shown to have progressed.

Exclusion:
1. Histologically confirmed recurrent or metastatic carcinoma of the nasopharynx and any salivary gland or non-squamous histology
2. Prior exposure to any PD-1 pathway targeting drug 2.2.4.2.6 Cohort 1b6: Pancreatic Cancer (Second Line)
Inclusion:
1. Histologically or cytologically documented localized or metastatic adenocarcinoma of the pancreas, which has failed (or are not indicated for) standard therapy
2. Patients who may have received prior surgery, radiation therapy for the management of locally advanced or metastatic adenocarcinoma of the pancreas providing that disease progression has been documented. All toxicities should be resolved, and the last fraction of radiation treatment was completed at least 4 weeks prior to first study drug administration Exclusion:
1. Patients with islet cell neoplasms, neuroendocrine or other primary tumors in the pancreas
2. Patients with active pancreatitis
3. Prior exposure to any PD-1 pathway targeting drug
4. Ascites of Grade 2 or higher 2.2.4.2.7 Cohort 1b7: Colorectal Cancer (Third line)
Inclusion:
1. Histologically or cytologically documented adenocarcinoma of colon or rectum
2. Metastatic CRC with documented disease progression after the last administration of standard therapies or intolerance to standard therapies (and approved therapies had to include a fluoropyrimidine, oxaliplatin, irinotecan, bevacizumab, and, if KRAS wild-type, cetuximab or panitumumab).

Exclusion:
1. Prior exposure to any PD-1 pathway targeting drug 2.2.4.2.8 Cohort 1b8: Malignant Glioma (First recurrence)
Inclusion:
1. Histologically or cytologically documented advanced World Health Organization (WHO) Grade IV malignant glioma (glioblastoma or gliosarcoma)
2. Previous treatment with surgery, radiotherapy and temozolomide
3. Documented first recurrence of GBM by diagnostic biopsy or contrast-enhanced MRI performed within 21 days of first study drug administration per Response Assessment in Neuro-oncology (RANO) criteria
4. If on steroids, dose must be stable or decreased for a minimum of 5 days prior to baseline MRI Exclusion:
1. Prior treatment with bevacizumab or another VEGF- or VEGFR-targeting agent
2. Recent evidence of more than Grade 1 CNS hemorrhage on baseline MRI scan
3. History or evidence upon physiological/neurological exam of CNS disease (e.g., seizures) unrelated to cancer unless adequately controlled by medication or potentially interfering with the study treatment
4. Patients unable to have a head contrast-enhanced MRI due to a pre-existing medical condition including a pacemaker or implantable cardioverter defibrillator (ICD) device
5. More than 1 recurrence of glioblastoma or gliosarcoma
6. Prior exposure to any PD-1 pathway targeting drug 2.3 Concomitant Medications All medications taken within 28 days before the administration of the first dose of any study drug and all concomitant therapy administered during the study until 100 days after last dose of any study drug will be recorded.

Information on all prior treatments indicated for advanced cancer, including chemotherapy, biochemotherapy, immunotherapy, radiation, surgery, biologic, and experimental therapy will be collected.

No concomitant medication information will be collected following patient discontinuation from the study except for concomitant medication use associated with study drug-related AEs or AEs that lead to discontinuation from the study.

2.3.1 Prohibited and/or Restricted Treatments

The following medications are prohibited during the study (unless utilized to treat a drug-related AE or specified in the eligibility section):

Immunosuppressive Agents

Immunosuppressive doses of systemic corticosteroids. Inhaled or topical steroids, and adrenal replacement steroid doses >10 mg daily prednisone equivalent, are permitted in the absence of active autoimmune disease. Steroids are also permitted to treat tumor-related AEs as clinically indicated.

Vaccines except as noted in Section 4.3.2

Statins for treatment of hypercholesterolemia. Statins will be allowed only if the patient is on a stable dose for over 3 months prior to the study and is in stable status without any CK elevations Other therapies including biologic, immunotherapy, extensive non-palliative radiation therapy, standard treatments, or investigational agents or devices 2.3.2 Permitted Therapy Patients are permitted to use of topical, ocular, intra-articular, intranasal, and inhaled corticosteroids (with minimal systemic absorption). Adrenal replacement steroid doses >10 mg daily prednisone are permitted. A brief (less than 3 weeks) course of corticosteroids for prophylaxis (e.g., contrast dye allergy) or for treatment of non-autoimmune conditions (e.g., delayed-type hypersensitivity reaction caused by a contact allergen) and also for the treatment of tumor-related AE is permitted.

Concomitant palliative and supportive care for disease-related symptoms (including bisphosphonates and RANK-L inhibitors) is allowed if initiated prior to first dose of study drug administration. Transfusions are permitted as needed.

The inactivated seasonal influenza vaccine can be given to subjects while on therapy without restriction. Influenza vaccines containing live virus or other clinically indicated vaccinations for infectious diseases (i.e., pneumovax, varicella, etc.) may be permitted; but must be discussed with the Sponsor's Medical Monitor and may require a study drug washout period prior to and after administration of the vaccine.

Concomitant use of statins will be allowed only if the patient is on a stable dose for over 3 months prior to the study and is in stable status without any CK elevations.

No routine premedication will be administered for initial Cabiralizumab and nivolumab doses. If a patient develops nausea, vomiting, or other infusion-related AEs, the patient may be pre-medicated with anti-emetics, steroids, or antihistamines prior to subsequent infusions of study drugs at the discretion of the Investigator. The treatment will be administered according to the institution's standard practice, and should be captured on the patient's CRF.

2.4 Discontinuation of Patients Following any Treatment with Study Drug

Patients MUST discontinue study drugs for any of the following reasons:

Withdrawal of informed consent (patient's decision to withdraw for any reason)

Any clinical significant AE, abnormal laboratory test results or intercurrent illness which, in the opinion of the Investigator, indicates that continued participation in the study is not in the best interest of the patient Patients who are required to have prohibited concomitant medications Pregnancy Termination of the study by the Sponsor Loss of ability to freely provide consent through imprisonment or involuntary incarceration for treatment of either a psychiatric or physical (e.g., infectious disease) illness Documented disease progression or clinical deterioration while receiving active study therapy Non-compliance by the patient All patients who discontinue study treatment should comply with protocol specified follow-up procedures as outlined in Section 6. The only exception to this requirement is when a patient withdraws consent for all study procedures or loses the ability to consent freely (i.e., is imprisoned or involuntarily incarcerated for the treatment of either a psychiatric or physical illness).

If a patient was withdrawn before completing the study, the reason for withdrawal must be entered on the appropriate CRF. The date and reason for cessation of Cabiralizumab and/or nivolumab will be documented, and the Investigator must make every effort to perform the Treatment Completion/Early Termination visit procedures. Patients will be followed for 100 days after the last dose of Cabiralizumab for safety and those with ongoing SAEs will be followed until either resolution or stabilization.

2.5 Post-Treatment Follow Up

Patients who discontinue treatment while still receiving clinical benefit (i.e., CR, PR or SD) should get follow-up tumor scans per-protocol to determine the duration of response, unless consent is withdrawn.

3 STUDY DRUGS

In this study, both the study drugs, Cabiralizumab and nivolumab, are considered Investigational [Medicinal] Products (IP/IMP). The product descriptions for Cabiralizumab and nivolumab are described in Table 3 and Table 4:

TABLE 3

Study Drug for Phase 1a Monotherapy Cohorts

| Product Description/Class and Dosage Form | Potency | IP | Open Label | Packaging/Appearance | Storage Conditions (per label) |
|---|---|---|---|---|---|
| Cabiralizumab Solution for Injection | 100 mg (20 mg/mL) | 5 mL per vial | X vials per carton/open-label | Sterile, aqueous, colorless, pyrogen-free solution in 5 mL Type 1 glass vials fitted with butyl rubber stoppers and flip-up aluminum seals | 2-8° C. (36-46° F.). Protect from freezing |

TABLE 4

Study Drugs for Phase 1a Combination Dose Escalation and Phase 1b Dose Expansion Cohorts

| Product Description/ Class and Dosage Form | Potency | IP | Open Label | Packaging/Appearance | Storage Conditions (per label) |
|---|---|---|---|---|---|
| Nivolumab Solution for Injection | 100 mg (10 mg/mL) | 10 mL per vial | 10 vials per carton/ Open-label | Clear to opalescent colorless to pale yellow liquid. May contain particles | 2-8° C. Protect from light and freezing |
| Cabiralizumab Solution for Injection | 100 mg (20 mg/mL) | 5 mL per vial | X vials per carton/open-label | Sterile, aqueous, colorless, pyrogen-free solution in 10 mL Type 1 glass vials fitted with butyl rubber stoppers and flip-up aluminum seals | 2-8° C. (36-46° F.). Protect from freezing |

3.1 Investigational Products

An investigational product, also known as investigational medicinal product in some regions, is defined as a pharmaceutical form of an active substance or placebo being tested or used as a reference in a clinical study, including products already with a marketing authorization but used or assembled (formulated or packaged) differently than the authorized form, or used for an unauthorized indication, or when used to gain further information about the authorized form. In this protocol, the investigational products are Cabiralizumab and nivolumab.

3.2 Study Drug Dosing and Dose Modification 3.2.1 Dosing

For the combination therapy, nivolumab should always be administered first as a 30-minute IV infusion, with a 30-minute rest between 2 infusions, followed by Cabiralizumab 30-minute infusion. Patients may be dosed no less than 12 days from the previous dose.

For the 4 mg/kg monotherapy cohort (1aM2) and combination dose escalation cohorts 1aC2 and 1aC3, the dose interval between the first and second patients in each cohort should be at least 24 hours for safety monitoring.

Dosing calculations should be based on the body weight assessed at Cycle 1 Day 1 prior to the first dose of study drug administration. It is not necessary to re-calculate subsequent doses if the patient's weight is within 10% of the weight used to calculate the previous dose. All doses should be rounded to the nearest milligram.

Patients should be carefully monitored for infusion reactions during study drug administration. If an acute infusion reaction is noted, patients should be managed according to the guidelines in Section 5.3.10 and Appendix E and F.

Doses of study drugs may be interrupted, delayed, or discontinued depending on how well the patient tolerates the treatment.

All vials are for single use only. Further instructions on study drug preparation and administration will be provided in the Pharmacy Manual.

3.2.1.1 Nivolumab Dosing

Patients in combination therapy cohorts will receive the nivolumab infusion first at a dose of 3 mg/kg as a 30-minute IV infusion, on Day 1 of each 14-day treatment cycle.

There will be no dose escalations or reductions of nivolumab allowed. Patients may be dosed no less than 12 days from the previous dose. There are no pre-medications recommended for nivolumab on the first cycle. Refer to the nivolumab IB for preparation and handling instructions.

3.2.1.2 Cabiralizumab Dosing

For patients in the combination therapy cohorts, the Cabiralizumab infusion will be administered 30 minutes after the end of the nivolumab infusion as a 30-minute IV infusion, on Day 1 of each 14-day treatment cycle. For patients in the monotherapy cohorts, the Cabiralizumab infusion can be initiated at any time as a 30-minute IV infusion on Day 1 of each 14-day treatment cycle.

Cabiralizumab dosing may be modified based on toxicities noted during the treatment period. If necessary, the dose will be adjusted based on the toxicity-modification table (Appendices E and F).

A research pharmacist (or other responsible personnel) will prepare the solution for administration. After calculating the number of vials, based on the patient's weight, the study drug product will be diluted with 0.9% Sodium Chloride Injection, USP. Prepared Cabiralizumab should be administered within 6 hours after preparation (ambient temperature). The IV administration setup for Cabiralizumab infusion must contain a 0.22 μm in-line filter or a 0.22 μm syringe filter. Cabiralizumab will be administered under medical supervision as a 30 minute (±5 minutes) IV infusion via a peripheral vein or central venous catheter. No incompatibilities between Cabiralizumab infusion and polyvinyl chloride (PVC), ethylene/propylene IV components, or glass bottles have been observed.

3.2.2 Dose Delay for Cabiralizumab and Nivolumab

Administration of Cabiralizumab in monotherapy or Cabiralizumab/nivolumab in combination therapy should be delayed for the following:

Any Grade 3 fatigue which does not resolve to Grade 1 or baseline before the next treatment visit Any Grade 2 or 3 drug-related laboratory abnormalities would not require a dose delay unless clinically indicated or specified in the protocol or Adverse Event Management table. Please discuss with the Sponsor's Medical Monitor or designee as needed.

For dose delays or modifications for all other AEs please refer to the AE Management tables in Appendix E.

Patients who require a dose delay of Cabiralizumab or Cabiralizumab+nivolumab should be re-evaluated weekly or more frequently if clinically indicated and resume study drug dosing when re-treatment criteria are met.

If a patient experiences an infusion reaction to Cabiralizumab, or nivolumab, or both study drugs, the infusion reaction should be treated following the infusion reaction treatment guidelines in Section 5.3.10 and Appendix E and F.

3.2.3 Criteria to Resume Treatment with Cabiralizumab and Nivolumab

Patients may resume treatment with Cabiralizumab or Cabiralizumab+nivolumab when the drug-related AE(s)

resolve(s) to Grade 1 or baseline as noted in the AE management tables in Appendices E and F.

3.2.4 Dose Reduction with Cabiralizumab

Dose reductions for Cabiralizumab may be permitted for patients on prolonged treatment beyond the DLT period in Phase 1a or any patient in Phase 1b per the guidelines in the appropriate AE management tables in Appendices E and F. If dose reductions or interruptions that do not fall within these guidelines are being considered by the Investigator, these will require discussion with and approval by the Sponsor, or designee.

3.2.5 Dose Discontinuation Criteria for Cabiralizumaband Nivolumab

Treatment of Cabiralizumab in monotherapy or Cabiralizumab in combination with nivolumab should be permanently discontinued for the following:

Any Grade 2 drug-related uveitis, eye pain or blurred vision that does not respond to topical therapy and does not improve to Grade 1 within the second re-treatment period OR that requires systemic treatment Any Grade 3 or higher infusion related reactions and hypersensitivity requiring discontinuation and re-initiation of therapy will require consultation with the Sponsor's Medical Monitor or designee.

Any Grade 3 non-skin, drug-related AE lasting >7 days, including drug-related uveitis, pneumonitis, hypoxia, bronchospasm, and endocrinopathies with the following exceptions:

Grade 3 drug-related endocrinopathies adequately controlled with only physiologic hormone replacement do not require discontinuation Grade 3 drug-related laboratory abnormalities do not require treatment discontinuation except:

Grade 3 drug-related thrombocytopenia >7 days or associated with Grade ≥2 bleeding requires discontinuation Any drug-related liver function test (LFT) abnormality that meets the following criteria requires discontinuation:

AST or ALT 10×ULN

Total bilirubin >3×ULN (>5×ULN with concurrent liver metastases)

AST or ALT >3×ULN AND total bilirubin >2×ULN, in the absence of a concurrent increase of alkaline phosphatase Any Grade 4 drug-related AE or laboratory abnormality, except for the following events which do not require discontinuation:

Grade 4 neutropenia ☐7 days

Grade 4 lymphopenia or leukopenia ☐7 days

Isolated Grade 4 amylase or lipase abnormalities that are not associated with symptoms or clinical manifestations of pancreatitis. The Sponsor's Medical Monitor should be consulted for Grade 4 amylase or lipase abnormalities.

Isolated Grade 4 electrolyte imbalances/abnormalities that are not associated with clinical sequelae and are corrected with supplementation/appropriate management within 72 hours of their onset Grade 4 drug-related endocrinopathy AEs, such as adrenal insufficiency, adrenocorticotropic hormone (ACTH) deficiency, hyper- or hypothyroidism, or glucose intolerance, which resolve or are adequately controlled with physiologic hormone replacement (corticosteroids, thyroid hormones) or glucose-controlling agents, respectively, may not require discontinuation after discussion with and approval from the Sponsor's Medical Monitor.

Any event that leads to delay in dosing lasting >6 weeks from the previous dose requires discontinuation, with the following exceptions:

Dosing delays to allow for prolonged steroid tapers to manage drug-related adverse events are allowed. Prior to re-initiating treatment in a patient with a dosing delay lasting >6 weeks from the previous dose, the Sponsor's Medical Monitor must be consulted. Tumor assessments should continue as per-protocol even if dosing is delayed. Periodic study visits to assess safety and laboratory studies should also continue per protocol, or more frequently if clinically indicated during such dosing delays or per the Investigator's discretion Dosing delays lasting >6 weeks from the previous dose that occur for non-drug-related reasons may be allowed if approved by the Sponsor's Medical Monitor. Prior to re-initiating treatment in a patient with a dosing delay lasting >6 weeks, the Sponsor's Medical Monitor must be consulted. Tumor assessments should continue per protocol every 8 weeks even if dosing is delayed. Periodic study visits to assess safety and laboratory studies should also continue per-protocol or more frequently if clinically indicated during such dosing delays or per the Investigator's discretion.

Any AE, laboratory abnormality, or intercurrent illness which, in the judgment of the Investigator, presents a substantial clinical risk to the patient with continued Cabiralizumab and/or nivolumab dosing Any Grade 3 or higher neurological toxicity Any Grade 3 or higher periorbital edema and persistent Grade 2 periorbital edema requiring 2 missed doses unless approved by Sponsor's Medical Monitor Any Grade 3 or higher drug-related diarrhea or colitis interfering with activities of daily living.

Any Grade 3 or 4 skin toxicity

Any Grade 3 or higher uveitis

If the causality of the adverse event requiring discontinuation is confirmed to be due to one of the study drugs in the combination therapy, the other drug may be continued per protocol schedule under the following scenarios:

Timely resolution of the adverse event based on the treatment modification table Clinical benefit is shown by the subject based on Investigator assessment 3.2.6 Infusion Delays and Missed Doses with Cabiralizumab and Nivolumab In the case that an infusion cannot be administered at a scheduled visit, it must be administered as soon as possible. If the delay is between 1 and 3 days, the procedures at the original scheduled visit should be performed. If the delay is more than 3 days, the procedures at the next visit should be performed, and subsequent visits will be reset to follow a 2-week dosing interval (the infusion at the original scheduled visit will be considered a missed dose). The time between two treatment cycles should be no less than 12 days.

Patients may miss up to 2 consecutive doses (up to 6 weeks between doses) and may resume the study drug if the event returns to baseline or ≤Grade 1 within 6 weeks of treatment interruption. Omission of additional dosing longer than 6 weeks for AEs will necessitate the patient's discontinuation from the study unless allowed by the Sponsor. Patients may miss doses in the course of participation in the study, including missed doses for scheduled vacations or other personal reasons as needed, but not more than 2 doses sequentially unless approved by the Sponsor's Medical Monitor.

3.2.7 Intra-patient Dose Escalation with Cabiralizumab and Nivolumab

Intra-patient dose escalation is not allowed for nivolumab or Cabiralizumab.

3.2.8 Treatment Beyond Disease Progression with Cabiralizumab and Nivolumab

Accumulating evidence indicates a minority of patients treated with immunotherapy may derive clinical benefit despite initial evidence of progressive disease (Wolchok, 2009)

Patients treated with Cabiralizumab and nivolumab will be permitted to continue Cabiralizumab and nivolumab treatment beyond initial RECIST v1.1 defined progressive disease, assessed by the Investigator, as long as the following criteria are met:

Patients who will be treated beyond disease progression must review and sign an ICF before continuing on study drug Investigator-assessed clinical benefit, and do not have rapid disease progression Tolerance of study drugs Stable performance status Treatment beyond progression will not delay an imminent intervention to prevent serious complications of disease progression (e.g., CNS metastases)

A radiographic assessment/scan should be performed approximately 8 weeks after initial Investigator-assessed progression to determine whether there has been a decrease in the tumor size or continued progressive disease. The assessment of clinical benefit should be balanced by clinical judgment as to whether the patient is clinically deteriorating and unlikely to receive any benefit from continued treatment with Cabiralizumab and nivolumab.

If the Investigator feels that the Cabiralizumab and nivolumab patient continues to achieve clinical benefit by continuing treatment, the patient should remain on the trial and continue to receive monitoring according to the time and event schedules per protocol.

For the patients who continue nivolumab study therapy beyond progression, further progression is defined as an additional 10% increase in tumor burden from time of initial progression. This includes an increase in the sum of diameters of all target lesions and/or the diameters of new measurable lesions compared to the time of initial progression. Cabiralizumab and nivolumab treatment should be discontinued permanently upon documentation of further progression.

Assessment for new lesions will follow guidelines in RECIST v1.1 (Appendix G).

3.2.9 Dose Modification Algorithms for Immuno-Oncology Agents

Immuno-oncology agents are associated with AEs that can differ in severity and duration compared to AEs caused by other therapeutic classes. Cabiralizumab and nivolumab are considered immuno-oncology agents in this protocol. Early recognition and management of AEs associated with immuno-oncology agents may mitigate severe toxicity. Management algorithms have been developed to assist Investigators in assessing and managing the following classes of AEs:

Gastrointestinal
Renal
Pulmonary
Hepatic
Endocrinopathy
Skin
Neurological
Infusion reaction
Periorbital edema
Uveitis 3.2.10 Treatment of Cabiralizumab and Nivolumab Related Infusion Reactions Cabiralizumab and nivolumab may induce infusion or hypersensitivity reactions. If such a reaction were to occur, it may manifest with fever, chills, rigors, headache, rash, pruritus, arthralgia, hypo- or hypertension, bronchospasm, or other symptoms.

Infusion reactions should be graded according to CTCAE v4.03 guidelines. Any Grade 3 or 4 infusion reaction should be reported within 24 hours to the study Medical Monitor and reported as an SAE if it meets the criteria.

The nivolumab infusion will be administered first, with a 30-minute rest between the 2 infusions, followed by Cabiralizumab 30-minute infusion. It may be unclear if an infusion reaction is due to Cabiralizumab, nivolumab, or to both study drugs. Therefore, one set of treatment recommendations (based on the most conservative treatments for infusion reactions due to either study drug) is provided below and may be modified based on clinical judgment, local treatment standards and guidelines, and/or specific symptoms, as appropriate:

For Grade 1 symptoms: (Mild reaction [e.g., localized cutaneous reactions including mild pruritus, flushing, rash], requires infusion rate to be decreased; intervention may be indicated.)

Decrease the rate of the study drug infusion until recovery from symptoms.

Remain at bedside and monitor the patient's vital signs until resolution of symptoms. Diphenhydramine 50 mg may be administered at the discretion of the treating physician.

When symptoms resolve, restart the infusion at the original infusion rate.

If a patient has an infusion reaction with nivolumab, Cabiralizumab can be given (without prophylactic medications) if the infusion reaction resolves within 3 hours. For scheduling purposes, Cabiralizumab infusion may be given the next day. Prophylactic pre-infusion medications should be given prior to all subsequent nivolumab infusions.

If a patient has an infusion reaction with Cabiralizumab, prophylactic pre-infusion medications should be given prior to all subsequent Cabiralizumab and nivolumab infusions.

The following prophylactic pre-infusion medications are recommended prior to future infusions of Cabiralizumab and nivolumab: diphenhydramine 50 mg (or equivalent) and/or paracetamol (acetaminophen) 325 to 1000 mg at least 30 minutes before additional study drug administrations.

For Grade 2 symptoms: (Moderate reaction [i.e., any symptom not listed above (mild symptoms) or below (severe symptoms) such as generalized pruritus, flushing, rash, dyspnea, hypotension with systolic blood pressure >80 mmHg], requires infusion interruption but responds promptly to symptomatic treatment [e.g., antihistamines, nonsteroidal anti-inflammatory drugs, narcotics, corticosteroids, IV fluids]; prophylactic pre-infusion medications indicated for ≤24 hours.)

Interrupt the study drug infusion.

Begin an IV infusion of normal saline, and treat the patient with diphenhydramine 50 mg IV (or equivalent) and/or paracetamol (acetaminophen) 325 to 1000 mg.

Remain at bedside and monitor the patient's vital signs until resolution of symptoms. Corticosteroid therapy may be administered at the discretion of the treating physician.

When symptoms resolve, restart the infusion at 50% of the original infusion rate; if no further complications ensue after 30 minutes, the rate may be increased to 100% of the original infusion rate.

Monitor the patient closely. If symptoms recur, immediately discontinue the infusion; no further study drug will be administered at that visit. Administer diphenhydramine 50 mg IV, and remain at bedside and monitor the patient until resolution of symptoms.

If a patient has an infusion reaction with nivolumab infusion, Cabiralizumab infusion can be given (without prophylactic medications) if the infusion reaction resolves within 3 hours. For scheduling purposes, the Cabiralizumab infusion may be given the next day. Prophylactic pre-infusion medications should be given prior to all subsequent nivolumab infusions.

If a patient has an infusion reaction with Cabiralizumab, prophylactic pre-infusion medications should be given prior to all subsequent Cabiralizumab and nivolumab infusions.

The following prophylactic pre-infusion medications are recommended prior to future infusions of Cabiralizumab and nivolumab: diphenhydramine 50 mg (or equivalent) and/or paracetamol (acetaminophen) 325 to 1000 mg should be administered at least 30 minutes before additional study drug administrations. If necessary, corticosteroids (up to 25 mg of SoluCortef or equivalent) may be used.

The amount of study drug infused must be recorded.

For Grade 3 or Grade 4 symptoms: (Severe reaction such as bronchospasm, generalized urticaria, systolic blood pressure <80 mmHg, or angioedema; Grade 3 symptoms including prolonged symptom, which requires 6 or more hours to respond to symptomatic medication and/or discontinuation of infusion; recurrence of symptoms following initial improvement; hospitalization indicated for other clinical sequelae, such as renal impairment, pulmonary infiltrates; Grade 4: life-threatening; pressor or ventilation support indicated.)

Immediately discontinue the study drug infusion. No further study drug will be administered. The amount of study drug infused must be recorded on the CRF.

Begin an IV infusion of normal saline, and treat the patient as follows: Recommend bronchodilators, epinephrine 0.2 to 1.0 mg of a 1:1,000 solution for subcutaneous administration or 0.1 to 0.25 mg of a 1:10,000 solution injected slowly for IV administration, and/or diphenhydramine 50 mg IV with methylprednisolone 100 mg IV (or equivalent), as needed.

Remain at bedside and monitor the patient's vital signs until recovery from symptoms.

The patient should be monitored until the Investigator is comfortable that the symptoms will not recur.

Investigators should follow their institutional guidelines for the treatment of anaphylaxis.

In the case of late-occurring hypersensitivity symptoms (e.g., appearance of a localized or generalized pruritus within 1 week after treatment), symptomatic treatment may be given (e.g., oral antihistamine, or corticosteroids).

3.3 Method of Assigning Patient Identification

Patients must be able to provide written informed consent and meet all eligibility criteria. No waivers of inclusion or exclusion criteria will be granted by Sponsor or its designee for any patient enrolled in the study. Before enrolling a patient, all eligibility criteria must be satisfied.

Patients who qualify for Phase 1a of the study will be enrolled as follows:

Three patients in the Phase 1aM1 monotherapy cohort will be enrolled first to be treated with 2 mg/kg Cabiralizumab every 14 days during the 28-day DLT period.

Once the above monotherapy cohort is fully enrolled, a cohort (1aC1) of 3 new patients will be enrolled to be treated with 1 mg/kg Cabiralizumab in combination with 3 mg/kg nivolumab every 14 days during the 28-day DLT period.

Dose escalation into the 4 mg/kg Cabiralizumab monotherapy cohort (1aM2) will proceed once the DLT period is cleared in the 2 mg/kg Cabiralizumab monotherapy cohort (1aM1).

Dose escalation into increasing dose levels of Cabiralizumab in combination with nivolumab will proceed until DLTs are observed either in the Cabiralizumab monotherapy or the Cabiralizumab in combination with nivolumab cohorts after discussion and agreement between the participating Investigators and Sponsor's Medical Monitor.

In Phase 1b, approximately 30 patients will be enrolled per cohort. Enrollment will be open for all cohorts in parallel and will continue until the enrollment target is reached. Once a cohort is filled, further enrollment will be restricted to the cohort(s) that have not been filled. A total of approximately 240 patients will be enrolled in the Phase 1b arm of the study.

The Investigator may repeat qualifying lab tests and vitals/ECGs prior to enrollment if a non-qualifying finding is considered an error or an acute finding is likely to meet eligibility criteria upon repeat testing.

3.4 Blinding/Unblinding

This is an open-label study and there will be no blinding or unblinding of patients during this study.

4 STUDY ASSESSMENTS AND PROCEDURES 4.1 Schedule of Assessments

The schedule of assessment tables are attached to the protocol as Appendices A, B, and C.

4.2 Study Procedures by Visit 4.2.1 Phase 1a Monotherapy 4.2.1.1 Screening Period (Day-28 to Day 0)

Patients who have fully consented to participation in the study will undergo Screening assessments within 28 days (4 weeks) prior to administration of the first infusion of Cabiralizumab (unless otherwise stated). To determine if the patient meets all inclusion criteria and does not violate any exclusion criteria, the following procedures will be performed (Appendix A):

Written, signed informed consent must be collected prior to any study-specific procedures Complete medical and disease history Demographic and baseline characteristics Complete physical examination, including height and weight Vital signs (blood pressure, pulse, respiratory rate, and temperature in supine position after 5 minutes rest)

ECOG performance status evaluation

Screening labs (as described in Appendix A, footnote g)

Clinical safety labs (as described in Appendix A, footnote h)

12-lead ECG (required at Screening, and if clinically indicated during the study)

Radiological imaging: CT/MRI is to be performed within 28 days prior to the first infusion of Cabiralizumab. If the MRI is performed as part of the patient's standard of care within 28 days of the first study infusion it does not need to be repeated if the documentation of results is provided and is adequate for an assessment.

Serum pregnancy test (β-hCG), for women of childbearing potential

Biopsy collection (for analyses described in Appendix D)

SAE reporting, if applicable

Document prior and concurrent medications 4.2.1.2 Cycle 1, Day 1

The following procedures will be performed:

Prior to Cabiralizumab infusion (within 72 hours unless otherwise stated):

Verification of eligibility

Update medical and disease history to capture any changes from Screening

Physical examination, including weight

Vital signs (blood pressure, pulse, respiratory rate and temperature in supine position after 5 minutes rest)

ECOG performance status evaluation

Clinical safety labs (as described in Appendix A, footnote h); results must be reviewed before dosing)

Serum β-hCG (evaluated by local laboratories) will be performed prior to the first dose of Cabiralizumab only on women of childbearing potential Blood collection for:

Serum (for analyses described in Appendix D, excluding nivolumab analyses)

Whole blood (for analyses described in Appendix D)

Frozen PBMC (for T cell phenotype analysis)

AE reporting, if applicable

Review of concomitant medications

Study drug administration: Cabiralizumab by IV infusion over 30 minutes

Post Cabiralizumab administration:

Post-dose vital signs (heart rate, blood pressure, and temperature in supine position after 5 minutes rest) at the following time points after completion of the IV infusion:

5 MINUTES, 15 MINUTES, 30 MINUTES, AND 1 HOUR 15 minutes (±5 minutes) post-dose:

Blood collection for serum (for Cabiralizumab PK)

4 hours (±60 minutes) post-dose:

Blood collection for serum (for Cabiralizumab PK)

4.2.1.3 Cycle 1, Day 2

Study patients will return to the study center on Day 2 for 24-hour (±6 hours) post-dose assessments. No treatment will be administered during this visit, but the following assessments will be completed:

Blood collection for:

Serum (for Cabiralizumab PK and cytokine multiplex panel)

Whole blood (for gene expression analysis)

AE reporting, if applicable

Review of concomitant medications 4.2.1.4 Cycle 1, Day 4

Study patients will return to the study center on Day 4 for 72-hour (±12 hours) post-dose assessments. No treatment will be administered during this visit, but the following assessments will be completed:

Blood collection

Serum (for Cabiralizumab PK)

Whole blood (for CD14$^+$/CD16$^+$ monocyte and gene expression analyses)

AE reporting, if applicable

Review of concomitant medications 4.2.1.5 Cycle 1, Day 8

Study patients will return to the study center on Day 8 for 168-hour (±24 hours) post-dose assessments. No treatment will be administered during this visit, but the following assessments will be completed:

Physical examination

Vital signs (blood pressure, pulse, respiratory rate, and temperature in supine position after 5 minutes rest)

Clinical safety labs (as described in Appendix A, footnote h)

Blood collection for:

Serum (for Cabiralizumab PK and cytokine multiplex panel)

Whole blood (for CD14$^+$/CD16$^+$ monocyte and gene expression analyses)

Frozen PBMC (for T cell phenotype analysis)

AE reporting, if applicable

Review of concomitant medications 4.2.1.6 Cycle 2, Day 1

The following procedures will be performed:

Prior to Cabiralizumab infusion (within 72 hours unless otherwise stated):

Physical examination, including weight

Vital signs (blood pressure, pulse, respiratory rate, and temperature in supine position after 5 minutes rest)

ECOG performance status evaluation

Clinical safety labs (as described in Appendix A, footnote h; results must be reviewed before dosing:

Blood collection for:

Serum (for analyses described in Appendix D, excluding nivolumab analyses)

Whole blood (for analyses described in Appendix D, except the MDSC panel)

Frozen PBMC (for T cell phenotype analysis)

AE reporting, if applicable

Review of concomitant medications

Study drug administration: Cabiralizumab by IV infusion over 30 minutes

Post Cabiralizumab administration:

Post-dose vital signs (blood pressure, pulse, respiratory rate, and temperature in supine position after 5 minutes rest) at the following time points after completion of the IV infusion:

5 minutes, 15 minutes, 30 minutes, and 1 hour 15 minutes (±5 minutes) post-dose:

Blood collection for serum (for Cabiralizumab PK)

4.2.1.7 End of Cycle 2

For Phase 1a patients in monotherapy cohort, if at the end of Cycle 2, the Investigator determines that the patient may benefit from continued dosing with Cabiralizumab, entry into the Extended Treatment Period may be offered.

If the patient is continuing onto the Extended Treatment Period (Cycle 3 and beyond), proceed to procedures outlined in Section 6.2.1.8.

If the patient does not qualify to receive further doses of Cabiralizumab, the patient will return to the clinic for the Treatment Completion/Early Termination visit outlined in Section 6.2.1.9.

4.2.1.8 Extended Treatment—Cycle 3 and Subsequent Cycles, Day 1

Phase 1a extended treatment for patients in monotherapy cohort may begin on Cycle 3, Day 1 (Study Day 29). Dosing will be discontinued if the patient experiences either disease progression or unacceptable toxicity.

At each infusion visit, patients are to remain at the study site after each administration of Cabiralizumab until completion of all post-dose assessments for safety monitoring. The following assessments will be performed at each visit unless otherwise noted (Appendix A):

Prior to each infusion of study drug (within 72 hours unless otherwise stated):

Physical examination, including weight

Vital signs (blood pressure, pulse, respiratory rate, and temperature in supine position after 5 minutes rest)

ECOG performance status evaluation

Clinical safety labs (as described in Appendix A, footnote h; results must be reviewed before dosing)

Radiological imaging: CT/MRI scan performed every 8 weeks for the first 12 months for patients who remain on treatment (and every 12 weeks thereafter) and 28 days (±7 days) after the last dose of study treatment.

Biopsy collection (prior to Cycle 3 only; for analyses described in Appendix D)

Blood collection for:

Serum (for analyses described in Appendix D) with the following exceptions:

Cabiralizumab PK for Cycles 3, 5, 9, 13, and 21

Cabiralizumab ADA for Cycles 3, 5, 13, and 21

ANA for Cycles 3, 5, 9, 13, 21, then every 6 cycles while on treatment

CSF1 and IL34 for Cycle 3 and 9

Cytokine multiplex panel for Cycles 3, 9, and 21

Whole blood (for analyses described in Appendix D) with the following exceptions:

$CD14^+/CD16^+$ monocytes for Cycle 3, and 9

MDSC panel for Cycle 3 only

Gene expression analysis for Cycle 3, 5, 9, 13, and 21

AE reporting, if applicable

Review of concomitant medications

Study drug administration: Cabiralizumab by IV infusion over 30 minutes

Post Cabiralizumab administration:

Post-dose vital signs (blood pressure, pulse, respiratory rate, and temperature in supine position after 5 minutes rest) at the following time points after completion of the IV infusion:

5 MINUTES, 15 MINUTES, 30 MINUTES, AND 1 HOUR 15 minutes (±5 minutes) post-dose:

Blood collection for serum (for analyses described in Appendix D) with the following exceptions:

Cabiralizumab PK for Cycle 8 only 4.2.1.9 Treatment Completion or Early Termination Visit Patients will return to the study center approximately 28 (±7) days after their last infusion of Cabiralizumab.

The following assessments will be performed:

Physical examination, including weight

Vital signs (blood pressure, pulse, respiratory rate, and temperature in supine position after 5 minutes rest)

ECOG performance status evaluation

Clinical safety labs (as described in Appendix A, footnote h)

12-lead ECG

Radiological imaging: CT/MRI scan does not need to be repeated if performed within 8 weeks prior to the Treatment Completion/Early Termination Visit or if tumor progression was previously determined.

Serum pregnancy test (β-hCG), if applicable

Biopsy for patients who progressed (for analyses described in Appendix D)

Blood collection

Serum (for analyses described in Appendix D, excluding nivolumab analyses)

Whole blood (for $CD14^+/CD16^+$ monocyte analysis and gene expression analysis only)

AE reporting, if applicable

Review of concomitant medications 4.2.2 Phase 1a Combination Dose Escalation 4.2.2.1 Screening Period (Day-28 to Day 0)

Patients who have consented to participation in the study will undergo screening assessments within 28 days (4 weeks) prior to administration of the first infusion of Cabiralizumab and nivolumab (unless otherwise stated). To determine if the patient meets all inclusion criteria and does not violate any exclusion criteria, the following procedures will be performed (Appendix B):

Written, signed informed consent must be collected prior to any study-specific procedures Complete medical and disease history Demographic and baseline characteristics Complete physical examination, including height and weight Vital signs (blood pressure, pulse, respiratory rate, and temperature in supine position after 5 minutes rest; pulse oximetry at rest and after exertion)

ECOG performance status evaluation

Screening labs (as described in Appendix B, footnote g)

Clinical safety labs (as described in Appendix B, footnote h)

12-lead ECG (required at Screening, and if clinically indicated during the study)

Radiological imaging: CT/MRI to be performed within 28 days prior to Cycle 1 Day 1. If the CT/MRI is performed as part of the patient's standard of care within 28 days of Cycle 1 Day 1, it does not need to be repeated if the documentation of results is provided and is adequate for RECIST 1.1

Serum pregnancy test (β-hCG), ≤5 days prior to Cycle 1, Day 1, for women of childbearing potential Biopsy collection (for analyses described in Appendix D)

SAE reporting, if applicable

Document prior and concurrent medications 4.2.2.2 Cycle 1, Day 1

The following procedures will be performed:

Prior to Cabiralizumab and nivolumab infusion (within 72 hours unless otherwise stated):

Verification of eligibility

Update medical and disease history to capture any changes from Screening

Physical examination, including weight

Vital signs (blood pressure, pulse, respiratory rate, and temperature in supine position after 5 minutes rest; pulse oximetry at rest and after exertion)

ECOG performance status evaluation

Clinical safety labs (as described in Appendix B, footnote h; results must be reviewed before dosing)

Serum β-hCG (evaluated by local laboratories) will be performed prior to the first dose of study drug only on women of childbearing potential Blood collection for:

Serum (for analyses described in Appendix D)

Whole blood (for analyses described in Appendix D)

Frozen PBMC (for T cell phenotype analysis)

AE reporting, if applicable

Review of concomitant medications

Study drug administration: Cabiralizumab and nivolumab will each be administered by IV infusion over 30 minutes. Nivolumab will be given first, with a 30-minute rest between the 2 infusions, followed by Cabiralizumab 30.

Post Cabiralizumab and nivolumab administration:

Post-dose vital signs (blood pressure, pulse, respiratory rate, and temperature in supine position after 5 minutes rest) at the following time points after completion of each IV infusion:

5 minutes and 15 minutes after nivolumab dose 5 minutes, 15 minutes, 30 minutes, and 1 hour after Cabiralizumab dose 15 minutes (±5 minutes) post-Cabiralizumab dose:
Blood collection for serum (for Cabiralizumab and nivolumab PK analysis)
4 hours (±60 minutes) post-Cabiralizumab dose:
Blood collection for serum (for Cabiralizumab PK only)

4.2.2.3 Cycle 1, Day 2

Study patients will return to the study center on Day 2 for 24-hour (±6 hours) post-dose assessments. No treatment will be administered during this visit, but the following assessments will be completed:
Blood collection for:
Serum (for Cabiralizumab PK and cytokine multiplex panel)
Whole blood (for gene expression analysis)
AE reporting, if applicable
Review of concomitant medications 4.2.2.4 Cycle 1, Day 4

Study patients will return to the study center on Day 4 for 72 hour (±12 hours) post-dose assessments. No treatment will be administered during this visit, but the following assessments will be completed:
Blood collection for:
Serum (for PK only)
Whole blood (for $CD14^+/CD16^+$ monocyte and gene expression analyses)
AE reporting, if applicable
Review of concomitant medications 4.2.2.5 Cycle 1, Day 8

Study patients will return to the study center on Day 8 for 168-hour (±24 hours) post-dose assessments. No treatment will be administered during this visit, but the following assessments will be completed:
Physical examination
Vital signs (blood pressure, pulse, respiratory rate, and temperature in supine position after 5 minutes rest; pulse oximetry at rest and after exertion)
Clinical safety labs (as described in Appendix B, footnote h)
Blood collection for:
Serum (for Cabiralizumab PK and cytokine multiplex panel)
Whole blood (for $CD14^+/CD16^+$ monocyte and gene expression analyses)
Frozen PBMC (for T cell phenotype analysis)
AE reporting, if applicable
Review of concomitant medications 4.2.2.6 Cycle 2, Day 1

The following procedures will be performed:
Prior to Cabiralizumab and nivolumab infusion (within 72 hours unless otherwise stated):
Physical examination, including weight
Vital signs (blood pressure, pulse, respiratory rate, and temperature in supine position after 5 minutes rest; pulse oximetry at rest and after exertion)
ECOG performance status evaluation
Clinical safety labs (as described in Appendix B, footnote h; results must be reviewed before dosing)
Blood collection for:
Serum (for analyses described in Appendix D)
Whole blood (for analyses described in Appendix D, except the MDSC panel)
Frozen PBMC (for T cell phenotype analysis)
AE reporting, if applicable
Review of concomitant medications
Study drug administration: Cabiralizumab and nivolumab will each be administered by IV infusion over 30 minutes. Nivolumab will be given first, with a 30-minute rest between the 2 infusions, followed by Cabiralizumab.
Post Cabiralizumab and nivolumab administration:
Post-dose vital signs (blood pressure, pulse, respiratory rate, and temperature in supine position after 5 minutes rest) at the following time points after completion of the IV infusion:
5 minutes and 15 minutes after nivolumab dose
5 minutes, 15 minutes, 30 minutes, and 1 hour after Cabiralizumab dose
15 minutes (±5 minutes) post-Cabiralizumab dose:
Blood collection for serum (for Cabiralizumab PK only)

4.2.2.7 End of Cycle 2

For Phase 1a patients in the combination cohort, if at the end of Cycle 2 the Investigator determines that the patient may benefit from continued dosing with Cabiralizumab and nivolumab, entry into the Extended Treatment Period may be offered.
If the patient is continuing onto the Extended Treatment Period (Cycle 3 and beyond), proceed to procedures outlined in Section 6.2.2.8.
If the patient does not qualify to receive further study drug, the patient will return to the clinic for the Treatment Completion/Early Termination visit outlined in Section 6.2.2.9.

4.2.2.8 Extended Treatment—Cycle 3 and Subsequent Cycles, Day 1

Phase 1a extended treatment for patients in combination dose escalation cohorts may begin on Cycle 3, Day 1 (Study Day 29).
At each infusion visit, patients are to remain at the study site after each administration of Cabiralizumab and nivolumab until completion of all post-dose assessments for safety monitoring. The following assessments will be performed at each visit unless otherwise noted (Appendix B):
Prior to each infusion of study drugs (within ≤72 hours unless otherwise stated):
Physical examination, including weight
Vital signs (blood pressure, pulse, respiratory rate, and temperature in supine position after 5 minutes rest; pulse oximetry at rest and after exertion)
ECOG performance status evaluation
Clinical safety labs (as described in Appendix B, footnote h; results must be reviewed before dosing)
Radiological imaging: CT/MRI scan performed every 8 weeks for the first 12 months for patients who remain on treatment (and every 12 weeks thereafter) and 28 days (±7 days) after the last dose of study treatment.
Biopsy collection (for analyses described in Appendix D)
Blood collection for:
Serum (for analyses described in Appendix D) with the following exceptions:
Cabiralizumab PK for Cycles 3, 5, 9, 13, and 21 only
Nivolumab PK for Cycles 3, 5, 9, 13, and 21 only
Cabiralizumab and nivolumab ADA for Cycles 3, 5, 13, and 21 only
ANA for Cycles 3, 5, 9, 13, 21, then every 6 cycles while on treatment
CSF1, IL34 for Cycle 3 and 9 only
Cytokine multiplex panel for Cycles 3, 9, and 21 only
Whole blood (for analyses described in Appendix D) with the following exceptions:
$CD14^+/CD16^+$ for Cycle 3 and 11 only
Myeloid-derived suppressor cell panel for Cycle 3 only
Gene expression analysis for Cycle 3, 5, 9, 13, and 21 only AE reporting, if applicable
Review of concomitant medications
Study drug administration: Cabiralizumab and nivolumab will each be administered by IV infusion over 30 minutes. Nivolumab will be given first, with a 30-minute rest between the 2 infusions, followed by Cabiralizumab.
Post Cabiralizumab and nivolumab administration:
Post-dose vital signs (blood pressure, pulse, respiratory rate, and temperature in supine position after 5 minutes rest) at the following time points after completion of the IV infusion:
5 minutes and 15 minutes after nivolumab dose
5 minutes, 15 minutes, 30 minutes, and 1 hour after Cabiralizumab dose
15 minutes (±5 minutes) post-Cabiralizumab dose:
Blood collection for serum (for analyses described in Appendix D) with the following exceptions:
Cabiralizumab and nivolumab PK for Cycle 8 only 4.2.2.9 Treatment Completion or Early Termination Visit Patients will return to the study center approximately 28 (±7) days after their last infusion of Cabiralizumab and nivolumab, or in the event a patient discontinues prematurely from the study.
The following assessments will be performed:
Physical examination, including weight
Vital signs (blood pressure, pulse, respiratory rate, and temperature in supine position after 5 minutes rest; pulse oximetry at rest and after exertion)
ECOG performance status evaluation
Clinical safety labs (as described in Appendix B, footnote h)
12-lead ECG
Radiological imaging: CT/MRI scan does not need to be repeated if performed within 8 weeks prior to the Treatment Completion/Early Termination Visit or if tumor progression was previously determined.
Serum pregnancy test (β-hCG), if applicable
Biopsy for patients who progressed (for analyses described in Appendix D)
Blood collection for:
Serum (for analyses described in Appendix D)
Whole blood (for CD14$^+$/CD16$^+$ monocyte analysis and gene expression by RNA sequencing only)
AE reporting, if applicable
Review of concomitant medications 4.2.3 Phase 1b Combination Dose Expansion 4.2.3.1 Screening Period (Day −28 to Day 0)

Patients who have fully consented to participation in the study will undergo Screening assessments within 28 days (4 weeks) prior to administration of the first infusion of Cabiralizumab and nivolumab (unless otherwise stated). To determine if the patient meets all inclusion criteria and does not violate any exclusion criteria, the following procedures will be performed (Appendix B):
Written, signed informed consent must be collected prior to any study-specific procedures
Complete medical and disease history
Demographic and baseline characteristics
Complete physical examination, including height and weight
Vital signs (blood pressure, pulse, respiratory rate, and temperature in supine position after 5 minutes rest; pulse oximetry at rest and after exertion)
ECOG performance status evaluation
Screening labs (as described in Appendix B, footnote g)
Clinical safety labs (as described in Appendix B, footnote h)
12-lead ECG (required at Screening, and if clinically indicated during the study)
Radiological imaging: CT/MRI to be performed within 28 days prior to the first infusion of study drug. If the MRI is performed as part of the patient's standard of care within 28 days of the first study infusion it does not need to be repeated if the documentation of results is provided and is adequate for RECIST 1.1.
Serum pregnancy test (β-HCG), 5 days prior to Cycle 1, Day 1, for women of childbearing potential
Biopsy collection (for analyses described in Appendix D)
SAE reporting, if applicable
Document prior and concurrent medications 4.2.3.2 Cycle 1, Day 1

The following procedures will be performed:
Prior to Cabiralizumab and nivolumab infusion (within 72 hours unless otherwise stated):
Verification of eligibility
Update medical and disease history to capture any changes from Screening
Physical examination, including weight
Vital signs (blood pressure, pulse, respiratory rate, and temperature in supine position after 5 minutes rest; pulse oximetry at rest and after exertion)
ECOG performance status evaluation
Clinical safety labs (as described in Appendix B, footnote h; results must be reviewed before dosing)
Serum β-hCG (evaluated by local laboratories) will be performed prior to the first dose of study drug only on women of childbearing potential
Blood collection for:
Serum (for analyses described in Appendix D)
Whole blood (for analyses described in Appendix D)
Frozen PBMC (for T cell phenotype analysis)
AE reporting, if applicable
Review of concomitant medications
Study drug administration: Cabiralizumab and nivolumab will each be administered by IV infusion over 30 minutes. Nivolumab will be given first, with a 30-minute rest between the 2 infusions, followed by Cabiralizumab.
Post-Cabiralizumab and nivolumab administration:
Post-dose vital signs (blood pressure, pulse, respiratory rate, and temperature in supine position after 5 minutes rest) at the following time points after completion of the IV infusion:
5 minutes and 15 minutes after nivolumab dose
5 minutes, 15 minutes, 30 minutes, and 1 hour after Cabiralizumab dose
15 minutes (±5 minutes) post-Cabiralizumab dose:
Blood collection for serum (for Cabiralizumab and nivolumab PK analysis)
4 hours (±60 minutes) post-Cabiralizumab dose:
Blood collection for serum (for Cabiralizumab PK only)

4.2.3.3 Cycle 1, Day 2

Study patients will return to the study center on Day 2 for 24-hour (±6 hours) post-dose assessments. No treatment will be administered during this visit, but the following assessments will be completed:
Blood collection for:
Serum (for Cabiralizumab PK and cytokine multiplex panel)
Whole blood (for gene expression analysis)
AE reporting, if applicable
Review of concomitant medications 4.2.3.4 Cycle 1, Day 4

Study patients will return to the study center on Day 4 for 72-hour (±12 hours) post-dose assessments. No treatment will be administered during this visit, but the following assessments will be completed:
Blood collection for:
Serum (for Cabiralizumab PK only)
Whole blood (for CD14+/CD16+ monocyte and gene expression analyses)
AE reporting, if applicable
Review of concomitant medications 4.2.3.5 Cycle 1, Day 8

Study patients will return to the study center on Day 8 for 168-hour (±24 hours) post-dose assessments. No treatment will be administered during this visit, but the following assessments will be completed:
Physical examination
Vital signs (blood pressure, pulse, respiratory rate, and temperature in supine position after 5 minutes rest; pulse oximetry at rest and after exertion)
Clinical safety labs (as described in Appendix B, footnote h)
Blood collection for:
Serum (for Cabiralizumab PK and cytokine multiplex panel)
Whole blood (for CD14+/CD16+ monocyte and gene expression analyses)
Frozen PBMC (for T cell phenotype analysis)
AE reporting, if applicable
Review of concomitant medications 4.2.3.6 Cycle 2, Day 1

The following procedures will be performed:
Prior to Cabiralizumab and nivolumab infusion (within 72 hours unless otherwise stated):
Physical examination, including weight
Vital signs (blood pressure, pulse, respiratory rate, and temperature in supine position after 5 minutes rest; pulse oximetry at rest and after exertion)
ECOG performance status evaluation
Clinical safety labs (as described in Appendix B, footnote h; results must be reviewed before dosing)
Blood collection for:
Serum (for analyses described in Appendix D)
Whole blood (for analyses described in Appendix D, except the MDSC panel)
Frozen PBMC (for T cell phenotype analysis)
AE reporting, if applicable
Review of concomitant medications
Study drug administration: Cabiralizumab and nivolumab will each be administered by IV infusion over 30 minutes. Nivolumab will be given first, with a 30-minute rest between the 2 infusions, followed by Cabiralizumab.
Post-Cabiralizumab and nivolumab administration:
Post-dose vital signs (blood pressure, pulse, respiratory rate, and temperature in supine position after 5 minutes rest) at the following time points after completion of the IV infusion:
5 minutes and 15 minutes after nivolumab dose
5 minutes, 15 minutes, 30 minutes, and 1 hour after Cabiralizumab dose
15 minutes (±5 minutes) post-Cabiralizumab dose:
Blood collection for serum (for Cabiralizumab PK only)

4.2.3.7 Cycle 3 and Subsequent Cycles, Day 1

At each infusion visit, patients are to remain at the study site after each administration of Cabiralizumab and nivolumab until completion of all post-dose assessments for safety monitoring. The following assessments will be performed at each visit unless otherwise noted (Appendix B):
Prior to each infusion of study drugs (within ≤72 hours unless otherwise stated):
Physical examination, including weight
Vital signs (blood pressure, pulse, respiratory rate, and temperature in supine position after 5 minutes rest; pulse oximetry at rest and after exertion)
ECOG performance status evaluation
Clinical safety labs (as described in Appendix B, footnote h; results must be reviewed before dosing)
Radiological imaging: CT/MRI scan performed every 8 weeks for the first 12 months for patients who remain on treatment (and every 12 weeks thereafter) and 28 days (±7 days) after the last dose of study treatment.
Biopsy collection (for analyses described in Appendix D)
Blood collection
Serum (for analyses described in Appendix D) with the following exceptions:
Cabiralizumab PK for Cycles 3, 5, 9, 13, and 21 only
Nivolumab PK for Cycles 3, 5, 9, 13, and 21 only
Cabiralizumab and nivolumab ADA for Cycles 3, 5, 13, and 21 only
ANA for Cycles 3, 5, 9, 13, 21, then every 6 cycles while on treatment
CSF1, IL34 for Cycle 3 and 9 only
Cytokine multiplex panel for Cycles 3, 9, and 21 only
Whole blood (for analyses described in Appendix D) with the following exceptions:
CD14+/CD16+ for Cycle 3 and 9 only
MDSC panel for Cycle 3 only
Gene expression analysis for Cycle 3, 5, 9, 13, and 21 only
AE reporting, if applicable
Review of concomitant medications
Study drug administration: Cabiralizumab and nivolumab will each be administered by IV infusion over 30 minutes. Nivolumab will be given first, with a 30-minute rest between the 2 infusions, followed by Cabiralizumab.
Post-Cabiralizumab and nivolumab administration:
Post-dose vital signs (blood pressure, pulse, respiratory rate, and temperature in supine position after 5 minutes rest) at the following time points after completion of the IV infusion:
5 minutes and 15 minutes after nivolumab dose
5 minutes, 15 minutes, 30 minutes, and 1 hour after Cabiralizumab dose
15 minutes (±5 minutes) post-Cabiralizumab dose:
Blood collection for serum (for analyses described in Appendix D) with the following exceptions:
Cabiralizumab and nivolumab PK for Cycle 8 only 4.2.3.8 Treatment Completion or Early Termination Visit Patients will return to the study center approximately 28 (±7) days after their last infusion of Cabiralizumab and nivolumab, or in the event a patient discontinues prematurely from the study.
The following assessments will be performed:
Physical examination, including weight
Vital signs (blood pressure, pulse, respiratory rate, and temperature in supine position after 5 minutes rest; pulse oximetry at rest and after exertion)
ECOG performance status evaluation
Clinical safety labs (as described in Appendix B, footnote h)
12-lead ECG
Radiological imaging: CT/MRI scan does not need to be repeated if performed within 8 weeks prior to the Treatment Completion/Early Termination Visit or if tumor progression was previously determined.

Serum pregnancy test (β-HCG)

Optional biopsy for patients who progressed (for analyses described in Appendix D)

Blood collection

Serum (for analyses described in Appendix D)

Whole blood (for CD14$^+$/CD16$^+$ monocyte analysis only)

AE reporting, if applicable

Review of concomitant medications 4.2.4 Follow-Up and Survival Follow-Up for All Patients After the Study Treatment Discontinuation Visit, each ongoing AE should be followed until the event has resolved to baseline grade, the event is assessed by the Investigator as stable, the patient is lost to follow-up, the patient withdraws consent, or when it has been determined that the study treatment is not the cause of the AE.

The occurrence of SAEs will be collected until 100 days after the last dose of study treatment or until resolved. Thereafter, only SAEs determined by the Investigator to be related to the study treatment will be collected.

In addition, serum will also be collected 100 days after last dose to analyze for Cabiralizumab PK, Cabiralizumab ADA, and nivolumab ADA.

Patients who have discontinued study treatment for reasons other than disease progression will continue to undergo tumor assessments approximately every 8 weeks (±2 weeks) from Study Treatment Discontinuation Visit until disease progression.

After the Study Treatment Discontinuation Visit, all patients (regardless of reason for discontinuation) will have anti-cancer therapies recorded and will be followed for survival every 3 months until death, loss to follow-up, withdrawal of consent, or study termination by the Sponsor.

For patients who withdraw their consent from the study but agree to participate in the survival follow-up, only survival information will be collected every 3 months.

4.3 Study Assessments 4.3.1 Safety Assessments

At baseline, a medical history will be obtained to capture relevant underlying conditions. The baseline examinations should include weight, height, ECOG Performance Status (Appendix G), ECG, blood pressure (BP), heart rate (HR), temperature, and oxygen saturation by pulse oximetry at rest (also monitor amount of supplemental oxygen, if applicable) within 28 days prior to first dose.

Safety assessments including serum hematology, chemistry, ECOG, weight and other assessments including ECG (if clinically indicated) will be done as part of standard care during each visit prior to dosing as noted in Appendices A, B, and C. The patient will also be monitored for any infusion-related AEs during dosing and followed up accordingly based on protocol guidelines. Pre-medications including steroids, antihistamines or other treatments will be given prior to future dosing if the patient develops infusion reactions per protocol guidelines.

Any patient who has received study drug will be evaluated for safety. Toxicity assessments will be continuous during the treatment phase and follow-up visits in-person. Once patients reach the survival follow-up phase, documented telephone calls/email correspondence to assess the patient's status are acceptable.

AEs and laboratory values will be graded according to the NCI CTCAE v4.03

Oxygen saturation by pulse oximetry at rest (also monitor amount of supplemental oxygen, if applicable) should be assessed at each on-study visit prior to dosing. If a patient shows changes on pulse oximetry or other pulmonary-related signs (hypoxia, fever) or symptoms (e.g. dyspnea, cough, fever) consistent with possible pulmonary AEs, the patient should be immediately evaluated to rule out pulmonary toxicity, according to the suspected pulmonary toxicity management table in Appendix E.

Physical examinations are to be performed as clinically indicated. If there are any new or worsening clinically significant changes since the last exam, report changes on the appropriate non-serious AE or SAE page.

Additional measures, including non-study required laboratory tests, should be performed as clinically indicated or to comply with local regulations. Laboratory toxicities (e.g., suspected drug induced liver enzyme evaluations) will be monitored during the follow-up phase via on site/local labs until all study drug-related toxicities resolve, return to baseline, or are deemed stable.

Some of the assessments referred to in this section may not be captured as data in the CRF. They are intended to be used as safety monitoring by the treating physician. Additional testing or assessments may be performed as clinically necessary or where required by institutional or local regulations.

4.3.2 Efficacy Assessments 4.3.2.1 Primary Efficacy Parameters

The primary efficacy parameter is the objective response rate (ORR; number of patients with confirmed response of CR or PR, divided by the total number of treated patients with measurable disease at baseline). Tumor response status will be assessed using RECIST v1.1 (Appendix F). Independent review of tumor assessments may be requested at the discretion of the Sponsor.

4.3.2.2 Additional Efficacy Parameters

Additional efficacy parameters may include the following: Overall Survival (OS, 1-year OS, and median OS), progression-free survival (PFS), and duration of response (DOR) for those patients with confirmed responses, based on RECIST v1.1.

CT/MRI (chest, abdomen, pelvis, and brain) will be performed at Screening, during the treatment and at the end of study/early termination per protocol. Measurements of change in tumor burden must be reviewed and documented after each measurement.

4.3.2.3 Tumor Biopsy

Biopsy at the primary tumor site will be collected at screening and also at 29 days on-treatment (prior to Cycle 3, Day 1) for all Phase 1a patients and 10 patients per cohort in Phase 1b. Patients in the Phase 1a portion of the study will also have post-treatment biopsy upon documented tumor progression. This post-progression biopsy will be optional for patients in Phase 1b. Biopsies will be assessed for tumor associated leukocytes, tumor proliferation, and cell death markers.

4.3.3 Pharmacokinetic Assessments

Blood samples for the PK evaluation of both Cabiralizumab and nivolumab will be collected from all patients (Phase 1a and 1b).

Blood samples will be collected for measurement of serum Cabiralizumab concentration during Cycle 1 on Days 1, 2, 4, and 8. Blood samples will be collected both before and at the end of the infusion for Cycle 2. In addition, blood samples will be collected at the end of the infusion for Cycle 8 and before the infusion on Cycles 3, 5, 9, 13, and 21. A blood sample will also be collected for PK analysis 100 days post-last dose and at the Treatment Completion/Early Termination visit.

Patients enrolled in dose escalation of phase 1a and phase 1b will have blood sampling for measurement of serum nivolumab concentration both before and at the end of infusion for Cycle 1. In addition, blood samples will be collected prior to infusion of Cycles 2, 3, 5, 9, 13, and 21. A blood sample will also be collected for PK analysis 100 days post-last dose and at the Treatment Completion/Early Termination visit.

Standard PK parameters will be determined based on serum Cabiralizumab concentration-time data, as appropriate. Potential pharmacokinetic drug-drug interaction between Cabiralizumab and nivolumab will be evaluated.

4.3.3.1 Pharmacokinetic Collection and Processing

Blood samples will be collected and processed for serum according to the instructions provided in a separate Laboratory Manual.

4.3.3.2 Pharmacokinetic Sample Analysis

Cabiralizumab concentration in serum will be determined in serum using a validated ELISA method. Nivolumab concentration in serum will be determined in serum using a validated ECLA method.

4.3.4 Immunogenicity Assessments

Blood samples will be collected before the infusion on Cycles 1, 2, 3, 5, 13, and 21, at 100 days post-last dose and at the Treatment Completion/Early Termination visit to measure ADA for Cabiralizumab and nivolumab. ADA for Cabiralizumab in serum will be measured by a validated bridging ECLA that utilizes Meso Scale Discovery (MSD) technology. ADA for nivolumab in serum will be measured by a validated ECLA method.

4.3.5 Biomarker Assessments

A variety of factors that could potentially predict clinical response to the combination of Cabiralizumab and nivolumab will be investigated in all peripheral blood and in tumor specimens taken from patients prior to and during treatment. Data from these investigations will be evaluated for associations with response and/or safety (AE) data. In addition, analyses of markers between the treatment arms will provide the necessary data to identify and validate biomarkers with predictive vs prognostic value. Complete instructions on the collection, processing, handling and shipment of all samples described herein will be provided in a Biomarker Manual.

4.3.5.1 Tumor Tissue Specimens

Tumor tissue specimens in the form of a paraffin embedded block or unstained slides will be submitted for central IHC assessment. These biopsy samples should be excisional, incisional or core needle as fine needle aspirates or other cytology specimens are insufficient for downstream biomarker analyses. Tissue samples are being collected to evaluate the PD effect of study drugs on the tumor microenvironment. These samples may also undergo gene sequencing to determine the effect of study drugs on gene pathways as well as identified gene signatures associated with resistance to response. These analyses may help predict future response to treatment. A summary of analyses to be performed are described in Appendix D.

Tumor biopsy specimens will be obtained before treatment, as well as on-treatment, to examine immune infiltrates and expression of selected tumor markers. The tumor tissue that is obtained from these samples will be divided as appropriate between a fresh frozen sample to be used for gene expression analysis, and a formalin fixed sample to be used for IHC.

Stained tissue sections will be submitted to the central lab, where they will be assessed by a pathologist and scored for PD-L1 positivity.

Samples may be assessed for the expression of immune or disease related genes, RNAs and/or proteins, as well as for the presence of immune cell populations using a variety of methodologies inclusive of, but not limited to IHC, qRT-PCR, genetic mutation detection and fluorescent in situ hybridization (FISH). Other methods of tumor biomarker expression are being evaluated.

4.3.5.2 Serum

Blood samples for exploratory serum biomarker analyses will be drawn at the time points indicated in the Schedule of Assessments (Appendices A, B, and C). Blood samples will be processed to collect serum and then put in frozen storage prior to analysis. In addition to the PK and ADA analyses mentioned above, serum samples will be analyzed to determine the PD effect of study drugs on cytokine and CSF1R ligand concentrations. Samples may be assessed by ELISA, seromics and/or other relevant multiplex-based protein assay methods. Serum marker analyses may also help establish a biomarker signature that may predict benefit or correlate with efficacy that can be used to inform this and future studies. Timings of sample collection are listed in Appendix C and analyses to be performed are described in Appendix D.

4.3.5.3 Whole Blood for Single Nucleotide Polymorphism (SNP) Assessment

Whole blood samples for exploratory pharmacogenetic assessment will be collected from all patients and put in frozen storage prior to analysis. Genomic DNA will be extracted and subsequently assessed for single nucleotide polymorphisms and other genetic variations in candidate genes that may predispose patients to benefit or AEs. Additional use of these data may include correlative analyses aimed at identifying genotypic associations with clinically-relevant biomarkers identified by other methodologies described in this section.

4.3.5.4 Flow Cytometry

Pre-treatment and on-treatment samples will be analyzed by flow cytometry to study the effects of Cabiralizumab and nivolumab on various peripheral blood immune cell subsets. Whole blood samples will be assessed to confirm the predicted PD effect of Cabiralizumab on the reduction of $CD16^+$ monocytes. PBMC samples will be analyzed to determine whether blockade of PD-1 combined with CSF1R targeting will impact peripheral T cell activation and function. PBMC samples may be assessed for the levels of myeloid-derived suppressor cells and for monocyte phenotype. Timings of sample collection are listed in Appendix C and analyses to be performed are described in Appendix D.

4.3.5.5 Gene Expression Profiling

Alterations in the pattern of gene expression in tumor samples will be assessed, using RNA sequencing and qPCR, with particular emphasis on pathways of immune function. All samples collected will be stored, and may be used for subsequent research relevant to tumor immune response.

5 STATISTICAL CONSIDERATIONS

All analyses will be descriptive and will be presented by dose group and overall as appropriate. Data collected in this study will be presented using summary tables and patient data listings. Continuous variables will be summarized using descriptive statistics, specifically the mean, median, standard deviation, minimum, and maximum. Categorical variables will be summarized by frequencies and percentages.

5.1 Sample Size Determination

Approximately 30 patients will be enrolled in Phase 1a (dose escalation); between 3 and 6 patients are expected to be treated at each dose escalation cohort according to the algorithm outlined in FIG. 6. Table 5 summarizes the probability of escalating to the next dose cohort for various true DLT rates.

TABLE 5

Probability of Dose Escalation and Dose Limiting Toxicities

| | True DLT rate | | | | |
|---|---|---|---|---|---|
| | 1% | 5% | 10% | 30% | 50% |
| Probability of dose escalation | 0.999 | 0.973 | 0.906 | 0.494 | 0.172 |

Objective Response Rate is the primary efficacy variable for the Phase 1b portion of the study. With approximately 30 patients in each disease type, the 95% confidence interval half-width for the corresponding response rate would be within 18%.

5.2 Populations for Analyses

All Enrolled Population: All patients who sign the ICF and were registered in IXRS.

Safety Population: All patients who receive at least one dose of Cabiralizumab and/or nivolumab.

PK Population: All patients who receive at least one dose of Cabiralizumab and have available serum concentration data evaluable for the determination of PK profile. All patients who received at least one dose of nivolumab, the peak and trough PK profile will be determined.

Biomarker Patients: All patients who receive at least one dose of Cabiralizumab and/or nivolumab and have available biomarker data.

Immunogenicity Patients: All patients who receive at least one dose of Cabiralizumab and/or nivolumab and have available ADA data.

5.3 Endpoints
5.3.1 Phase 1a Endpoints
5.3.1.1 Primary
Safety

The incidence of Grade 3 and Grade 4 AEs and clinical laboratory abnormalities defined as DLTs.

The incidence of AEs, clinical laboratory abnormalities, and ECG abnormalities 5.3.1.2 Secondary
Pharmacokinetic The following PK parameters will be derived from concentration-time data for Cabiralizumab when appropriate and applicable. Other parameters, such as dose dependency and accumulation ratio, may also be calculated. The potential pharmacokinetic drug-drug interaction between Cabiralizumab and nivolumab will be assessed as appropriate.

Area under serum concentration-time curve (AUC)
Maximum serum concentration ($C_{max}$)
Minimum serum concentration ($C_{max}$)
Volume of distribution at steady state ($V_{ss}$)

The peak and trough concentration PK profile will be derived from nivolumab serum concentration data when appropriate and applicable.

Immunogenicity

Immunogenicity, defined as an immune response to either Cabiralizumab or nivolumab, will be assessed by measurement of total anti-Cabiralizumab antibodies and total anti-nivolumab antibodies from all patients. Immunogenicity testing will consist of screening, confirmation, and titration for both Cabiralizumab and nivolumab.

Pharmacodynamic Biomarkers

Changes in whole blood monocyte subsets by flow cytometry

Changes in cytokine levels multiplex analysis

Biomarker expression levels in tumor biopsy samples as measured by IHC 5.3.1.3 Exploratory
Pharmacodynamic Biomarkers Changes in serum levels of selected markers Changes in peripheral T cell and other leukocyte phenotypes by flow cytometry Levels of peripheral MDSC by flow cytometry Changes in gene expression in whole blood or PBMC 5.3.2 Phase 1b Endpoints
5.3.2.1 Primary
Efficacy The objective response rate (ORR) will be defined as the total number of patients with confirmed responses of either CR or PR divided by the total number of response-evaluable patients Safety The incidence of AEs, SAES, clinical laboratory abnormalities, and ECG abnormalities The incidence of treatment discontinuations, modifications, interruptions due to adverse events Grade 3 and Grade 4 AEs and clinical laboratory abnormalities 5.3.2.2 Secondary
Pharmacokinetic The following PK parameters will be derived from concentration-time data for Cabiralizumab when appropriate and applicable. Other parameters, such as dose dependency and accumulation ratio, may also be calculated. The potential pharmacokinetic drug-drug interaction between Cabiralizumab and nivolumab will be assessed as appropriate.

Area under serum concentration-time curve (AUC)
Maximum serum concentration ($C_{max}$)
Minimum serum concentration ($C_{max}$)
Volume of distribution at steady state ($V_{ss}$)

The peak and trough concentration PK profile will be derived from nivolumab serum concentration data when appropriate and applicable.

Immunogenicity

Immunogenicity, defined as an immune response to either Cabiralizumab or nivolumab, will be assessed by measurement of total anti-Cabiralizumab antibodies and total anti-nivolumab antibodies from all patients. Immunogenicity testing will consist of screening, confirmation, and titration for both Cabiralizumab and nivolumab.

Pharmacodynamic Biomarkers

Changes in whole blood monocyte subsets by flow cytometry

Changes in cytokine levels multiplex analysis

Biomarker expression levels in tumor biopsy samples as measured by IHC

Efficacy

Overall Survival (OS) will be defined as the time between the first dose of study drug and death.

One-year OS
Median OS

Duration of response (DOR) will be defined as the time from response (CR or PR) until the onset of PD that is subsequently confirmed.

Progression-free survival (PFS) will be defined for each patient as the time from the first dose to the first observation of disease progression or death due to any cause.

5.3.2.3 Exploratory
Pharmacodynamic Biomarkers
Changes in serum levels of selected markers
Changes in peripheral T cell and other leukocyte phenotypes by flow cytometry
Levels of peripheral MDSC by flow cytometry
Changes in gene expression in whole blood or PBMC 5.4 Analyses 5.4.1 Demographics and Baseline Characteristics Demographic data, medical history, other baseline characteristics, concomitant disease, and concomitant medication will be summarized by cohort and overall. To determine whether the criteria for study conduct are met, corresponding tables and listings will be provided. These will include an assessment of protocol deviations, study drug accountability, and other data that may impact the general conduct of the study.

5.4.2 Efficacy Analyses

For each disease type, response to treatment will be summarized by ORR, defined as the ratio of the number of patients that achieve an objective response to the number of patients enrolled. Exact confidence interval will be constructed for the response rate. Overall Survival, survival at 1 year, and median survival will be estimated by the Kaplan-Meier method. The corresponding confidence interval will also be presented.

5.4.3 Safety Analyses

Safety analyses will be performed for patients included in the safety population. AEs, clinical laboratory information, vital signs, ECOG performance status, weight, and ECGs will be tabulated and summarized.

AEs will be summarized overall and with separate summaries for SAEs, AEs leading to discontinuation, AEs leading to death, and NCI-CTCAE version 4.03 Grade 3 or higher AEs.

Weight and vital signs will be summarized descriptively (n, mean, standard deviation, median, minimum, and maximum). ECOG performance status will be summarized categorically and descriptively.

Shift tables displaying patient counts and percentages classified by baseline grade and maximum grade on treatment will be provided for laboratory data by cohort and overall. A marked laboratory change is defined as a shift from a baseline Grade 0 to Grade 3 (non-hematologic) or Grade 4 (hematologic) on treatment, or a shift from a baseline Grade 1 to Grade 4 on treatment. The number and percentage of patients with marked laboratory changes will be tabulated by cohort and overall.

5.4.4 Pharmacokinetic Analyses

Individual and mean serum concentration of Cabiralizumab and nivolumab versus time data will be plotted by dose level. Summary statistics will be tabulated for the serum concentration-time data and estimated PK parameters of Cabiralizumab, as appropriate. Potential PK drug-drug interaction between Cabiralizumab and nivolumab will be evaluated.

For Cabiralizumab, PK parameters including $C_{max}$, AUC, $C_{trough}$, CL, and $V_{ss}$ will be estimated. Other PK parameters as well as inter-patient variability, Cabiralizumab accumulation and dose proportionality will be evaluated when data are available. PK data (Cabiralizumab and/or nivolumab) collected from this study may be used in combination with other studies for exposure-response or population PK modeling, which will be part of a separate report.

5.4.5 Immunogenicity

A listing will be provided of all available immunogenicity data for both Cabiralizumab and nivolumab. Additionally, a listing of immunogenicity data from those patients with at least one positive ADA at any time point will be provided by dose level. The frequency of patients with at least one positive ADA assessment, and frequency of patients who develop ADA after a negative baseline assessment will be provided by dose. To examine the potential relationship between immunogenicity and safety, the frequency and type of AEs of special interest may be examined by overall immunogenicity status. Associations between pre-dose concentrations of Cabiralizumab or nivolumab and corresponding ADA assessments may be explored.

5.4.6 Biomarker Analyses

To assess the PD effects of Cabiralizumab and nivolumab on various exploratory biomarkers (such as soluble factors, peripheral blood immune cell subsets, and other markers as assessed by IHC) summary statistics for these markers and their changes (or percent changes) from baseline will be tabulated by visit and dose. In addition, the time course of exploratory biomarker outcomes will be investigated graphically, by summary plots or individual patient plots over time. Patterns of change in these biomarker values over time and how the patterns differed among dose levels may be additionally investigated using appropriate modeling, for example, by linear mixed effects models.

Possible associations of biomarker measures with clinical efficacy measures including OS will be investigated based on data availability. Methods such as, but not limited to, logistic regression may be used to further investigate such associations.

If, at the time of database lock for the primary and secondary endpoints, biomarker data related to the exploratory objectives are not available, these biomarker analyses results may not be included in the CSR but reported separately.

Selected Serum Marker Expression:

Analyses of expression are descriptive in nature and intended to examine the distribution of expression and assess potential associations between expression and efficacy measures. If there is an indication of a meaningful association, future work will evaluate expression as a predictive biomarker, including selection of an optimal expression cut-off to classify patients as positive or negative. Cut-off selection and validation will be conducted across studies and reported outside of individual CSRs. Additionally, analyses detailed below may be reported outside of the CSR in order to ensure the integrity of any potential validation analyses using data from this study.

The following analyses will be performed:
Listing of selected biomarker data
Summary of tumor specimen acquisition and characteristics
Summary statistics of expression by select subgroups, and overall
Box plot of expression by treatment group and overall
OS curves for each treatment group will be estimated using the Kaplan-Meier (KM) product limit method for each Expression Quartile subgroup and for the subgroup of patients with an unknown or indeterminate IHC result. Expression quartiles will be defined based on overall population. Two-sided, 95% confidence intervals for median OS will be computed by Brookmeyer and Crowley method.

Investigator-determined PFS curves for each treatment group will be estimated using the KM product-limit method for each Expression Quartile subgroup and for the subgroup of patients with an unknown or indeterminate IHC result. Expression quartiles will be defined based on overall population. Two-sided, 95% confidence intervals for median PFS will be computed by Brookmeyer and Crowley method.

Investigator-determined ORRs will be computed by treatment group along with exact 95% CIs using the Clopper-Pearson method for each Expression Quartile subgroup and for the subgroup of patients with an unknown or indeterminate expression result. Expression quartiles will be defined based on overall population. Associated odds ratios and 95% CIs will be calculated.

Box plots of expression versus Response Status by treatment group

Cumulative distribution plot of expression versus population percentile by treatment group and overall Waterfall plots of individual expression by treatment group Forest plot of OS and PFS Hazard Ratios with 95% CIs for each Expression Quartile subgroup and for the subgroup of patients with an unknown or indeterminate IHC result. Expression Quartiles will be defined based on overall population.

5.5 Interim Analysis

No formal interim analysis is planned.

The Sponsor (and/or designee) and Investigator(s) will review safety data from each dose cohort prior to dose escalation or de-escalation. In addition, an interim data summary may be performed at several times prior to completion of the study in order to facilitate program decisions and to support presentations or publications.

| Term | Definition |
| --- | --- |
| ACTH | Adrenocorticotropic hormone |
| ADA | Anti-drug antibody |
| AE | Adverse event |
| ALT | Alanine aminotransferase |
| ANA | Antinuclear antibody |
| ANC | Absolute neutrophil count |
| AST | Aspartate aminotransferase |
| AT | Aminotransferases |
| AUC | Area under the concentration-time curve |
| AUC(INF) | Area under the concentration-time curve from time zero extrapolated |
| β-HCG | Beta-human chorionic gonadotropin |
| BID | Bis in die; twice daily |
| BMI | Body mass index |
| BMS | Bristol-Myers Squibb |
| BP | Blood pressure |
| BTLA | B- and T-lymphocyte attenuator |
| BUN | Blood urea nitrogen |
| ° C. | Degrees Celsius |
| CBC | Complete blood count |
| CD | Cluster of differentiation |
| CFR | Code of Federal Regulations |
| CHO | Chinese hamster ovary |
| CI | Confidence interval |
| CK | Creatinine kinase |
| CL | Clearance |
| $C_{max}$, CMAX | Maximum observed concentration |
| $C_{min}$, CMIN | Trough observed concentration |
| CMV | Cytomegalovirus |
| CNS | Central nervous system |
| CR | Complete response |
| CRC | Colorectal cancer |
| CRF | Case report form, may be paper or electronic |
| CRO | Contract research organization |
| CRP | C-reactive protein |
| CSF1 | Colony stimulating factor 1 |
| CSF1R | Colony stimulating factor 1 receptor |
| CSR | Clinical study report |
| CT | Computed tomography |
| CTA | Clinical trials agreement |
| CTCAE v4.03 | Common Terminology Criteria for Adverse Events, version 4.03 |
| CTLA-4 | Cytotoxic T lymphocyte antigen 4 |

-continued

| Term | Definition |
| --- | --- |
| $C_{trough}$ | Trough observed plasma concentration |
| CTX | C-terminal collagen crosslink peptides |
| CV | Coefficient of variation |
| DC | Dendritic cell |
| DEHP | Di-(2-ethylhexyl)phthalate |
| DILI | Drug-induced liver injury |
| dL | Deciliter |
| DLT | Dose-limiting toxicity |
| DMARD | Disease-modifying anti-rheumatic drug |
| DNA | Deoxyribonucleic acid |
| DOR | Duration of response |
| $EC_{50}$ | Half-maximal effective concentration |
| ECG | electrocardiogram |
| ECLA | Electrochemiluminescence assay |
| ECM | Extracellular matrix |
| ECOG | Eastern Cooperative Oncology Group |
| eCRF | Electronic case report form |
| EDC | Electronic data capture |
| e.g. | exempli gratia (for example) |
| ELISA | Enzyme-linked immunosorbent assay |
| ePPND | Enhanced pre- and post-natal development |
| ESR | Erythrocyte sedimentation rate |
| ° F. | Degrees Fahrenheit |
| FACS | Fluorescent-activated cell sorter |
| Fc | Fragment crystallizable |
| FDA | Food and Drug Administration |
| FFPE | Formalin-fixed, paraffin-embedded |
| FISH | Fluorescent in situ hybridization |
| FivePrime | Five Prime Therapeutics, Inc. |
| FSH | Follicle stimulating hormone |
| g | Gram |
| GBM | Glioblastoma multiforme |
| GCP | Good Clinical Practice |
| GI | Gastrointestinal |
| h | Hour |
| HBcAg | Hepatitis B core antigen |
| HBsAg | Hepatitis B surface antigen |
| HBV | Hepatitis B virus |
| HCV | Hepatitis C virus |
| HIV | Human Immunodeficiency Virus |
| HR | Heart rate |
| HRP | Horseradish peroxidase |
| HRT | Hormone replacement therapy |
| IB | Investigator's Brochure |
| $IC_{50}$ | Half-maximal inhibitory concentration |
| ICD | Implantable Cardioverter Defibrillator |
| ICF | Informed consent form |
| ICH | International Conference on Harmonisation |
| ICOS | Inducible co-stimulator |
| ID | Infectious disease |
| i.e. | id est (that is) |
| IEC | Independent ethics committee |
| IFN | Interferon |
| IgG | Immunoglobulin G |
| IHC | Immunohistochemistry |
| IL | Interleukin |
| IM | Intramuscular |
| IMP | Investigational medicinal product |
| IND | Investigational new drug |
| INR | International normalized ratio |
| I-O | Immuno-oncology |
| irAE | Immune-related adverse event |
| IRB | Institutional review board |
| ITIM | Immunoreceptor tyrosine inhibitory motif |
| ITSM | Immunoreceptor tyrosine-based switch motif |
| IU | International unit |
| IV | Intravenous |
| IXRS | Integrated voice and web response system |
| kg | Kilogram |
| KM | Kaplan-Meier |
| LAG-3 | Lymphocyte-activate gene 3 |
| LDH | Lactate dehydrogenase |
| LFT | Liver function test |
| LLOQ | Lower limit of quantification |
| MABEL | Minimum anticipated biological effect level |
| mCRPC | Metastatic castration-resistant prostate cancer |
| MDSC | Myeloid-derived suppressor cell |

| Term | Definition |
|---|---|
| mg | Milligram |
| min | Minute |
| μL | Microliter |
| mL | Milliliter |
| MLR | Mixed lymphocyte reaction |
| μM | Micrometer |
| mM | Millimolar |
| mm$^3$ | Cubic millimeters |
| mmHg | millimeters of mercury |
| MRI | Magnetic resonance imaging |
| MSD | Meso Scale Discovery |
| MTD | Maximum tolerated dose |
| N | Number of patients or observations |
| NCA | Non-compartmental analysis |
| NCI | National Cancer Institute |
| ng | Nanogram |
| NOAEL | No-observable-adverse-effect level |
| NSCLC | Non-small cell lung cancer |
| NYHA | New York Heart Association |
| NSAID | Non-steroidal, anti-inflammatory drug |
| ORR | Objective response rate |
| OS | Overall survival |
| PBMC | Peripheral blood mononuclear cell |
| PD | Pharmacodynamics |
| PD-1 | Programmed death 1 |
| PDAC | Pancreatic ductal adenocarcinoma |
| PD-L1 | Programmed death ligand 1 |
| PD-L2 | Programmed death ligand 2 |
| PFS | Progression-free survival |
| PK | Pharmacokinetics |
| PO | Per os; by mouth |
| PPK | Population pharmacokinetics |
| PR | Partial response |
| PTT (aPTT) | Partial thromboplastin time |
| PVC | Polyvinyl chloride |
| q2w | Every two weeks |
| qPCR | Quantitative real-time polymerase chain reaction |
| qRT-PCR | Quantitative reverse-transcription polymerase chain reaction |
| QTcF | Fridericia's correction formula for QT interval |
| RBC | Red blood cell |
| RCC | Renal cell carcinoma |
| RD | Recommended Dose |
| RECIST v1.1 | Response Evaluation Criteria in Solid Tumors, version 1.1 |
| RNA | Ribonucleic acid |
| SAE | Serious adverse event |
| SAP | Statistical analysis plan |
| SCCHN | Squamous-cell carcinoma of the head and neck |
| SD | Stable disease |
| SkTnI | Skeletal troponin |
| SOP | Standard operating procedure |
| T$_3$ | Triiodothyronine |
| T$_4$ | Thyroxine |
| TAM | Tumor-associated macrophage |
| TB | Tuberculosis |
| TCR | T-cell receptor |
| TIL | Tumor-infiltrating lymphocyte |
| T$_{max}$, TMAX | Time of maximum observed concentration |
| TNF | Tumor necrosis factor |
| Trap5b | Tartrate resistant acid phosphatases 5b |
| ULN | Upper limit of normal |
| USP | United States Pharmacopeia |
| Vss | Volume of distribution at steady state |
| Vz | Volume of distribution of terminal phase (if IV and if multi- |
| WBC | White blood cell |
| WHO | World Health Organization |
| WOCBP | Women of childbearing potential |

6 REFERENCES

Ansari M J, Salama A D, Chitnis T, Smith R N, Yagita H, Akiba H, et al. The programmed death-1 (PD-1) pathway regulates autoimmune diabetes in nonobese diabetic (NOD) mice. J Exp Med. 2003; 198(1):63-9.

Blazar B R, Carreno B M, Panoskaltsis-Mortari A, Carter L, Iwai Y, Yagita H, et al. Blockade of programmed death-1 engagement accelerates graft-versus-host disease lethality by an IFN-α-dependent mechanism. J Immunol. 2003; 171:1272-7.

Carter L L, Fouser L A, Jussif J, Fitz L, Deng B, Wood C R, et al. PD-1:PD-L inhibitory pathway affects both CD4$^+$ and CD8$^+$ T cells and is overcome by IL-2. Eur J Immunol. 2002; 32(3):634-43.

Cassier P, Gomez-Roca C, Italiano A, Cannarile M, Ries C, Brillouet A, et al. Phase 1 study of RG7155, a novel anti-CSF1R antibody, in patients with locally advanced pigmented villonodular synovitis (PVNS). J Clin Oncol suppl. 2014; 32:5 abstract 10504.

Chemnitz J M, Parry R V, Nichols K E, June C H, Riley J L. SHP-1 and SHP-2 associate with immunoreceptor tyrosine-based switch motif of programmed death 1 upon primary human T cell stimulation, but only receptor ligation prevents T cell activation. J Immunol. 2004; 173:945-54.

Dai X, Ryan G, Hapel A, Dominguez M, Russell R, Kapp S, et al. Targeted disruption of the mouse colony-stimulating factor 1 receptor gene results in osteopetrosis, mononuclear phagocyte deficiency, increased primitive progenitor cell frequencies, and reproductive defects. Blood. 2002; 99:111-20.

Dunn G P, Bruce A T, Ikeda H, Old L J, Schreiber R D. Cancer immunoediting: from immunosurveillance to tumor escape. Nat Immunol. 2002; 3:991-8.

Freeman G J, Long A J, Iwai Y, Bourque K, Chernova T, Nishimura H, et al. Engagement of the PD 1 immunoinhibitory receptor by a novel B7 family member leads to negative regulation of lymphocyte activation. J Exp Med. 2000; 192(7):1027-34.

Gabbay M B, Thomas J, Gibbs A, Hold P. A randomized crossover trial of the impact of additional spermicide on condom failure rates. Sex Transm Dis. 2008; 35:862-8.

Greenwald R J, Freeman G H, Sharpe A H. The B7 family revisited. Annu Rev Immunol. 2004; 23:515-48.

Habicht A, Dada S, Jurewicz M, Fife B T, Yagita H, Azuma M, et al. A link between PDL1 and T regulatory cells in fetomaternal tolerance. J Immunol. 2007; 179:5211-9.

Hamilton J, Achuthan A. Colony stimulating factors and myeloid cell biology in health and disease. Trends in Immunology, 2013; 34:81-89.

Kaufmann D E, Walker B D. Programmed death-1 as a factor in immune exhaustion and activation in HIV infection. Curr Opin HIV Aids. 2008; 3(3):362-7.

Kestelman P, Trussel, J. Efficacy of the simultaneous use of condoms and spermicides. Family Planning Perspectives. 1991; 23(5):226-7.

Komohara Y, Jinushi M, Takeya M. Clinical significance of macrophage heterogeneity in human malignant tumors. Cancer Sci. 2014; 105:1-8.

Kuang D M, Zhao Q, Peng C, Xu J, Zhang J P, Wu C, et al. Activated monocytes in peritumoral stroma of hepatocellular carcinoma foster immune privilege and disease progression through PD-L1. J Exp Med. 2009; 206(6): 1327-37.

Latchman Y, Wood C R, Chernova T, Chaudhary D, Borde M, Chernova I, et al., PD-L2 is a second ligand for PD-1 and inhibits T cell activation. Nat Immunol. 2001; 2(3): 261-268.

Lavin Y, Merad M. Macrophages: gatekeepers of tissue integrity. Cancer Immunol Res. 2013; 1(4):201-9.

Lavin Y, Winter D, Blecher-Gonen R, David E, Keren-Shaul H, Merad M, et al. Tissue-dependent macrophage enhancer landscapes are shaped by the local microenvironment. Cell. 2014; 159:1312-26.

Llosa N J, Cruise M, Tam A, Wicks E C, Hechenbleikner E M, Taube J M, et al. The vigorous immune microenvironment of microsatellite instable colon cancer is balanced by multiple counter-inhibitory checkpoints. Cancer Discov. 2015; 5(1):43-51.

Masteller E, Wong, B. Targeting IL-34 in chronic inflammation. Drug Discov Today, 2014; 19:1212-16.

Nishimura H, Nose M, Hiai H, Minato N, Honjo T. Development of lupus-like autoimmune diseases by disruption of the PD-1 gene encoding an ITIM motif-carrying immunoreceptor. Immunity. 1999; 11:141-51.

Nishimura H, Honjo T. PD-1: an inhibitory immunoreceptor involved in peripheral tolerance. Trends Immunol. 2001a; 22: 265-8.

Nishimura H, Okazaki T, Tanaka Y, Nakatani K, Hara M, Matsumori A, et al. Autoimmune dilated cardiomyopathy in PD-1 receptor-deficient mice. Science. 2001b; 291: 319-22.

Nivolumab Investigator's Brochure. Version 13. Bristol-Myers Squibb. 21 Jul. 2014

Noy R, Pollard J. Tumor-associated macrophages: from mechanisms to therapy. Immunity. 2014; 41:49-61.

Okazaki T, Tanaka Y, Nishio R, Mitsuiye T, Mizoguchi A, Wang J, et al. Autoantibodies against cardiac troponin I are responsible for dilated cardiomyopathy in PD-1-deficient mice. Nat Med. 2003; 9:1477-83.

Opdivo [package insert]. Princeton, N.J.: Bristol-Myers Squibb Company; March, 2015.

Pardoll D. Does the immune system see tumors as foreign or self? Annu Rev Immunol. 2003; 21:807-39.

Pyonteck S, Akkari L, Schuhmacher A, Bowman R, Sevenich L, Quail D, et al. CSF-1R inhibition alters macrophage polarization and blocks glioma progression. Nat Med. 2013; 19:1264-72.

Radi Z, Guzman R, Bell R. Increased connective tissue extracellular matrix in the op/op model of osteopetrosis. Pathobiology. 2009; 76:199-203

Radi Z, Koza-Taylor P, Bell R, Obert L, Runnels H, Beebe J, et al. Increased serum enzyme levels associated with Kupffer cell reduction with no signs of hepatic or skeletal muscle injury. Am J Pathol. 2011; 179: 240-247.

Ries C, Cannarile M, Hoves S, Benz J, Wartha K, Runza V, et al. Targeting tumor-associated macrophages with anti-CSF-1R antibody reveals a strategy for cancer therapy. Cancer Cell. 2014; 25:846-59.

Rizvi N A, Mazeires J, Planchard D, Stinchcombe T E, Dy G K, Antonia S J, et al. Activity and safety of nivolumab, an anti-PD-1 immune checkpoint inhibitor, for patients with advanced, refractory squamous non-small-cell lung cancer (CheckMate 063): a phase 2, single-arm trial. Lancet Oncol. 2015; 16(3):257-65.

Ruffell B, Coussens L M. Macrophages and therapeutic resistance in cancer. Cancer Cell. 2015; 27:462-72.

Rutebemberwa A, Ray S C, Astemborski J L, Levine J, Liu L, Dowd K A, et al. High-programmed death-1 levels on hepatitis C virus-specific T cells during acute infection are associated with viral persistence and require preservation of cognate antigen during chronic infection. J Immunol. 2008; 181:8215-25.

Sadis S, Mukherjee A, Olson S, Dokmanovich M, Maher R, Cai C, et al. Safety, pharmacokinetics, and pharmacodynamics of PD-0360324, a human monoclonal antibody to monocyte/macrophage colony stimulating factor, in healthy volunteers. ACR/ARHP Scientific Meeting 2009 Oct. 17-21, Philadelphia, Pa., Poster 408.

Salama A D, Chitnis T, Imitola J, Ansari M J, Akiba H, Tushima F, et al. Critical role of the programmed death-1 (PD-1) pathway in regulation of experimental autoimmune encephalomyelitis. J Exp Med. 2003; 198:71-8.

Sharpe A H, Wherry E J, Ahmed R, Freeman G J. The function of programmed cell death 1 and its ligands in regulating autoimmunity and infection. Nature Immunol. 2007; 8:239-45.

Sheppard K A, Fitz L J, Lee J M, Benander C, George J A, Wooters J, et al. PD-1 inhibits T-cell receptor induced phosphorylation of the ZAP70/CD3zeta signalosome and downstream signaling to PKC-theta. FEBS Letters. 2004; 574:37-41.

Tumeh P C, Harview C L, Yearley J H, Shintaku I P, Taylor E J M, Robert L, et al. PD-1 blockade induces responses by inhibiting adaptive immune resistance. Nature. 2014; 515:568-71.

Velu V, Titanji K, Zhu B, Husain S, Pladevega A, Lai L, et al. Enhancing SIV-specific immunity in vivo by PD-1 blockade. Nature. 2009; 458:206-10.

Wang C, Thudium K B, Han M, Wang X T, Huang H, Feingersh D, et al. In vitro characterization of the anti-PD-1 antibody nivolumab, BMS-936558, and in vivo toxicology in non-human primates. Cancer Immunol Res. 2014; 2:846-56.

Weber J S, D'Angelo S P, Minor D, Hodi F S, Gutzmer R, Neyns B, et al. Nivolumab versus chemotherapy in patients with advanced melanoma who progressed after anti-CTLA-4 treatment (CheckMate 037): a randomised, controlled, open-label, phase 3 trial. Lancet Oncol. 2015; 16(4):375-84.

Wolchok J D, Hoos A, O'Day S, Weber J S, Hamid O, Lebbe C. Guidelines for the evaluation of immune therapy activity in solid tumors: immune-related response criteria. Clin Cancer Res. 2009; 15:7412-20.

Zitvogel L, Tesniere A, Kroemer G. Cancer despite immunosurveillance: immunoselection and immunosubversion. Nat Rev Immunol. 2006; 6:715-27.

Zhu Y, Knolhoff B, Meyer M, Nywening T, West B, Luo J, et al. CSF1/CSF1R blockade reprograms tumor-infiltrating macrophages and improves response to T-cell checkpoint immunotherapy in pancreatic cancer models. Cancer Res. 2014; 74:5057-69.

APPENDIX A

Schedule of Assessments
Phase 1a Cabiralizumab Monotherapy and Combination - Schedule of Patient Assessments

| Procedure[a,b] | Screening Day −28 to Day 0 Week 0 | Cycle 1 Day 1 | Cycle 1 Day 2 Week 1 | Cycle 1 Day 4 | Cycle 1 Day 8 Week 2 | Cycle 2 Day 1 Week 3 | Cycle x[r] Day 1 Week ≥5 | Treatment Completion/ Early Termination Visit |
|---|---|---|---|---|---|---|---|---|
| Informed Consent | x | | | | | | | |
| Review/Confirm Eligibility | x | x | | | | | | |
| Medical History/ | x | x | | | | | | |
| Physical Examination[c] | x | x | | | x | x | x | x |
| Height and Weight[d] | x | x | | | | x | x | x |
| Vital Signs[e] | x | x | | | x | x | x | x |
| ECOG Performance Status[f] | x | x | | | | x | x | x |
| Screening Labs[g] | x | | | | | | | |
| Clinical Safety Labs[h] | x | x | | | x | x | x | x |
| 12-Lead ECG[i] | x | | | | | | | x |
| CT/MRI Tumor Assessment[j,k] | x | | | | | | x | x |
| Serum Pregnancy Test[l] | x | x | | | | | | x |
| Biopsy[m] | x | | | | | | x | x |
| PK Sampling[n,o] | | x | x | x | x | x | x | x |
| PD Sampling[n] | | x | x | x | x | x | x | x |
| ADA Sampling[n] | | x | | | | x | x | x |
| ANA Testing[p] | | x | | | | x | x | x |
| Study Drug(s)[q] | | x | | | | x | x | |
| Adverse Events | x------------------------------------------------------------------------------------------------------------------x | | | | | | | x |
| Prior/Concomitant | x------------------------------------------------------------------------------------------------------------------x | | | | | | | x |

Notes for Phase 1a Schedule of Assessments

[a] Unless specified, procedure is to be completed within ±72 hours of scheduled time point and to be synchronized with administration day of Cabiralizumab infusion.

[b] Any clinical assessment, laboratory study, or additional non-specified tests may be obtained at any time, if clinically indicated.

[c] Standard physical examination will be performed as determined by the Investigator, particularly to follow physical findings to resolution. Targeted physical exams should be conducted at any time to follow up on AE reports.

[d] Height is only required to be recorded at Screening (for BMI calculation). Weight is required to be recorded at Day 1 of each cycle. Dose will be adjusted only if weight change is >10% from first dose on Cycle 1 Day 1.

[e] Vital signs include pulse, respiratory rate, blood pressure, and temperature in the supine position. Measure prior to dose and after completion of each IV infusion at the following time points: 5 minutes, 15 minutes, 30 minutes, and 1 hour post-dose (30 minutes and 1 hour after Cabiralizumab only). Pulse oximetry is performed at rest and after exertion prior to dosing only.

[f] Patient ECOG Status assessments are to be performed within 72 hours prior to dosing (Day 1 of each cycle).

[g] Screening labs include serology for Hepatitis B (HBsAg and HBcAb), Hepatitis C (HCV antibody), HIV antibody, and Quantiferon test (for latent TB).

[h] Clinical Safety Labs:

Hematology including CBC with differential, platelets, hemoglobin, hematocrit, RBC, and RBC indices Chemistry includes CK (creatinine kinase), AST (aspartate transaminase), ALT (alanine transaminase), bicarbonate, bilirubin, (direct and total), BUN (blood urea nitrogen), calcium, chloride, creatinine, glucose, LDH (lactate dehydrogenase), phosphorus, potassium, sodium, and, if applicable, serum pregnancy. If CK is elevated at any time, obtain troponins (cardiac and skeletal), CK isoenzymes, aldolase, and ECG; repeat CK and these additional tests daily or other interval as clinically indicated, until resolved or stable. If either AST or ALT is elevated, obtain total serum bilirubin, alkaline phosphatase; repeat daily or other interval, as clinically indicated, until resolved or stable. Additional tests may be obtained at any time, if clinically indicated.

Urinalysis will only be done at Screening, and when clinically indicated.

[i] Obtain ECG records at Screening and Treatment Completion/Early Termination Visit (after PK blood draw, record exact time). Additional ECGs should be obtained at any time, if serum CK or cardiac troponin is elevated; if abnormal (excluding sinus tachycardia), ECGs should be obtained (if clinically indicated), until the abnormality is resolved or clinically stable. Additional ECGs may be obtained at any time, if clinically indicated. ECGs for each patient should be obtained from the same machine whenever possible. To minimize variability, it is important that patients be in a resting position for at least 5 minutes prior to each ECG evaluation. Body position should be consistently maintained for each ECG evaluation to prevent changes in heart rate. Environmental distractions (e.g., television, radio, conversation) should be avoided during the pre-ECG resting period and during ECG recording.

[j] CT/MRI of the Tumor sites measured as per Response Evaluation Criteria in Solid Tumors (RECIST) v1.1. If patient terminates prior to scheduled CT/MRI scans, subject should have scans done at Treatment Completion/Early Termination Visit. The same measuring modality should be used by the site to maintain consistency across the various time points.

[k] Performed every 8 weeks for the first 12 months for patients who remain on treatment (and every 12 weeks thereafter) and 28 days (±7 days) after the last dose of study treatment. CT/MRI scans do not need to be repeated if performed within 8 weeks prior to the Treatment Completion/Early Termination Visit or if tumor progression was previously determined.

[l] All women of childbearing potential (including those who have had a tubal ligation) will have a serum pregnancy test at Screening, on Cycle 1 Day 1, and at Treatment Completion/Early Termination Visit and when clinically indicated.

[m] Biopsy at primary tumor or metastatic tumor site will be collected at Screening and prior to Cycle 3, Day 1 dose. It is recommended that patients who have documented progression receive another biopsy at the end of treatment. Biopsies will be assessed for tumor associated leukocytes, tumor proliferation and cell death markers.

[n] Samples will be collected for PK, PD, and ADA analyses. Not all visits will require collection of all three - see Appendix C for collection schedule.

[o] Blood will be collected to evaluate Cmax & Cmin on day 1 of study drugs on Cycles 1, 2, 3, 5, 8, 9, 13, 21, and at the end of treatment.

[p] Antinuclear antibody (ANA) testing by indirect fluorescent antibody (IFA). If the titer is positive, check erythrocyte sedimentation rate (ESR) and C-reactive protein (CRP) to confirm result. Will be checked prior to dose at Cycles 1, 2, 3, 5, 9, 13, 21, then every 6 cycles while on treatment and at Treatment Completion/Early Termination Visit.

[q] Cabiralizumab +/− nivolumab study drug will be administered every 2 weeks in 14-day cycles for 4 weeks. The dosing may continue until PD or unacceptable toxicity.

[r] These assessments are to be performed prior to each subsequent dose (with the exceptions noted in Appendix B) for those patients who continue treatment without signs of progressive disease or toxicity

APPENDIX B

Schedule of Assessments
Phase 1b Cabiralizumab + Nivolumab - Schedule of Patient Assessments

| Procedure[a,b] | Screening Day -28 to Day 0 Week 0 | Cycle 1 Day 1 | Cycle 1 Day 2 Week 1 | Cycle 1 Day 4 | Cycle 1 Day 8 Week 2 | Cycle 2 Day 1 Week 3 | Cycle x[s] Day 1 Week ≥5 | Treatment Completion/ Early Termination Visit |
|---|---|---|---|---|---|---|---|---|
| Informed Consent | x | | | | | | | |
| Review/Confirm Eligibility | x | x | | | | | | |
| Medical History/Demographics | x | x | | | | | | |
| Physical Examination[c] | x | x | | | x | x | x | x |
| Height and Weight[d] | x | x | | | | x | x | x |
| Vital Signs[e] | x | x | | | x | x | x | x |
| ECOG Performance Status[f] | x | x | | | | x | x | x |
| Screening Labs[g] | x | | | | | | | |
| Clinical Safety Labs[h] | x | x | | | x | x | x | x |
| 12-Lead ECG[i] | x | | | | | | | x |
| CT/MRI Tumor Assessment[j,k] | x | | | | | | x | x |
| Serum Pregnancy Test[l] | x | x | | | | | | x |
| Biopsy[m] | x | | | | | | x | x |
| PK Sampling[n,o] | | x | x | x | x | x | x | x |
| PD Sampling[n] | | x | x | x | x | x | x | x |
| ADA Sampling[n] | | x | | | | x | x | x |
| ANA Testing[p] | | x | | | | x | x | x |
| Study Drug(s)[q,r] | | x | | | | x | x | |
| Adverse Events | x------------------------------------------------------------------------------------------------------------x | | | | | | | x |
| Prior/Concomitant | x------------------------------------------------------------------------------------------------------------x | | | | | | | x |

Notes for Phase 1b Schedule of Assessments

[a]Unless specified, procedure is to be completed within ±72 hours of scheduled time point and to be synchronized with administration day of Cabiralizumab infusion.

[b]Any clinical assessment, laboratory study, or additional non-specified tests may be obtained at any time, if clinically indicated.

[c]Standard physical examination will be performed as determined by the Investigator, particularly to follow physical findings to resolution. Targeted physical exams should be conducted at any time to follow up on AE reports. A photo of the subject's eyes will be taken at baseline, and subsequently at follow up visits, as clinically indicated.

[d]Height is only required to be recorded at Screening (for BMI calculation). Weight is required to be recorded at Day 1 of each cycle. Dose will be adjusted only if weight change is >10% from first dose.

[e]Vital signs include pulse, respiratory rate, blood pressure, and temperature in the supine position. Measure prior to dose and after completion of the IV infusion at the following time points: 5 minutes, 15 minutes, 30 minutes, and 1 hour post-dose (30 minutes and 1 hour for Cabiralizumab only). Pulse oximetry is performed at rest and after exertion prior to dosing only.

[f]Patient ECOG Status assessments are to be performed within 96 hours prior to dosing (Day 1 of each cycle).

[g]Screening labs include serology for Hepatitis B (HBsAg and HBcAb), Hepatitis C (HCV antibody), HIV antibody, and Quantiferon test (for latent TB).

[h]Clinical Safety Labs:

Hematology including CBC with differential, platelets, hemoglobin, hematocrit, RBC, and RBC indices Chemistry includes CK (creatinine kinase), AST (aspartate transaminase), ALT (alanine transaminase), bicarbonate, bilirubin, (direct and total), BUN (blood urea nitrogen), calcium, chloride, creatinine, glucose, LDH (lactate dehydrogenase), phosphorus, potassium, sodium, and, if applicable, serum pregnancy. If CK is elevated at any time, obtain troponins (cardiac and skeletal), CK isoenzymes, aldolase, and ECG; repeat CK and these additional tests daily or other interval as clinically indicated, until resolved or stable. If either AST or ALT is elevated, obtain total serum bilirubin, alkaline phosphatase; repeat daily or other interval, as clinically indicated, until resolved or stable. Additional tests may be obtained at any time, if clinically indicated.

Urinalysis will only be done at Screening, and when clinically indicated.

[i]Obtain ECG records at Screening and Treatment Completion/Early Termination Visit (after PK/PD blood draw, record exact time). Additional ECGs should be obtained at any time, if serum CK or cardiac troponin is elevated; if abnormal (excluding sinus tachycardia), ECGs should be obtained (if clinically indicated), until the abnormality is resolved or clinically stable. Additional ECGs may be obtained at any time, if clinically indicated. ECGs for each patient should be obtained from the same machine whenever possible. To minimize variability, it is important that patients be in a resting position for at least 5 minutes prior to each ECG evaluation. Body position should be consistently maintained for each ECG evaluation to prevent changes in heart rate. Environmental distractions (e.g., television, radio, conversation) should be avoided during the pre-ECG resting period and during ECG recording. Additional tests may be obtained at any time, if clinically indicated.

[j]CT/MRI of the Tumor sites measured as per Response Evaluation Criteria in Solid Tumors (RECIST) v1.1. If subject terminates prior to scheduled CT/MRI scan, subject should have scans done at Treatment Completion/Early Termination Visit. Response per CT/MRI will be assessed using RECIST v1.1. In the case of PD-1 resistant melanoma and squamous lung cancer, CT scans need to be done at the end of Cycles 4 and 6. The same measuring modality should be preferably used by the site to maintain consistency across the various time points. The tumor assessments for all other cancer types will be done every 2 months (4 cycles) apart unless clinically indicated.

[k]Performed every 8 weeks for the first 12 months for subjects who remain on treatment (and every 12 weeks thereafter) and 28 days (±7 days) after the last dose of study treatment. CT/MRI scans do not need to be repeated if performed within 8 weeks prior to the Treatment Completion/Early Termination Visit or if tumor progression was previously determined.

[l]All women of childbearing potential (including those who have had a tubal ligation) will have a serum pregnancy test at Screening and at Treatment Completion/Early Termination Visit and when clinically indicated.

[m]Biopsy at primary tumor or metastatic tumor site will be collected at Screening and prior to Cycle 3, Day 1 dose. It is recommended that subjects who have documented progression receive another biopsy at the end of treatment. Biopsies will be assessed for tumor associated leukocytes, tumor proliferation and cell death markers.

[n]Samples will be collected for PK, PD, and ADA analyses. Not all visits will require collection of all three - see Appendix C for collection schedule.

[o]Blood will be collected to evaluate Cmax & Cmin on day 1 of study drugs on Cycles 1, 2, 3, 5, 8, 9, 13, 21, and at the end of treatment.

[p]Antinuclear antibody (ANA) testing by indirect fluorescent antibody (IFA). If the titer is positive, check erythrocyte sedimentation rate (ESR) and C- reactive protein (CRP) to confirm result. Will be checked prior to dose at Cycles 1, 2, 3, 5, 9, 13, 21, then every 6 cycles while on treatment and at Treatment Completion/Early Termination Visit.

[q]Cabiralizumab and nivolumab will both be administered by IV infusion over 30 minutes. Nivolumab will be given first, with a 30-minute rest between the 2 infusions, followed by Cabiralizumab 30- minute infusion.

[r]Cabiralizumab + nivolumab study drug will be administered every 2 weeks in 14-day cycles and will continue until PD or unacceptable toxicity.

[s]These assessments are to be performed prior to each subsequent dose (with exceptions noted in Appendix B) for patients who continue treatment without signs of progressive disease or toxicity.

APPENDIX C

Schedule of Sample Collection
Phase 1a/b: Study Flowchart for Pharmacokinetic and Pharmacodynamic Blood Sample Collections

| Study Cycle | Study Day | Time point | Type of Sample |
|---|---|---|---|
| Screening | Screening (Day-28) | Screening | Biopsy Tissue |
| Cycle 1 | Day 1 | Prior to infusion | Cabiralizumab & Nivo PK (serum) |
| | | | Cabiralizumab & Nivo ADA (serum) |
| | | | Selected serum markers (serum) |
| | | | ANA (serum) |
| | | | $CD14^+/CD16^+$ monocytes, MDSC panel (whole blood) |
| | | | Gene expression by RNAseq (whole Blood) |
| | | | T cell phenotype (frozen PBMC) |
| | | | Cytokine multiplex panel (serum) |
| | | 15 min after infusion | Cabiralizumab & Nivo PK (serum) |
| | | 4 hr after infusion | Cabiralizumab PK (serum) |
| | Day 2 | 24 hr after infusion | Cabiralizumab PK (serum) |
| | | | Gene expression by RNASeq (whole blood) |
| | | | Cytokine multiplex panel (serum) |
| | Day 4 | 72 hr after infusion | Cabiralizumab PK (serum) |
| | | | $CD14^+/CD16^+$ monocytes, (whole blood) |
| | | | Gene expression by RNASeq (whole blood) |
| | Day 8 | 168 hr after infusion | Cabiralizumab PK (serum) |
| | | | $CD14^+/CD16^+$, (whole blood) |
| | | | Gene expression (whole blood) |
| | | | T cell phenotype (frozen PBMC) |
| | | | Cytokine multiplex panel (serum) |
| Cycles 2-3 | Day 1 | Prior to infusion | Biopsy Tissue (to be taken prior to Cycle 3, Day 1 dose) |
| | | | Cabiralizumab & Nivo PK(serum) |
| | | | Cabiralizumab & Nivo ADA (serum) |
| | | | Selected serum markers (serum) |
| | | | ANA (serum) |
| | | | $CD14^+/CD16^+$ monocytes, (whole blood) |
| | | | Gene expression by RNAseq (whole blood) |
| | | | MDSC panel (whole blood) (Cycle 3 only) |
| | | | T cell phenotype (frozen PBMC), (prior to Cycle 3 only; should correspond to tissue biopsy) |
| | | | Cytokine multiplex panel (serum) |
| | | 15 min after infusion | Cabiralizumab PK (serum) (Cycle 2 only) |
| Cycle 8 | Day 1 | 15 min after infusion | Cabiralizumab PK and Nivo PK (serum) |
| Cycles 5, 9, 13, 21 | Day 1 | Prior to infusion | Cabiralizumab and Nivo PK (serum) |
| | | | Selected serum markers (serum) (prior to Cycle 9) |
| | | | ANA (serum) (and every 6 cycles starting after Cycle 21) |
| | | | $CD14^+/CD16^+$ monocytes (whole blood) (prior to Cycle 9) |
| | | | Gene expression by RNAseq (whole blood) |
| | | | Cabiralizumab & Nivo ADA (serum) (prior to dose for cycles 5, 13, and 21) |
| | | | Cytokine multiplex panel (serum) (prior to dose for Cycles 9 and 21) |
| Treatment Completion/ Early Termination | Study discontinuation/ PD | Post treatment | Biopsy tissue for patients who have documented disease progression |
| | | | Cabiralizumab & Nivo PK (serum) |
| | | | Cabiralizumab & Nivo ADA (serum) |
| | | | Selected serum markers (serum) |
| | | | ANA (serum) |
| | | | $CD14^+/CD16^+$ monocytes, (whole blood) |
| | | | Cytokine multiplex panel (serum) |
| | | | Gene expression by RNASeq (whole blood) |
| 100 days post-last dose | | | Cabiralizumab & Nivo ADA (serum) |
| | | | Cabiralizumab PK (serum) |

Appendix D—Sample Collection for PD Analyses
  Blood samples
    Whole blood analyses
      CD14⁺/CD16⁺ monocytes
      Gene expression
      DNA for SNP analysis
    Serum analyses
      PK of Cabiralizumab
      PK of nivolumab
      ADA of Cabiralizumab
      ADA of nivolumab
      ANA (if result is positive, check ESR and CRP to confirm)
      Serum cytokine multiplex
      Selected serum markers
    Frozen PBMC analysis for characterization of T cells, monocytes and myeloid-derived suppressor cells by flow cytometry
  Tumor biopsy samples
    IHC analysis of selected biomarkers
    Gene expression analysis
    T-cell receptor clonality
    Neo-antigen analysis Example 5

Results from the Phase 1a/1b Monotherapy and Combined Cabiralizumab and Nivolumab Combination Therapy Trial In the above study, 24 solid tumor patients receiving cabiralizumab were evaluated and 205 solid tumor patients receiving cabiralizumab and nivolumab combination therapy were evaluated. The baseline characteristics of the patients are as shown below:

TABLE 6

|  | Cabiralizumab Monotherapy (n = 24) | Cabiralizumab + Nivolumab (n = 205) |
|---|---|---|
| Median age (range), years | 65.5 (48-88) | 64 (25-85) |
| <65 years, n (%) | 10 (42) | 110 (54) |
| Male, n (%) | 13 (54) | 100 (49) |
| ECOG performance status, n (%) | | |
| 0 | 7 (29) | 55 (27) |
| 1 | 17 (71) | 145 (71) |
| 2 | 0 | 4 (2) |
| Not reported | 0 | 1 (<1%) |
| No. of prior regimens, n (%) | | |
| 0 | 0 | 7 (3) |
| 1 | 5 (21) | 47 (23) |
| 2 | 2 (8) | 58 (28) |
| ≥3 | 17 (71) | 93 (45) |
| No. of prior regimens for metastatic disease, n (%) | | |
| 0 | 7 (29) | 77 (38) |
| 1 | 6 (25) | 28 (14) |
| 2 | 3 (13) | 44 (21) |
| ≥3 | 8 (33) | 56 (27) |

The safety profile of the combination was generally consistent with that of nivolumab (Brahmer J. et al. *N. Engl. J. Med.* 373: 123-135 (2015); Ferris R L et al. *N. Engl. J. Med.* 375: 1856-67 (2016)) and cabiralizumab monotherapy. The most common treatment related adverse events were elevations in creatine kinase and serum liver enzymes (without elevation in bilirubin). These may be secondary to cabiralizumab's depletion of Kupffer cells (macrophages). A summary of the safety profile is provided in the table below.

TABLE 7

|  | Cabiralizumab Monotherapy (n = 24) | | Cabiralizumab + Nivolumab (n = 205) | |
|---|---|---|---|---|
|  | Any Grade, n (%) | Grade 3-4, n (%) | Any Grade, n (%) | Grade 3-4, n (%) |
| Any treatment-related AE (TRAE) | 15 (63) | 13 (54) | 184 (90) | 100 (49) |
| AEs leading to discontinuation | 3 (13) | 2 (8) | 15 (7) | 10 (5) |
| Clinical TRAEs (≥15% of pts treated with combination) | | | | |
| Periorbital edema | 5 (21) | 0 | 84 (41) | 1 (<1) |
| Fatigue | 7 (29) | 0 | 74 (36) | 11 (5) |
| Rash | 1 (4) | 1 (4) | 38 (19) | 8 (4) |
| Pruritus | 2 (8) | 0 | 34 (17) | 2 (1) |
| Nausea | 3 (13) | 0 | 30 (15) | 0 |

TABLE 7-continued

|  | Cabiralizumab Monotherapy (n = 24) | | Cabiralizumab + Nivolumab (n = 205) | |
| --- | --- | --- | --- | --- |
|  | Any Grade, n (%) | Grade 3-4, n (%) | Any Grade, n (%) | Grade 3-4, n (%) |
| Treatment-related laboratory abnormalities of interest |  |  |  |  |
| Serum enzyme elevations[a] | 10 (42) | 9 (38) | 103 (50) | 40 (20) |
| Pancreatic enzyme elevations[b] | 3 (13) | 2 (8) | 42 (20) | 24 (12) |
| Treatment-related deaths |  | 0 |  | 3 (1.5)[c] |

[a]Includes AE terms indicative of elevated CPK, AST, ALT, and LDH.
[b]Includes AE terms indicative of elevated amylase and lipase.
[c]Includes pneumonitis (n = 1, cabiralizumab 1 mg/kg + nivolumab), respiratory distress (n = 1, cabiralizumab 4 mg/kg + nivolumab), and acute respiratory distress (n = 1, cabiralizumab 4 mg/kg + nivolumab)
AE = adverse event;
ALT = alanine aminotransferase;
AST = aspartate aminotransferase;
CPK = creatine phosphokinase;
LDH = lactate dehydrogenase The clearance of cabiralizumab is similar when administered as a monotherapy or in combination with nivolumab. The PK of cabiralizumab at doses at or above 4 mg/kg Q2W approaches the linear dose range, suggesting saturation of target-mediated clearance. Exposure with the cabiralizumab 4 mg/kg dose in the presence of nivolumab was similar across tumor types tested. Cabiralizumab with or without nivolumab also showed low immunogenicity. (The PK and immunogenicity data are not shown.)

Concentrations of CD14+CD16++ nonclassical monocytes per microliter of peripheral blood after a first dose of either cabiralizumab or cabiralizumab plus nivolumab were obtained in 34 patients with advanced solid tumors. (See FIGS. 3A and 3B.) As shown in FIG. 3A, monotherapy of at least 2 mg/kg cabiralizumab or combination therapy of at least 4 mg/kg cabiralizumab plus 3 mg/kg nivolumab Q2W is sufficient for levels of CD14+CD16++ monocytes to fall to below 10 monocytes per microliter within 3 days of initial dosing and to also remain below that threshold for a period of at least 10 days, or until the next scheduled dose at day 14. Dose-dependent reduction of levels of circulating CD14+CD16++ nonclassical monocytes reached a maximum at dosages of 4 mg/kg cabiralizumab Q2W. FIG. 3B shows that these levels remained below 10 monocytes per microliter of peripheral blood in the pancreatic cancer cohort of patients and in the remaining other cancer patients.

Within the pancreatic cancer cohort from this trial, the patient demographics and safety profile were as shown in the tables below. Of the 33 patients listed, 31 were response evaluable.

TABLE 8

|  | Cabiralizumab 4 mg/kg + Nivolumab 3 mg/kg Pancreatic Cancer (n = 33) |
| --- | --- |
| Median age (range), years | 64 (37-85) |
| <65 years, n (%) | 17 (52) |
| Male, n (%) | 17 (52) |
| ECOG performance status, n (%) |  |
| 0 | 13 (39) |
| 1 | 19 (58) |
| 2 | 1 (3) |

TABLE 8-continued

|  | Cabiralizumab 4 mg/kg + Nivolumab 3 mg/kg Pancreatic Cancer (n = 33) |
| --- | --- |
| No. of prior regimens, n (%) |  |
| 0 | 1 (3)* |
| 1 | 3 (9) |
| 2 | 14 (42) |
| ≥3 | 15 (45) |
| No. of prior regimens for metastatic disease, n (%) |  |
| 0 | 7 (21) |
| 1 | 4 (12) |
| 2 | 12 (36) |
| ≥3 | 10 (30) |

*Patient was ineligible or refused standard therapy.

TABLE 9

|  | Cabiralizumab 4 mg/kg + Nivolumab 3 mg/kg Pancreatic Cancer (n = 33) | |
| --- | --- | --- |
|  | Any Grade n (%) | Grade ¾ n (%) |
| Any TRAE | 31 (94) | 20 (61) |
| AEs leading to discontinuation | 3 (9) | 3 (9) |
| Clinical TRAEs in ≥15% of patients |  |  |
| Fatigue | 14 (42) | 1 (3) |
| Periorbital edema | 10 (30) | 0 |
| Rash | 7 (21) | 0 |
| Vomiting | 7 (21) | 0 |
| Hyponatremia | 6 (18) | 3 (9) |
| Diarrhea | 5 (15) | 1 (3) |
| Rash maculopapular | 5 (15) | 3 (9) |
| Treatment-related laboratory abnormalities of interest |  |  |
| Serum enzyme elevations[a] | 17 (52) | 11 (33) |
| Pancreatic enzyme elevations[b] | 2 (6) | 1 (3) |
| Treatment-related deaths |  | 0 |

[a]Includes AE terms indicative of elevated CPK, AST, ALT, and LDH.
[b]Includes AE terms indicative of elevated amylase and lipase.

Responses for patients with pancreatic cancer observed in the trial are shown in a scatter plot in FIG. 4. Out of 31 evaluable patients, 5 showed durable clinical benefit (16%) and the confirmed objective response rate (ORR) was 10% (3 confirmed responses). All three confirmed responses were observed in patients with microsatellite stable (MSS) disease who historically had not shown benefit with anti-PD-1/PD-L1 inhibitor treatment. Responses were accompanied by steep declines in tumor burden over baseline, for example, a percent reduction of at least 30% within 50 to 100 days of the start of treatment. (See FIG. 4.)

Furthermore, one heavily pretreated patient with MSS pancreatic cancer that had metastasized to the liver showed a 75% reduction in tumor burden from the metastasized tumor. (See FIG. 5.) Specifically, a 58 year old male patient who received 4 chemotherapy regimens including FOLFIRINOX, gemcitabine/nab-paclitaxel, 5-FU/leucovorin/liposomal irinotecan, and liposomal irinotecan regimens, achieved a partial response with a best change in tumor burden of −52%, with a decline of 99% in CA19-9 levels. In addition, a 63-year old male patient who received 4 prior chemotherapy regimens (adjuvant FOLFIRINOX, FOLFIRINOX, capecitabine, and gemcitabine plus nab-paclitaxel) also showed a durable partial response. (See FIG. 14.) As shown in FIG. 14, lesions in the lung observed prior to treatment with cabiralizumab and nivolumab had significantly reduced after several months of treatment (February 2017 vs. July 2017 scans; see white arrows in February 2017 scan). This patient achieved a partial response with a best change in tumor burden of −50%. CA19-9 levels declined 96% from baseline. As of November 2017, this patient's response was ongoing.

Example 6

Phase II Clinical Trial of Cabiralizumab and Nivolumab in Combination in Pancreatic Cancer Patients, with and without Chemotherapy An open-label, randomized, Phase II clinical trial is conducted to evaluate the efficacy, safety, tolerability, pharmacokinetics, and pharmacodynamics of a combination of cabiralizumab and nivolumab with and without chemotherapy in advanced pancreatic cancer patients. For example, treatment options for advanced pancreatic cancer patients in the US are currently limited. Gemcitabine combined with nab-paclitaxel (Abraxane®), for example, is approved for first-line treatment of advanced pancreatic cancer. A combination of 5-FU, leucovorin, and irinotecan liposome (Onivyde®) chemotherapy has also been approved for patients who have progressed despite treatment with gemcitabine-based chemotherapy. In this study, advanced metastatic cancer patients who have previously received treatment with standard, first-line treatment options based on gemcitabine or 5-fluorouracil (5-FU), but have progressed after that treatment, will receive cabiralizumab in combination with nivolumab either with or without gemcitabine/Abraxane® or FOLFOX (combination oxaliplatin, 5-FU, leucovorin) chemotherapy.

The study will evaluate the median progression free survival (PFS) at 6, 9, and 12 months, overall survival rate (OSR) at 6 months, 1 year and 2 years, objective response rate (ORR), and median duration of response (mDOR), and incidence of adverse events and serious adverse events (AEs and SAEs). PFS is defined as the time from the first dosing date the first recorded disease progression or death due to any cause, whichever is first. The ORR and mDOR will be assessed according to the RECIST v1.1 criteria.

Overall there will be 40 patients in each treatment arm of the study and 4 treatment arms in total. In Arm A, the investigator's choice of chemotherapy regimen will be administered until withdrawal of consent, death, or initiation of another anti-cancer therapy: either gemcitabine/nab-paclitaxel (Abraxane®) or 5-FU/leucovorin/irinotecan liposome (Onivyde®) chemotherapy. In Arm B, patients will receive 4 mg/kg cabrializumab every 2 weeks and 480 mg nivolumab every 4 weeks until withdrawal of consent, death, or initiation of another anti-cancer therapy. In Arm C, patients will receive 4 mg/kg cabrializumab every 2 weeks and 480 mg nivolumab every 4 weeks plus gemcitabine/Abraxane® chemotherapy until withdrawal of consent, death, or initiation of another anti-cancer therapy. In Arm D, patients will receive 4 mg/kg cabrializumab every 2 weeks and 480 mg nivolumab every 4 weeks plus oxaliplatin/5-FU/leucovorin (FOLFOX) chemotherapy until withdrawal of consent, death, or initiation of another anti-cancer therapy. Specifically, the treatment protocols for each arm are as follows:

TABLE 10

| Treatment Arm | Treatment | Dose | Frequency |
| --- | --- | --- | --- |
| A | Investigator choice of chemotherapy | As appropriate | As appropriate |
| B, C, D | Cabiralizumab | 4 mg/kg IV | Q2W |
| B, C, D | Nivolumab | 480 mg IV | Q4W |
| C | Gemcitabine | 1000 mg/m$^2$ IV | Day 1, 8, 15 Q4W |
| C | Nab-paclitaxel (Abraxane ®) | 125 mg/m$^2$ IV | Day 1, 8, 15 Q4W |
| D | Oxaliplatin | 85 mg/m$^2$ IV | Day 1, 15 Q4W |
| D | 5-FU | 400 mg/m$^2$ bolus AND 2400 mg/m$^2$ IV | Day 1, 15 Q4W |
| D | Leucovorin | 400 mg/m$^2$ IV | Day 1, 15 Q4W |

For the cabiralizumab and nivolumab combination therapy (Arms B, C, D), nivolumab is administered first as a 30 minute IV, followed by a 30 minute IV of cabiralizumab. The time between the two IV infusions is generally 30 minutes but can be more or less depending on the situation. Cabiralizumab will be administered once every 2 weeks (Q2W; i.e. 14 plus or minus 2 days) and nivolumab will be administered once every 4 weeks (Q4W; i.e. 28 plus or minus 2 days) until progression of disease or discontinuation due to toxicity, withdrawal of consent, or study closure. Subjects may be administered cabiralizumab no less than 12 days from the previous dose of cabiralizumab and may be administered nivolumab no less than 24 days from the previous dose of nivolumab. Dosages are based on body weight at cycle 1 day 1 prior to administration of the first dose of cabiralizumab. In Arms C and D, chemotherapy regimens will be administered after nivolumab and cabiralizumab treatment with a further 30 minute rest period beforehand. In Arm A, the dosing regimen for irinotecan liposome injection (Onivyde®) with 5-fluorouracil and leucovorin is irinotecan liposome injection 70 mg/m$^2$ over 90 minutes, followed by leucovorin 400 mg/m$^2$ over 30 minutes, and 5-fluorouracil 2400 mg/m$^2$ over 46 hours Q2W. Nab-paclitaxel (Abraxane®) is dosed at 125 mg/m$^2$ administered as an IV infusion over 30 to 40 minutes on Days 1, 8, and 15 of each 28-day cycle. Gemcitabine is administered in Arms A and C 1000 mg/m$^2$ over 30 to 40 minutes immediately after nab-paclitaxel on Days 1, 8, and 15 of each 28-day cycle. In Arm D, FOLFOX is given as follows: each of (oxaliplatin 85 mg/m² on Day 1 over 2 hours; leucovorin 400 mg/m² over 2 hours on Day 1 [leucovorin may be given concurrently with oxaliplatin]; 5-FU 400 mg/m² bolus on Day 1, followed by 2400 mg/m² over 46 hours continuous infusion) on Days 1 and 15 of a 28-day cycle.

The first six patients in Arms C and D will be evaluated for safety before those arms continue and more patients are enrolled. Blood, urine, tumor samples and echocardiograms will be collected for patients at 30, 60 and 100 days of treatment. Tumor progression or response endpoints will be assessed using RECIST v1.1 for solid tumors.

Inclusion criteria for the trial include the following:
At least 18 years old and have histological or cytological confirmed
Diagnosis of locally advanced or metastatic adenocarcinoma of the pancreas, which has progressed during or after at least one line of systemic chemotherapy (gemcitabine or 5-fluoruracil-based regimens
Minimum time from first systemic therapy for recurrent/metastatic adenocarcinoma of pancreas to progression should be at least 3 months
Measurable disease by RECIST v1.1 and at least one lesion available for biopsy in addition to the target lesion
Prior palliative radiotherapy must have been completed at least 2 weeks prior to the first dose of the study treatment. Participants with symptomatic tumor lesions at baseline that may require palliative radiotherapy within 4 weeks of the first dose of study treatment are strongly encouraged to receive palliative radiotherapy prior to enrollment
Eastern Cooperative Oncology Group (ECOG) performance status of ≤1
Ability to undergo mandatory pre- and on-treatment biopsies
Adequate marrow function as defined by the following:
  i) White blood cell (WBC) ≥2000 μL (stable off any growth factor within 4 weeks of first study treatment administration);
  ii) Neutrophils ≥1500 μL (stable off any growth factor within 4 weeks of first study treatment administration);
  iii) Platelets ≥100×10³ μL (transfusion to achieve this level is not permitted within 2 weeks of first study treatment administration);
  iv) Hemoglobin ≥8.5 g/dL (transfusion to achieve this level is not permitted within 2 weeks of first study treatment administration).
Adequate other organ functions as defined by the following:
  i) Alanine aminotransferase (ALT) and aspartate aminotransferase (AST) ≤3× institutional ULN
  ii) Total bilirubin ≤1.5× institutional ULN (except participants with Gilbert's Syndrome who must have normal direct bilirubin)
  iii) Serum creatinine ≤1.5×ULN or creatinine clearance (CLcr) ≥40 mL/min (measured using the Cockcroft-Gault formula below):

Female CLcr=((140−age in years)×weight in kg×0.85)/(72×serum creatinine in mg/dL)

Male CLcr=((140−age in years)×weight in kg×1.00)/(72×serum creatinine in mg/dL)

Ability to comply with study visits, treatment, procedures, PK and PD sample collection, and required study follow-up.
Women of childbearing potential must have a negative serum or urine pregnancy test within 24 hours of the first treatment and must not be breastfeeding and must follow instructions for contraception methods for the duration of the study and for a total of 5 months after treatment completion
Men who are sexually active must agree to follow instructions for contraception for the duration of the study and for 7 months after treatment completion and to refrain from sperm donation during this time.

Exclusion criteria include the following:
Suspected, known, or progressive CNS metastases (imaging required only if participants are symptomatic).
Participants with active, known, or suspected autoimmune disease. Participants with vitiligo, type I diabetes mellitus, residual hypothyroidism due to autoimmune condition only requiring hormone replacement, euthyroid participants with a history of Grave's disease (participants with suspected autoimmune thyroid disorders must be negative for thyroglobulin and thyroid peroxidase antibodies and thyroid stimulating immunoglobulin prior to first dose of study treatment), psoriasis not requiring systemic treatment, or conditions not expected to recur in the absence of an external trigger are permitted to enroll after discussing with the Medical Monitor for the trial.
Participants with a condition requiring systemic treatment with either corticosteroids (>10 mg daily prednisone equivalents) or other immunosuppressive medications within 14 days of study treatment administration except for adrenal replacement steroid doses >10 mg daily prednisone equivalent in the absence of active autoimmune disease.
Interstitial lung disease that is symptomatic or may interfere with the detection or management of suspected treatment-related pulmonary toxicity.
Current or history of clinically significant muscle disorders (eg, myositis), recent unresolved muscle injury, or any condition known to elevate serum CK levels.
Uncontrolled or significant cardiovascular disease including, but not limited to, any of the following:
  i) Myocardial infarction or stroke/transient ischemic attack within the past 6 months
  ii) Uncontrolled angina within the past 3 months
  iii) Any history of clinically significant arrhythmias (such as ventricular tachycardia, ventricular fibrillation, or torsades de pointes)
  iv) History of other clinically significant heart disease (eg, cardiomyopathy, congestive heart failure with New York Heart Association functional classification III to IV, pericarditis, significant pericardial effusion, or myocarditis)
  v) Cardiovascular disease-related requirement for daily supplemental oxygen therapy.
History of any chronic hepatitis as evidenced by the following:
  i) Positive test for hepatitis B surface antigen
  ii) Positive test for qualitative hepatitis C viral load (by polymerase chain reaction [PCR]).
Previous malignancies (except non-melanoma skin cancers, and in situ bladder, gastric, colorectal, endometrial, cervical/dysplasia, melanoma, or breast cancers) unless complete remission was achieved at least 2 years prior to study entry and no additional therapy is required during the study period.
Prior organ allograft or allogeneic bone marrow transplantation.

Any major surgery within 4 weeks of study treatment. Participants must have recovered from the effects of major surgery or significant traumatic injury at least 14 days before the first dose of study treatment.

All toxicities attributed to prior anti-cancer therapy other than alopecia and fatigue must have resolved to Grade 1 (National Cancer Institute Common Terminology Criteria for Adverse Events [NCI CTCAE] v4.03) or baseline before administration of study treatment.

Participants with toxicities attributed to prior anti-cancer therapy that are not expected to resolve and result in long lasting sequelae, such as neuropathy after platinum-based therapy, are permitted to enroll.

Evidence of uncontrolled, active infection, requiring parenteral anti-bacterial, anti-viral or anti-fungal therapy ≤7 days prior to administration of study medication.

Any uncontrolled inflammatory GI disease including Crohn's Disease and ulcerative colitis.

Known history of testing positive for human immunodeficiency virus (HIV) or known acquired immunodeficiency syndrome (Testing for HIV must be performed at sites mandated by local requirements.)

Any uncontrolled medical condition or psychiatric disorder which, in the opinion of the Investigator, would pose a risk to patient safety or interfere with study participation or interpretation of individual patient results.

Current or recent (within 3 months of study drug administration) gastrointestinal disease that could impact upon the absorption of study drug.

Transfusion completed within 72 hours prior to first dose of study drug administration Any GI surgery that could impact upon the absorption of study drug.

Inability to tolerate oral medication.

Inability to be venipunctured and/or tolerate venous access.

Positive test for latent tuberculosis (TB) at screening (e.g., T-SPOT or Quantiferon® test) or evidence of active TB.

Prior exposure to prior therapy with immune cell-modulating antibody regimens, such as, but not limited to, anti-CSF1R, anti-PD-1, anti-PD-L1, anti PD-L2, anti-CTLA-4 antibodies.

Any anti-cancer therapy (eg, chemotherapy, biologics, vaccines, or hormonal treatment) including investigational drugs within 4 weeks prior to the first dose of study treatment administration, except for non-cytotoxic therapies, for which at least 4 weeks or 5 half-lives (whichever is shorter) must have elapsed between last dose and first treatment with any study treatments; if 5 half-lives are shorter than 4 weeks, agreement with the Medical Monitor must be obtained.

Treatment with botanical preparations (eg, herbal supplements, including potential drugs of abuse, or traditional Chinese medicines) intended for general health support or to treat the disease under study within 2 weeks prior to randomization/treatment.

Concomitant use of statins while on study. However, a patient using statins for over 3 months prior to study drug administration and in stable status without CK rise may be permitted to enroll.

Non-oncology vaccine therapies for prevention of infectious diseases (e.g., human papilloma virus vaccine) within 4 weeks of study drug administration. The inactivated seasonal influenza vaccine can be given to patients before treatment and while on therapy without restriction. Influenza vaccines containing live virus or other clinically indicated vaccinations for infectious diseases (i.e., pneumovax, varicella, etc) may be permitted, but must be discussed with the Medical Monitor and may require a study drug washout period prior to and after administration of vaccine.

Patients with abnormal serum chemistry values, which in the opinion of the investigator are considered to be clinically significant, will be excluded from the study. This will include patients who show clinical signs and symptoms related to their abnormal serum chemistry values, as well as patients whose serum chemistry values are asymptomatic but clinically significant (e.g., hypokalemia or hyponatremia).

Evidence of coagulopathy or bleeding diathesis

Ascites needing paracentesis or medical management

Peripheral Neuropathy greater than Grade 1 (for Arm B receiving nab-paclitaxel)

Albumin less than 3 g/dL

Evidence of organ dysfunction or any clinically significant deviation from normal in physical examination, vital signs, ECG, or clinical laboratory determinations beyond what is consistent with the target population Known history of sensitivity to infusions containing Tween 20 (polysorbate 20) and Tween 80 (polysorbate 80)

History of allergy to study treatments or any of its components of the study arm that participant is enrolling Consumption of non-pasteurized milk while on study drug and for 30 days after discontinuing study drug Pregnant or breastfeeding Participants who are compulsorily detained for treatment of either a psychiatric or physical (eg, infectious disease) illness Example 7

Profiling of Responsive and Nonresponsive Patients Treated with Cabiralizumab and Nivolumab Patient cohorts for a dose escalation and dose expansion Phase Ia/Ib study of cabiralizumab and nivolumab, as described in Examples 3 and 4, are shown in FIG. 6a and FIG. 6b. Initial results showed that the combination was tolerable with preliminary evidence of durable clinical benefit in heavily pretreated patients with advanced MSS pancreatic cancer. (See Wainberg, Z. A., et al. *J. Immunother. Cancer* 5(suppl 3): Abstract 042 (2017).) This example summarizes further characterization of patients treated in the clinical study.

Tumor mutation burden (TMB) was measured in patients treated during the dose expansion phase by whole exome sequence analysis of archival or fresh biopsy samples. FIG. 7 shows TMB in patients treated during the expansion phase, broken down by tumor type: glioma, SCCHN, NSCLCn (NSCLC PD-1 naïve), NSCLCr (NSCLC de novo or acquired resistance), ovarian, pancreatic, and renal. Genomic analysis of tumor mutation burden was performed on 94 patients. As shown in FIG. 7, nearly all patients had a low TMB, as designated by the arrow shown to the left of the y-axis of the graph which marks a TMB level of 200 total missense mutations as determined by whole exome sequencing (WES), which is equivalent to a TMB of 10 mutations/megabase determined by a Foundation One® CDx™ assay (Foundation Medicine, Inc.). The equivalence was determined by measuring the number of mutations using both methods on some of the same samples. Most patients also had a TMB of less than 10 mutations per megabase by the Foundation One® assay, as designated by the arrow shown to the left of the y-axis. 91 of the 94 patients had a low TMB of less than 10 mutations per megabase by that assay. All but one of these patients had a microsatellite stable tumor. Four patients with pancreatic cancer included in the analysis who responded to the combination treatment each had low TMB and were also MSS, a phenotype that historically has not shown benefit with anti-PD-1/PD-L1 therapy.

Changes in peripheral concentration of CSF-1 and IL-34 were measured by ELISA, and are shown in FIG. 8A. Changes in peripheral $CD14^+CD16^{++}$ (or $CD14^{DIM}CD16^{BRIGHT}$) nonclassical monocyte levels were measured by flow cytometry, and are shown in FIG. 8B. Both were analyzed in patients treated with 1, 2, 4, or 6 mg/kg cabiralizumab plus 3 mg/kg novolumab Q2W. A similar dose-dependent increase in IL-34 was observed in patients on the Q2W schedule (data not shown). As shown in FIG. 8B, a durable depletion of nonclassical $CD14^+$ $CD16^{++}$ monocytes was observed in patients treated with at least 4 mg/kg cabiralizumab and 3 mg/kg nivolumab.

FIGS. 9A and 9B show a comparison of patients on a Q2W and on a Q3W dosing regimen with respect to CSF-1 and nonclassical $CD14^+CD16^{++}$ monocyte levels. As shown in FIG. 9A, CSF-1 increases were similar in both dosage schedules. But, as shown in FIG. 9B, $CD14^+CD16^{++}$ nonclassical monocytes decreased consistently in the Q2W regimen but varied in the Q3W regimen.

Peripheral and tumor biomarker expression was measured at the protein level by immunohistochemistry (IHC) or at the RNA level transcriptomic analysis in patients that received 4 mg/kg cabiralizumab plus 3 mg/kg nivolumab Q2W during dose expansion. The IHC and transcriptome analyses were performed using pre-treatment (baseline) and post-treatment (roughly after 4 weeks treatment; or two doses) biopsies.

CSF1R and CD163 levels were measured by IHC and both showed pronounced decreases from baseline with cabiralizumab plus nivolumab treatment. For example, after 4 weeks of treatment, CSF1R protein levels determined by IHC decreased from baseline in 76% of 51 patients sampled with a median change from baseline of −60% (P=0.0089), CD163 protein levels determined by IHC decreased from baseline in 59% of 51 patients sampled, with a median decrease of −43% (P=0.207), and CD68 protein levels determined by IHC decreased from baseline in 60% of 52 patients sampled, with a median decrease of −16% (P=0.263). On the other hand, increases in expression of CSF1R, CD163, and/or CD68 of up to 200% were observed in 5, 7, and 6 patients, respectively. (See FIG. 12 for a graph of these data.) IHC staining of baseline and on-treatment biopsy samples also showed decreases in CSF1R+ macrophages within tumor epithelium in ovarian and pancreatic cancer subjects (not shown). Effector T cell levels also increased in tumors of treated patients compared to baseline by a median of 38% (out of 52 patients; P=0.029), with 58% of patients showing an increase in effector T cell levels, based on IHC measurement of CD8. (See FIG. 13 for a graph of these data.)

RNA expression levels of a variety of biomarkers including CSF1R-related markers (CSF-1, CSF1R, and IL-34), pro-inflammatory markers (CCL19, CCL5, CCL8, CCR7, CD86, CXCL10, CXCL11, CXCL13, CXCL9, IFNG, IL23A, STAT1, and TNF) and anti-inflammatory markers (ARG1, C5AR1, CD14, CD163, CXCR1, CXCR2, IL1A, IL1RN, IL8, MRC1, MSR1, PF4, PPBP, S100A12, S100A8, SAA1, S100A9, and TGFB1) were assessed by transcriptome analysis, as shown in FIGS. 10A-B. Changes in RNA expression levels of the markers for responders (FIG. 10A) and non-responders (FIG. 10B) are shown. In general, no significant changes in marker expression levels were found in non-responders, while significant increases in expression of CSF-1 and IL-34 and pro-inflammatory markers were observed in cabiralizumab plus nivolumab responders. Levels of B cell markers (CD72, CD79A, CD79B, MS4A1, TNFRSF17), CD8 T cell markers (CD3D, CD8A, CD8B), effector T cell (Teff) cytolytic markers (GZMM, APOL3, CTSW, GNLY, GZMA, GZMH, KLRB1, KLRD1, KLRK1, NKG7, PRF1), and Teff inhibitory receptor markers (BTLA, CD244, CD96, CTLA4, LAG3, PDCD1, TIGIT, FOXP3) were also assessed at the RNA level by transcriptome analysis, as shown in FIGS. 11A (responders) and 11B (nonresponders). Similarly, significant increases in expression of CD8 T cell and T effector cytolytic and inhibitory receptor markers were observed in patients who responded to cabiralizumab plus nivolumab (FIG. 11A), while no significant changes were observed in nonresponders (FIG. 11B).

These analyses demonstrated a cabrializumab-mediated CSF1R blockade in the periphery and tumor microenvironment in patients with advanced cancer treated with at least 4 mg/kg cabiralizumab and with 3 mg/kg nivolumab Q2W, as circulating CSF-1 levels increased and nonclassical monocyte levels decreased, while, in tumors, CSF1R, CD163, and CD68 levels decreased and effector T cell levels (measured by CD8) increased. Tumor-based pharmacodynamic responses with the combination were consistent with cabiralizumab's mechanism of action and correlated with increased expression of genes that promote a pro-inflammatory tumor microenvironment. Furthermore, most patients in the analysis had low TMB tumors, which are not typically responsive to treatment with nivolumab monotherapy.

As a summary of this Example, pharmacodynamic activity of cabiralizumab plus nivolumab in patients with advanced tumors treated in a phase 1a/b trial (NCT02526017) was evaluated using peripheral and tumor biomarkers. Cabiralizumab plus nivolumab-associated increases in serum CSF-1 and decreases in peripheral nonclassical monocytes were sustained during a 2-week dose interval. IHC analysis of pre- and on-treatment biopsies across tumor types showed increases in CD8 T-cell infiltrates and decreases in macrophage markers CSF1R and CD163. Transcriptomes of paired biopsies showed increased CD8 and cytolytic gene signatures, with concurrent increased expression of M1 macrophage-associated genes, supporting blockade of CSF1R-driven M2 responses. Genomic analyses demonstrated that 91 of 94 patients had low tumor mutation burden (TMB) below 10 mutations/megabase as determined with the Foundation One® CDx™ assay (or less than 200 total missense mutations as determined by WES) with only 1 patient having microsatellite instability. Treatment responses were observed across tumor types. In 4 partial responses observed in patients with pancreatic cancer, all were microsatellite stable (MSS) and low TMB. Orthogonal IHC and transcriptome-wide analyses demonstrated cabiralizumab-mediated CSF1R blockade in the periphery and tumor microenvironment in patients with advanced cancer. These data support further clinical development of cabiralizumab plus nivolumab in multiple indications, including MSS pancreatic cancer (see NCT03336216).

Table of Sequences

Table 11 provides certain sequences discussed herein. All polypeptide and antibody sequences are shown without leader sequences, unless otherwise indicated.

TABLE 11

Sequences and Descriptions

| SEQ ID NO | Description | Sequence |
|---|---|---|
| 1 | hCSF1R (full-length, no leader sequence) | IPVIEPSVPE LVVKPGATVT LRCVGNGSVE WDGPPSPHWT LYSDGSSSIL STNNATFQNT GTYRCTEPGD PLGGSAAIHL YVKDPARPWN VLAQEVVVFE DQDALLPCLL TDPVLEAGVS LVRVRGRPLM RHTNYSFSPW HGFTIHRAKF IQSQDYQCSA LMGGRKVMSI SIRLKVQKVI PGPPALTLVP AELVRIRGEA AQIVCSASSV DVNFDVFLQH NNTKLAIPQQ SDFHNNRYQK VLTLNLDQVD FQHAGNYSCV ASNVQGKHST SMFFRVVESA YLNLSSEQNL IQEVTVGEGL NLKVMVEAYP GLQGFNWTYL GPFSDHQPEP KLANATTKDT YRHTFTLSLP RLKPSEAGRY SFLARNPGGW RALTFELTLR YPPEVSVIWT FINGSGTLLC AASGYPQPNV TWLQCSGHTD RCDEAQVLQV WDDPYPEVLS QEPFHKVTVQ SLLTVETLEH NQTYECRAHN SVGSGSWAFI PISAGAHTHP PDEFLFTPVV VACMSIMALL LLLLLLLLYK YKQKPKYQVR WKIIESYEGN SYTFIDPTQL PYNEKWEFPR NNLQFGKTLG AGAFGKVVEA TAFGLGKEDA VLKVAVKMLK STAHADEKEA LMSELKIMSH LGQHENIVNL LGACTHGGPV LVITEYCCYG DLLNFLRRKA EAMLGPSLSP GQDPEGGVDY KNIHLEKKYV RRDSGFSSQG VDTYVEMRPV STSSNDSFSE QDLDKEDGRP LELRDLLHFS SQVAQGMAFL ASKNCIHRDV AARNVLLTNG HVAKIGDFGL ARDIMNDSNY IVKGNARLPV KWMAPESIFD CVYTVQSDVW SYGILLWEIF SLGLNPYPGI LVNSKFYKLV KDGYQMAQPA FAPKNIYSIM QACWALEPTH RPTFQQICSF LQEQAQEDRR ERDYTNLPSS SRSGGSGSSS SELEEESSSE HLTCCEQGDI AQPLLQPNNY QFC |
| 2 | hCSFER (full-length, +leader sequence) | MGPGVLLLLL VATAWHGQGI PVIEPSVPEL VVKPGATVTL RCVGNGSVEW DGPPSPHWTL YSDGSSSILS TNNATFQNTG TYRCTEPGDP LGGSAAIHLY VKDPARPWNV LAQEVVVFED QDALLPCLLT DPVLEAGVSL VRVRGRPLMR HTNYSFSPWH GFTIHRAKFI QSQDYQCSAL MGGRKVMSIS IRLKVQKVIP GPPALTLVPA ELVRIRGEAA QIVCSASSVD VNFDVFLQHN NTKLAIPQQS DFHNNRYQKV LTLNLDQVDF QHAGNYSCVA SNVQGKHSTS MFFRVVESAY LNLSSEQNLI QEVTVGEGLN LKVMVEAYPG LQGFNWTYLG PFSDHQPEPK LANATTKDTY RHTFTLSLPR LKPSEAGRYS FLARNPGGWR ALTFELTLRY PPEVSVIWTF INGSGTLLCA ASGYPQPNVT WLQCSGHTDR CDEAQVLQVW DDPYPEVLSQ EPFHKVTVQS LLTVETLEHN QTYECRAHNS VGSGSWAFIP ISAGAHTHPP DEFLFTPVVV ACMSIMALLL LLLLLLYKY KQKPKYQVRW KIIESYEGNS YTFIDPTQLP YNEKWEFPRN NLQFGKTLGA GAFGKVVEAT AFGLGKEDAV LKVAVKMLKS TAHADEKEAL MSELKIMSHL GQHENIVNLL GACTHGGPVL VITEYCCYGD LLNFLRRKAE AMLGPSLSPG QDPEGGVDYK NIHLEKKYVR RDSGFSSQGV DTYVEMRPVS TSSNDSFSEQ DLDKEDGRPL ELRDLLHFSS QVAQGMAFLA SKNCIHRDVA ARNVLLTNGH VAKIGDFGLA RDIMNDSNYI VKGNARLPVK WMAPESIFDC VYTVQSDVWS YGILLWEIFS LGLNPYPGIL VNSKFYKLVK DGYQMAQPAF APKNIYSIMQ ACWALEPTHR PTFQQICSFL QEQAQEDRRE RDYTNLPSSS RSGGSGSSSS ELEEESSSEH LTCCEQGDIA QPLLQPNNYQ FC |
| 3 | Ab light chain leader sequence | METDTLLLWV LLLWVPGSTG |
| 4 | Ab heavy chain leader sequence | MAVLGLLLCL VTFPSCVLS |
| 5 | Cabiralizumab heavy chain CDR1 | GYTFTDNYMI |
| 6 | Cabiralizumab heavy chain CDR2 | DINPYNGGTT FNQKFKG |
| 7 | Cabiralizumab heavy chain CDR3 | ESPYFSNLYV MDY |
| 8 | Cabiralizumab light chain CDR1 | KASQSVDYDG DNYMN |
| 9 | Cabiralizumab light chain CDR2 | AASNLES |
| 10 | Cabiralizumab light chain CDR3 | HLSNEDLST |

TABLE 11-continued

Sequences and Descriptions

| SEQ ID NO | Description | Sequence |
|---|---|---|
| 11 | Cabiralizumab heavy chain variable region | QVQLVQSGAE VKKPGSSVKV SCKASGYTFT DNYMIWVRQA PGQGLEWMGD INPYNGGTTF NQKFKGRVTI TADKSTSTAY MELSSLRSED TAVYYCARES PYFSNLYVMD YWGQGTLVTV SS |
| 12 | Cabiralizumab light chain variable region | EIVLTQSPAT LSLSPGERAT LSCKASQSVD YDGDNYMNWY QQKPGQAPRL LIYAASNLES GIPARFSGSG SGTDFTLTIS SLEPEDFAVY YCHLSNEDLS TFGGGTKVEI K |
| 13 | Cabiralizumab heavy chain | QVQLVQSGAE VKKPGSSVKV SCKASGYTFT DNYMIWVRQA PGQGLEWMGD INPYNGGTTF NQKFKGRVTI TADKSTSTAY MELSSLRSED TAVYYCARES PYFSNLYVMD YWGQGTLVTV SSASTKGPSV FPLAPCSRST SESTAALGCL VKDYFPEPVT VSWNSGALTS GVHTFPAVLQ SSGLYSLSSV VTVPSSSLGT KTYTCNVDHK PSNTKVDKRV ESKYGPPCPP CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 14 | Cabiralizumab light chain | EIVLTQSPAT LSLSPGERAT LSCKASQSVD YDGDNYMNWY QQKPGQAPRL LIYAASNLES GIPARFSGSG SGTDFTLTIS SLEPEDFAVY YCHLSNEDLS TFGGGTKVEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 15 | Human CSF1 | EEVSEYCSHM IGSGHLQSLQ RLIDSQMETS CQITFEFVDQ EQLKDPVCYL KKAFLLVQDI MEDTMRFRDN TPNAIAIVQL QELSLRLKSC FTKDYEEHDK ACVRTFYETP LQLLEKVKNV FNETKNLLDK DWNIFSKNCN NSFAECSSQG HERQSEGS |
| 16 | Human IL-34 | NEPLEMWPLT QNEECTVTGF LRDKLQYRSR LQYMKHYFPI NYKISVPYEG VFRIANVTRL QRAQVSEREL RYLWVLVSLSATESVQDVLL EGHPSWKYLQ EVQTLLLLNVQ QGLTDVEVSP KVESVLSLLN APGPNLKLVR PKALLDNCFR VMELLYCSCC KQSSVLNWQD CEVPSPQSCS PEPSLQYAAT QLYPPPPWSP SSPPHSTGSV RPVRAQGEGL LP |
| 17 | Human IgG4 S241P | ASTKGPSVFP LAPCSRSTSE STAALGCLVK DYFPEPVTVS WNSGALTSGV HTFPAVLQSS GLYSLSSVVT VPSSSLGTKT YTCNVDHKPS NTKVDKRVES KYGPPCPPCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVYT LPPSQEEMTK NQVSLTCLVK GFYPSDIAVE WESNGQPENN YKTTPPVLDS DGSFFLYSRL TVDKSRWQEG NVFSCSVMHE ALHNHYTQKS LSLSLGK |
| 18 | Human Igκ | RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGEC |
| 19 | human PD-1 precursor (with signal sequence) UniProtKB/Swiss-Prot: Q15I163, 1 OCT. 2014 | MQIPQAPWPV VWAVLQLGWR PGWFLDSPDR PWNPPTFSPA LLVVTEGDNA TFTCSFSNTS ESFVLNWYRM SPSNQTDKLA AFPEDRSQPG QDCRFRVTQL PNGRDFHMSV VRARRNDSGT YLCGAISLAP KAQIKESLRA ELRVTERRAE VPTAHPSPSP RPAGQFQTLV VGVVGGLLGS LVLLVWVLAV ICSRAARGTI GARRTGQPLK EDPSAVPVFS VDYGELDFQW REKTPEPPVP CVPEQTEYAT IVFPSGMGTS SPARRGSADG PRSAQPLRPE DGHCSWPL |
| 20 | human PD-1 (mature, without signal sequence) | PGWFLDSPDR PWNPPTFSPA LLVVTEGDNA TFTCSFSNTS ESFVLNWYRM SPSNQTDKLA AFPEDRSQPG QDCRFRVTQL PNGRDFHMSV VRARRNDSGT YLCGAISLAP KAQIKESLRA ELRVTERRAE VPTAHPSPSP RPAGQFQTLV VGVVGGLLGS LVLLVWVLAV ICSRAARGTI GARRTGQPLK EDPSAVPVFS VDYGELDFQW REKTPEPPVP CVPEQTEYAT IVFPSGMGTS SPARRGSADG PRSAQPLRPE DGHCSWPL |
| 21 | human PD-L1 precursor (with signal sequence) UniProtKB/Swiss-Prot: Q9NZQ7.1, 1 OCT. 2014 | MRIFAVFIFM TYWHLLNAFT VTVPKDLYVV EYGSNMTIEC KFPVEKQLDL AALIVYWEME DKNIIQFVHG EEDLKVQHSS YRQRARLLKD QLSLGNAALQ ITDVKLQDAG VYRCMISYGG ADYKRITVKV NAPYNKINQR ILVVDPVTSE HELTCQAEGY PKAEVIWTSS DHQVLSGKTT TTNSKREEKL FNVTSTLRIN TTTNEIFYCT FRRLDPEENH TAELVIPELP LAHPPNERTH LVILGAILLC LGVALTFIFR LRKGRMMDVK KCGIQDTNSK KQSDTHLEET |

TABLE 11-continued

Sequences and Descriptions

| SEQ ID NO | Description | Sequence |
|---|---|---|
| 22 | human PD-L1 (mature, without signal sequence) | FT VTVPKDLYVV EYGSNMTIEC KFPVEKQLDL AALIVYWEME DKNIIQFVHG EEDLKVQHSS YRQRARLLKD QLSLGNAALQ ITDVKLQDAG VYRCMISYGG ADYKRITVKV NAPYNKINQR ILVVDPVTSE HELTCQAEGY PKAEVIWTSS DHQVLSGKTT TTNSKREEKL FNVTSTLRIN TTTNEIFYCT FRRLDPEENH TAELVIPELP LAHPPNERTH LVILGAILLC LGVALTFIFR LRKGRMMDVK KCGIQDTNSK KQSDTHLEET |
| 23 | Nivolumab heavy chain variable region | QVQLVESGGGVVQPGRSLRLDCKASGITFSNSGMHWVRQAPGKGLEWVAVIWYD GSKRYYADSVKGRFTISRDNSKNTLFLQMNSLRAEDTAVYYCATNDDYWGQGTL VTVSS |
| 24 | Nivolumab heavy chain constant region | ASTKGPSVFPLAPCSRSTSESTAALGCLVKDYFPEPVTVSWNSGALTSGVHTFP AVLQSSGLYSLSSVVTVPSSSLGTKTYTCNVDHKPSNTKVDKRVESKYGPPCPP CPAPEFLGGPSVFLFPPKPKDTLMISRTPEVTCVVVDVSQEDPEVQFNWYVDGV EVHNAKTKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESNGQPENN YKTTPPVLDSDGSFFLYSRLTVDKSRWQEGNVFSCSVMHEALHNHYTQKSLSLS LGK |
| 25 | Nivolumab light chain variable region | EIVLTQSPATLSLSPGERATLSCRASQSVSSYLAWYQQKPGQAPRLLIYDASNR ATGIPARFSGSGSGTDFTLTISSLEPEDFAVYYCQQSSNWPRTFGQGTKVEIK |
| 26 | Nivolumab light chain constant region | RTVAAPSVFIFPPSDEQLKSGTASVVCLLNNFYPREAKVQWKVDNALQSGNSQE SVTEQDSKDSTYSLSSTLTLSKADYEKHKVYACEVTHQGLSSPVTKSFNRGEC |
| 27 | Nivolumab heavy chain variable region FR1 | QVQLVESGGGVVQPGRSLRLDCKASGITFS |
| 28 | Nivolumab heavy chain CDR1 | NSGMH |
| 29 | Nivolumab heavy chain FR2 | WVRQAPGKGLEWVA |
| 30 | Nivolumab heavy chain CDR2 | VIWYDGSKRYYADSVKG |
| 31 | Nivolumab heavy chain FR3 | RFTISRDNSKNTLFLQMNSLRAEDTAVYYCAT |
| 32 | Nivolumab heavy chain CDR3 | NDDY |
| 33 | Nivolumab heavy chain FR4 | WGQGTLVTVSS |
| 34 | Nivolumab light chain FR1 | EIVLTQSPATLSLSPGERATLSC |
| 35 | Nivolumab light chain CDR1 | RASQSVSSYLA |
| 36 | Nivolumab light chain FR2 | WYQQKPGQAPRLLIY |
| 37 | Nivolumab light chain CDR2 | DASNRAT |
| 38 | Nivolumab light chain FR3 | GIPARFSGSGSGTDFTLTISSLEPEDFAVYYC |
| 39 | Nivolumab light chain CDR3 | QQSSNWPRT |

TABLE 11-continued

Sequences and Descriptions

| SEQ ID NO | Description | Sequence |
|---|---|---|
| 40 | Nivolumab light chain FR4 | FGQGTKVEIK |

---

The invention claimed is:

1. A method of treating pancreatic cancer in a subject, wherein the cancer has been determined to be microsatellite-stable (MSS), and wherein the cancer has been determined to have: (a) a tumor mutation burden (TMB) of less than 20 mutations/megabase, less than 15 mutations/megabase, or less than 10 mutations/megabase, as determined with a comprehensive genomic profiling assay, and/or (b) a TMB of less than 400, less than 300 or less than 200 missense mutations as determined by whole exome sequencing (WES), comprising administering to the subject 2, 3, or 4 mg/kg of an anti-CSF1R antibody once every two weeks and 400-600 mg of an anti-PD-1 antibody once every four weeks, wherein the anti-CSF1R antibody comprises a heavy chain comprising a heavy chain (HC) CDR1 having the sequence of SEQ ID NO: 5, an HC CDR2 having the sequence of SEQ ID NO: 6, and an HC CDR3 having the sequence of SEQ ID NO: 7, and a light chain comprising a light chain (LC) CDR1 having the sequence of SEQ ID NO: 8, a LC CDR2 having the sequence of SEQ ID NO: 9, and a LC CDR3 having the sequence of SEQ ID NO: 10; and wherein the anti-PD-1 antibody comprises a heavy chain comprising a heavy chain (HC) CDR1 having the sequence of SEQ ID NO: 28, an HC CDR2 having the sequence of SEQ ID NO: 30, and an HC CDR3 having the sequence of SEQ ID NO: 32, and a light chain comprising a light chain (LC) CDR1 having the sequence of SEQ ID NO: 35, a LC CDR2 having the sequence of SEQ ID NO: 37, and a LC CDR3 having the sequence of SEQ ID NO: 39.

2. A method of treating pancreatic cancer in a subject, wherein the cancer has been determined to be microsatellite-stable (MSS), and wherein the cancer has been determined to have: (a) a tumor mutation burden (TMB) of less than 20 mutations/megabase, less than 15 mutations/megabase, or less than 10 mutations/megabase, as determined with a comprehensive genomic profiling assay, and/or (b) a TMB of less than 400, less than 300 or less than 200 missense mutations as determined by whole exome sequencing (WES), comprising administering to the subject 2, 3, or 4 mg/kg of an anti-CSF1R antibody once every two weeks and 400-600 mg of an anti-PD-1 antibody once every four weeks in combination with chemotherapy comprising gemcitabine or 5-fluorouracil (5-FU), wherein the anti-CSF1R antibody comprises a heavy chain comprising a heavy chain (HC) CDR1 having the sequence of SEQ ID NO: 5, an HC CDR2 having the sequence of SEQ ID NO: 6, and an HC CDR3 having the sequence of SEQ ID NO: 7, and a light chain comprising a light chain (LC) CDR1 having the sequence of SEQ ID NO: 8, a LC CDR2 having the sequence of SEQ ID NO: 9, and a LC CDR3 having the sequence of SEQ ID NO: 10; and wherein the anti-PD-1 antibody comprises a heavy chain comprising a heavy chain (HC) CDR1 having the sequence of SEQ ID NO: 28, an HC CDR2 having the sequence of SEQ ID NO: 30, and an HC CDR3 having the sequence of SEQ ID NO: 32, and a light chain comprising a light chain (LC) CDR1 having the sequence of SEQ ID NO: 35, a LC CDR2 having the sequence of SEQ ID NO: 37, and a LC CDR3 having the sequence of SEQ ID NO: 39.

3. The method of claim 2, wherein the subject is administered 4 mg/kg of the anti-CSF1R antibody once every two weeks and 450-500 mg the anti-PD-1 antibody once every four weeks.

4. The method of claim 3, wherein the subject is administered 4 mg/kg of the anti-CSF1R antibody once every two weeks and 480 mg the anti-PD-1 antibody once every four weeks.

5. The method of claim 2, wherein the subject is administered chemotherapy comprising gemcitabine and nab-paclitaxel.

6. The method of claim 2, wherein the subject is administered chemotherapy comprising FOLFOX.

7. The method of claim 2, wherein the anti-CSF1R antibody and/or the anti-PD-1 antibody is a Fab, an Fv, an scFv, a Fab', or a (Fab')$_2$ fragment.

8. The method of claim 2, wherein (a) the anti-PD-1 antibody heavy chain comprises a heavy chain variable region comprising the sequence of SEQ ID NO: 23 and wherein the anti-PD-1 antibody light chain comprises a light chain variable region comprising the sequence of SEQ ID NO: 25; (b) the anti-PD-1 antibody comprises a heavy chain comprising the sequence of each of SEQ ID NOs: 23 and 24 and wherein the anti-PD-1 antibody comprises a light chain comprising the sequence of each of SEQ ID NOs: 25 and 26; or (c) the anti-PD-1 antibody is nivolumab.

9. The method of claim 2, wherein (a) the anti-CSF1R antibody comprises a heavy chain variable region comprising the sequence of SEQ ID NO: 11 and wherein the anti-CSF1R antibody comprises a light chain variable region comprising the sequence of SEQ ID NO: 12; (b) the anti-CSF1R antibody comprises a heavy chain comprising the sequence of SEQ ID NO: 13 and wherein the anti-CSF1R antibody comprises a light chain comprising the sequence of SEQ ID NO: 14; or (c) the anti-CSF1R antibody is cabiralizumab.

10. The method of claim 2, wherein the subject meets one or more of the following criteria:

has previously failed treatment with a standard therapy for pancreatic cancer or is not indicated for treatment with a standard therapy;

has previously received a PD-1/PD-L1 inhibitor therapy;

is a PD-1/PD-L1 inhibitor inadequate responder;

is refractory to a PD-1/PD-L1 inhibitor, e.g., after at least 2 doses;

has a localized adenocarcinoma of the pancreas;

has metastatic adenocarcinoma of the pancreas;

does not have active pancreatitis or ascites of Grade 2 or higher;

has a pancreatic tumor that is PD-L1 positive;

has reduced circulating $CD14^+CD16^{++}$ nonclassical monocytes after at least one dose of each of the anti-CSF1R antibody and the anti-PD-antibody; and has a pancreatic cancer that has progressed after at least one gemcitabine-based or 5-fluorouracil-based chemotherapy regimen.

11. The method of claim 2, wherein the subject has advanced pancreatic cancer.

12. A method of treating cancer in a subject, wherein the cancer has been determined to be microsatellite-stable (MSS), and wherein the cancer has been determined to have: (a) a tumor mutation burden (TMB) of less than 20 mutations/megabase, less than 15 mutations/megabase, or less than 10 mutations/megabase, as determined with a comprehensive genomic profiling assay, and/or (b) a TMB of less than 400, less than 300 or less than 200 missense mutations as determined by whole exome sequencing (WES), comprising:

a) Administering to the subject at least one dose of an anti-CSF1R antibody and an anti-PD-1 antibody, wherein the expression level of at least one marker gene is determined to increase following the administration, the at least one marker gene comprising one or more of: CCL19, CCL5, CCL8, CCR7, CD86, CXCL10, CXCL11, CXCL13, CXCL9, IFNG, IL23A, STAT1, TNF, CD72, CD79A, CD79B, MS4A1, TNFRSF17, CD3D, CD8A, CD8B, GZMM, APOL3, CTSW, GNLY, GZMA, GZMH, KLRB1, KLRD1, KLRK1, NKG7, PRF1, BTLA, CD244, CD96, CTLA4, LAGS, PDCD1, TIGIT, and FOXP3; and b) continuing to administer the anti-CSF1R antibody and anti-PD-1 antibody to the subject.

13. The method of claim 12, further comprising measuring the expression level of one or more of CSF1R, CSF-1 and IL-34, wherein increases in CSF-1 and IL-34 expression levels following administration indicate that the subject is responsive to treatment with the anti-CSF1R antibody and anti-PD-1 antibody while a decrease in CSF1R expression level indicates that the subject is not responsive to treatment with the anti-CSF1R antibody and anti-PD-1 antibody.

14. The method of claim 12, wherein the at least one marker gene comprises:

a. at least one pro-inflammatory marker gene comprising: CCL19, CCL5, CCL8, CCR7, CD86, CXCL10, CXCL11, CXCL13, CXCL9, IFNG, IL23A, STAT1, and TNF;

b. at least one B cell marker comprising: CD72, CD79A, CD79B, MS4A1, and TNFRSF17;

c. at least one CD8 T cell marker comprising: CD3D, CD8A, and CD8B;

d. at least one effector T cell cytolytic marker comprising: GZMM, APOL3, CTSW, GNLY, GZMA, GZMH, KLRB1, KLRD1, KLRK1, NKG7, and PRF1; and/or e. at least one effector T cell receptor marker comprising: BTLA, CD244, CD96, CTLA4, LAGS, PDCD1, TIGIT, and FOXP3.

15. A method of treating cancer in a subject, wherein the cancer has been determined to be microsatellite-stable (MSS), and wherein the cancer has been determined to have: (a) a tumor mutation burden (TMB) of less than 20 mutations/megabase, less than 15 mutations/megabase, or less than 10 mutations/megabase, as determined with a comprehensive genomic profiling assay, and/or (b) a TMB of less than 400, less than 300 or less than 200 missense mutations as determined by whole exome sequencing (WES), comprising: a) administering to the subject at least one dose of an anti-CSF1R antibody and an anti-PD-1 antibody, wherein the expression level of at least one marker gene comprising one or both of CSF-1 and IL-34 is determined to increase following the administration, and b) continuing to administer the anti-CSF1R antibody and anti-PD-1 antibody to the subject.

* * * * *

UNITED STATES PATENT AND TRADEMARK OFFICE
CERTIFICATE OF CORRECTION

PATENT NO. : 11,421,034 B2
APPLICATION NO. : 16/646690
DATED : August 23, 2022
INVENTOR(S) : Katherine E. Lewis et al.

It is certified that error appears in the above-identified patent and that said Letters Patent is hereby corrected as shown below:

In the Claims

In Claim 12, Column 189, Line 43, delete "LAGS" and insert --LAG3--

In Claim 14, Column 190, Line 24, delete "LAGS" and insert --LAG3--

Signed and Sealed this
Eleventh Day of October, 2022

Katherine Kelly Vidal
*Director of the United States Patent and Trademark Office*

SEQUENCE LISTING

<160> NUMBER OF SEQ ID NOS: 40

<210> SEQ ID NO 1
<211> LENGTH: 953
<212> TYPE: PRT
<213> ORGANISM: Homo sapiens

<400> SEQUENCE: 1

```
Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
            20                  25                  30

Gly Pro Pro Ser Pro His Trp Thr Leu Tyr Ser Asp Gly Ser Ser Ser
        35                  40                  45

Ile Leu Ser Thr Asn Asn Ala Thr Phe Gln Asn Thr Gly Thr Tyr Arg
    50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125

Leu Met Arg His Thr Asn Tyr Ser Phe Ser Pro Trp His Gly Phe Thr
    130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys
    210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
            260                 265                 270

Phe Phe Arg Val Val Glu Ser Ala Tyr Leu Asn Leu Ser Ser Glu Gln
        275                 280                 285

Asn Leu Ile Gln Glu Val Thr Val Gly Glu Gly Leu Asn Leu Lys Val
```

-continued

```
                290               295               300
Met Val Glu Ala Tyr Pro Gly Leu Gln Gly Phe Asn Trp Thr Tyr Leu
305                 310               315                 320

Gly Pro Phe Ser Asp His Gln Pro Glu Pro Lys Leu Ala Asn Ala Thr
                325               330               335

Thr Lys Asp Thr Tyr Arg His Thr Phe Thr Leu Ser Leu Pro Arg Leu
                340               345               350

Lys Pro Ser Glu Ala Gly Arg Tyr Ser Phe Leu Ala Arg Asn Pro Gly
                355               360               365

Gly Trp Arg Ala Leu Thr Phe Glu Leu Thr Leu Arg Tyr Pro Pro Glu
                370               375               380

Val Ser Val Ile Trp Thr Phe Ile Asn Gly Ser Gly Thr Leu Leu Cys
385                 390               395                 400

Ala Ala Ser Gly Tyr Pro Gln Pro Asn Val Thr Trp Leu Gln Cys Ser
                405               410               415

Gly His Thr Asp Arg Cys Asp Glu Ala Gln Val Leu Gln Val Trp Asp
                420               425               430

Asp Pro Tyr Pro Glu Val Leu Ser Gln Glu Pro Phe His Lys Val Thr
                435               440               445

Val Gln Ser Leu Leu Thr Val Glu Thr Leu Glu His Asn Gln Thr Tyr
                450               455               460

Glu Cys Arg Ala His Asn Ser Val Gly Ser Gly Ser Trp Ala Phe Ile
465                 470               475                 480

Pro Ile Ser Ala Gly Ala His Thr His Pro Pro Asp Glu Phe Leu Phe
                485               490               495

Thr Pro Val Val Val Ala Cys Met Ser Ile Met Ala Leu Leu Leu Leu
                500               505               510

Leu Leu Leu Leu Leu Tyr Lys Tyr Lys Gln Lys Pro Lys Tyr Gln
                515               520               525

Val Arg Trp Lys Ile Ile Glu Ser Tyr Glu Gly Asn Ser Tyr Thr Phe
                530               535               540

Ile Asp Pro Thr Gln Leu Pro Tyr Asn Glu Lys Trp Glu Phe Pro Arg
545                 550               555                 560

Asn Asn Leu Gln Phe Gly Lys Thr Leu Gly Ala Gly Ala Phe Gly Lys
                565               570               575

Val Val Glu Ala Thr Ala Phe Gly Leu Gly Lys Glu Asp Ala Val Leu
                580               585               590

Lys Val Ala Val Lys Met Leu Lys Ser Thr Ala His Ala Asp Glu Lys
                595               600               605

Glu Ala Leu Met Ser Glu Leu Lys Ile Met Ser His Leu Gly Gln His
                610               615               620

Glu Asn Ile Val Asn Leu Leu Gly Ala Cys Thr His Gly Gly Pro Val
625                 630               635                 640

Leu Val Ile Thr Glu Tyr Cys Cys Tyr Gly Asp Leu Leu Asn Phe Leu
                645               650               655

Arg Arg Lys Ala Glu Ala Met Leu Gly Pro Ser Leu Ser Pro Gly Gln
                660               665               670

Asp Pro Glu Gly Gly Val Asp Tyr Lys Asn Ile His Leu Glu Lys Lys
                675               680               685

Tyr Val Arg Arg Asp Ser Gly Phe Ser Ser Gln Gly Val Asp Thr Tyr
                690               695               700

Val Glu Met Arg Pro Val Ser Thr Ser Ser Asn Asp Ser Phe Ser Glu
705                 710               715                 720
```

-continued

```
Gln Asp Leu Asp Lys Glu Asp Gly Arg Pro Leu Glu Leu Arg Asp Leu
                725                 730                 735

Leu His Phe Ser Ser Gln Val Ala Gln Gly Met Ala Phe Leu Ala Ser
            740                 745                 750

Lys Asn Cys Ile His Arg Asp Val Ala Ala Arg Asn Val Leu Leu Thr
        755                 760                 765

Asn Gly His Val Ala Lys Ile Gly Asp Phe Gly Leu Ala Arg Asp Ile
    770                 775                 780

Met Asn Asp Ser Asn Tyr Ile Val Lys Gly Asn Ala Arg Leu Pro Val
785                 790                 795                 800

Lys Trp Met Ala Pro Glu Ser Ile Phe Asp Cys Val Tyr Thr Val Gln
                805                 810                 815

Ser Asp Val Trp Ser Tyr Gly Ile Leu Leu Trp Glu Ile Phe Ser Leu
            820                 825                 830

Gly Leu Asn Pro Tyr Pro Gly Ile Leu Val Asn Ser Lys Phe Tyr Lys
        835                 840                 845

Leu Val Lys Asp Gly Tyr Gln Met Ala Gln Pro Ala Phe Ala Pro Lys
    850                 855                 860

Asn Ile Tyr Ser Ile Met Gln Ala Cys Trp Ala Leu Glu Pro Thr His
865                 870                 875                 880

Arg Pro Thr Phe Gln Gln Ile Cys Ser Phe Leu Gln Glu Gln Ala Gln
                885                 890                 895

Glu Asp Arg Arg Glu Arg Asp Tyr Thr Asn Leu Pro Ser Ser Ser Arg
            900                 905                 910

Ser Gly Gly Ser Gly Ser Ser Ser Glu Leu Glu Glu Glu Ser Ser
        915                 920                 925

Ser Glu His Leu Thr Cys Cys Glu Gln Gly Asp Ile Ala Gln Pro Leu
    930                 935                 940

Leu Gln Pro Asn Asn Tyr Gln Phe Cys
945                 950

<210> SEQ ID NO 2
<211> LENGTH: 972
<212> TYPE: PRT
<213> ORGANISM: Homo sapiens

<400> SEQUENCE: 2

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
            35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
    115                 120                 125

Leu Thr Asp Pro Val Leu Glu Ala Gly Val Ser Leu Val Arg Val Arg
```

```
            130                 135                 140
Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
                180                 185                 190

Leu Lys Val Gln Lys Val Ile Pro Gly Pro Ala Leu Thr Leu Val
                195                 200                 205

Pro Ala Glu Leu Val Arg Ile Arg Gly Glu Ala Ala Gln Ile Val Cys
210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
                260                 265                 270

Ala Gly Asn Tyr Ser Cys Val Ala Ser Asn Val Gln Gly Lys His Ser
                275                 280                 285

Thr Ser Met Phe Phe Arg Val Val Glu Ser Ala Tyr Leu Asn Leu Ser
290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
                340                 345                 350

Asn Ala Thr Thr Lys Asp Thr Tyr Arg His Thr Phe Thr Leu Ser Leu
                355                 360                 365

Pro Arg Leu Lys Pro Ser Glu Ala Gly Arg Tyr Ser Phe Leu Ala Arg
                370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
                420                 425                 430

Gln Cys Ser Gly His Thr Asp Arg Cys Asp Glu Ala Gln Val Leu Gln
                435                 440                 445

Val Trp Asp Asp Pro Tyr Pro Glu Val Leu Ser Gln Glu Pro Phe His
                450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
                500                 505                 510

Phe Leu Phe Thr Pro Val Val Ala Cys Met Ser Ile Met Ala Leu
                515                 520                 525

Leu Leu Leu Leu Leu Leu Leu Leu Tyr Lys Tyr Lys Gln Lys Pro
                530                 535                 540

Lys Tyr Gln Val Arg Trp Lys Ile Ile Glu Ser Tyr Glu Gly Asn Ser
545                 550                 555                 560
```

```
Tyr Thr Phe Ile Asp Pro Thr Gln Leu Pro Tyr Asn Glu Lys Trp Glu
                565                 570                 575

Phe Pro Arg Asn Asn Leu Gln Phe Gly Lys Thr Leu Gly Ala Gly Ala
            580                 585                 590

Phe Gly Lys Val Val Glu Ala Thr Ala Phe Gly Leu Gly Lys Glu Asp
        595                 600                 605

Ala Val Leu Lys Val Ala Val Lys Met Leu Lys Ser Thr Ala His Ala
    610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                645                 650                 655

Gly Pro Val Leu Val Ile Thr Glu Tyr Cys Cys Tyr Gly Asp Leu Leu
            660                 665                 670

Asn Phe Leu Arg Arg Lys Ala Glu Ala Met Leu Gly Pro Ser Leu Ser
        675                 680                 685

Pro Gly Gln Asp Pro Glu Gly Gly Val Asp Tyr Lys Asn Ile His Leu
    690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
                725                 730                 735

Phe Ser Glu Gln Asp Leu Asp Lys Glu Asp Gly Arg Pro Leu Glu Leu
            740                 745                 750

Arg Asp Leu Leu His Phe Ser Ser Gln Val Ala Gln Gly Met Ala Phe
        755                 760                 765

Leu Ala Ser Lys Asn Cys Ile His Arg Asp Val Ala Ala Arg Asn Val
    770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
                805                 810                 815

Leu Pro Val Lys Trp Met Ala Pro Glu Ser Ile Phe Asp Cys Val Tyr
            820                 825                 830

Thr Val Gln Ser Asp Val Trp Ser Tyr Gly Ile Leu Leu Trp Glu Ile
        835                 840                 845

Phe Ser Leu Gly Leu Asn Pro Tyr Pro Gly Ile Leu Val Asn Ser Lys
    850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
                885                 890                 895

Pro Thr His Arg Pro Thr Phe Gln Gln Ile Cys Ser Phe Leu Gln Glu
            900                 905                 910

Gln Ala Gln Glu Asp Arg Arg Glu Arg Asp Tyr Thr Asn Leu Pro Ser
        915                 920                 925

Ser Ser Arg Ser Gly Gly Ser Gly Ser Ser Ser Glu Leu Glu Glu
    930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
                965                 970
```

```
<210> SEQ ID NO 3
<211> LENGTH: 20
<212> TYPE: PRT
<213> ORGANISM: Artificial Sequence
<220> FEATURE:
<223> OTHER INFORMATION: Ab light chain leader sequence

<400> SEQUENCE: 3

Met Glu Thr Asp Thr Leu Leu Leu Trp Val Leu Leu Leu Trp Val Pro
1               5                   10                  15

Gly Ser Thr Gly
            20

<210> SEQ ID NO 4
<211> LENGTH: 19
<212> TYPE: PRT
<213> ORGANISM: Artificial Sequence
<220> FEATURE:
<223> OTHER INFORMATION: Ab heavy chain leader sequence

<400> SEQUENCE: 4

Met Ala Val Leu Gly Leu Leu Leu Cys Leu Val Thr Phe Pro Ser Cys
1               5                   10                  15

Val Leu Ser

<210> SEQ ID NO 5
<211> LENGTH: 10
<212> TYPE: PRT
<213> ORGANISM: Artificial Sequence
<220> FEATURE:
<223> OTHER INFORMATION: Cabiralizumab heavy chain CDR1

<400> SEQUENCE: 5

Gly Tyr Thr Phe Thr Asp Asn Tyr Met Ile
1               5                   10

<210> SEQ ID NO 6
<211> LENGTH: 17
<212> TYPE: PRT
<213> ORGANISM: Artificial Sequence
<220> FEATURE:
<223> OTHER INFORMATION: Cabiralizumab heavy chain CDR2

<400> SEQUENCE: 6

Asp Ile Asn Pro Tyr Asn Gly Gly Thr Thr Phe Asn Gln Lys Phe Lys
1               5                   10                  15

Gly

<210> SEQ ID NO 7
<211> LENGTH: 13
<212> TYPE: PRT
<213> ORGANISM: Artificial Sequence
<220> FEATURE:
<223> OTHER INFORMATION: Cabiralizumab heavy chain CDR3

<400> SEQUENCE: 7

Glu Ser Pro Tyr Phe Ser Asn Leu Tyr Val Met Asp Tyr
1               5                   10

<210> SEQ ID NO 8
<211> LENGTH: 15
<212> TYPE: PRT
<213> ORGANISM: Artificial Sequence
<220> FEATURE:
<223> OTHER INFORMATION: Cabiralizumab light chain CDR1
```

```
<400> SEQUENCE: 8

Lys Ala Ser Gln Ser Val Asp Tyr Asp Gly Asp Asn Tyr Met Asn
1               5                   10                  15

<210> SEQ ID NO 9
<211> LENGTH: 7
<212> TYPE: PRT
<213> ORGANISM: Artificial Sequence
<220> FEATURE:
<223> OTHER INFORMATION: Cabiralizumab light chain CDR2

<400> SEQUENCE: 9

Ala Ala Ser Asn Leu Glu Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Cabiralizumab light chain CDR3

<400> SEQUENCE: 10

His Leu Ser Asn Glu Asp Leu Ser Thr
1               5

<210> SEQ ID NO 11
<211> LENGTH: 122
<212> TYPE: PRT
<213> ORGANISM: Artificial Sequence
<220> FEATURE:
<223> OTHER INFORMATION: Cabiralizumab heavy chain variable region

<400> SEQUENCE: 11

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Asn
            20                  25                  30

Tyr Met Ile Trp Val Arg Gln Ala Pro Gly Gln Gly Leu Glu Trp Met
        35                  40                  45

Gly Asp Ile Asn Pro Tyr Asn Gly Gly Thr Thr Phe Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Pro Tyr Phe Ser Asn Leu Tyr Val Met Asp Tyr Trp
            100                 105                 110

Gly Gln Gly Thr Leu Val Thr Val Ser Ser
        115                 120

<210> SEQ ID NO 12
<211> LENGTH: 111
<212> TYPE: PRT
<213> ORGANISM: Artificial Sequence
<220> FEATURE:
<223> OTHER INFORMATION: Cabiralizumab light chain variable region

<400> SEQUENCE: 12

Glu Ile Val Leu Thr Gln Ser Pro Ala Thr Leu Ser Leu Ser Pro Gly
1               5                   10                  15
```

Glu Arg Ala Thr Leu Ser Cys Lys Ala Ser Gln Ser Val Asp Tyr Asp
            20                  25                  30

Gly Asp Asn Tyr Met Asn Trp Tyr Gln Gln Lys Pro Gly Gln Ala Pro
        35                  40                  45

Arg Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys His Leu Ser Asn
                85                  90                  95

Glu Asp Leu Ser Thr Phe Gly Gly Gly Thr Lys Val Glu Ile Lys
            100                 105                 110

<210> SEQ ID NO 13
<211> LENGTH: 449
<212> TYPE: PRT
<213> ORGANISM: Artificial Sequence
<220> FEATURE:
<223> OTHER INFORMATION: Cabiralizumab heavy chain

<400> SEQUENCE: 13

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Asn
            20                  25                  30

Tyr Met Ile Trp Val Arg Gln Ala Pro Gly Gln Gly Leu Glu Trp Met
        35                  40                  45

Gly Asp Ile Asn Pro Tyr Asn Gly Gly Thr Thr Phe Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Pro Tyr Phe Ser Asn Leu Tyr Val Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

```
Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 14
<211> LENGTH: 218
<212> TYPE: PRT
<213> ORGANISM: Artificial Sequence
<220> FEATURE:
<223> OTHER INFORMATION: Cabiralizumab light chain

<400> SEQUENCE: 14

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
            20                  25                  30

Gly Asp Asn Tyr Met Asn Trp Tyr Gln Gln Lys Pro Gly Gln Ala Pro
        35                  40                  45

Arg Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys His Leu Ser Asn
                85                  90                  95

Glu Asp Leu Ser Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
```

```
                   180                 185                 190
His Lys Val Tyr Ala Cys Glu Val Thr His Gln Gly Leu Ser Ser Pro
            195                 200                 205

Val Thr Lys Ser Phe Asn Arg Gly Glu Cys
            210                 215

<210> SEQ ID NO 15
<211> LENGTH: 158
<212> TYPE: PRT
<213> ORGANISM: Homo sapiens

<400> SEQUENCE: 15

Glu Glu Val Ser Glu Tyr Cys Ser His Met Ile Gly Ser Gly His Leu
1               5                   10                  15

Gln Ser Leu Gln Arg Leu Ile Asp Ser Gln Met Glu Thr Ser Cys Gln
            20                  25                  30

Ile Thr Phe Glu Phe Val Asp Gln Glu Gln Leu Lys Asp Pro Val Cys
        35                  40                  45

Tyr Leu Lys Lys Ala Phe Leu Leu Val Gln Asp Ile Met Glu Asp Thr
    50                  55                  60

Met Arg Phe Arg Asp Asn Thr Pro Asn Ala Ile Ala Ile Val Gln Leu
65                  70                  75                  80

Gln Glu Leu Ser Leu Arg Leu Lys Ser Cys Phe Thr Lys Asp Tyr Glu
                85                  90                  95

Glu His Asp Lys Ala Cys Val Arg Thr Phe Tyr Glu Thr Pro Leu Gln
            100                 105                 110

Leu Leu Glu Lys Val Lys Asn Val Phe Asn Glu Thr Lys Asn Leu Leu
        115                 120                 125

Asp Lys Asp Trp Asn Ile Phe Ser Lys Asn Cys Asn Asn Ser Phe Ala
    130                 135                 140

Glu Cys Ser Ser Gln Gly His Glu Arg Gln Ser Glu Gly Ser
145                 150                 155

<210> SEQ ID NO 16
<211> LENGTH: 222
<212> TYPE: PRT
<213> ORGANISM: Homo sapiens

<400> SEQUENCE: 16

Asn Glu Pro Leu Glu Met Trp Pro Leu Thr Gln Asn Glu Glu Cys Thr
1               5                   10                  15

Val Thr Gly Phe Leu Arg Asp Lys Leu Gln Tyr Arg Ser Arg Leu Gln
            20                  25                  30

Tyr Met Lys His Tyr Phe Pro Ile Asn Tyr Lys Ile Ser Val Pro Tyr
        35                  40                  45

Glu Gly Val Phe Arg Ile Ala Asn Val Thr Arg Leu Gln Arg Ala Gln
    50                  55                  60

Val Ser Glu Arg Glu Leu Arg Tyr Leu Trp Val Leu Val Ser Leu Ser
65                  70                  75                  80

Ala Thr Glu Ser Val Gln Asp Val Leu Leu Glu Gly His Pro Ser Trp
                85                  90                  95

Lys Tyr Leu Gln Glu Val Gln Thr Leu Leu Asn Val Gln Gln Gly
            100                 105                 110

Leu Thr Asp Val Glu Val Ser Pro Lys Val Glu Ser Val Leu Ser Leu
        115                 120                 125

Leu Asn Ala Pro Gly Pro Asn Leu Lys Leu Val Arg Pro Lys Ala Leu
```

```
            130                 135                 140
Leu Asp Asn Cys Phe Arg Val Met Glu Leu Leu Tyr Cys Ser Cys Cys
145                 150                 155                 160

Lys Gln Ser Ser Val Leu Asn Trp Gln Asp Cys Glu Val Pro Ser Pro
                165                 170                 175

Gln Ser Cys Ser Pro Glu Pro Ser Leu Gln Tyr Ala Ala Thr Gln Leu
            180                 185                 190

Tyr Pro Pro Pro Trp Ser Pro Ser Pro His Ser Thr Gly
        195                 200                 205

Ser Val Arg Pro Val Arg Ala Gln Gly Glu Gly Leu Leu Pro
        210                 215                 220

<210> SEQ ID NO 17
<211> LENGTH: 327
<212> TYPE: PRT
<213> ORGANISM: Homo sapiens

<400> SEQUENCE: 17

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285
```

```
Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 18
<211> LENGTH: 107
<212> TYPE: PRT
<213> ORGANISM: Homo sapiens

<400> SEQUENCE: 18

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 19
<211> LENGTH: 288
<212> TYPE: PRT
<213> ORGANISM: Homo sapiens

<400> SEQUENCE: 19

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175
```

```
Leu Leu Gly Ser Leu Val Leu Val Trp Val Leu Ala Val Ile Cys
            180                 185                 190
Ser Arg Ala Ala Arg Gly Thr Ile Gly Ala Arg Arg Thr Gly Gln Pro
            195                 200                 205
Leu Lys Glu Asp Pro Ser Ala Val Pro Val Phe Ser Val Asp Tyr Gly
            210                 215                 220
Glu Leu Asp Phe Gln Trp Arg Glu Lys Thr Pro Glu Pro Pro Val Pro
225                 230                 235                 240
Cys Val Pro Glu Gln Thr Glu Tyr Ala Thr Ile Val Phe Pro Ser Gly
                245                 250                 255
Met Gly Thr Ser Ser Pro Ala Arg Arg Gly Ser Ala Asp Gly Pro Arg
            260                 265                 270
Ser Ala Gln Pro Leu Arg Pro Glu Asp Gly His Cys Ser Trp Pro Leu
            275                 280                 285

<210> SEQ ID NO 20
<211> LENGTH: 268
<212> TYPE: PRT
<213> ORGANISM: Homo sapiens

<400> SEQUENCE: 20

Pro Gly Trp Phe Leu Asp Ser Pro Asp Arg Pro Trp Asn Pro Pro Thr
1               5                   10                  15
Phe Ser Pro Ala Leu Leu Val Val Thr Glu Gly Asp Asn Ala Thr Phe
            20                  25                  30
Thr Cys Ser Phe Ser Asn Thr Ser Glu Ser Phe Val Leu Asn Trp Tyr
            35                  40                  45
Arg Met Ser Pro Ser Asn Gln Thr Asp Lys Leu Ala Ala Phe Pro Glu
            50                  55                  60
Asp Arg Ser Gln Pro Gly Gln Asp Cys Arg Phe Arg Val Thr Gln Leu
65                  70                  75                  80
Pro Asn Gly Arg Asp Phe His Met Ser Val Val Arg Ala Arg Arg Asn
                85                  90                  95
Asp Ser Gly Thr Tyr Leu Cys Gly Ala Ile Ser Leu Ala Pro Lys Ala
            100                 105                 110
Gln Ile Lys Glu Ser Leu Arg Ala Glu Leu Arg Val Thr Glu Arg Arg
            115                 120                 125
Ala Glu Val Pro Thr Ala His Pro Ser Pro Ser Pro Arg Pro Ala Gly
            130                 135                 140
Gln Phe Gln Thr Leu Val Val Gly Val Val Gly Gly Leu Leu Gly Ser
145                 150                 155                 160
Leu Val Leu Leu Val Trp Val Leu Ala Val Ile Cys Ser Arg Ala Ala
                165                 170                 175
Arg Gly Thr Ile Gly Ala Arg Arg Thr Gly Gln Pro Leu Lys Glu Asp
            180                 185                 190
Pro Ser Ala Val Pro Val Phe Ser Val Asp Tyr Gly Glu Leu Asp Phe
            195                 200                 205
Gln Trp Arg Glu Lys Thr Pro Glu Pro Pro Val Pro Cys Val Pro Glu
            210                 215                 220
Gln Thr Glu Tyr Ala Thr Ile Val Phe Pro Ser Gly Met Gly Thr Ser
225                 230                 235                 240
Ser Pro Ala Arg Arg Gly Ser Ala Asp Gly Pro Arg Ser Ala Gln Pro
                245                 250                 255
Leu Arg Pro Glu Asp Gly His Cys Ser Trp Pro Leu
            260                 265
```

<210> SEQ ID NO 21
<211> LENGTH: 290
<212> TYPE: PRT
<213> ORGANISM: Homo sapiens

<400> SEQUENCE: 21

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 22
<211> LENGTH: 272
<212> TYPE: PRT
<213> ORGANISM: Homo sapiens

<400> SEQUENCE: 22

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
                20                  25                  30

Ala Ala Leu Ile Val Tyr Trp Glu Met Glu Asp Lys Asn Ile Ile Gln
            35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Thr His Leu Val
    210                 215                 220

Ile Leu Gly Ala Ile Leu Leu Cys Leu Gly Val Ala Leu Thr Phe Ile
225                 230                 235                 240

Phe Arg Leu Arg Lys Gly Arg Met Met Asp Val Lys Lys Cys Gly Ile
                245                 250                 255

Gln Asp Thr Asn Ser Lys Lys Gln Ser Asp Thr His Leu Glu Glu Thr
            260                 265                 270

<210> SEQ ID NO 23
<211> LENGTH: 113
<212> TYPE: PRT
<213> ORGANISM: Artificial Sequence
<220> FEATURE:
<223> OTHER INFORMATION: Nivolumab heavy chain variable region

<400> SEQUENCE: 23

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

-continued

```
<210> SEQ ID NO 24
<211> LENGTH: 327
<212> TYPE: PRT
<213> ORGANISM: Artificial Sequence
<220> FEATURE:
<223> OTHER INFORMATION: Nivolumab heavy chain constant region

<400> SEQUENCE: 24

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 25
<211> LENGTH: 107
<212> TYPE: PRT
<213> ORGANISM: Artificial Sequence
<220> FEATURE:
```

-continued

<223> OTHER INFORMATION: Nivolumab light chain variable region

<400> SEQUENCE: 25

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 26
<211> LENGTH: 107
<212> TYPE: PRT
<213> ORGANISM: Artificial Sequence
<220> FEATURE:
<223> OTHER INFORMATION: Nivolumab light chain constant region

<400> SEQUENCE: 26

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 27
<211> LENGTH: 30
<212> TYPE: PRT
<213> ORGANISM: Artificial Sequence
<220> FEATURE:
<223> OTHER INFORMATION: Nivolumab heavy chain variable region FR1

<400> SEQUENCE: 27

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser
            20                  25                  30

<210> SEQ ID NO 28
<211> LENGTH: 5
<212> TYPE: PRT
<213> ORGANISM: Artificial Sequence
<220> FEATURE:
<223> OTHER INFORMATION: Nivolumab heavy chain CDR1

```
<400> SEQUENCE: 28

Asn Ser Gly Met His
1               5

<210> SEQ ID NO 29
<211> LENGTH: 14
<212> TYPE: PRT
<213> ORGANISM: Artificial Sequence
<220> FEATURE:
<223> OTHER INFORMATION: Nivolumab heavy chain FR2

<400> SEQUENCE: 29

Trp Val Arg Gln Ala Pro Gly Lys Gly Leu Glu Trp Val Ala
1               5                   10

<210> SEQ ID NO 30
<211> LENGTH: 17
<212> TYPE: PRT
<213> ORGANISM: Artificial Sequence
<220> FEATURE:
<223> OTHER INFORMATION: Nivolumab heavy chain CDR2

<400> SEQUENCE: 30

Val Ile Trp Tyr Asp Gly Ser Lys Arg Tyr Tyr Ala Asp Ser Val Lys
1               5                   10                  15

Gly

<210> SEQ ID NO 31
<211> LENGTH: 32
<212> TYPE: PRT
<213> ORGANISM: Artificial Sequence
<220> FEATURE:
<223> OTHER INFORMATION: Nivolumab heavy chain FR3

<400> SEQUENCE: 31

Arg Phe Thr Ile Ser Arg Asp Asn Ser Lys Asn Thr Leu Phe Leu Gln
1               5                   10                  15

Met Asn Ser Leu Arg Ala Glu Asp Thr Ala Val Tyr Tyr Cys Ala Thr
                20                  25                  30

<210> SEQ ID NO 32
<211> LENGTH: 4
<212> TYPE: PRT
<213> ORGANISM: Artificial Sequence
<220> FEATURE:
<223> OTHER INFORMATION: Nivolumab heavy chain CDR3

<400> SEQUENCE: 32

Asn Asp Asp Tyr
1

<210> SEQ ID NO 33
<211> LENGTH: 11
<212> TYPE: PRT
<213> ORGANISM: Artificial Sequence
<220> FEATURE:
<223> OTHER INFORMATION: Nivolumab heavy chain FR4

<400> SEQUENCE: 33

Trp Gly Gln Gly Thr Leu Val Thr Val Ser Ser
1               5                   10

<210> SEQ ID NO 34
<211> LENGTH: 23
```

```
<212> TYPE: PRT
<213> ORGANISM: Artificial Sequence
<220> FEATURE:
<223> OTHER INFORMATION: Nivolumab light chain FR1

<400> SEQUENCE: 34

Glu Ile Val Leu Thr Gln Ser Pro Ala Thr Leu Ser Leu Ser Pro Gly
1               5                   10                  15
Glu Arg Ala Thr Leu Ser Cys
            20

<210> SEQ ID NO 35
<211> LENGTH: 11
<212> TYPE: PRT
<213> ORGANISM: Artificial Sequence
<220> FEATURE:
<223> OTHER INFORMATION: Nivolumab light chain CDR1

<400> SEQUENCE: 35

Arg Ala Ser Gln Ser Val Ser Ser Tyr Leu Ala
1               5                   10

<210> SEQ ID NO 36
<211> LENGTH: 15
<212> TYPE: PRT
<213> ORGANISM: Artificial Sequence
<220> FEATURE:
<223> OTHER INFORMATION: Nivolumab light chain FR2

<400> SEQUENCE: 36

Trp Tyr Gln Gln Lys Pro Gly Gln Ala Pro Arg Leu Leu Ile Tyr
1               5                   10                  15

<210> SEQ ID NO 37
<211> LENGTH: 7
<212> TYPE: PRT
<213> ORGANISM: Artificial Sequence
<220> FEATURE:
<223> OTHER INFORMATION: Nivolumab light chain CDR2

<400> SEQUENCE: 37

Asp Ala Ser Asn Arg Ala Thr
1               5

<210> SEQ ID NO 38
<211> LENGTH: 32
<212> TYPE: PRT
<213> ORGANISM: Artificial Sequence
<220> FEATURE:
<223> OTHER INFORMATION: Nivolumab light chain FR3

<400> SEQUENCE: 38

Gly Ile Pro Ala Arg Phe Ser Gly Ser Gly Ser Gly Thr Asp Phe Thr
1               5                   10                  15
Leu Thr Ile Ser Ser Leu Glu Pro Glu Asp Phe Ala Val Tyr Tyr Cys
            20                  25                  30

<210> SEQ ID NO 39
<211> LENGTH: 9
<212> TYPE: PRT
<213> ORGANISM: Artificial Sequence
<220> FEATURE:
<223> OTHER INFORMATION: Nivolumab light chain CDR3

<400> SEQUENCE: 39

Gln Gln Ser Ser Asn Trp Pro Arg Thr
1               5
```

-continued

```
<210> SEQ ID NO 40
<211> LENGTH: 10
<212> TYPE: PRT
<213> ORGANISM: Artificial Sequence
<220> FEATURE:
<223> OTHER INFORMATION: Nivolumab light chain FR4

<400> SEQUENCE: 40

Phe Gly Gln Gly Thr Lys Val Glu Ile Lys
1               5                   10
```